US012655210B2

(12) United States Patent
Beconi et al.

(10) Patent No.: US 12,655,210 B2
(45) Date of Patent: Jun. 16, 2026

(54) ANTI-HEMOJUVELIN (HJV) ANTIBODIES FOR TREATING ANEMIA OF CHRONIC DISEASE

(71) Applicants: Disc Medicine, Inc., Watertown, MA (US); AbbVie Deutschland GmbH & Co. KG, Wiesbaden (DE); AbbVie Inc., North Chicago, IL (US)

(72) Inventors: Maria Beconi, Cambridge, MA (US); John Quisel, Cambridge, MA (US); Brian MacDonald, Newton Square, PA (US); Steven Robinette, Fremont, NH (US); Bernhard Mueller, Hannover (DE); Andreas Popp, Sprockhovel (DE); Jennifer M. Perez, Worcester, MA (US)

(73) Assignees: Disc Medicine, Inc., Watertown, MA (US); AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 661 days.

(21) Appl. No.: 17/924,660

(22) PCT Filed: May 13, 2021

(86) PCT No.: PCT/US2021/032345
§ 371 (c)(1),
(2) Date: Nov. 10, 2022

(87) PCT Pub. No.: WO2021/231800
PCT Pub. Date: Nov. 18, 2021

(65) Prior Publication Data
US 2023/0183339 A1     Jun. 15, 2023

Related U.S. Application Data

(60) Provisional application No. 63/164,307, filed on Mar. 22, 2021, provisional application No. 63/047,844, filed on Jul. 2, 2020, provisional application No. 63/035,634, filed on Jun. 5, 2020, provisional application No. 63/024,427, filed on May 13, 2020.

(51) Int. Cl.
*C07K 16/28*     (2006.01)
*A61K 39/00*     (2006.01)
*A61P 7/06*     (2006.01)

(52) U.S. Cl.
CPC ................ *C07K 16/28* (2013.01); *A61P 7/06* (2018.01); *A61K 2039/505* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,526,938 A | 7/1985 | Churchill et al. |
| 4,554,101 A | 11/1985 | Hopp |
| 4,628,027 A | 12/1986 | Gay |
| 4,704,692 A | 11/1987 | Ladner |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,223,409 A | 6/1993 | Ladner et al. |
| 5,225,539 A | 7/1993 | Winter |
| 5,241,070 A | 8/1993 | Law |
| 5,258,498 A | 11/1993 | Huston et al. |
| 5,290,540 A | 3/1994 | Prince et al. |
| 5,294,404 A | 3/1994 | Grandone et al. |
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,524 A | 6/1996 | Buechler et al. |
| 5,530,101 A | 6/1996 | Queen et al. |
| 5,543,524 A | 8/1996 | Mattingly et al. |
| 5,565,362 A | 10/1996 | Rosen et al. |

(Continued)

FOREIGN PATENT DOCUMENTS

| | | |
|---|---|---|
| CA | 2855840 A1 | 6/2013 |
| CA | 3116900 A1 | 4/2020 |

(Continued)

OTHER PUBLICATIONS

Extended European Search Report for Application No. 20867029.9, mailed Aug. 7, 2023.

(Continued)

*Primary Examiner* — Ruixiang Li
(74) *Attorney, Agent, or Firm* — Wolf, Greenfield & Sacks, P.C.

(57)     ABSTRACT

Aspects of the application provide anti-hemojuvelin antibodies and methods of using the same in treating anemias of chronic disease, iron-restricted anemias, and/or conditions associated with anemia.

20 Claims, 28 Drawing Sheets

Specification includes a Sequence Listing.

(56) References Cited

U.S. PATENT DOCUMENTS

| | | | |
|---|---|---|---|
| 5,571,698 A | 11/1996 | Ladner et al. |
| 5,573,904 A | 11/1996 | Mattingly |
| 5,580,717 A | 12/1996 | Dower et al. |
| 5,585,089 A | 12/1996 | Queen et al. |
| 5,585,097 A | 12/1996 | Bolt et al. |
| 5,593,896 A | 1/1997 | Adamczyk et al. |
| 5,624,821 A | 4/1997 | Winter et al. |
| 5,627,052 A | 5/1997 | Schrader |
| 5,648,260 A | 7/1997 | Winter et al. |
| 5,658,727 A | 8/1997 | Barbas et al. |
| 5,677,425 A | 10/1997 | Bodmer et al. |
| 5,679,377 A | 10/1997 | Bernstein et al. |
| 5,679,526 A | 10/1997 | Buechler et al. |
| 5,693,762 A | 12/1997 | Queen et al. |
| 5,693,780 A | 12/1997 | Newman et al. |
| 5,698,426 A | 12/1997 | Huse |
| 5,714,352 A | 2/1998 | Jakobobits et al. |
| 5,723,323 A | 3/1998 | Kauffman et al. |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,780,225 A | 7/1998 | Wigler et al. |
| 5,783,699 A | 7/1998 | Mattingly et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,849,992 A | 12/1998 | Meade et al. |
| 5,851,776 A | 12/1998 | Valkirs |
| 5,855,913 A | 1/1999 | Hanes et al. |
| 5,869,046 A | 2/1999 | Presta et al. |
| 5,874,064 A | 2/1999 | Edwards et al. |
| 5,885,527 A | 3/1999 | Buechler |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Lloyd et al. |
| 5,939,272 A | 8/1999 | Buechler et al. |
| 5,939,598 A | 8/1999 | Kucherlapati et al. |
| 5,947,124 A | 9/1999 | Buechler et al. |
| 5,969,108 A | 10/1999 | Mccafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,998,209 A | 12/1999 | Jokobovits et al. |
| 6,017,517 A | 1/2000 | Park |
| 6,019,944 A | 2/2000 | Buechler |
| 6,019,968 A | 2/2000 | Platz et al. |
| 6,075,181 A | 6/2000 | Kucherlapati et al. |
| 6,091,001 A | 7/2000 | Jakobovits et al. |
| 6,096,311 A | 8/2000 | Fanger et al. |
| 6,111,166 A | 8/2000 | Van de winkel |
| 6,113,855 A | 9/2000 | Buechler |
| 6,114,598 A | 9/2000 | Kucherlapati et al. |
| 6,121,022 A | 9/2000 | Presta et al. |
| 6,130,364 A | 10/2000 | Jakobovits et al. |
| 6,143,576 A | 11/2000 | Buechler |
| 6,165,745 A | 12/2000 | Ward et al. |
| 6,180,370 B1 | 1/2001 | Queen et al. |
| 6,194,551 B1 | 2/2001 | Idusogie et al. |
| 6,204,023 B1 | 3/2001 | Robinson et al. |
| 6,270,765 B1 | 8/2001 | Deo et al. |
| 6,277,375 B1 | 8/2001 | Ward |
| 6,303,755 B1 | 10/2001 | Deo et al. |
| 6,365,116 B1 | 4/2002 | Barham et al. |
| 6,410,690 B1 | 6/2002 | Deo et al. |
| 6,632,926 B1 | 10/2003 | Chen et al. |
| 6,660,843 B1 | 12/2003 | Feige et al. |
| 6,682,928 B2 | 1/2004 | Keler et al. |
| 6,699,658 B1 | 3/2004 | Wittrup et al. |
| 6,737,056 B1 | 5/2004 | Presta |
| 6,890,763 B2 | 5/2005 | Jackowski et al. |
| 6,914,128 B1 | 7/2005 | Salfeld et al. |
| 6,925,389 B2 | 8/2005 | Hitt et al. |
| 6,984,720 B1 | 1/2006 | Korman et al. |
| 6,989,100 B2 | 1/2006 | Norton |
| 7,335,667 B2 | 2/2008 | Rodgers et al. |
| 7,411,048 B2 | 8/2008 | Kulaksiz et al. |
| 7,511,018 B2 | 3/2009 | Goldberg et al. |
| 7,528,143 B2 | 5/2009 | Noronha et al. |
| 7,534,764 B2 | 5/2009 | Ganz et al. |
| 7,598,257 B2 | 10/2009 | Rodgers et al. |
| 7,612,041 B2 | 11/2009 | Knopf et al. |
| 7,612,181 B2 | 11/2009 | Wu et al. |
| 7,658,921 B2 | 2/2010 | Dall'Acqua et al. |
| 7,709,605 B2 | 5/2010 | Knopf et al. |
| 7,763,634 B2 | 7/2010 | Young et al. |
| 7,767,816 B2 | 8/2010 | Farmer et al. |
| 7,820,163 B2 | 10/2010 | Leung et al. |
| 7,825,246 B2 | 11/2010 | Noronha et al. |
| 7,834,022 B2 | 11/2010 | Rodgers et al. |
| 7,842,663 B2 | 11/2010 | Knopf et al. |
| 7,906,293 B2 | 3/2011 | Mattingly et al. |
| 7,960,343 B2 | 6/2011 | Knopf et al. |
| 7,968,091 B2 | 6/2011 | Woolf et al. |
| 7,988,973 B2 | 8/2011 | Sherman |
| 8,058,229 B2 | 11/2011 | Seehra et al. |
| 8,088,767 B2 | 1/2012 | Galan et al. |
| 8,138,199 B2 | 3/2012 | Noronha et al. |
| 8,138,339 B2 | 3/2012 | Bauer et al. |
| 8,158,616 B2 | 4/2012 | Rodgers et al. |
| 8,183,245 B2 | 5/2012 | Guerin et al. |
| 8,183,346 B2 | 5/2012 | Leung et al. |
| 8,193,189 B2 | 6/2012 | Gerspacher et al. |
| 8,202,881 B2 | 6/2012 | Purandare et al. |
| 8,258,144 B2 | 9/2012 | Song et al. |
| 8,278,335 B2 | 10/2012 | Machacek et al. |
| 8,293,881 B2 | 10/2012 | Seehra et al. |
| 8,304,258 B2 | 11/2012 | Kulaksiz et al. |
| 8,309,566 B2 | 11/2012 | Bhamidipati et al. |
| 8,309,718 B2 | 11/2012 | Li et al. |
| 8,318,167 B2 | 11/2012 | Lin et al. |
| 8,323,649 B2 | 12/2012 | Garcia-Martinez et al. |
| 8,328,308 B2 | 12/2012 | Kurashina et al. |
| 8,338,377 B2 | 12/2012 | Seehra |
| 8,344,144 B2 | 1/2013 | Machacek et al. |
| 8,349,851 B2 | 1/2013 | Abraham et al. |
| 8,349,865 B2 | 1/2013 | Siu et al. |
| 8,354,408 B2 | 1/2013 | Bourke et al. |
| 8,367,078 B2 | 2/2013 | Sayeski et al. |
| 8,367,706 B2 | 2/2013 | Altman et al. |
| 8,415,346 B2 | 4/2013 | Altman et al. |
| 8,415,362 B2 | 4/2013 | Rodgers et al. |
| 8,415,364 B2 | 4/2013 | Epstein et al. |
| 8,420,089 B2 | 4/2013 | Smith |
| 8,420,695 B2 | 4/2013 | Wilson et al. |
| 8,431,569 B2 | 4/2013 | Young et al. |
| 8,440,663 B2 | 5/2013 | Mann et al. |
| 8,440,679 B2 | 5/2013 | McAllister et al. |
| 8,445,199 B2 | 5/2013 | Collier et al. |
| 8,486,902 B2 | 7/2013 | Rodgers et al. |
| 8,486,941 B2 | 7/2013 | Burns et al. |
| 8,501,735 B2 | 8/2013 | Rosales et al. |
| 8,507,435 B2 | 8/2013 | Goldberg et al. |
| 8,507,501 B2 | 8/2013 | Yu et al. |
| 8,513,270 B2 | 8/2013 | Arvantis et al. |
| 8,530,619 B2 | 9/2013 | Kaplan et al. |
| 8,563,539 B2 | 10/2013 | Baldino et al. |
| 8,580,802 B2 | 11/2013 | Salituro et al. |
| 8,591,886 B2 | 11/2013 | Ponath et al. |
| 8,604,043 B2 | 12/2013 | Li et al. |
| 8,609,817 B2 | 12/2013 | Leung et al. |

(56)  References Cited

U.S. PATENT DOCUMENTS

| | | | |
|---|---|---|---|
| 8,629,168 | B2 | 1/2014 | Gerspacher et al. |
| 8,629,250 | B2 | 1/2014 | Sasu et al. |
| 8,633,205 | B2 | 1/2014 | Ledeboer et al. |
| 8,633,206 | B2 | 1/2014 | Promo et al. |
| 8,637,023 | B2 | 1/2014 | Lin et al. |
| 8,637,526 | B2 | 1/2014 | Blaney et al. |
| 8,648,069 | B2 | 2/2014 | Akritopoulou-Zanze et al. |
| 8,673,891 | B2 | 3/2014 | Fujihara et al. |
| 8,691,807 | B2 | 4/2014 | Yao et al. |
| 8,710,016 | B2 | 4/2014 | Seehra et al. |
| 8,716,303 | B2 | 5/2014 | Rodgers et al. |
| 8,722,693 | B2 | 5/2014 | Rodgers et al. |
| 8,741,912 | B2 | 6/2014 | Ledeboer et al. |
| 8,765,385 | B2 | 7/2014 | Kumar et al. |
| 8,765,727 | B2 | 7/2014 | Combs et al. |
| 8,765,734 | B2 | 7/2014 | Huang et al. |
| 8,779,001 | B2 | 7/2014 | Tweardy et al. |
| 8,795,665 | B2 | 8/2014 | Seo et al. |
| 8,809,359 | B2 | 8/2014 | Burns |
| 8,814,840 | B2 | 8/2014 | Evans et al. |
| 8,822,481 | B1 | 9/2014 | Rodgers et al. |
| 8,829,013 | B1 | 9/2014 | Rodgers et al. |
| 8,841,431 | B2 | 9/2014 | Sell et al. |
| 8,846,908 | B2 | 9/2014 | Singh et al. |
| 8,865,168 | B2 | 10/2014 | Lin et al. |
| 8,871,753 | B2 | 10/2014 | Combs et al. |
| 8,895,002 | B2 | 11/2014 | Lin et al. |
| 8,901,145 | B2 | 12/2014 | Baldino et al. |
| 8,912,200 | B2 | 12/2014 | Brasca et al. |
| 8,915,875 | B2 | 12/2014 | Passlock-Deetjen et al. |
| 8,921,376 | B2 | 12/2014 | Ledeboer et al. |
| 8,933,085 | B2 | 1/2015 | Rodgers et al. |
| 8,937,064 | B2 | 1/2015 | Ledeboer et al. |
| 8,937,065 | B2 | 1/2015 | Becker et al. |
| 8,957,065 | B2 | 2/2015 | Cha et al. |
| 8,962,803 | B2 | 2/2015 | Mueller et al. |
| 8,980,582 | B2 | 3/2015 | Seo et al. |
| 8,999,998 | B2 | 4/2015 | Gibbons et al. |
| 9,034,311 | B2 | 5/2015 | Eastwood et al. |
| 9,034,884 | B2 | 5/2015 | Rodgers et al. |
| 9,035,074 | B2 | 5/2015 | Brown et al. |
| 9,040,052 | B1 | 5/2015 | Clube |
| 9,051,382 | B2 | 6/2015 | Trentmann et al. |
| 9,079,912 | B2 | 7/2015 | Rodgers et al. |
| 9,085,615 | B2 | 7/2015 | Garcia-Martinez et al. |
| 9,133,200 | B2 | 9/2015 | Gonzalez Rodriguez et al. |
| 9,175,075 | B2 | 11/2015 | Mueller |
| 9,175,078 | B2 | 11/2015 | Arvedson et al. |
| 9,181,271 | B2 | 11/2015 | Li et al. |
| 9,187,562 | B1 | 11/2015 | Clube |
| 9,193,733 | B2 | 11/2015 | Rodgers et al. |
| 9,206,183 | B2 | 12/2015 | Bach Tana et al. |
| 9,206,188 | B2 | 12/2015 | Vankayalapati et al. |
| 9,228,188 | B2 | 1/2016 | Bettecourt et al. |
| 9,249,145 | B2 | 2/2016 | Rodgers et al. |
| 9,249,454 | B2 | 2/2016 | Woolf et al. |
| 9,265,825 | B2 | 2/2016 | Smith |
| 9,283,224 | B2 | 3/2016 | Brasca et al. |
| 9,315,577 | B2 | 4/2016 | Foltz et al. |
| 9,358,229 | B2 | 6/2016 | Vannucchi et al. |
| 9,359,358 | B2 | 6/2016 | Rodgers et al. |
| 9,371,320 | B2 | 6/2016 | Nara et al. |
| 9,382,231 | B2 | 7/2016 | Li et al. |
| 9,439,963 | B2 | 9/2016 | Clube |
| 9,452,227 | B2 | 9/2016 | Garcia-Martinez et al. |
| 9,469,613 | B2 | 10/2016 | Brown et al. |
| 9,469,654 | B2 | 10/2016 | Pandey et al. |
| 9,518,027 | B2 | 12/2016 | Silverman |
| 9,526,759 | B2 | 12/2016 | Knopf et al. |
| 9,533,986 | B2 | 1/2017 | Pandey et al. |
| 9,540,367 | B2 | 1/2017 | Tung |
| 9,556,251 | B2 | 1/2017 | Lin et al. |
| 9,605,069 | B2 | 3/2017 | Mueller et al. |
| 9,610,356 | B2 | 4/2017 | Hohlbaum et al. |
| 9,617,258 | B2 | 4/2017 | Thorarensen et al. |
| 9,636,398 | B2 | 5/2017 | Belligere et al. |
| 9,637,483 | B2 | 5/2017 | Yoshida et al. |
| 9,650,399 | B2 | 5/2017 | Gunning et al. |
| 9,657,098 | B2 | 5/2017 | Westerman et al. |
| 9,676,756 | B2 | 6/2017 | Bauer et al. |
| 9,682,983 | B2 | 6/2017 | Alimardanov et al. |
| 9,688,661 | B2 | 6/2017 | Brasca et al. |
| 9,701,747 | B2 | 7/2017 | Smith |
| 9,708,379 | B2 | 7/2017 | Lin et al. |
| 9,724,410 | B2 | 8/2017 | Smith et al. |
| 9,738,636 | B2 | 8/2017 | Hopkins et al. |
| 9,803,011 | B2 | 10/2017 | Westerman et al. |
| 9,814,722 | B2 | 11/2017 | Rodgers et al. |
| 9,862,764 | B2 | 1/2018 | Cong et al. |
| 9,884,900 | B2 | 2/2018 | Kumar et al. |
| 9,949,971 | B2 | 4/2018 | Hamdy et al. |
| 9,993,480 | B2 | 6/2018 | Vannucchi et al. |
| 10,001,571 | B2 | 6/2018 | Rowland et al. |
| 10,011,571 | B2 | 7/2018 | Lu et al. |
| 10,016,429 | B2 | 7/2018 | Rodgers et al. |
| 10,064,866 | B2 | 9/2018 | Scherle et al. |
| 10,106,602 | B2 | 10/2018 | Mueller et al. |
| 10,111,897 | B2 | 10/2018 | Wood et al. |
| 10,112,933 | B2 | 10/2018 | Tweardy et al. |
| 10,118,958 | B2 | 11/2018 | Mueller et al. |
| 10,189,882 | B2 | 1/2019 | Attie et al. |
| 10,202,356 | B2 | 2/2019 | Mollard et al. |
| 10,206,931 | B2 | 2/2019 | Romero et al. |
| 10,233,186 | B2 | 3/2019 | Brooijmans et al. |
| 10,239,941 | B2 | 3/2019 | Westerman et al. |
| 10,245,268 | B2 | 4/2019 | Koh et al. |
| 10,246,462 | B2 | 4/2019 | Beck et al. |
| 10,273,273 | B2 | 4/2019 | Lin et al. |
| 10,294,226 | B2 | 5/2019 | Koudriakova et al. |
| 10,307,426 | B2 | 6/2019 | Zak et al. |
| 10,307,455 | B2 | 6/2019 | Kumar et al. |
| 10,323,088 | B2 | 6/2019 | Westerman |
| 10,391,094 | B2 | 8/2019 | Jayan et al. |
| 10,392,441 | B2 | 8/2019 | Durum |
| 10,428,148 | B2 | 10/2019 | Katagiri et al. |
| 10,669,277 | B2 | 6/2020 | Wilson et al. |
| 10,822,403 | B2 | 11/2020 | Mueller et al. |
| 12,098,189 | B2 | 9/2024 | Mueller et al. |
| 12,098,192 | B2 | 9/2024 | Mueller et al. |
| 12,365,729 | B2 | 7/2025 | Mueller et al. |
| 12,497,452 | B2 | 12/2025 | Mueller et al. |
| 2003/0170881 | A1 | 9/2003 | Davis et al. |
| 2003/0186374 | A1 | 10/2003 | Hufton et al. |
| 2004/0018577 | A1 | 1/2004 | Emerson et al. |
| 2005/0042664 | A1 | 2/2005 | Wu et al. |
| 2005/0054078 | A1 | 3/2005 | Miller et al. |
| 2006/0104968 | A1 | 5/2006 | Bookbinder et al. |
| 2006/0106020 | A1 | 5/2006 | Rodgers et al. |
| 2006/0153852 | A1 | 7/2006 | Coleman et al. |
| 2006/0160164 | A1 | 7/2006 | Miller et al. |
| 2007/0004618 | A1 | 1/2007 | Ganz et al. |
| 2007/0149506 | A1 | 6/2007 | Arvantis et al. |
| 2008/0020401 | A1 | 1/2008 | Grenier et al. |
| 2008/0021013 | A1 | 1/2008 | Dobrzanski et al. |
| 2008/0213277 | A1 | 9/2008 | Sasu et al. |
| 2008/0287475 | A1 | 11/2008 | Feng et al. |
| 2008/0312259 | A1 | 12/2008 | Rodgers et al. |
| 2009/0062302 | A1 | 3/2009 | Buser-Doepner et al. |
| 2009/0104187 | A1 | 4/2009 | Kovacevich et al. |
| 2009/0238825 | A1 | 9/2009 | Kovacevich et al. |
| 2010/0008918 | A1 | 1/2010 | Sherman et al. |
| 2010/0028340 | A1 | 2/2010 | Mueller et al. |
| 2010/0035875 | A1 | 2/2010 | Zhu et al. |
| 2010/0048557 | A1 | 2/2010 | Zhu et al. |
| 2010/0093760 | A1 | 4/2010 | Yu et al. |
| 2010/0160287 | A1 | 6/2010 | Wannamaker et al. |
| 2010/0204246 | A1 | 8/2010 | Davies et al. |
| 2010/0322941 | A1 | 12/2010 | Fischer et al. |
| 2010/0324040 | A1 | 12/2010 | Davies et al. |
| 2011/0020775 | A1 | 1/2011 | Cecil |
| 2011/0070233 | A1 | 3/2011 | Seehra et al. |
| 2011/0085973 | A1 | 4/2011 | Kao et al. |
| 2011/0135664 | A1 | 6/2011 | Mueller |
| 2011/0201628 | A1 | 8/2011 | Chuaqui et al. |

(56) References Cited

U.S. PATENT DOCUMENTS

| | | |
|---|---|---|
| 2011/0243853 A1 | 10/2011 | Jamieson et al. |
| 2011/0293526 A1 | 12/2011 | Plikus et al. |
| 2012/0055573 A1 | 3/2012 | Adams |
| 2012/0064076 A1 | 3/2012 | Lin et al. |
| 2012/0115930 A1 | 5/2012 | Monia et al. |
| 2012/0164140 A1 | 6/2012 | Lin et al. |
| 2012/0196853 A1 | 8/2012 | Duerrenberger et al. |
| 2012/0202806 A1 | 8/2012 | Duerrenberger et al. |
| 2012/0214798 A1 | 8/2012 | Duerrenberger et al. |
| 2012/0214803 A1 | 8/2012 | Buhr et al. |
| 2013/0089512 A1 | 4/2013 | Eastwood et al. |
| 2013/0216498 A1 | 8/2013 | Eastwood et al. |
| 2013/0243743 A1 | 9/2013 | Seehra et al. |
| 2013/0330343 A1 | 12/2013 | Mueller et al. |
| 2013/0330359 A1 | 12/2013 | Beligere et al. |
| 2014/0057970 A1 | 2/2014 | Schwobel et al. |
| 2014/0073643 A1 | 3/2014 | Smith et al. |
| 2014/0073645 A1 | 3/2014 | Linder et al. |
| 2014/0086919 A1 | 3/2014 | Lin et al. |
| 2014/0127325 A1 | 5/2014 | Bettencourt et al. |
| 2014/0170110 A1 | 6/2014 | Eastwood et al. |
| 2014/0199314 A1 | 7/2014 | Lin et al. |
| 2014/0286964 A1 | 9/2014 | Hubbard et al. |
| 2015/0024046 A1 | 1/2015 | Bartholomaus et al. |
| 2015/0166672 A1 | 6/2015 | Clube |
| 2015/0197525 A1 | 7/2015 | Silverman et al. |
| 2015/0291675 A1 | 10/2015 | Trentmann et al. |
| 2015/0306112 A1 | 10/2015 | Wu et al. |
| 2015/0361163 A1 | 12/2015 | Kumar et al. |
| 2015/0369821 A1 | 12/2015 | Trentmann et al. |
| 2016/0115167 A1 | 4/2016 | Yu et al. |
| 2016/0122409 A1 | 5/2016 | Ganz et al. |
| 2016/0186172 A1 | 6/2016 | Bettencourt et al. |
| 2016/0263117 A1 | 9/2016 | Yu et al. |
| 2016/0317632 A1 | 11/2016 | Albrecht et al. |
| 2017/0029499 A1 | 2/2017 | Kakkar et al. |
| 2017/0190705 A1 | 7/2017 | Yu et al. |
| 2017/0196878 A1 | 7/2017 | Centore et al. |
| 2017/0197968 A1 | 7/2017 | Lee et al. |
| 2017/0224819 A1 | 8/2017 | Hamdy et al. |
| 2017/0239451 A1 | 8/2017 | Berkowitz |
| 2017/0247448 A1 | 8/2017 | Westerman |
| 2017/0274077 A1 | 9/2017 | Kumar et al. |
| 2017/0305883 A1 | 10/2017 | Yu et al. |
| 2017/0313754 A1 | 11/2017 | Bourne et al. |
| 2017/0333406 A1 | 11/2017 | Adler et al. |
| 2018/0001633 A1 | 1/2018 | Silverbrook et al. |
| 2018/0002328 A1 | 1/2018 | Li et al. |
| 2018/0016332 A1 | 1/2018 | Schurpf et al. |
| 2018/0021340 A1 | 1/2018 | Yu et al. |
| 2018/0050085 A1 | 2/2018 | Kumar et al. |
| 2018/0057812 A1 | 3/2018 | Peyssonnaux et al. |
| 2018/0118835 A1 | 5/2018 | Katagiri et al. |
| 2018/0148491 A1 | 5/2018 | Han et al. |
| 2018/0317602 A1 | 11/2018 | Rothbaum et al. |
| 2019/0040068 A1 | 2/2019 | Yin et al. |
| 2019/0135807 A1 | 5/2019 | Anderson et al. |
| 2019/0152949 A1 | 5/2019 | Cyr et al. |
| 2019/0169208 A1 | 6/2019 | Cui et al. |
| 2019/0204427 A1 | 7/2019 | Abari et al. |
| 2019/0218214 A1 | 7/2019 | Hopkins et al. |
| 2019/0241650 A1 | 8/2019 | Devalaraja et al. |
| 2019/0282663 A1 | 9/2019 | Seehra et al. |
| 2019/0284183 A1 | 9/2019 | Hopkins et al. |
| 2019/0322665 A1 | 10/2019 | Bacani et al. |
| 2019/0328857 A1 | 10/2019 | Andersen et al. |
| 2020/0054643 A1 | 2/2020 | Hopkins et al. |
| 2020/0055919 A1 | 2/2020 | Kumar et al. |
| 2020/0071303 A1 | 3/2020 | Wang et al. |
| 2020/0095250 A1 | 3/2020 | Vechorkin et al. |
| 2020/0101134 A1 | 4/2020 | Laadem et al. |
| 2020/0199131 A1 | 6/2020 | Pan et al. |
| 2021/0380669 A1 | 12/2021 | Nicholls et al. |
| 2022/0372135 A1 | 11/2022 | Quisel et al. |
| 2022/0372136 A1 | 11/2022 | Quisel et al. |
| 2023/0174645 A1 | 6/2023 | Beconi et al. |
| 2024/0417458 A1 | 12/2024 | MacDonald et al. |
| 2025/0084162 A1 | 3/2025 | Mueller et al. |
| 2025/0179159 A1 | 6/2025 | Mueller et al. |
| 2025/0304678 A1 | 10/2025 | Mueller et al. |
| 2025/0312445 A1 | 10/2025 | Buch et al. |

FOREIGN PATENT DOCUMENTS

| | | |
|---|---|---|
| CN | 1484652 A | 3/2004 |
| CN | 101778864 A | 7/2010 |
| CN | 101816674 A | 9/2010 |
| CN | 103655542 A | 3/2014 |
| CN | 104136462 A | 11/2014 |
| CN | 104144947 A | 11/2014 |
| CN | 109789184 A | 5/2019 |
| EP | 404097 A2 | 12/1990 |
| EP | 471293 A2 | 2/1992 |
| EP | 2335708 A1 | 6/2011 |
| HN | 2010/000752 A | 8/2012 |
| JP | 2002-542770 A | 12/2002 |
| JP | 2015-502753 A | 1/2015 |
| JP | 2011-512806 A | 4/2024 |
| WO | WO 1990/002809 A1 | 3/1990 |
| WO | WO 1991/005548 A1 | 5/1991 |
| WO | WO 1991/010737 A1 | 7/1991 |
| WO | WO 1991/010741 A1 | 7/1991 |
| WO | WO 1991/017271 A1 | 11/1991 |
| WO | WO 1992/001047 A1 | 1/1992 |
| WO | WO 1992/002551 A1 | 2/1992 |
| WO | WO 1992/009690 A2 | 6/1992 |
| WO | WO 1992/015679 A1 | 9/1992 |
| WO | WO 1992/018619 A1 | 10/1992 |
| WO | WO 1992/019244 A2 | 11/1992 |
| WO | WO 1992/020791 A1 | 11/1992 |
| WO | WO 1992/022324 A1 | 12/1992 |
| WO | WO 1993/001288 A1 | 1/1993 |
| WO | WO 1993/011161 A1 | 6/1993 |
| WO | WO 1993/011236 A1 | 6/1993 |
| WO | WO 1994/002602 A1 | 2/1994 |
| WO | WO 1994/029351 A2 | 12/1994 |
| WO | WO 1995/015982 A2 | 6/1995 |
| WO | WO 1995/020401 A1 | 8/1995 |
| WO | WO 1996/020698 A2 | 7/1996 |
| WO | WO 1996/033735 A1 | 10/1996 |
| WO | WO 1996/034096 A1 | 10/1996 |
| WO | WO 1997/029131 A1 | 8/1997 |
| WO | WO 1997/032572 A2 | 9/1997 |
| WO | WO 1997/034631 A1 | 9/1997 |
| WO | WO 1997/044013 A1 | 11/1997 |
| WO | WO 1998/016654 A1 | 4/1998 |
| WO | WO 1998/023289 A1 | 6/1998 |
| WO | WO 1998/024893 A2 | 6/1998 |
| WO | WO 1998/031346 A1 | 7/1998 |
| WO | WO 1998/031700 A1 | 7/1998 |
| WO | WO 1998/050433 A2 | 11/1998 |
| WO | WO 1999/015154 A1 | 4/1999 |
| WO | WO 1999/020253 A1 | 4/1999 |
| WO | WO 1999/025044 A1 | 5/1999 |
| WO | WO 1999/045031 A2 | 9/1999 |
| WO | WO 1999/053049 A1 | 10/1999 |
| WO | WO 1999/058572 A1 | 11/1999 |
| WO | WO 1999/066903 A2 | 12/1999 |
| WO | WO 2000/009560 A2 | 2/2000 |
| WO | WO 2000/037504 A2 | 6/2000 |
| WO | WO 2000/042072 A2 | 7/2000 |
| WO | WO 2000/056772 A1 | 9/2000 |
| WO | WO 2001/058956 A2 | 8/2001 |
| WO | WO 2002/002773 A2 | 1/2002 |
| WO | WO 2002/016436 A2 | 2/2002 |
| WO | WO 2002/060919 A2 | 8/2002 |
| WO | WO 2004/078140 A2 | 9/2004 |
| WO | WO 2005/047307 A2 | 5/2005 |
| WO | WO 2006/088972 A2 | 8/2006 |
| WO | WO 2007/024715 A2 | 3/2007 |
| WO | WO 2007/039256 A2 | 4/2007 |
| WO | WO 2008/047831 A1 | 4/2008 |
| WO | WO 2008/117050 A1 | 10/2008 |
| WO | WO 2008/124768 A1 | 10/2008 |

(56) References Cited

FOREIGN PATENT DOCUMENTS

| WO | WO 2008/132502 A1 | 11/2008 |
|----|----|----|
| WO | WO 2008/144757 A1 | 11/2008 |
| WO | WO 2009/016410 A2 | 2/2009 |
| WO | WO 2009/017838 A2 | 2/2009 |
| WO | WO 2009/017954 A1 | 2/2009 |
| WO | WO 2009/027736 A2 | 3/2009 |
| WO | WO 2009/030500 A1 | 3/2009 |
| WO | WO 2007/024715 A9 | 4/2009 |
| WO | WO 2009/046416 A1 | 4/2009 |
| WO | WO 2009/049028 A1 | 4/2009 |
| WO | WO 2009/055674 A1 | 4/2009 |
| WO | WO 2009/095712 A2 | 8/2009 |
| WO | WO 2009/106356 A1 | 9/2009 |
| WO | WO 2010/020810 A1 | 2/2010 |
| WO | WO 2010/056981 A2 | 5/2010 |
| WO | WO 2010/065077 A2 | 6/2010 |
| WO | WO 2010/065079 A2 | 6/2010 |
| WO | WO 2010/065496 A1 | 6/2010 |
| WO | WO 2010/072823 A1 | 7/2010 |
| WO | WO 2010/141062 A1 | 12/2010 |
| WO | WO 2011/023722 A1 | 3/2011 |
| WO | WO 2011/029832 A1 | 3/2011 |
| WO | WO 2011/066369 A2 | 6/2011 |
| WO | WO 2011/066371 A2 | 6/2011 |
| WO | WO 2011/070045 A1 | 6/2011 |
| WO | WO 2011/153586 A1 | 12/2011 |
| WO | WO 2012/150973 A1 | 11/2012 |
| WO | WO 2013/063110 A1 | 5/2013 |
| WO | WO 2013/090633 A2 | 6/2013 |
| WO | WO 2013/090635 A2 | 6/2013 |
| WO | WO 2014/020531 A1 | 2/2014 |
| WO | WO 2014/058516 A1 | 4/2014 |
| WO | WO 2014/065661 A1 | 5/2014 |
| WO | WO 2015/051135 A2 | 4/2015 |
| WO | WO 2015/091531 A1 | 6/2015 |
| WO | WO 2015/118434 A1 | 8/2015 |
| WO | WO 2015/171691 A2 | 11/2015 |
| WO | WO 2016/090188 A1 | 6/2016 |
| WO | WO 2016/146651 A1 | 9/2016 |
| WO | WO 2016/180784 A1 | 11/2016 |
| WO | WO 2017/143014 A1 | 8/2017 |
| WO | WO 2017/191437 A1 | 11/2017 |
| WO | WO 2017/196261 A1 | 11/2017 |
| WO | WO 2017/216724 A1 | 12/2017 |
| WO | WO 2018/009624 A1 | 1/2018 |
| WO | WO 2018/022762 A1 | 2/2018 |
| WO | WO 2018/053234 A1 | 3/2018 |
| WO | WO 2018/067740 A1 | 4/2018 |
| WO | WO 2018/096525 A2 | 5/2018 |
| WO | WO 2018/128828 A1 | 7/2018 |
| WO | WO 2018/136634 A1 | 7/2018 |
| WO | WO 2018/165186 A1 | 9/2018 |
| WO | WO 2018/185341 A1 | 10/2018 |
| WO | WO 2018/200855 A1 | 11/2018 |
| WO | WO 2019/057112 A1 | 3/2019 |
| WO | WO 2019/069844 A1 | 4/2019 |
| WO | WO 2019/079649 A1 | 4/2019 |
| WO | WO 2019/094751 A1 | 5/2019 |
| WO | WO 2019/107943 A1 | 6/2019 |
| WO | WO 2019/140283 A1 | 7/2019 |
| WO | WO 2019/161157 A1 | 8/2019 |
| WO | WO 2019/161162 A1 | 8/2019 |
| WO | WO 2019/204427 A1 | 10/2019 |
| WO | WO 2020/009740 A2 | 1/2020 |
| WO | WO 2020/041466 A1 | 2/2020 |
| WO | WO 2020/065252 A1 | 4/2020 |
| WO | WO 2020/068729 A1 | 4/2020 |
| WO | WO 2020/086730 A1 | 4/2020 |
| WO | WO 2020/086736 A1 | 4/2020 |
| WO | WO 2020/086963 A1 | 4/2020 |
| WO | WO 2020/092523 A1 | 5/2020 |
| WO | WO 2020/097396 A1 | 5/2020 |
| WO | WO 2020/097398 A1 | 5/2020 |
| WO | WO 2020/112086 A1 | 6/2020 |
| WO | WO 2021/062163 A1 | 4/2021 |
| WO | WO 2021/062171 A1 | 4/2021 |
| WO | WO 2021/231798 A1 | 11/2021 |
| WO | WO 2021/231800 A2 | 11/2021 |
| WO | WO 2023/091968 A1 | 5/2023 |

OTHER PUBLICATIONS

International Search Report and Written Opinion for Application No. PCT/US2020/052732 mailed Jan. 11, 2021.

International Preliminary Report on Patentability for Application No. PCT/US2020/052732 mailed Apr. 7, 2022.

International Search Report and Written Opinion for Application No. PCT/US2020/052748 mailed Jan. 12, 2021.

International Preliminary Report on Patentability for Application No. PCT/US2020/052748 mailed Apr. 7, 2022.

Invitation to Pay Additional Fees for Application No. PCT/US2021/032345 mailed Aug. 24, 2021.

International Search Report and Written Opinion for Application No. PCT/US2021/032345 mailed Nov. 26, 2021.

International Preliminary Report on Patentability for Application No. PCT/US2021/032345 mailed Nov. 24, 2022.

Invitation to Pay Additional Fees for Application No. PCT/US2021/032343 mailed Aug. 16, 2021.

International Search Report and Written Opinion for Application No. PCT/US2021/032343 mailed Oct. 29, 2021.

International Preliminary Report on Patentability for Application No. PCT/US2021/032343 mailed Nov. 24, 2022.

International Search Report and Written Opinion for Application No. PCT/US2022/079987 mailed Mar. 6, 2023.

[No Author Listed] Know About Different Types of Wounds, Wound Care Surgeons, 2022, https://www.woundcaresurgeons.org/blogs/know-about-different-types-of-wounds, 5 pages.

Akinc et al., Targeting the Hepcidin Pathway with RNAi Therapeutics for the Treatment of Anemia. Blood. Nov. 18, 2011;118(21):688. doi: http://doi.org/10.1182/blood.V118.21.688.688.

Alshemmari et al., Molecular Pathogenesis and Clinical Significance of Driver Mutations in Primary Myelofibrosis: A Review. Med Princ Pract. 2016;25(6):501-509. doi: 10.1159/000450956. Epub Sep. 21, 2016.

Amylon et al., Prednisone stimulation of erythropoiesis in leukemic children during remission. Am J Hematol. Oct. 1986;23(2):179-81. doi: 10.1002/ajh.2830230213.

Asshoff et al., Momelotinib inhibits ACVR1/ALK2, decreases hepcidin production, and ameliorates anemia of chronic disease in rodents. Blood. Mar. 30, 2017;129(13):1823-1830. doi: 10.1182/blood-2016-09-740092. Epub Feb. 10, 2017.

Babbitt et al., Mechanisms of anemia in Ckd. J Am Soc Nephrol. Oct. 2012;23(10):1631-4. doi: 10.1681/ASN.2011111078. Epub Aug. 30, 2012.

Babbitt et al., Bone morphogenetic protein signaling by hemojuvelin regulated hepcidin expression. Nature Genetics. May 2006;38(5):531. doi:10.1038/ng1777. Epub Apr. 9, 2006.

Birgegard et al., Inflammatory functional iron deficiency common in myelofibrosis, contributes to anaemia and impairs quality of life. From the Nordic MPN study Group. Eur J Haematol. Mar. 2019;102(3):235-240. doi: 10.1111/ejh.13198. Epub Jan. 1, 2019.

Boser et al., Anti-repulsive Guidance Molecule C (RGMc) Antibodies Increases Serum Iron in Rats and Cynomolgus Monkeys by Hepcidin Downregulation. AAPS J. Jul. 2015;17(4):930-8. doi: 10.1208/s12248-015-9770-4. Epub Apr. 22, 2015.

Braunstein et al., Anemia of Chronic Disease. John Hopkins University School of Medicine. Sep. 2021. https://www.merckmanuals.com/professional/hematology-and-oncology/anemias-caused-by-deficient-erythropoiesis/anemia-of-chronic-disease [last accessed Nov. 16, 2022].

Bruhns et al., Specificity and affinity of human Fcgamma receptors and their polymorphic variants for human IgG subclasses. Blood. Apr. 16, 2009;113(16):3716-25. doi: 10.1182/blood-2008-09-179754. Epub Nov. 18, 2008.

Calpe et al., Comparison of newly developed anti-bone morphogenetic protein 4 llama-derived antibodies with commercially avail-

(56) References Cited

OTHER PUBLICATIONS able BMP4 inhibitors. MAbs. May-Jun. 2016;8(4):678-88. doi: 10.1080/19420862.2016.1158380.

Canali et al., Activin B Induces Noncanonical SMAD1/5/8 Signaling via BMP Type I Receptors in Hepatocytes: Evidence for a Role in Hepcidin Induction by Inflammation in Male Mice. Endocrinology. Mar. 2016;157(3):1146-62. doi: 10.1210/en.2015-1747. Epub Jan. 6, 2016.

Capellini et al., Iron deficiency across chronic inflammatory conditions: International expert opinion on definition, diagnosis, and management. Am J Hematol. Oct. 2017;92(10):1068-1078. doi: 10.1002/ajh.24820. Epub Jul. 7, 2017.

Carvalho et al., ALK2 inhibitors display beneficial effects in preclinical models of ACVR1 mutant diffuse intrinsic pontine glioma. Commun Biol. May 9, 2019;2:156. doi: 10.1038/s42003-019-0420-8.

Cazzola, et al., From Janus kinase 2 to calreticulin: the clinically relevant genomic landscape of myeloproliferative neoplasms. Blood. Jun. 12, 2014;123(24):3714-9. doi: 10.1182/blood-2014-03-530865. Epub Apr. 30, 2014.

Chai et al., Danazol: An Effective and Underutilised Treatment Option in Diamond-Blackfan Anaemia. Case Rep Hematol. Jul. 1, 2019;2019:4684156. doi: 10.1155/2019/4684156.

Chelius et al., Formation of pyroglutamic acid from N-terminal glutamic acid in immunoglobulin gamma antibodies. Anal Chem. Apr. 1, 2006;78(7):2370-6. doi: 10.1021/ac051827k.

Chen et al., Differential roles for bone morphogenetic protein (BMP) receptor type IB and IA in differentiation and specification of mesenchymal precursor cells to osteoblast and adipocyte lineages. J Cell Biol. Jul. 13, 1998;142(1):295-305. doi: 10.1083/jcb.142.1.295.

Cheng et al., Hepcidin expression in anemia of chronic disease and concomitant iron-deficiency anemia. Clin Exp Med. Mar. 2011;11(1):33-42. doi: 10.1007/s10238-010-0102-9. Epub May 25, 2010.

Cokic et al., Proinflammatory Cytokine IL-6 and JAK-STAT Signaling Pathway in Myeloproliferative Neoplasms. Mediators Inflamm. 2015;2015:453020. doi: 10.1155/2015/453020. Epub Sep. 29, 2015.

Cooke et al., A fully human anti-hepcidin antibody modulates iron metabolism in both mice and nonhuman primates. Blood. Oct. 24, 2013;122(17):3054-61. Doi: 10.1182/blood-2013-06- 505792. Epub Aug. 14, 2013.

Cullis, Diagnosis and management of anaemia of chronic disease: current status. Br J Haematol. Aug. 2011;154(3):289-300. doi: 10.1111/j.1365-2141.2011.08741.x. Epub May 25, 2011.

Daher et al., Heterozygous mutations in BMP-6 Pro-peptide Lead to Inappropriate Hepcidin Synethesis and Moderate Iron Overload in Humans. Gastroenterology. Mar. 2016;150(3): 672-683.e4. doi: 10.1053/j.gastro.2015.10.049. Epub Nov. 12, 2015.

Dall'Acqua et al., Properties of human IgGls engineered for enhanced binding to the neonatal Fc receptor (FcRn). J Biol Chem. Aug. 18, 2006;281(33):23514-24. doi: 10.1074/jbc.M604292200. Epub Jun. 21, 2006.

De Falco et al., Iron refractory iron deficiency anemia. Haemotologica. 2013;98(6): 845-53. doi: 10.3324/haematol.2012.075515.

Du et al., The serine protease TMPRSS6 is required to sense iron deficiency. Science. May 23, 2008;320(5879):1088-92. doi: 10.1126/science.1157121. Epub May 1, 2008. Author Manuscript, 9 pages.

Elala et al., 1599 Driver Mutations and Prognosis in 502 Patients with Essential Thrombocythemia. ASH. Dec. 5, 2015. Retrieved from internet: https://ash.confex.com/ash/2015/webprogramscheduler/Paper79911.html. [last accessed Nov. 22, 2022].

Emanuel et al., Myeloproliferative neoplasm (MPN) symptom assessment form total symptom score: prospective international assessment of an abbreviated symptom burden scoring system among patients with MPNs. J Clin Oncol. Nov. 20, 2012;30(33):4098-103. doi: 10.1200/JCO.2012.42.3863. Epub Oct. 15, 2012. Erratum in: J Clin Oncol. Dec. 20, 2012;30(36):4590. Ferarri, Maria L [corrected to Ferrari, Maria L].

Feder et al., A novel MHC class I-like gene is mutated in pateints with hereditary haemochromatosis. Nat Genet. Aug. 1996;13(4):399-408. doi: 10.1038/ng0896-399.

Finberg et al., Down-regulation of Bmp/Smad signaling by Tmprss6 is required for maintenance of systemic iron homeostasis. Blood. May 6, 2010;115(18):3817-26. doi: 10.1182/blood-2009-05-224808. Epub Mar. 3, 2010.

Fung et al., High-throughput screening of small molecules identifies hepcidin antagonists. Mol Pharmacol. Mar. 2013;83(3):681-90. doi: 10.1124/mol.112.083428. Epub Jan. 4, 2013.

Fung et al., Manipulation of the hepcidin pathway for therapeutic purposes. Haematologica. Nov. 2013;98(11):1667-76. doi: 10.3324/haematol.2013.084624.

Genbank Submission; NIH/NCBI, Gene ID 148738, HJV hemojuvelin BMP co-receptor [*Homo sapiens* (human)], Jun. 15, 2023, 7 pages.

Genbank Submission; NIH/NCBI, Gene ID 310681, Hjv hemojuvelin BMP co-receptor [*Rattus norvegicus* (Norway rat)], Jun. 15, 2023, 4 pages.

Genbank Submission; NIH/NCBI, Gene ID 69585, Hjv hemojuvelin BMP co-receptor [*Mus musculus* (house mouse)], Apr. 12, 2023.

Genbank Submission; NIH/NCBI, Gene ID 698805, HJV hemojuvelin BMP co-receptor [*Macaca mulatta* (Rhesus monkey)], Aug. 15, 2022, 3pages.

Gomez-Puerto et al., Bone morphogenetic protein receptor signal transduction in human disease. J Pathol. Jan. 2019;247(1):9-20. doi: 10.1002/path.5170. Epub Nov. 27, 2018.

Gorrell et al., Identification of a bone mophogenic protein type 2 receptor neutralizing antibody. BMC Res Notes. 2019; 12-331. doi: 10.1186/s13104-019-4367-0.

Guglielmelli et al., Anaemia characterises patients with myelofibrosis harbouring Mpl mutation. Br J Haematol. May 2007;137(3):244-7. doi: 10.1111/j.1365-2141.2007.06565.x.

Harrison et al., Momelotinib versus best available therapy in patients with myelofibrosis is previously treated with ruxolitinib (SIMPLIFY 2): a randomized, open-label, phase 3 trial. Lancet Haematol. Feb. 2018;5(2):e73-e81. doi: 10.1016/S2352-3026(17)30237-5. Epub Dec. 20, 2017.

Hinton et al., Engineered Human IgG Antibodies with Longer Serum Half-lives in Primates, J Biol Chem. Feb. 20, 2004;279(8):6213-6. doi: 10.1074/jbc.C300470200. Epub Dec. 29, 2003.

Holliger et al., "Diabodies": small bivalent and bispecific antibody fragments. Proc Natl Acad Sci U S A. Jul. 15, 1993;90(14):6444-8. doi: 10.1073/pnas.90.14.6444.

Hudson et al., Novel Quinazolinone Inhibitors of ALK2 Flip between Alternate Binding Modes: Structure-Activity Relationship, Structural Characterization, Kinase Profiling, and Cellular Proof of Concept. J Med Chem. Aug. 23, 2018;61(16):7261-7272. doi: 10.1021/acs.jmedchem.8b00782. Epub Aug. 7, 2018.

Jabara et al., A missense mutaton in TFRC, encoding transferrin receptor 1, causes combined immunodeficiency. Nat Genet. Jan. 2016;48(1):74-8. doi: 10.1038/ng.3465. Epub Dec. 7, 2015.

Kang et al., BMP2 accelerates the motility and invasiveness of gastric cancer cells via activation of the phosphatidylinositol 3-kinase (PI3K)/Akt pathway. Exp Cell Res. Jan. 1, 2010;316(1):24-37. doi: 10.1016/j.yexcr.2009.10.010. Epub Oct. 14, 2009.

Katsarou et al., Hepcidin Therapeutics. Pharmaceuticals (Basel). Nov. 21, 2018;11(4):127. doi: 10.3390/ph11040127.

Kawakami et al., BMP signaling during bone pattern determination in the developing limb. Development. Nov. 1996;122(11):3557-66. doi: 10.1242/dev.122.11.3557.

Kinsley et al., Molecular characterization of a third case of human astransferrinemia. Blood. Oct. 15, 2004;104(8):2607.doi: 10.1182/blood-2004-05-1751.

Klampfl et al. Somatic mutations of calreticulin in myeloproliferative neoplasms. N Engl J Med. Dec. 19, 2013;369(25):2379-90. doi: 10.1056/NEJMoa1311347. Epub Dec. 10, 2013.

Kovac et al. Anti-Hemojuvelin Antibody Corrects Anemia Caused by Inappropriately High Hepcidin Level. Haematologica. May 2016;101(5):e173-6. doi: 10.3324/haematol.2015.140772. Epub Mar. 4, 2016.

Kralovics et al., A gain-of-function mutation of JAK2 in myeloproliferative disorders. N Engl J Med. Apr. 28, 2005;352(17):1779-90. doi: 10.1056/NEJMoa051113.

(56) References Cited

OTHER PUBLICATIONS

Kundranda et al., Role of Hepcidin in Anemia of Waldenstrom Macroglobulinemia. Blood. Nov. 11, 2010;116(21):4984. doi:https://doi.org/10.1182/blood.V116.21.4984.4984.

Kuns-Hashimoto et al., Selective Binding of RGMc/hemojuvelin, a Key Protein in Systemic Iron Metabolism, to BMP-2 and Neogenin. Am J Physiol Cell Physiol. Apr. 2008;294(4):C994-C1003. doi: 10.1152/ajpcell.00563.2007. Epub Feb. 20, 2008.

Lasho et al., SF3B1 mutations in primary myelofibrosis: clinical, histopathology and genetic correlates among 155 patients. Leukemia. May 2012;26(5):1135-7. doi: 10.1038/leu.2011.320. Epub Nov. 8, 2011.

Lefranc et al., IMGT, the international ImMunoGeneTics database. Nucleic Acids Res. Jan. 1, 1999;27(1):209-12. doi: 10.1093/nar/27.1.209.

Lin et al., Competitive Regulation of Hepcidin mRNA by Soluble and Cell-Associated Hemojuvelin. Blood. Oct. 15, 2005;106(8):2884-9. doi: 10.1182/blood-2005-05-1845. Epub Jul. 5, 2005.

Locatelli et al., Kidney Disease: Improving Global Outcomes guidelines on anaemia management in chronic kidney disease: a European Renal Best Practice position statement. Nephrol Dial Transplant. Jun. 2013;28(6):1346-59. doi: 10.1093/ndt/gft033. Epub Apr. 12, 2013.

Macdougall et al., FIND-CKD: a randomized trial of intravenous ferric carboxymaltose versus oral iron in patients with chronic kidney disease and iron deficiency anaemia. Nephrol Dial Transplant. Nov. 2014;29(11):2075-84. doi: 10.1093/ndt/gfu201. Epub Jun. 2, 2014.

Madu et al., Anaemia of Chronic Disease: An In-Depth Review. Med Princ Pract. Jan. 2017;26(1):1-9. doi: 10.1159/000452104. Epub Sep. 28, 2016.

Maes et al., In anemia of multiple myeloma, hepcidin is induced by increased bone morphogenetic protein 2. Blood. Nov. 4, 2010;116(18):3635-44. doi: 10.1182/blood-2010-03-274571. Epub Aug. 2, 2010.

Maliken et al., The hepcidin circuits act: balancing iron and inflammation. Hepatology. May 2011;53(5):1764-6. doi: 10.1002/hep.24267. Author Manuscript, 5 pages.

Mesa et al., The Myelofibrosis Symptom Assessment Form (MFSAF): an evidence-based brief inventory to measure quality of life and symptomatic response to treatment in myelofibrosis. Leuk Res. Sep. 2009;33(9):1199-203. doi: 10.1016/j.leukres.2009.01.035. Epub Feb. 27, 2009. Author Manuscript, 10 pages.

Meynard et al., Lack of the bone morphogenetic protein BMP6 induces massive iron overload. Nat Genet. Apr. 2009;41(4):478-81. doi: 10.1038/ng.320. Epub Mar. 1, 2009.

Nangalia et al., Somatic CALR mutations in myeloproliferative neoplasms with nonmutated JAK2. N Engl J Med. Dec. 19, 2013;369(25):2391-2405. doi: 10.1056/NEJMoa1312542. Epub Dec. 10, 2013.

Naymagon et al., Myelofibrosis-Related Anemia and Emergings Therapeutic Strategies. HemaSphere. Dec. 20, 2017;1(1):e1. doi: 10.1097/HS9.0000000000000001.

Nemeth et al., Anti-hepcidin therapy for iron-restricted anemias. Blood. 2013;122(17):2929-31. doi: https://doi.org/10.1182/blood-2013-08-522466.

Nemeth et al., Hepcidin regulates cellular iron efflux by binding to ferroportin and inducing its internalization. Science. Dec. 17, 2004;306(5704):2090-3. doi: 10.1126/science.1104742. Epub Oct. 28, 2004.

Neubauer et al., Jak2 deficiency defines an essential developmental checkpoint in definitive hematopoiesis. Cell. May 1, 1998;93(3):397-409. doi: 10.1016/s0092-8674(00)81168-x.

O'Mara et al., Anemia in patients with Chronic Kidney Disease. Diabetes Spectrum. 2008;21(1):12-19. doi: https://doi.org/10.2337/diaspect.21.1.12.

Ogun et al., Biochemistry, Transferrin. Nov. 16, 2022. In: StatPearls [Internet]. Treasure Island (FL): StatPearls Publishing; Jan. 2023. 4 pages.

Oh et al., Hepcidin Suppression by Momelotinib Is Associated with Increased Iron Availability and Erythropoiesis in Transfusion-Dependent Myelofibrosis Patients. Blood. Nov. 29, 2018;132:4282. doi: https://doi.org/10.1182/blood-2018-99-111349.

Papanikolaou et al., Mutations in HFE2 cause iron overload in chromosome 1q-linked juvenile hemochromatosis. Nature Genetics. Jan. 2004;36(1):77-82. doi:10.1038/ng1274. Epub Nov. 30, 2003.

Pardanani et al., Associations and prognostic interactions between circulating levels of hepcidin, ferritin and inflammatory cytokines in primary myelofibrosis. Am J Hematol. Apr. 2013;88(4):312-6. doi: 10.1002/ajh.23406. Epub Feb. 28, 2013.

Parganas et al., Jak2 is essential for signaling through a variety of cytokine receptors. Cell. May 1, 1998;93(3):385-95. doi: 10.1016/s0092-8674(00)81167-8.

Passamonti et al., A dynamic prognostic model to predict survival in primary myelofibrosis: a study by the IWG-MRT (International Working Group for Myeloproliferative Neoplasms Research and Treatment). Blood. Mar. 4, 2010;115(9):1703-8. doi: 10.1182/blood-2009-09-245837. Epub Dec. 14, 2009.

Poljak, Production and structure of diabodies. Structure. Dec. 15, 1995;2(12):1121-3. doi: 10.1016/s0969-2126(94)00113-8.

Pouliot et al., Overexpression of a dominant negative type II bone morphogenetic protein receptor inhibits the growth of human breast cancer cells. Cancer Res. Jan. 15, 2003;63(2):277-81.

Qiao et al., Hepcidin-induced endocytosis of ferroportin is dependent on ferroportin ubiquitination. Cell Metab. Jun. 6, 2012;15(6):918-24. doi: 10.1016/j.cmet.2012.03.018.

Rameshwar et al., Systemic transforming growth factor-beta in patients with bone marrow fibrosis-pathophysiological implications. Am J Hematol. Oct. 1998; 59(2):133-42. doi: 10.1002/(sici)1096-8652(199810)59:2<133::aid-ajh6>3.0.co;2-z.

Ramos et al., Minihepcidins prevent iron overload in a hepcidin-deficient mouse model of severe hemochromatosis. Blood. Nov. 1, 2012;120(18):3829-36. doi: 10.1182/blood-2012-07-440743. Epub Sep. 18, 2012.

Roetto et al., Mutant antimicrobial peptide hepcidin is associated with severe juvenile hemochromatosis. Nat Genet. Jan. 2003;33(1):21-2. doi: 10.1038/ng1053. Epub Dec. 9, 2002.

Ross et al., Identification of Antibody and Small Molecule Antagonists of Ferroportin-Hepcidin Interaction. Front Pharmacol. Nov. 21, 2017;8:838. doi: 10.3389/fphar.2017.00838.

Rotwein et al., Variation in the repulsive guidance molecule family in human populations. Physiol Rep. Feb. 2019;7(3):e13959. DOI:10.14814/phy2.13959. Epub Feb. 11, 2019.

Schwoebel et al., The effects of the anti-hepcidin Spiegelmer NOX-H94 on inflammation-induced anemia in cynomolgus monkeys. Blood. Mar. 21, 2013;121(12):2311-5. doi: 10.1182/blood-2012-09-456756. Epub Jan. 24, 2013.

Shi et al., BMP6 and BMP4 expression in patients with cancer-related anemia and its relationship with hepcidin and s-HJV. Genet Mol Res. Mar. 31, 2016;15(1). doi: 10.4238/gmr.15017130.

Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. doi: 10.1074/jbc.M009483200. Epub Nov. 28, 2000.

Smith et al., Mouse model recapitulating human Fcγ receptor structural and functional diversity. Proc Natl Acad Sci U S A. Apr. 17, 2012;109(16):6181-6. doi: 10.1073/pnas.1203954109. Epub Apr. 2, 2012.

Tapper et al., Genetic variation at MECOM, TERT, JAK2 and HBS1L-MYB predisposes to myeloproliferative neoplasms. Nat Commun. Apr. 7, 2015;6:6691. doi: 10.1038/ncomms7691.

Tefferi et al., An overview on CALR and CSF3R mutations and a proposal for revision of WHO diagnostic criteria for myeloproliferative neoplasms. Leukemia. Jul. 2014;28(7):1407-13. doi: 10.1038/leu.2014.35. Epub Jan. 20, 2014.

Tefferi et al., Targeted deep sequencing in primary myelofibrosis. Blood Adv. Nov. 30, 2016;1(2):105-111. doi: 10.1182/bloodadvances.2016000208.

Vadhan-Raj et al., Phase 1 Study of a Hepcidin Antagonist, LY2787106, in Cancer-Associated Anemia. Blood. Dec. 3, 2015;126(23):537. doi:http://doi.org/10.1182/blood.V126.23.537.537.

(56) References Cited

OTHER PUBLICATIONS

Vannucchi et al., Mutations and prognosis in primary myelofibrosis. Leukemia. Sep. 2013;27(9):1861-9. doi: 10.1038/leu.2013.119. Epub Apr. 26, 2013.

Vela et al., Differential regulation of hepcidin in cancer and non-cancer tissues and its clinical implications. Exp Mol Med. Feb. 2, 2018;50(2):e436. doi: 10.1038/emm.2017.273.

Verstovsek et al., A double-blind, placebo-controlled trial of ruxolitinib for myelofibrosis. N Engl J Med. Mar. 1, 2012;366(9):799-807. doi: 10.1056/NEJMoa1110557. Author Manuscript, 17 pages.

Verstovsek et al., Safety and efficacy of INCB018424, a JAK1 and JAK2 inhibitor, in myelofibrosis. N Engl J Med. Sep. 16, 2010;363(12):1117-27. doi: 10.1056/NEJMoa1002028.

Wang, Hepcidin regulation in the anemia of inflammation. Curr Opin Hematol. May 2016;23(3):189-97. doi: 10.1097/MOH. 0000000000000236. Author Manuscript, 15 pages.

Webster et al., Chronic Kidney Disease. Lancet. Mar. 25, 2017;389(10075):1238-1252. doi: 10.1016/S0140-6736(16)32064-5. Epub Nov. 23, 2016.

Wish et al., Positive Iron Balance in Chronic Kidney Disease: How Much is Too Much and How to Tell? Am J Nephrol. 2018;47(2):72-83. doi: 10.1159/000486968. Epub Feb. 13, 2018.

Xia et al., Hemojuvelin regulates hepcidin expression via a selective subset of BMP ligands and receptors independently of neogenin. Blood. May 15, 2008;111(10):5195-204. doi: 10.1182/blood-2007-09-111567. Epub Mar. 7, 2008.

Xu et al., In vitro characterization of five humanized OKT3 effector function variant antibodies. Cell Immunol. Feb. 25, 2000;200(1):16-26. doi: 10.1006/cimm.2000.1617.

Zhang et al., The Role of Hepatocyte Hemojuvelin in the Regulation of Bone Morphogenic Protein-6 and Hepcidin Expression in Vivo. J Biol Chem. May 28, 2010;285(22):16416-23. doi: 10.1074/jbc. M110.109488. Epub Apr. 2, 2010.

Zhang, Control of Systemic Iron Homeostasis by the Hemojuvelin-Hepcidin Axis. Adv Nutr. Nov. 2010;1(1):38-45. doi: 10.3945/an. 110.1009. Epub Nov. 16, 2010.

Zhao et al., Neogenin Facilitates the Induction of Hepcidin Expression by Hemojuvelin in the Liver. J Biol Chem. Jun. 3, 2016;291(23):12322-35. doi: 10.1074/jbc.M116.721191. Epub Apr. 12, 2016.

Zhou et al., Hepcidin is elevated in primary and secondary myelofibrosis and remains elevated in patients treated with ruxolitinib. Blood. Nov. 29, 2018;132 (Supp 1):1760. 4 pages.

Zoller et al., Iron in Cancer Infection, Kidney and Liver Diseases: Innocent Bystander or Therapeutic Target? Bio Iron. May 6, 2019. Retrieved from internet: https://bioironforum.org/wp-content/uploads/2018/10/7.-Iron-in-cancer-infection-kidney-and-liver-diseases.Theurl-Zoller.pdf.

U.S. Appl. No. 17/764,142, filed Mar. 25, 2022, Disc Medicine Inc.

U.S. Appl. No. 17/764,143, filed Mar. 25, 2022, Quisel et al.

U.S. Appl. No. 17/924,672, filed Nov. 10, 2022, Beconi et al.

EP 20867029.9, Aug. 7, 2023, Extended European Search Report.

PCT/US2020/052732, Jan. 11, 2021, International Search Report and Written Opinion.

PCT/US2020/052732, Apr. 7, 2022, International Preliminary Report on Patentability.

PCT/US2020/052748, Jan. 12, 2021, International Search Report and Written Opinion.

PCT/US2020/052748, Apr. 7, 2022, International Preliminary Report on Patentability.

PCT/US2021/032345, Aug. 24, 2021, Invitation to Pay Additional Fees.

PCT/US2021/032345, Nov. 26, 2021, International Search Report and Written Opinion.

PCT/US2021/032345, Nov. 24, 2022, International Preliminary Report on Patentability.

PCT/US2021/032343, Aug. 16, 2021, Invitation to Pay Additional Fees.

PCT/US2021/032343, Oct. 29, 2021, International Search Report and Written Opinion.

PCT/US2021/32343, Nov. 24, 2022, International Preliminary Report on Patentability.

PCT/US2022/079987, Mar. 6, 2023, International Search Report and Written Opinion.

Extended European Search Report for Application No. 20869747.4, mailed Sep. 18, 2023.

Extended European Search Report for Application No. EP21803135. 9, mailed May 2, 2024.

Extended European Search Report for Application No. EP21804008. 7, mailed Apr. 8, 2024.

International Preliminary Report on Patentability for Application No. PCT/US2022/079987 mailed May 30, 2024.

International Search Report and Written Opinion for Application No. PCT/US2023/068107 mailed Oct. 17, 2023.

International Preliminary Report on Patentability for Application No. PCT/US2023/068107 mailed Dec. 19, 2024.

[No Author Listed] Leukemia & Lymphoma Society, Myelofibrosis Facts, <URL: https://www.lls.org/sites/default/files/file_assets/FS14_Myelofibrosis_Fact%20Sheet_Final9.12.pdf> [retrieved on Feb. 26, 2025], Apr. 2012. 9 pages.

[No Author Listed] National Kidney Foundation. K/DOQI clinical practice guidelines for chronic kidney disease: evaluation, classification, and stratification. Am J Kidney Dis. Feb. 2002;39(2 Suppl 1):S1-266.

Alwahaibi et al., Spectrum of glomerular diseases in Arab countries: A systematic review. Saudi J Kidney Dis Transpl. Nov.-Dec. 2018;29(6):1256-1266. doi: 10.4103/1319-2442.248285.

Andriopoulos et al., BMP6 is a key endogenous regulator of hepcidin expression and iron metabolism. Nat Genet. Apr. 2009;41(4):482-7. doi: 10.1038/ng.335. Epub Mar. 1, 2009. Author Manuscript, 16 pages.

Blanchette et al., Modulation of hepcidin to treat iron deregulation: potential clinical applications. Expert Rev Hematol. 2016;9(2):169-86. doi: 10.1586/17474086.2016.1124757. Epub Dec. 15, 2015.

Brasse-Lagnel et al., Immunoassay for human serum hemojuvelin. Haematologica. Dec. 2010;95(12):2031-7. doi: 10.3324/haematol. 2010.022129. Epub Aug. 16, 2010.

Brorson et al., Therapeutic monoclonal antibodies and consistent ends: terminal heterogeneity, detection, and impact on quality. Curr Opin Biotechnol. Dec. 2014;30:140-6. doi: 10.1016/j.copbio.2014. 06.012. Epub Jul. 12, 2014.

Browne et al., Potential role of bone morphogenetic protein (BMP) signalling as a potential therapeutic target for modification of iron balance. Nephrology Dialysis Transplantation. Jan. 1, 2009;24(1):28-30.

Chiu et al., Antibody Structure and Function: The Basis for Engineering Therapeutics. Antibodies (Basel). Dec. 3, 2019;8(4):55. doi: 10.3390/antib8040055.

Chothia et al., Canonical structures for the hypervariable regions of immunoglobulins. J Mol Biol. Aug. 20, 1987;196(4):901-17. doi: 10.1016/0022-2836(87)90412-8.

Coyne, Hepcidin: clinical utility as a diagnostic tool and therapeutic target. Kidney Int. Aug. 2011;80(3):240-4. doi: 10.1038/ki.2011. 141. Epub Jun. 15, 2011.

D'Angelo, Role of hepcidin in the pathophysiology and diagnosis of anemia. Blood Res. Mar. 2013;48(1):10-5. doi: 10.5045/br.2013.48. 1.10. Epub Mar. 25, 2013.

De Pascalis et al., Grafting of "abbreviated" complementarity-determining regions containing specificity-determining residues essential for ligand contact to engineer a less immunogenic humanized monoclonal antibody. the Journal of Immunology. Sep. 15, 2002;169(6):3076-84.

Eleftheriadis et al., The role of hepcidin in iron homeostasis and anemia in hemodialysis patients. Semin Dial. Jan.-Feb. 2009;22(1):70-7. doi: 10.1111/j.1525-139X.2008.00532.x.

Fujita et al., The roles of RGMa-neogenin signaling in inflammation and angiogenesis. Inflamm Regen. Mar. 8, 2017;37:6. doi: 10.1186/s41232-017-0037-6.

Ganz et al., The Hepcidin-Ferroportin System as a Therapeutic Target in Anemias and Iron Overload Disorders. Hematology Am Soc Hematol Educ Program. 2011:538-42. doi: 10.1182/asheducation-2011.1.538.

(56)          References Cited

OTHER PUBLICATIONS

Ganz, Anemia of Inflammation. N Engl J Med. Sep. 19, 2019;381(12):1148-1157. doi: 10.1056/NEJMra1804281.

Ganz, Hepcidin and iron regulation, 10 years later. Blood. Apr. 28, 2011;117(17):4425-33. doi: 10.1182/blood-2011-01-258467. Epub Feb. 23, 2011.

Katagiri et al., Bone Morphogenetic Proteins. Cold Spring Harb Perspect Biol. Jun. 1, 2016;8(6):a021899. doi: 10.1101/cshperspect. a021899.

Kroot et al., Hepcidin in human iron disorders: diagnostic implications. Clin Chem. Dec. 2011;57(12):1650-69. doi: 10.1373/clinchem.2009.140053. Epub Oct. 11, 2011.

Kuninger et al., Complex biosynthesis of the muscle-enriched iron regulator RGMc. J Cell Sci. Aug. 15, 2006;119(Pt 16):3273-83. doi: 10.1242/jcs.03074. Epub Jul. 25, 2006.

Lee et al., Neogenin inhibits HJV secretion and regulates BMP-induced hepcidin expression and iron homeostasis. Blood. Apr. 15, 2010;115(15):3136-45. doi: 10.1182/blood-2009-11-251199. Epub Jan. 11, 2010. Erratum in: Blood. Jul. 8, 2010;116(1):151. Lee, Dai-Hoon [corrected to Lee, Dae-Hoon]; Zhou, Li-Juau [corrected to Zhou, Li-Juan]; Xie, Jiau-Xiu [corrected to Xie, Jian- Xin].

Litchford et al., Nutritional issues in the patient with diabetes and foot ulcers. In: Levin and O'Neal's The Diabetic Foot, Jan. 1, 2008 (pp. 199-217), Mosby.

Metzgeroth et al., Iron deficiency anemia and anemia of chronic disorders. Internist (Berl). Aug. 1, 2015;56(9):978-88. German. doi: 10.1007/s00108-015-3711-2.

Mleczko-Sanecka et al., SMAD7 controls iron metabolism as a potent inhibitor of hepcidin expression. Blood. Apr. 1, 2010;115(13):2657-65. doi: 10.1182/blood-2009-09-238105. Epub Dec. 29, 2009.

Mueller et al., The role of repulsive guidance molecules in the embryonic and adult vertebrate central nervous system. Philos Trans R Soc Lond B Biol Sci. Sep. 29, 2006;361(1473):1513-29. doi: 10.1098/rstb.2006.1888.

Murtagh et al., Dialysis or not? A comparative survival study of patients over 75 years with chronic kidney disease stage 5. Nephrol Dial Transplant. Jul. 2007;22(7):1955-62. doi: 10.1093/ndt/gfm153. Epub Apr. 4, 2007.

NCBI Submission, Gene ID: 148738, HJV hemojuvelin BMP co-receptor [Homo sapiens (human)], Accessed online: https://www. ncbi.nlm.nih.gov/gene/148738?report=full_report&format=text. Last updated Nov. 25, 2025, 5 pages.

NCBI Submission, Gene ID: 310681, Hjv hemojuvelin BMP co-receptor [Rattus norvegicus (Norway rat)], Accessed online: https:// www.ncbi.nlm.nih.gov/gene/310681?report=full_report&format= text. Last updated on Nov. 19, 2025, 3 pages.

NCBI Submission, Gene ID: 69585, Hjv hemojuvelin BMP co-receptor [Mus musculus (house mouse)], Accessed online: https:// www.ncbi.nlm.nih.gov/gene/69585?report=full_report&format= text. Last updated on Nov. 19, 2025, 5 pages.

NCBI Submission, Gene ID: 698805, HJV hemojuvelin BMP co-receptor [Macaca mulatta (Rhesus monkey)], Accessed online: https://www.ncbi.nlm.nih.gov/gene/?term=698805&report=full_ report&format=text, Last updated Aug. 17, 2024, 2 pages.

Nemeth, Targeting the hepcidin-ferroportin axis in the diagnosis and treatment of anemias. Adv Hematol. 2010;2010:750643. doi: 10.1155/2010/750643. Epub Dec. 24, 2009.

Nili et al., Soluble repulsive guidance molecule c/hemojuvelin is a broad spectrum bone morphogenetic protein (BMP) antagonist and inhibits both BMP2- and BMP6-mediated signaling and gene expression. J Biol Chem. Aug. 6, 2010;285(32):24783-92. doi: 10.1074/jbc.M110.130286. Epub Jun. 8, 2010.

Petzer et al., Established and Emerging Concepts to Treat Imbalances of Iron Homeostasis in Inflammatory Diseases. Pharmaceuticals (Basel). Dec. 11, 2018;11(4):135. doi: 10.3390/ph11040135.

Pietrangelo, Hepcidin in human iron disorders: therapeutic implications. J Hepatol. Jan. 2011;54(1):173-81. doi: 10.1016/j.jhep.2010. 08.004. Epub Aug. 26, 2010.

Preza et al., Minihepcidins are rationally designed small peptides that mimic hepcidin activity in mice and may be useful for the treatment of iron overload. J Clin Invest. Dec. 2011;121(12):4880-8. doi: 10.1172/JCI57693.

Sebastiani et al., Pharmacological Targeting of the Hepcidin/Ferroportin Axis. Front Pharmacol. Jun. 21, 2016;7:160. doi: 10.3389/fphar.2016.00160.

Sheetz et al., Targeting the hepcidin-ferroportin pathway in anaemia of chronic kidney disease. Br J Clin Pharmacol. May 2019;85(5):935-948. doi: 10.1111/bcp.13877. Epub Mar. 4, 2019.

Sullivan, Stored iron and vascular reactivity. Arterioscler Thromb Vasc Biol. Aug. 2005;25(8):1532-5. doi: 10.1161/01.ATV.0000174124. 20147.22.

Sun et al., A hepcidin lowering agent mobilizes iron for incorporation into red blood cells in an adenine-induced kidney disease model of anemia in rats. Nephrol Dial Transplant. Jul. 2013;28(7):1733-43. doi: 10.1093/ndt/gfs584. Epub Jan. 22, 2013.

Tattersall et al., When to start dialysis: updated guidance following publication of the Initiating Dialysis Early and Late (IDEAL) study. Nephrol Dial Transplant. Jul. 2011;26(7):2082-6. doi: 10.1093/ndt/gfr168. Epub May 5, 2011.

Theurl et al., Pharmacologic inhibition of hepcidin expression reverses anemia of chronic inflammation in rats. Blood. Nov. 3, 2011;118(18):4977-84. doi: 10.1182/blood-2011-03-345066. Epub Jul. 5, 2011.

Tian et al., Repulsive guidance molecules (RGMs) and neogenin in bone morphogenetic protein (BMP) signaling. Mol Reprod Dev. Sep. 2013;80(9):700-17. doi: 10.1002/mrd.22199. Epub Jul. 19, 2013.

Toft et al., Anemia and clinical outcomes in patients with non-dialysis dependent or dialysis dependent severe chronic kidney disease: a Danish population-based study. J Nephrol. Feb. 2020;33(1):147-156. doi: 10.1007/s40620-019-00652-9. Epub Oct. 5, 2019.

Wang et al., Prognostic implications of predialysis patients' symptoms in peritoneal dialysis patients. Ren Fail. Dec. 2021;43(1):216-222. doi: 10.1080/0886022X.2021.1871920.

Wu et al., DISC-0974, An Anti-Hemojuvelin (HJV) Monoclonal Antibody, Reduced Hepcidin And Improved Anemia In A Rat Model Of Chronic Kidney Disease. American Society of Hematology, Blood, Nov. 15, 2022; vol. 140, (Supplement 1): 8153-8154. https://ashpublications.org/blood/article/140/Supplement%201/8153/489647/DISC-0974-an-Anti-Hemojuvelin-HJV-Monoclonal.

Xiao et al., Bone morphogenic proteins in iron homeostasis. Bone. Sep. 2020;138:115495. doi: 10.1016/j.bone.2020.115495. Epub Jun. 23, 2020. Author Manuscript, 27 pages.

Yu et al., Chapter 10-Antibody glycosylation. In, Antibody Fc: Linking Adaptive and Innate Immunity. Editors: Ackerman, ME Nimmerjahn, F. 2014, p. 179-194.

Zipfel et al., Complement Inhibitors in Clinical Trials for Glomerular Diseases. Front Immunol. Sep. 27, 2019;10:2166. doi: 10.3389/fimmu.2019.02166.

In vivo immunization in rats and hybridoma screening & selection [a]  ⟹  HA (anti-hemojuvelin mAb; rat IgG1/κ)

Humanization by CDR grafting [b]

hHA [humanized hemojuvelin mAb; hIgG1 mut(L234A,L235A)/κ]

Affinity maturation by in vitro yeast display [c]

hHA [affinity matured humanized hemojuvelin; hIgG1 mut(L234A,L235A)/κ]

hHA-008-QL

Reducing effector function mut(L234A,L235A)
mut(T250Q,M428L)

Enhancing FcRn binding thus extending $t_{1/2}$ hIgG1 mut(L234A,L235A)
/mut(T250Q,M428L)

Mutations to the IgG1 Fc Region

VH          CH1          Hinge          CH2          CH3 hHA-008
L234A
L235A
attenuated immune signaling hHA-008-QL
T250Q          M428L
L234A
L235A          improved PK characteristics High Hepcidin Disorder Initiating myeloid mutations
•JAK2, CALR, others (Myelofibrosis)
•Genomic instability (Myeloma)

Myeloid proliferation and
macrophage activation

Macrophage
iron loading

⇧ IL6,
OncM
BMP6

⇧ Hepcidin

Iron sequestration anemia

SEQUENCE LISTING

```
<160> NUMBER OF SEQ ID NOS: 129

<210> SEQ ID NO 1
<211> LENGTH: 5
<212> TYPE: PRT
<213> ORGANISM: Artificial Sequence
<220> FEATURE:
<223> OTHER INFORMATION: Synthethic Polypeptide

<400> SEQUENCE: 1

Asn Tyr Gly Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthethic Polypeptide

<400> SEQUENCE: 2

Met Ile Tyr Tyr Asp Ser Ser Glu Lys His Tyr Ala Asp Ser Val Lys
1               5                   10                  15

Gly

<210> SEQ ID NO 3
<211> LENGTH: 6
<212> TYPE: PRT
<213> ORGANISM: Artificial Sequence
<220> FEATURE:
<223> OTHER INFORMATION: Synthethic Polypeptide

<400> SEQUENCE: 3

Gly Thr Thr Pro Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthethic Polypeptide

<400> SEQUENCE: 4

Arg Ser Ser Gln Ser Leu Glu Thr Ser Asp Gly Asp Thr Phe Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 5

Glu Val Ser Thr Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthethic Polypeptide

<400> SEQUENCE: 6
```

-continued

```
Phe Gln Val Thr His Asp Pro Met Thr
1               5
```

<210> SEQ ID NO 7
<211> LENGTH: 115
<212> TYPE: PRT
<213> ORGANISM: Artificial Sequence
<220> FEATURE:
<223> OTHER INFORMATION: Synthethic Polypeptide

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115
```

<210> SEQ ID NO 8
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 8

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Thr Ser
            20                  25                  30

Asp Gly Asp Thr Phe Leu Glu Trp Phe Gln Gln Arg Pro Gly Gln Ser
        35                  40                  45

Pro Arg Leu Leu Ile Tyr Glu Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Thr His Asp Pro Met Thr Phe Gly Gln Gly Thr Lys Leu Glu Ile Lys
            100                 105                 110
```

<210> SEQ ID NO 9
<211> LENGTH: 5
<212> TYPE: PRT
<213> ORGANISM: Artificial Sequence
<220> FEATURE:
<223> OTHER INFORMATION: Synthethic Polypeptide

<400> SEQUENCE: 9

```
Tyr Tyr Gly Met Asn
```

-continued

```
1               5

<210> SEQ ID NO 10
<211> LENGTH: 17
<212> TYPE: PRT
<213> ORGANISM: Artificial Sequence
<220> FEATURE:
<223> OTHER INFORMATION: Synthethic Polypeptide

<400> SEQUENCE: 10

Met Ile Tyr Tyr Asp Ser Ser Asp Lys His Tyr Ala Asp Ser Val Lys
1               5                   10                  15

Gly

<210> SEQ ID NO 11
<211> LENGTH: 6
<212> TYPE: PRT
<213> ORGANISM: Artificial Sequence
<220> FEATURE:
<223> OTHER INFORMATION: Synthethic Polypeptide

<400> SEQUENCE: 11

Gly Thr Thr Pro Asp Val
1               5

<210> SEQ ID NO 12
<211> LENGTH: 6
<212> TYPE: PRT
<213> ORGANISM: Artificial Sequence
<220> FEATURE:
<223> OTHER INFORMATION: Synthethic Polypeptide

<400> SEQUENCE: 12

Gly Thr Thr Pro Asp Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthethic Polypeptide

<400> SEQUENCE: 13

Gly Ser Thr Pro Asp Tyr
1               5

<210> SEQ ID NO 14
<211> LENGTH: 16
<212> TYPE: PRT
<213> ORGANISM: Artificial Sequence
<220> FEATURE:
<223> OTHER INFORMATION: Synthethic Polypeptide

<400> SEQUENCE: 14

Arg Ser Ser Gln Ser Leu Glu Ser Ser Asp Gly Asp Thr Phe Leu Glu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthethic Polypeptide

<400> SEQUENCE: 15
```

-continued

Arg Ser Ser Gln Ser Leu Glu Glu Ser Asp Gly Tyr Thr Phe Leu Glu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthethic Polypeptide

<400> SEQUENCE: 16

Arg Ser Ser Gln Ser Leu Glu Asp Ser Asp Gly Gly Thr Phe Leu Glu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthethic Polypeptide

<400> SEQUENCE: 17

Arg Ser Ser Gln Ser Leu Glu Glu Ser Asp Gly Tyr Thr Phe Leu His
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 18

Glu Val Ser Asn Arg Phe Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 19

Asp Val Ser Thr Arg Phe Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 20

Asp Val Ser Glu Arg Phe Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 21

Asp Val Ser Ser Arg Phe Ser

```
1               5

<210> SEQ ID NO 22
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 22

Ala Val Ser His Arg Phe Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 23

Glu Val Ser His Arg Phe Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthethic Polypeptide

<400> SEQUENCE: 24

Met Gln Val Thr His Asp Pro Leu Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthethic Polypeptide

<400> SEQUENCE: 25

Phe Gln Val Thr His Asp Pro Val Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Synthethic Polypeptide

<400> SEQUENCE: 26

Phe Gln Ala Thr Tyr Asp Pro Leu Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthethic Polypeptide

<400> SEQUENCE: 27

Phe Gln Ala Thr His Asp Pro Leu Thr
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: Synthethic Polypeptide

<400> SEQUENCE: 28

Phe Gln Ala Thr His Asp Pro Val Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Synthethic Polypeptide

<400> SEQUENCE: 29

Phe Gln Ala Thr His Asp Pro Leu Ser
1               5

<210> SEQ ID NO 30
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 30

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Thr Ser
            20                  25                  30

Asp Gly Asp Thr Phe Leu Glu Trp Phe Gln Gln Arg Pro Gly Gln Ser
        35                  40                  45

Pro Arg Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Thr His Asp Pro Leu Thr Phe Gly Gln Gly Thr Lys Leu Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 31

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Thr Ser
            20                  25                  30

Asp Gly Asp Thr Phe Leu Glu Trp Phe Gln Gln Arg Pro Gly Gln Ser
        35                  40                  45

Pro Arg Leu Leu Ile Tyr Glu Val Ser Asn Arg Phe Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Thr His Asp Pro Val Thr Phe Gly Gln Gly Thr Lys Leu Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 32

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Ser Ser
                20                  25                  30

Asp Gly Asp Thr Phe Leu Glu Trp Phe Gln Gln Arg Pro Gly Gln Ser
            35                  40                  45

Pro Arg Leu Leu Ile Tyr Asp Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Thr His Asp Pro Val Thr Phe Gly Gln Gly Thr Lys Leu Glu Ile Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 33

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Glu Ser
                20                  25                  30

Asp Gly Tyr Thr Phe Leu Glu Trp Phe Gln Gln Arg Pro Gly Gln Ser
            35                  40                  45

Pro Arg Leu Leu Ile Tyr Asp Val Ser Glu Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr Tyr Asp Pro Leu Thr Phe Gly Gln Gly Thr Lys Leu Glu Ile Lys
            100                 105                 110

<210> SEQ ID NO 34
<211> LENGTH: 115
<212> TYPE: PRT
<213> ORGANISM: Artificial Sequence
<220> FEATURE:
<223> OTHER INFORMATION: Synthethic Polypeptide
```

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Gly Met Asn Trp Ile Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115
```

<210> SEQ ID NO 35
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 35

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asp Ser
            20                  25                  30

Asp Gly Gly Thr Phe Leu Glu Trp Phe Gln Gln Arg Pro Gly Gln Ser
        35                  40                  45

Pro Arg Leu Leu Ile Tyr Asp Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110
```

<210> SEQ ID NO 36
<211> LENGTH: 115
<212> TYPE: PRT
<213> ORGANISM: Artificial Sequence
<220> FEATURE:
<223> OTHER INFORMATION: Synthethic Polypeptide

<400> SEQUENCE: 36

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
        35                  40                  45

Gly Met Ile Tyr Tyr Asp Ser Ser Asp Lys His Tyr Ala Asp Ser Val
    50                  55                  60
```

```
Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gly Thr Thr Pro Asp Val Trp Gly Gln Gly Thr Met Val Thr
            100                 105                 110

Val Ser Ser
        115
```

<210> SEQ ID NO 37
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 37

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Glu Ser
            20                  25                  30

Asp Gly Tyr Thr Phe Leu His Trp Phe Gln Gln Arg Pro Gly Gln Ser
            35                  40                  45

Pro Arg Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Phe Gln Ala
                85                  90                  95

Thr His Asp Pro Val Thr Phe Gly Gln Gly Thr Lys Leu Glu Ile Lys
            100                 105                 110
```

<210> SEQ ID NO 38
<211> LENGTH: 115
<212> TYPE: PRT
<213> ORGANISM: Artificial Sequence
<220> FEATURE:
<223> OTHER INFORMATION: Synthethic Polypeptide

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
        50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115
```

<210> SEQ ID NO 39
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 39

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Glu Ser
            20                  25                  30

Asp Gly Tyr Thr Phe Leu His Trp Phe Gln Gln Arg Pro Gly Gln Ser
        35                  40                  45

Pro Arg Leu Leu Ile Tyr Glu Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110

<210> SEQ ID NO 40
<211> LENGTH: 1338
<212> TYPE: DNA
<213> ORGANISM: Artificial Sequence
<220> FEATURE:
<223> OTHER INFORMATION: Synthethic Polynucleotide

<400> SEQUENCE: 40
gaagtacagt tggtagaaag cggcggagga cttgtgcagc caggtggatc tctcagactt      60
tcatgtgccg caagcggttt tacttttagt aactatggaa tgaactgggt tagacaagcg     120
cccggaaaag gattggaatg gataggaatg atatactacg acagctccga gaaacattat     180
gccgactcag ttaaaggaag atttacaata tcaagagaca atagcaaaaa cacactttat     240
cttcaaatga attcactgcg agccgaggat acagcagtct attattgcgc aaaaggctcg     300 accccgatt actggggtca aggaacaatg gtaaccgtgt caagcgcgtc gaccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagccgcgg gggaccgtc agtcttcctc     720 ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac acaggtgta caccctgccc ccatcccgcg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200

```
tccttcttcc tctacagcaa gctcaccgtg acaagagca ggtggcagca ggggaacgtc      1260
ttctcatgct ccgtgatgca tgaggctctg cacaaccact acacgcagaa gagcctctcc      1320
ctgtctccgg gtaaatga                                                    1338
```

<210> SEQ ID NO 41
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 41

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Asp Ser
            20                  25                  30

Asp Gly Asp Thr Phe Leu His Trp Phe Gln Gln Arg Pro Gly Gln Ser
        35                  40                  45

Pro Arg Leu Leu Ile Tyr Ala Val Ser His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Val Thr Phe Gly Gln Gly Thr Lys Leu Glu Ile Lys
            100                 105                 110
```

<210> SEQ ID NO 42
<211> LENGTH: 115
<212> TYPE: PRT
<213> ORGANISM: Artificial Sequence
<220> FEATURE:
<223> OTHER INFORMATION: Synthethic Polypeptide

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Lys Trp Gly Gln Gly Thr Met Val Thr
            100                 105                 110

Val Ser Ser
        115
```

<210> SEQ ID NO 43
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 43

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Glu Ser
            20                  25                  30

Asp Gly Tyr Thr Phe Leu Glu Trp Phe Gln Gln Arg Pro Gly Gln Ser
            35                  40                  45

Pro Arg Leu Leu Ile Tyr Glu Val Ser His Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110

<210> SEQ ID NO 44
<211> LENGTH: 115
<212> TYPE: PRT
<213> ORGANISM: Artificial Sequence
<220> FEATURE:
<223> OTHER INFORMATION: Synthethic Polypeptide

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Thr Pro Asp Tyr Trp Gly Gln Gly Thr Met Val Thr
            100                 105                 110

Val Ser Ser
        115

<210> SEQ ID NO 45
<211> LENGTH: 112
<212> TYPE: PRT
<213> ORGANISM: Artificial Sequence
<220> FEATURE:
<223> OTHER INFORMATION: Synthethic Polypeptide

<400> SEQUENCE: 45

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asp Ser
            20                  25                  30

Asp Gly Gly Thr Phe Leu Glu Trp Phe Gln Gln Arg Pro Gly Gln Ser
        35                  40                  45

Pro Arg Leu Leu Ile Tyr Asp Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Ser Phe Gly Gln Gly Thr Lys Leu Glu Ile Lys
                100                 105                 110

<210> SEQ ID NO 46
<211> LENGTH: 330
<212> TYPE: PRT
<213> ORGANISM: Artificial Sequence
<220> FEATURE:
<223> OTHER INFORMATION: Synthethic Polypeptide

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

-continued

```
Gln Lys Ser Leu Ser Leu Ser Pro Gly Lys
            325                 330

<210> SEQ ID NO 47
<211> LENGTH: 107
<212> TYPE: PRT
<213> ORGANISM: Homo sapiens

<400> SEQUENCE: 47

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 48
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Gln Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190
```

-continued

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
                325                 330
```

```
<210> SEQ ID NO 49
<211> LENGTH: 7
<212> TYPE: PRT
<213> ORGANISM: Artificial Sequence
<220> FEATURE:
<223> OTHER INFORMATION: Synthethic Polypeptide

<400> SEQUENCE: 49

Glu Val Ser Ser Arg Phe Ser
1               5
```

```
<210> SEQ ID NO 50
<211> LENGTH: 16
<212> TYPE: PRT
<213> ORGANISM: Artificial Sequence
<220> FEATURE:
<223> OTHER INFORMATION: Synthethic Polypeptide

<400> SEQUENCE: 50

Arg Ser Ser Gln Ser Leu Ala Asp Ser Asp Gly Asp Thr Phe Leu His
1               5                   10                  15
```

```
<210> SEQ ID NO 51
<211> LENGTH: 445
<212> TYPE: PRT
<213> ORGANISM: Artificial Sequence
<220> FEATURE:
<223> OTHER INFORMATION: Synthethic Polypeptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                     85                    90                    95

Ala Lys Gly Thr Thr Pro Asp Tyr Trp Gly Gln Gly Thr Met Val Thr
                100                   105                   110

Val Ser Ser Ala Ser Thr Lys Gly Pro Ser Val Phe Pro Leu Ala Pro
            115                   120                   125

Ser Ser Lys Ser Thr Ser Gly Gly Thr Ala Ala Leu Gly Cys Leu Val
        130                   135                   140

Lys Asp Tyr Phe Pro Glu Pro Val Thr Val Ser Trp Asn Ser Gly Ala
145                   150                   155                   160

Leu Thr Ser Gly Val His Thr Phe Pro Ala Val Leu Gln Ser Ser Gly
                165                   170                   175

Leu Tyr Ser Leu Ser Ser Val Val Thr Val Pro Ser Ser Ser Leu Gly
                180                   185                   190

Thr Gln Thr Tyr Ile Cys Asn Val Asn His Lys Pro Ser Asn Thr Lys
            195                   200                   205

Val Asp Lys Lys Val Glu Pro Lys Ser Cys Asp Lys Thr His Thr Cys
        210                   215                   220

Pro Pro Cys Pro Ala Pro Glu Ala Ala Gly Gly Pro Ser Val Phe Leu
225                   230                   235                   240

Phe Pro Pro Lys Pro Lys Asp Thr Leu Met Ile Ser Arg Thr Pro Glu
                245                   250                   255

Val Thr Cys Val Val Val Asp Val Ser His Glu Asp Pro Glu Val Lys
                260                   265                   270

Phe Asn Trp Tyr Val Asp Gly Val Glu Val His Asn Ala Lys Thr Lys
                275                   280                   285

Pro Arg Glu Glu Gln Tyr Asn Ser Thr Tyr Arg Val Val Ser Val Leu
        290                   295                   300

Thr Val Leu His Gln Asp Trp Leu Asn Gly Lys Glu Tyr Lys Cys Lys
305                   310                   315                   320

Val Ser Asn Lys Ala Leu Pro Ala Pro Ile Glu Lys Thr Ile Ser Lys
                325                   330                   335

Ala Lys Gly Gln Pro Arg Glu Pro Gln Val Tyr Thr Leu Pro Pro Ser
                340                   345                   350

Arg Glu Glu Met Thr Lys Asn Gln Val Ser Leu Thr Cys Leu Val Lys
            355                   360                   365

Gly Phe Tyr Pro Ser Asp Ile Ala Val Glu Trp Glu Ser Asn Gly Gln
        370                   375                   380

Pro Glu Asn Asn Tyr Lys Thr Thr Pro Pro Val Leu Asp Ser Asp Gly
385                   390                   395                   400

Ser Phe Phe Leu Tyr Ser Lys Leu Thr Val Asp Lys Ser Arg Trp Gln
                405                   410                   415

Gln Gly Asn Val Phe Ser Cys Ser Val Met His Glu Ala Leu His Asn
                420                   425                   430

His Tyr Thr Gln Lys Ser Leu Ser Leu Ser Pro Gly Lys
            435                   440                   445
```

<210> SEQ ID NO 52
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 52

Asp Val Val Leu Thr Gln Ser Pro Leu Ser Leu Pro Val Thr Leu Gly

-continued

```
1                5                    10                   15

Gln Pro Ala Ser Ile Ser Cys Arg Ser Ser Gln Ser Leu Glu Thr Ser
             20                   25                   30

Asp Gly Asp Thr Phe Leu Glu Trp Phe Gln Gln Arg Pro Gly Gln Ser
             35                   40                   45

Pro Arg Leu Leu Ile Tyr Glu Val Ser Thr Arg Phe Ser Gly Val Pro
         50                   55                   60

Asp Arg Phe Ser Gly Ser Gly Ser Gly Thr Asp Phe Thr Leu Lys Ile
65                   70                   75                   80

Ser Arg Val Glu Ala Glu Asp Val Gly Val Tyr Tyr Cys Phe Gln Val
                 85                   90                   95

Thr His Asp Pro Met Thr Phe Gly Gln Gly Thr Lys Leu Glu Ile Lys
             100                  105                  110

Arg Thr Val Ala Ala Pro Ser Val Phe Ile Phe Pro Pro Ser Asp Glu
             115                  120                  125

Gln Leu Lys Ser Gly Thr Ala Ser Val Val Cys Leu Leu Asn Asn Phe
         130                  135                  140

Tyr Pro Arg Glu Ala Lys Val Gln Trp Lys Val Asp Asn Ala Leu Gln
145                  150                  155                  160

Ser Gly Asn Ser Gln Glu Ser Val Thr Glu Gln Asp Ser Lys Asp Ser
                 165                  170                  175

Thr Tyr Ser Leu Ser Ser Thr Leu Thr Leu Ser Lys Ala Asp Tyr Glu
             180                  185                  190

Lys His Lys Val Tyr Ala Cys Glu Val Thr His Gln Gly Leu Ser Ser
             195                  200                  205

Pro Val Thr Lys Ser Phe Asn Arg Gly Glu Cys
         210                  215
```

```
<210> SEQ ID NO 53
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 53
```

```
Asp Val Val Leu Thr Gln Ser Pro Leu Ser Leu Pro Val Thr Leu Gly
1                5                    10                   15

Gln Pro Ala Ser Ile Ser Cys Arg Ser Ser Gln Ser Leu Glu Thr Ser
             20                   25                   30

Asp Gly Asp Thr Phe Leu Glu Trp Phe Gln Gln Arg Pro Gly Gln Ser
             35                   40                   45

Pro Arg Leu Leu Ile Tyr Glu Val Ser Ser Arg Phe Ser Gly Val Pro
         50                   55                   60

Asp Arg Phe Ser Gly Ser Gly Ser Gly Thr Asp Phe Thr Leu Lys Ile
65                   70                   75                   80

Ser Arg Val Glu Ala Glu Asp Val Gly Val Tyr Tyr Cys Met Gln Val
                 85                   90                   95

Thr His Asp Pro Leu Thr Phe Gly Gln Gly Thr Lys Leu Glu Ile Lys
             100                  105                  110

Arg Thr Val Ala Ala Pro Ser Val Phe Ile Phe Pro Pro Ser Asp Glu
             115                  120                  125

Gln Leu Lys Ser Gly Thr Ala Ser Val Val Cys Leu Leu Asn Asn Phe
         130                  135                  140

Tyr Pro Arg Glu Ala Lys Val Gln Trp Lys Val Asp Asn Ala Leu Gln
```

-continued

```
      145              150              155              160

Ser Gly Asn Ser Gln Glu Ser Val Thr Glu Gln Asp Ser Lys Asp Ser
                 165              170              175

Thr Tyr Ser Leu Ser Ser Thr Leu Thr Leu Ser Lys Ala Asp Tyr Glu
                 180              185              190

Lys His Lys Val Tyr Ala Cys Glu Val Thr His Gln Gly Leu Ser Ser
                 195              200              205

Pro Val Thr Lys Ser Phe Asn Arg Gly Glu Cys
        210              215

<210> SEQ ID NO 54
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 54

Asp Val Val Leu Thr Gln Ser Pro Leu Ser Leu Pro Val Thr Leu Gly
1               5               10              15

Gln Pro Ala Ser Ile Ser Cys Arg Ser Ser Gln Ser Leu Glu Thr Ser
                 20              25              30

Asp Gly Asp Thr Phe Leu Glu Trp Phe Gln Gln Arg Pro Gly Gln Ser
           35              40              45

Pro Arg Leu Leu Ile Tyr Glu Val Ser Asn Arg Phe Ser Gly Val Pro
        50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Phe Gln Val
                 85              90              95

Thr His Asp Pro Val Thr Phe Gly Gln Gly Thr Lys Leu Glu Ile Lys
                 100             105             110

Arg Thr Val Ala Ala Pro Ser Val Phe Ile Phe Pro Pro Ser Asp Glu
                 115             120             125

Gln Leu Lys Ser Gly Thr Ala Ser Val Val Cys Leu Leu Asn Asn Phe
        130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
                 165             170             175

Thr Tyr Ser Leu Ser Ser Thr Leu Thr Leu Ser Lys Ala Asp Tyr Glu
                 180             185             190

Lys His Lys Val Tyr Ala Cys Glu Val Thr His Gln Gly Leu Ser Ser
                 195             200             205

Pro Val Thr Lys Ser Phe Asn Arg Gly Glu Cys
        210             215

<210> SEQ ID NO 55
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 55

Asp Val Val Leu Thr Gln Ser Pro Leu Ser Leu Pro Val Thr Leu Gly
1               5               10              15
```

```
Gln Pro Ala Ser Ile Ser Cys Arg Ser Ser Gln Ser Leu Glu Ser Ser
        20                  25                  30

Asp Gly Asp Thr Phe Leu Glu Trp Phe Gln Gln Arg Pro Gly Gln Ser
        35                  40                  45

Pro Arg Leu Leu Ile Tyr Asp Val Ser Thr Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Thr His Asp Pro Val Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

```
<210> SEQ ID NO 56
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 56
```

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Glu Ser
        20                  25                  30

Asp Gly Tyr Thr Phe Leu Glu Trp Phe Gln Gln Arg Pro Gly Gln Ser
        35                  40                  45

Pro Arg Leu Leu Ile Tyr Asp Val Ser Glu Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr Tyr Asp Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160
```

-continued

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 57
<211> LENGTH: 445
<212> TYPE: PRT
<213> ORGANISM: Artificial Sequence
<220> FEATURE:
<223> OTHER INFORMATION: Synthethic Polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
                20                  25                  30

Gly Met Asn Trp Ile Arg Gln Ala Pro Gly Lys Gly Leu Glu Trp Ile
            35                  40                  45

Gly Met Ile Tyr Tyr Asp Ser Ser Glu Lys His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
                130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
                210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
                290                 295                 300
```

-continued

```
Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
                325             330             335

Ala Lys Gly Gln Pro Arg Glu Pro Gln Val Tyr Thr Leu Pro Pro Ser
            340             345             350

Arg Glu Glu Met Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
        370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
                405             410             415

Gln Gly Asn Val Phe Ser Cys Ser Val Met His Glu Ala Leu His Asn
                420             425             430

His Tyr Thr Gln Lys Ser Leu Ser Leu Ser Pro Gly Lys
        435             440             445

<210> SEQ ID NO 58
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 58

Asp Val Val Leu Thr Gln Ser Pro Leu Ser Leu Pro Val Thr Leu Gly
1               5               10              15

Gln Pro Ala Ser Ile Ser Cys Arg Ser Ser Gln Ser Leu Glu Asp Ser
                20              25              30

Asp Gly Gly Thr Phe Leu Glu Trp Phe Gln Gln Arg Pro Gly Gln Ser
            35              40              45

Pro Arg Leu Leu Ile Tyr Asp Val Ser Ser Arg Phe Ser Gly Val Pro
        50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Phe Gln Ala
                85              90              95

Thr His Asp Pro Leu Thr Phe Gly Gln Gly Thr Lys Leu Glu Ile Lys
            100             105             110

Arg Thr Val Ala Ala Pro Ser Val Phe Ile Phe Pro Pro Ser Asp Glu
        115             120             125

Gln Leu Lys Ser Gly Thr Ala Ser Val Val Cys Leu Leu Asn Asn Phe
        130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
                165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
        210             215
```

```
<210> SEQ ID NO 59
<211> LENGTH: 445
<212> TYPE: PRT
<213> ORGANISM: Artificial Sequence
<220> FEATURE:
<223> OTHER INFORMATION: Synthethic Polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
            35                  40                  45

Gly Met Ile Tyr Tyr Asp Ser Ser Asp Lys His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Val Trp Gly Gln Gly Thr Met Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365
```

-continued

```
Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly Lys
        435             440             445
```

```
<210> SEQ ID NO 60
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 60
```

```
Asp Val Val Leu Thr Gln Ser Pro Leu Ser Leu Pro Val Thr Leu Gly
1               5               10              15

Gln Pro Ala Ser Ile Ser Cys Arg Ser Ser Gln Ser Leu Glu Glu Ser
            20              25              30

Asp Gly Tyr Thr Phe Leu His Trp Phe Gln Gln Arg Pro Gly Gln Ser
        35              40              45

Pro Arg Leu Leu Ile Tyr Glu Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Phe Gln Ala
            85              90              95

Thr His Asp Pro Val Thr Phe Gly Gln Gly Thr Lys Leu Glu Ile Lys
            100             105             110

Arg Thr Val Ala Ala Pro Ser Val Phe Ile Phe Pro Pro Ser Asp Glu
        115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
        180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215
```

```
<210> SEQ ID NO 61
<211> LENGTH: 445
<212> TYPE: PRT
<213> ORGANISM: Artificial Sequence
<220> FEATURE:
<223> OTHER INFORMATION: Synthethic Polypeptide

<400> SEQUENCE: 61
```

```
Glu Val Gln Leu Val Glu Ser Gly Gly Gly Leu Val Gln Pro Gly Gly
1               5               10              15
```

-continued

```
Ser Leu Arg Leu Ser Cys Ala Ala Ser Gly Phe Thr Phe Ser Asn Tyr
        20              25              30

Gly Met Asn Trp Val Arg Gln Ala Pro Gly Lys Gly Leu Glu Trp Ile
        35              40              45

Gly Met Ile Tyr Tyr Asp Ser Ser Glu Lys His Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Gly Thr Thr Pro Asp Tyr Trp Gly Gln Gly Thr Met Val Thr
            100             105             110

Val Ser Ser Ala Ser Thr Lys Gly Pro Ser Val Phe Pro Leu Ala Pro
        115             120             125

Ser Ser Lys Ser Thr Ser Gly Gly Thr Ala Ala Leu Gly Cys Leu Val
    130             135             140

Lys Asp Tyr Phe Pro Glu Pro Val Thr Val Ser Trp Asn Ser Gly Ala
145             150             155             160

Leu Thr Ser Gly Val His Thr Phe Pro Ala Val Leu Gln Ser Ser Gly
            165             170             175

Leu Tyr Ser Leu Ser Ser Val Val Thr Val Pro Ser Ser Ser Leu Gly
            180             185             190

Thr Gln Thr Tyr Ile Cys Asn Val Asn His Lys Pro Ser Asn Thr Lys
        195             200             205

Val Asp Lys Lys Val Glu Pro Lys Ser Cys Asp Lys Thr His Thr Cys
    210             215             220

Pro Pro Cys Pro Ala Pro Glu Ala Ala Gly Gly Pro Ser Val Phe Leu
225             230             235             240

Phe Pro Pro Lys Pro Lys Asp Thr Leu Met Ile Ser Arg Thr Pro Glu
            245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
        275             280             285

Pro Arg Glu Glu Gln Tyr Asn Ser Thr Tyr Arg Val Val Ser Val Leu
    290             295             300

Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
            325             330             335

Ala Lys Gly Gln Pro Arg Glu Pro Gln Val Tyr Thr Leu Pro Pro Ser
            340             345             350

Arg Glu Glu Met Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
        370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430
```

-continued

```
His Tyr Thr Gln Lys Ser Leu Ser Leu Ser Pro Gly Lys
        435                 440                 445

<210> SEQ ID NO 62
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 62

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Glu Ser
            20                  25                  30

Asp Gly Tyr Thr Phe Leu His Trp Phe Gln Gln Arg Pro Gly Gln Ser
        35                  40                  45

Pro Arg Leu Leu Ile Tyr Glu Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 63
<211> LENGTH: 445
<212> TYPE: PRT
<213> ORGANISM: Artificial Sequence
<220> FEATURE:
<223> OTHER INFORMATION: Synthethic Polypeptide

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
        210                 215                 220

Pro Pro Cys Pro Ala Pro Glu Ala Ala Gly Gly Pro Ser Val Phe Leu
225                 230                 235                 240

Phe Pro Pro Lys Pro Lys Asp Gln Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Leu His Glu Ala Leu His Asn
                420                 425                 430

His Tyr Thr Gln Lys Ser Leu Ser Leu Ser Pro Gly Lys
                435                 440                 445
```

<210> SEQ ID NO 64
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 64

-continued

```
gacgtagtac tgacccaaag cccccttctc ctcccagtaa ccctcggaca accagcctca      60
atttcatgca gatcatcaca atcacttgag gacagcgacg gaggcacttt tcttgagtgg     120
ttccaacaaa gacccggaca aagcccacgc ctgcttattt acgacgtatc aagcagattc     180
tcaggagttc cagacagatt ttcaggcagc ggatccggca cagacttcac ccttaaaatt     240
agcagagtag aagcagaaga tgtaggagtg tattattgtt tccaagccac ccacgacccc     300
ctcagcttcg gacaaggaac taagctcgaa atcaaaagaa cggtggctgc accatctgtc     360
ttcatcttcc cgccatctga tgagcagttg aaatctggaa ctgcctctgt tgtgtgcctg     420
ctgaataact ctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttga     660
```

<210> SEQ ID NO 65
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 65

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Asp Ser
            20                  25                  30

Asp Gly Asp Thr Phe Leu His Trp Phe Gln Gln Arg Pro Gly Gln Ser
        35                  40                  45

Pro Arg Leu Leu Ile Tyr Ala Val Ser His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Val Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 66
<211> LENGTH: 445
<212> TYPE: PRT

<213> ORGANISM: Artificial Sequence
<220> FEATURE:
<223> OTHER INFORMATION: Synthethic Polypeptide

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Lys Trp Gly Gln Gly Thr Met Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 67
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 67

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Glu Ser
                20                  25                  30

Asp Gly Tyr Thr Phe Leu Glu Trp Phe Gln Gln Arg Pro Gly Gln Ser
            35                  40                  45

Pro Arg Leu Leu Ile Tyr Glu Val Ser His Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 68
<211> LENGTH: 445
<212> TYPE: PRT
<213> ORGANISM: Artificial Sequence
<220> FEATURE:
<223> OTHER INFORMATION: Synthethic Polypeptide

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30
```

```
Gly Met Asn Trp Val Arg Gln Ala Pro Gly Lys Gly Leu Glu Trp Ile
    35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Thr Pro Asp Tyr Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
    435                 440                 445
```

```
<210> SEQ ID NO 69
<211> LENGTH: 219
<212> TYPE: PRT
<213> ORGANISM: Artificial Sequence
<220> FEATURE:
<223> OTHER INFORMATION: Synthethic Polypeptide

<400> SEQUENCE: 69

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asp Ser
            20                  25                  30

Asp Gly Gly Thr Phe Leu Glu Trp Phe Gln Gln Arg Pro Gly Gln Ser
        35                  40                  45

Pro Arg Leu Leu Ile Tyr Asp Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 70
<211> LENGTH: 345
<212> TYPE: DNA
<213> ORGANISM: Artificial Sequence
<220> FEATURE:
<223> OTHER INFORMATION: Synthethic Polynucleotide

<400> SEQUENCE: 70
gaagtacagt tggtagaaag cggcggagga cttgtgcagc caggtggatc tctcagactt      60
tcatgtgccg caagcggttt tactttttagt aactatggaa tgaattggat tagacaagcg     120
cccggaaaag gattggaatg gataggaatg atatactacg atagctcaga aaaacattat      180
gccgactcag ttaaaggaag atttacaata tcaagagaca atagcaaaaa cacactttat      240
cttcaaatga attcactgcg agccgaggat acagcagtct attattgcgc aaaaggaaca      300
acaccagatt attggggtca aggaacaatg gtaaccgtgt caagc                     345

<210> SEQ ID NO 71
<211> LENGTH: 1338
<212> TYPE: DNA
<213> ORGANISM: Artificial Sequence
<220> FEATURE:
```

-continued

<223> OTHER INFORMATION: Synthethic Polynucleotide

<400> SEQUENCE: 71

```
gaagtacagt tggtagaaag cggcggagga cttgtgcagc caggtggatc tctcagactt      60
tcatgtgccg caagcggttt tacttttagt aactatggaa tgaattggat tagacaagcg     120
cccggaaaag gattggaatg gataggaatg atatactacg atagctcaga aaaacattat     180
gccgactcag ttaaaggaag atttacaata tcaagagaca atagcaaaaa cacactttat     240
cttcaaatga attcactgcg agccgaggat acagcagtct attattgcgc aaaaggaaca     300
acaccagatt attggggtca aggaacaatg gtaaccgtgt caagcgcgtc gaccaagggc     360
ccatcggtct tccccctggc accctcctcc aagagcacct ctggggggcac agcggccctg     420 ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagccgcgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccgcg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaatga                                                 1338
```

<210> SEQ ID NO 72
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 72

```
gacgtagtac tgacccaaag ccccctttct ctcccagtaa ccctcggaca accagcctca      60
atttcatgca gatcatcaca atcacttgag acgagcgacg gagacacttt tcttgagtgg     120
ttccaacaaa gacccggaca aagcccacgc ctgcttattt acgaggtatc aacgagattc     180
tcaggagttc cagacagatt ttcaggcagc ggatccggca cagacttcac ccttaaaatt     240
agcagagtag aagcagaaga tgtaggagtg tattattgtt ttcaagtcac ccacgacccc     300
atgacgttcg gacaaggaac taagctcgaa atcaaa                               336
```

<210> SEQ ID NO 73
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 73
gacgtagtac tgacccaaag cccccttct ctcccagtaa ccctcggaca accagcctca    60
atttcatgca gatcatcaca atcacttgag acgagcgacg gagacacttt tcttgagtgg   120
ttccaacaaa gacccggaca aagcccacgc ctgcttattt acgaggtatc aacgagattc   180
tcaggagttc cagacagatt ttcaggcagc ggatccggca cagacttcac ccttaaaatt   240
agcagagtag aagcagaaga tgtaggagtg tattattgtt ttcaagtcac ccacgacccc   300
atgacgttcg gacaaggaac taagctcgaa atcaaaagaa cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct caacaggggg agagtgttga   660

<210> SEQ ID NO 74
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 74
gacgtagtac tgacccaaag cccccttct ctcccagtaa ccctcggaca accagcctca    60
atttcatgca gatcatcaca atcacttgag acgagcgacg gagacacttt tcttgagtgg   120
ttccaacaaa gacccggaca aagcccacgc ctgcttattt acgaggtatc aagcagattc   180
tcaggagttc cagacagatt ttcaggcagc ggatccggca cagacttcac ccttaaaatt   240
agcagagtag aagcagaaga tgtaggagtg tattattgta tgcaagtcac ccacgacccc   300
ctgaccttcg gacaaggaac taagctcgaa atcaaa                              336

<210> SEQ ID NO 75
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 75
gacgtagtac tgacccaaag cccccttct ctcccagtaa ccctcggaca accagcctca    60
atttcatgca gatcatcaca atcacttgag acgagcgacg gagacacttt tcttgagtgg   120
ttccaacaaa gacccggaca aagcccacgc ctgcttattt acgaggtatc aagcagattc   180
tcaggagttc cagacagatt ttcaggcagc ggatccggca cagacttcac ccttaaaatt   240
agcagagtag aagcagaaga tgtaggagtg tattattgta tgcaagtcac ccacgacccc   300
ctgaccttcg gacaaggaac taagctcgaa atcaaaagaa cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct caacaggggg agagtgttga   660

<210> SEQ ID NO 76
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 76
gacgtagtac tgacccaaag ccccctttct ctcccagtaa ccctcggaca accagcctca        60
atttcatgca gatcatcaca atcacttgag accagcgacg gagatacttt tcttgagtgg       120
ttccaacaaa gacccggaca aagcccacgc ctgcttattt acgaggtatc aaacagattc       180
tcaggagttc cagacagatt ttcaggcagc ggatccggca cagacttcac ccttaaaatt       240
agcagagtag aagcagaaga tgtaggagtg tattattgtt ccaagtcac ccacgacccc        300 gtcacgttcg gacaaggaac taagctcgaa atcaaa                                 336

<210> SEQ ID NO 77
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 77
gacgtagtac tgacccaaag ccccctttct ctcccagtaa ccctcggaca accagcctca        60
atttcatgca gatcatcaca atcacttgag accagcgacg gagatacttt tcttgagtgg       120
ttccaacaaa gacccggaca aagcccacgc ctgcttattt acgaggtatc aaacagattc       180
tcaggagttc cagacagatt ttcaggcagc ggatccggca cagacttcac ccttaaaatt       240
agcagagtag aagcagaaga tgtaggagtg tattattgtt ccaagtcac ccacgacccc        300 gtcacgttcg gacaaggaac taagctcgaa atcaaaagaa cggtggctgc accatctgtc       360
ttcatcttcc cgccatctga tgagcagttg aaatctggaa ctgcctctgt tgtgtgcctg       420
ctgaataact ctatcccag agaggccaaa gtacagtgga aggtggataa cgccctccaa        480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct caacaggggg agagtgttga       660

<210> SEQ ID NO 78
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 78
gacgtagtac tgacccaaag ccccctttct ctcccagtaa ccctcggaca accagcctca        60
atttcatgca gatcatcaca atcacttgag tccagcgacg gagacacttt tcttgagtgg       120
ttccaacaaa gacccggaca aagcccacgc ctgcttattt acgatgtatc aactagattc       180
tcaggagttc cagacagatt ttcaggcagc ggatccggca cagacttcac ccttaaaatt       240
agcagagtag aagcagaaga tgtaggagtg tattattgtt ttcaagtcac ccatgacccc       300
gtgaccttcg gacaaggaac taagctcgaa atcaaa                                 336

<210> SEQ ID NO 79
<211> LENGTH: 660

<212> TYPE: DNA
<213> ORGANISM: Artificial Sequence
<220> FEATURE:
<223> OTHER INFORMATION: Synthethic Polynucleotide

<400> SEQUENCE: 79
gacgtagtac tgacccaaag ccccctttct ctcccagtaa ccctcggaca accagcctca        60
atttcatgca gatcatcaca atcacttgag tccagcgacg gagacacttt tcttgagtgg       120
ttccaacaaa gacccggaca aagcccacgc ctgcttattt acgatgtatc aactagattc       180
tcaggagttc cagacagatt ttcaggcagc ggatccggca cagacttcac ccttaaaatt       240
agcagagtag aagcagaaga tgtaggagtg tattattgtt ttcaagtcac ccatgacccc       300
gtgaccttcg gacaaggaac taagctcgaa atcaaaagaa cggtggctgc accatctgtc       360
ttcatcttcc cgccatctga tgagcagttg aaatctggaa ctgcctctgt tgtgtgcctg       420
ctgaataact tctatcccag agaggccaaa gtacagtgga aggtggataa cgccctccaa       480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct caacaggggg agagtgttga       660

<210> SEQ ID NO 80
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 80
gacgtagtac tgacccaaag ccccctttct ctcccagtaa ccctcggaca accagcctca        60
atttcatgca gatcatcaca atcacttgag gaaagcgacg gatacacttt tcttgaatgg       120
ttccaacaaa gacccggaca aagcccacgc ctgcttattt acgatgtatc agaaagattc       180
tcaggagttc cagacagatt ttcaggcagc ggatccggca cagacttcac ccttaaaatt       240
agcagagtag aagcagaaga tgtaggagtg tattattgtt ccaagcgac ctacgacccc       300 ctcaccttcg gacaaggaac taagctcgaa atcaaa                                 336

<210> SEQ ID NO 81
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 81
gacgtagtac tgacccaaag ccccctttct ctcccagtaa ccctcggaca accagcctca        60
atttcatgca gatcatcaca atcacttgag gaaagcgacg gatacacttt tcttgaatgg       120
ttccaacaaa gacccggaca aagcccacgc ctgcttattt acgatgtatc agaaagattc       180
tcaggagttc cagacagatt ttcaggcagc ggatccggca cagacttcac ccttaaaatt       240
agcagagtag aagcagaaga tgtaggagtg tattattgtt ccaagcgac ctacgacccc       300 ctcaccttcg gacaaggaac taagctcgaa atcaaaagaa cggtggctgc accatctgtc       360
ttcatcttcc cgccatctga tgagcagttg aaatctggaa ctgcctctgt tgtgtgcctg       420
ctgaataact tctatcccag agaggccaaa gtacagtgga aggtggataa cgccctccaa       480
tcgggtaact cccaggagag tgtcacagag caggacagca aggacagcac ctacagcctc       540

-continued

```
agcagcaccc tgacgctgag caaagcagac tacgagaaac acaaagtcta cgcctgcgaa        600
gtcacccatc agggcctgag ctcgcccgtc acaaagagct tcaacagggg agagtgttga        660

<210> SEQ ID NO 82
<211> LENGTH: 345
<212> TYPE: DNA
<213> ORGANISM: Artificial Sequence
<220> FEATURE:
<223> OTHER INFORMATION: Synthethic Polynucleotide

<400> SEQUENCE: 82
gaagtacagt tggtagaaag cggcggagga cttgtgcagc caggtggatc tctcagactt         60
tcatgtgccg caagcggttt tacttttagt tactatggaa tgaactggat tagacaagcg        120
cccggaaaag gattggaatg dataggcatg atatactacg acagctcgga gaaacattat        180
gccgactcag ttaaaggaag atttacaata tcaagagaca atagcaaaaa cacactttat        240
cttcaaatga attcactgcg agccgaggat acagcagtct attattgcgc aaaagggacg        300
acgcccgatt actggggtca aggaacaatg gtaaccgtgt caagc                        345

<210> SEQ ID NO 83
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 83
gacgtagtac tgacccaaag ccccctttct ctcccagtaa ccctcggaca accagcctca         60
atttcatgca gatcatcaca atcacttgag dacagcgacg gaggaacttt tcttgagtgg        120
ttccaacaaa daccccggaca aagcccacgc ctgcttattt acgacgtatc aagcagattc        180
tcaggagttc cagacagatt ttcaggcagc ggatccggca cagacttcac ccttaaaatt        240
agcagagtag aagcagaaga tgtaggagtg tattattgtt ttcaagcgac ccacgacccc        300
ctgacgttcg gacaaggaac taagctcgaa atcaaa                                   336

<210> SEQ ID NO 84
<211> LENGTH: 1338
<212> TYPE: DNA
<213> ORGANISM: Artificial Sequence
<220> FEATURE:
<223> OTHER INFORMATION: Synthethic Polynucleotide

<400> SEQUENCE: 84
gaagtacagt tggtagaaag cggcggagga cttgtgcagc caggtggatc tctcagactt         60
tcatgtgccg caagcggttt tacttttagt tactatggaa tgaactggat tagacaagcg        120
cccggaaaag gattggaatg dataggcatg atatactacg acagctcgga gaaacattat        180
gccgactcag ttaaaggaag atttacaata tcaagagaca atagcaaaaa cacactttat        240
cttcaaatga attcactgcg agccgaggat acagcagtct attattgcgc aaaagggacg        300
acgcccgatt actggggtca aggaacaatg gtaaccgtgt caagcgcgtc gaccaagggc        360
ccatcggtct tccccctggc accctcctcc aagagcacct ctgggggcac agcggccctg        420
ggctgcctgg tcaaggacta cttccccgaa ccggtgacgg tgtcgtggaa ctcaggcgcc        480
ctgaccagcg gcgtgcacac cttcccggct gtcctacagt cctcaggact ctactccctc        540
agcagcgtgg tgaccgtgcc ctccagcagc ttgggcaccc agacctacat ctgcaacgtg        600
aatcacaagc ccagcaacac caaggtggac aagaaagttg agcccaaatc ttgtgacaaa        660
```
actcacacat gcccaccgtg cccagcacct gaagccgcgg ggggaccgtc agtcttcctc          720
ttccccccaa aacccaagga caccctcatg atctcccgga cccctgaggt cacatgcgtg          780
gtggtggacg tgagccacga agaccctgag gtcaagttca actggtacgt ggacggcgtg          840
gaggtgcata atgccaagac aaagccgcgg gaggagcagt acaacagcac gtaccgtgtg          900
gtcagcgtcc tcaccgtcct gcaccaggac tggctgaatg gcaaggagta caagtgcaag          960
gtctccaaca aagccctccc agcccccatc gagaaaacca tctccaaagc caaagggcag         1020
ccccgagaac cacaggtgta caccctgccc ccatcccgcg aggagatgac caagaaccag         1080
gtcagcctga cctgcctggt caaaggcttc tatcccagcg acatcgccgt ggagtgggag         1140
agcaatgggc agccggagaa caactacaag accacgcctc ccgtgctgga ctccgacggc         1200
tccttcttcc tctacagcaa gctcaccgtg gacaagagca ggtggcagca ggggaacgtc         1260
ttctcatgct ccgtgatgca tgaggctctg cacaaccact acacgcagaa gagcctctcc         1320
ctgtctccgg gtaaatga                                                      1338

<210> SEQ ID NO 85
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 85
gacgtagtac tgacccaaag ccccctttct ctcccagtaa ccctcggaca accagcctca           60
atttcatgca gatcatcaca atcacttgag gacagcgacg gaggaacttt tcttgagtgg          120
ttccaacaaa gacccggaca aagcccacgc ctgcttattt acgacgtatc aagcagattc          180
tcaggagttc cagacagatt ttcaggcagc ggatccggca cagacttcac ccttaaaatt          240
agcagagtag aagcagaaga tgtaggagtg tattattgtt ttcaagcgac ccacgacccc          300
ctgacgttcg gacaaggaac taagctcgaa atcaaaagaa cggtggctgc accatctgtc          360
ttcatcttcc cgccatctga tgagcagttg aaatctggaa ctgcctctgt tgtgtgcctg          420
ctgaataact ctatcccag agaggccaaa gtacagtgga aggtggataa cgccctccaa          480
tcgggtaact cccaggagag tgtcacagag caggacagca aggacagcac ctacagcctc          540
agcagcaccc tgacgctgag caaagcagac tacgagaaac acaaagtcta cgcctgcgaa          600
gtcacccatc agggcctgag ctcgcccgtc acaaagagct tcaacagggg agagtgttga          660

<210> SEQ ID NO 86
<211> LENGTH: 345
<212> TYPE: DNA
<213> ORGANISM: Artificial Sequence
<220> FEATURE:
<223> OTHER INFORMATION: Synthethic Polynucleotide

<400> SEQUENCE: 86
gaagtacagt tggtagaaag cggcggagga cttgtgcagc caggtggatc tctcagactt           60
tcatgtgccg caagcggttt tacttttagt aactatggaa tgaactggat aagacaagcg          120 cccgaaaag gattggaatg gataggcatg atatactacg acagctcgga caaacattat          180
gccgactcag ttaaaggaag atttacaata tcaagagaca atagcaaaaa cacactttat          240
cttcaaatga attcactgcg agccgaggat acagcagtct attattgcgc aaaagggacg          300
acgccggatg tatggggtca aggaacaatg gtaaccgtgt caagc                        345

-continued

```
<210> SEQ ID NO 87
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 87
gacgtagtac tgacccaaag ccccctttct ctcccagtaa ccctcggaca accagcctca      60
atttcatgca gatcatcaca atcacttgaa gagagcgacg gatacacttt tcttcattgg     120
ttccaacaaa gacccggaca aagcccacgc ctgcttattt acgaggtatc aaacagattc     180
tcaggagttc cagacagatt ttcaggcagc ggatccggca cagacttcac ccttaaaatt     240
agcagagtag aagcagaaga tgtaggagtg tattattgtt ccaagccac ccacgacccc      300 gtgacgttcg gacaaggaac taagctcgaa atcaaa                               336

<210> SEQ ID NO 88
<211> LENGTH: 1338
<212> TYPE: DNA
<213> ORGANISM: Artificial Sequence
<220> FEATURE:
<223> OTHER INFORMATION: Synthethic Polynucleotide

<400> SEQUENCE: 88
gaagtacagt tggtagaaag cggcggagga cttgtgcagc caggtggatc tctcagactt      60
tcatgtgccg caagcggttt tactttttagt aactatggaa tgaactggat aagacaagcg     120
cccggaaaag gattggaatg gataggcatg atatactacg acagctcgga caaacattat     180
gccgactcag ttaaaggaag atttacaata tcaagagaca atagcaaaaa cacacttttat    240 cttcaaatga attcactgcg agccgaggat acagcagtct attattgcgc aaaagggacg      300
acgccggatg tatgggggtca aggaacaatg gtaaccgtgt caagcgcgtc gaccaagggc     360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagccgcgg ggggaccgtc agtcttcctc      720
ttccccccaa aacccaagga cacccttcatg atctcccgga cccctgaggt cacatgcgtg    780
gtggtggacg tgagccacga agaccctgag gtcaagttca actggtacgt ggacggcgtg      840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag      960
gtctccaaca aagccctccc agcccccatc gagaaaacca tctccaaagc caaagggcag     1020 cccgagaac acaggtgta caccctgccc ccatcccgcg aggagatgac caagaaccag       1080
gtcagcctga cctgcctggt caaaggcttc tatcccagcg acatcgccgt ggagtgggag     1140
agcaatgggc agccggagaa caactacaag accacgcctc ccgtgctgga ctccgacggc     1200
tccttcttcc tctacagcaa gctcaccgtg gacaagagca ggtggcagca ggggaacgtc     1260
ttctcatgct ccgtgatgca tgaggctctg cacaaccact acacgcagaa gagcctctcc     1320
ctgtctccgg gtaaatga                                                  1338
```

```
<210> SEQ ID NO 89
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 89
gacgtagtac tgacccaaag ccccctttct ctcccagtaa ccctcggaca accagcctca      60
atttcatgca gatcatcaca atcacttgaa gagagcgacg gatacacttt tcttcattgg     120
ttccaacaaa gacccggaca aagcccacgc ctgcttattt acgaggtatc aaacagattc     180
tcaggagttc cagacagatt ttcaggcagc ggatccggca cagacttcac ccttaaaatt     240
agcagagtag aagcagaaga tgtaggagtg tattattgtt ccaagccac ccacgacccc      300 gtgacgttcg gacaaggaac taagctcgaa atcaaaagaa cggtggctgc accatctgtc     360
ttcatcttcc cgccatctga tgagcagttg aaatctggaa ctgcctctgt tgtgtgcctg     420
ctgaataact ctatcccag agaggccaaa gtacagtgga aggtggataa cgccctccaa      480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttga     660

<210> SEQ ID NO 90
<211> LENGTH: 345
<212> TYPE: DNA
<213> ORGANISM: Artificial Sequence
<220> FEATURE:
<223> OTHER INFORMATION: Synthethic Polynucleotide

<400> SEQUENCE: 90
gaagtacagt tggtagaaag cggcggagga cttgtgcaac caggtggatc tctcagactt      60
tcatgtgccg caagcggttt tactttttagt aactatggaa tgaactgggt tagacaagcg     120 cccgggaaaag gattggaatg gataggcatg atatattacg acagctcgga gaaacattat     180
gccgactcag ttaaaggaag atttacaata tcaagagaca atagcaaaaa cacactttat     240
cttcaaatga attcactgcg agccgaggat acagcagtct attattgcgc aaaagggacc     300
acccccgatt actggggtca aggaacaatg gtaaccgtgt caagc                     345

<210> SEQ ID NO 91
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 91
gacgtagtac tgacccaaag cccccttct ctcccagtaa ccctcggaca accagcctca       60
atttcatgca gatcatcaca atcacttgaa gaaagcgacg gatacacttt tcttcactgg     120
ttccaacaaa gacccggaca aagcccacgc ctgcttattt acgaggtatc aaccagattc     180
tcaggagttc cagacagatt ttcaggcagc ggatccggca cagacttcac ccttaaaatt     240
agcagagtag aagcagaaga tgtaggagtg tattattgtt ccaagccac ccacgacccc      300 ctgaccttcg gacaaggaac taagctcgaa atcaaa                               336

<210> SEQ ID NO 92
<211> LENGTH: 1338
<212> TYPE: DNA
```

```
<213> ORGANISM: Artificial Sequence
<220> FEATURE:
<223> OTHER INFORMATION: Synthethic Polynucleotide

<400> SEQUENCE: 92
gaagtacagt tggtagaaag cggcggagga cttgtgcaac caggtggatc tctcagactt      60
tcatgtgccg caagcggttt tacttttagt aactatggaa tgaactgggt tagacaagcg     120
cccggaaaag gattggaatg gataggcatg atatattacg acagctcgga gaaacattat     180
gccgactcag ttaaaggaag atttacaata tcaagagaca atagcaaaaa cacactttat     240
cttcaaatga attcactgcg agccgaggat acagcagtct attattgcgc aaaagggacc     300
acccccgatt actgggtgtca aggaacaatg gtaaccgtgt caagcgcgtc gaccaagggc     360
ccatcggtct tcccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagccgcgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccgcg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaatga                                                  1338

<210> SEQ ID NO 93
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 93
gacgtagtac tgacccaaag ccccctttct ctcccagtaa ccctcggaca accagcctca      60
atttcatgca gatcatcaca atcacttgaa gaaagcgacg gatacacttt tcttcactgg     120
ttccaacaaa gacccggaca agcccacgc ctgcttattt acgaggtatc aaccagattc     180
tcaggagttc cagacagatt ttcaggcagc ggatccggca cagacttcac ccttaaaatt     240
agcagagtag aagcagaaga tgtaggagtg tattattgtt ccaagccac ccacgacccc      300 ctgaccttcg gacaaggaac taagctcgaa atcaaaagaa cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
```
agcagcaccc tgacgctgag caaagcagac tacgagaaac acaaagtcta cgcctgcgaa     600
gtcacccatc agggcctgag ctcgcccgtc acaaagagct tcaacagggg agagtgttga     660

<210> SEQ ID NO 94
<211> LENGTH: 1338
<212> TYPE: DNA
<213> ORGANISM: Artificial Sequence
<220> FEATURE:
<223> OTHER INFORMATION: Synthethic Polynucleotide

<400> SEQUENCE: 94
gaagtacagt tggtagaaag cggcggagga cttgtgcaac caggtggatc tctcagactt      60
tcatgtgccg caagcggttt tactttagt aactatggaa tgaactgggt tagacaagcg     120
cccggaaaag gattggaatg gataggcatg atatattacg acagctcgga gaaacattat     180
gccgactcag ttaaaggaag atttacaata tcaagagaca atagcaaaaa cacactttat     240
cttcaaatga attcactgcg agccgaggat acagcagtct attattgcgc aaaagggacc     300 accccgatt actggggtca aggaacaatg gtaaccgtgt caagcgcgtc gaccaagggc     360
ccatcggtct tcccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagccgcgg gggaccgtc agtcttcctc     720 ttcccccca aacccaagga ccaactcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccgcg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgctgca tgaggctctg cacaaccact acacgcagaa gagcctctcc    1320
ctgtctccgg gtaaatga                                                 1338

<210> SEQ ID NO 95
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 95
gacgtagtac tgacccaaag ccccctttct ctcccagtaa ccctcggaca accagcctca      60
atttcatgca gatcatcaca atcacttgcg gacagcgacg gagatacttt tcttcactgg     120
ttccaacaaa gacccggaca aagcccacgc ctgcttattt acgcggtatc acacagattc     180
tcaggagttc cagacagatt ttcaggcagc ggatccggca cagacttcac ccttaaaatt     240

-continued

```
agcagagtag aagcagaaga tgtaggagtg tattattgtt tccaagccac ccatgacccc      300
gtcacgttcg gacaaggaac taagctcgaa atcaaa                                336

<210> SEQ ID NO 96
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 96
gacgtagtac tgacccaaag cccccttct ctcccagtaa ccctcggaca accagcctca        60
atttcatgca gatcatcaca atcacttgcg gacagcgacg gagatacttt tcttcactgg      120
ttccaacaaa gacccggaca aagcccacgc ctgcttattt acgcggtatc acacagattc      180
tcaggagttc cagacagatt ttcaggcagc ggatccggca cagacttcac ccttaaaatt      240
agcagagtag aagcagaaga tgtaggagtg tattattgtt tccaagccac ccatgacccc      300
gtcacgttcg gacaaggaac taagctcgaa atcaaaagaa cggtggctgc accatctgtc      360
ttcatcttcc cgccatctga tgagcagttg aaatctggaa ctgcctctgt tgtgtgcctg      420
ctgaataact ctatcccag agaggccaaa gtacagtgga aggtggataa cgccctccaa       480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct caacaggggg agagtgttga      660

<210> SEQ ID NO 97
<211> LENGTH: 345
<212> TYPE: DNA
<213> ORGANISM: Artificial Sequence
<220> FEATURE:
<223> OTHER INFORMATION: Synthethic Polynucleotide

<400> SEQUENCE: 97
gaagtacagt tggtagaaag cggcggagga cttgtgcagc caggtggatc tctcagactt       60
tcatgtgccg caagcggttt tacttttagt aactatggaa tgaactgggt tagacaagcg      120
cccggaaaag gattggaatg gataggcatg atatactacg acagctccga gaaacattat      180
gccgactcag ttaaaggaag atttacaata tcaagagaca atagcaaaaa cacactttat      240
cttcaaatga attcactgcg agccgaggat acagcagtct attattgcgc aaaaggcacg      300
acgcccgata aatggggtca aggaacaatg gtaaccgtgt caagc                      345

<210> SEQ ID NO 98
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 98
gacgtagtac tgacccaaag cccccttct ctcccagtaa ccctcggaca accagcctca        60
atttcatgca gatcatcaca atcacttgag gagagcgacg gatacacttt tcttgagtgg      120
ttccaacaaa gacccggaca aagcccacgc ctgcttattt acgaggtatc acatagattc      180
tcaggagttc cagacagatt ttcaggcagc ggatccggca cagacttcac ccttaaaatt      240
agcagagtag aagcagaaga tgtaggagtg tattattgtt tccaagcgac ccacgacccc      300
ctgacgttcg gacaaggaac taagctcgaa atcaaa                                336
```

<210> SEQ ID NO 99
<211> LENGTH: 1338
<212> TYPE: DNA
<213> ORGANISM: Artificial Sequence
<220> FEATURE:
<223> OTHER INFORMATION: Synthethic Polynucleotide

<400> SEQUENCE: 99
gaagtacagt tggtagaaag cggcggagga cttgtgcagc caggtggatc tctcagactt      60
tcatgtgccg caagcggttt tactttttagt aactatggaa tgaactgggt tagacaagcg     120
cccggaaaag gattggaatg gataggcatg atatactacg acagctccga gaaacattat      180
gccgactcag ttaaaggaag atttacaata tcaagagaca atagcaaaaa cacactttat      240
cttcaaatga attcactgcg agccgaggat acagcagtct attattgcgc aaaaggcacg      300
acgcccgata aatggggtca aggaacaatg gtaaccgtgt caagcgcgtc gaccaagggc      360
ccatcggtct ccccctggc acccctcctc aagagcacct ctgggggcac agcggccctg       420
ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagaaagttg agcccaaatc ttgtgacaaa      660
actcacacat gcccaccgtg cccagcacct gaagccgcgg ggggaccgtc agtcttcctc      720
ttccccccaa aacccaagga caccctcatg atctcccgga cccctgaggt cacatgcgtg      780
gtggtggacg tgagccacga agaccctgag gtcaagttca actggtacgt ggacggcgtg      840
gaggtgcata atgccaagac aaagccgcgg gaggagcagt acaacagcac gtaccgtgtg      900
gtcagcgtcc tcaccgtcct gcaccaggac tggctgaatg gcaaggagta caagtgcaag      960
gtctccaaca aagccctccc agcccccatc gagaaaacca tctccaaagc caaagggcag     1020 cccccgagaac cacaggtgta caccctgccc ccatcccgcg aggagatgac caagaaccag    1080
gtcagcctga cctgcctggt caaaggcttc tatcccagcg acatcgccgt ggagtgggag     1140
agcaatgggc agccggagaa caactacaag accacgcctc ccgtgctgga ctccgacggc     1200
tccttcttcc tctacagcaa gctcaccgtg gacaagagca ggtggcagca ggggaacgtc     1260
ttctcatgct ccgtgatgca tgaggctctg cacaaccact acacgcagaa gagcctctcc    1320
ctgtctccgg gtaaatga                                                   1338

<210> SEQ ID NO 100
<211> LENGTH: 660
<212> TYPE: DNA
<213> ORGANISM: Artificial Sequence
<220> FEATURE:
<223> OTHER INFORMATION: Synthethic Polynucleotide

<400> SEQUENCE: 100
gacgtagtac tgacccaaag cccccttttct ctcccagtaa ccctcggaca accagcctca     60
atttcatgca gatcatcaca atcacttgag gagagcgacg gatacacttt tcttgagtgg      120
ttccaacaaa gacccggaca aagcccacgc ctgcttattt acgaggtatc acatagattc      180
tcaggagttc cagacagatt ttcaggcagc ggatccggca cagacttcac ccttaaaatt      240
agcagagtag aagcagaaga tgtaggagtg tattattgtt ccaagcgac ccacgacccc       300 ctgacgttcg gacaaggaac taagctcgaa atcaaaagaa cggtggctgc accatctgtc      360

-continued

```
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgttga      660
```

```
<210> SEQ ID NO 101
<211> LENGTH: 345
<212> TYPE: DNA
<213> ORGANISM: Artificial Sequence
<220> FEATURE:
<223> OTHER INFORMATION: Synthethic Polynucleotide

<400> SEQUENCE: 101
gaagtacagt tggtagaaag cggcggagga cttgtgcagc caggtggatc tctcagactt       60
tcatgtgccg caagcggttt tacttttagt aactatggaa tgaactgggt tagacaagcg      120
cccggaaaag gattggaatg gataggaatg atatactacg acagctccga gaaacattat      180
gccgactcag ttaaggaag atttacaata tcaagagaca atagcaaaaa cacactttat        240
cttcaaatga attcactgcg agccgaggat acagcagtct attattgcgc aaaaggctcg      300
accccggatt actggggtca aggaacaatg gtaaccgtgt caagc                      345
```

```
<210> SEQ ID NO 102
<211> LENGTH: 336
<212> TYPE: DNA
<213> ORGANISM: Artificial Sequence
<220> FEATURE:
<223> OTHER INFORMATION: Synthethic Polynucleotide

<400> SEQUENCE: 102
gacgtagtac tgacccaaag ccccctttct ctcccagtaa ccctcggaca accagcctca       60
atttcatgca gatcatcaca atcacttgag gacagcgacg gaggcacttt tcttgagtgg      120
ttccaacaaa gacccggaca aagcccacgc ctgcttattt acgacgtatc aagcagattc      180
tcaggagttc cagacagatt ttcaggcagc ggatccggca cagacttcac ccttaaaatt      240
agcagagtag aagcagaaga tgtaggagtg tattattgtt ccaagccac ccacgacccc       300 ctcagcttcg acaaggaac taagctcgaa atcaaa                                 336
```

```
<210> SEQ ID NO 103
<211> LENGTH: 330
<212> TYPE: PRT
<213> ORGANISM: Homo sapiens

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
            130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
            210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
            290             295             300

Val Phe Ser Cys Ser Val Met His Glu Ala Leu His Asn His Tyr Thr
305             310             315             320

Gln Lys Ser Leu Ser Leu Ser Pro Gly Lys
                325             330
```

```
<210> SEQ ID NO 104
<211> LENGTH: 19
<212> TYPE: PRT
<213> ORGANISM: Artificial Sequence
<220> FEATURE:
<223> OTHER INFORMATION: Synthethic Polypeptide

<400> SEQUENCE: 104

Met Glu Phe Gly Leu Ser Trp Leu Phe Leu Val Ala Ile Leu Lys Gly
1               5               10              15

Val Gln Cys
```

```
<210> SEQ ID NO 105
<211> LENGTH: 5
<212> TYPE: PRT
<213> ORGANISM: Artificial Sequence
<220> FEATURE:
<223> OTHER INFORMATION: Synthethic Polypeptide
<220> FEATURE:
<221> NAME/KEY: misc_feature
<222> LOCATION: (1)..(1)
<223> OTHER INFORMATION: Xaa can be Asn or Tyr

<400> SEQUENCE: 105

Xaa Tyr Gly Met Asn
1               5
```

```
<210> SEQ ID NO 106
<211> LENGTH: 17
<212> TYPE: PRT
<213> ORGANISM: Artificial Sequence
<220> FEATURE:
<223> OTHER INFORMATION: Synthethic Polypeptide
<220> FEATURE:
<221> NAME/KEY: misc_feature
<222> LOCATION: (8)..(8)
<223> OTHER INFORMATION: Xaa can be Glu or Asp

<400> SEQUENCE: 106

Met Ile Tyr Tyr Asp Ser Ser Xaa Lys His Tyr Ala Asp Ser Val Lys
1               5                   10                  15

Gly

<210> SEQ ID NO 107
<211> LENGTH: 6
<212> TYPE: PRT
<213> ORGANISM: Artificial Sequence
<220> FEATURE:
<223> OTHER INFORMATION: Synthethic Polypeptide
<220> FEATURE:
<221> NAME/KEY: misc_feature
<222> LOCATION: (2)..(2)
<223> OTHER INFORMATION: Xaa can be Thr or Ser
<220> FEATURE:
<221> NAME/KEY: misc_feature
<222> LOCATION: (6)..(6)
<223> OTHER INFORMATION: Xaa can be Tyr, Val, or Lys

<400> SEQUENCE: 107

Gly Xaa Thr Pro Asp Xaa
1               5

<210> SEQ ID NO 108
<211> LENGTH: 16
<212> TYPE: PRT
<213> ORGANISM: Artificial Sequence
<220> FEATURE:
<223> OTHER INFORMATION: Synthethic Polypeptide
<220> FEATURE:
<221> NAME/KEY: misc_feature
<222> LOCATION: (7)..(7)
<223> OTHER INFORMATION: Xaa can be Ala or Glu
<220> FEATURE:
<221> NAME/KEY: misc_feature
<222> LOCATION: (8)..(8)
<223> OTHER INFORMATION: Xaa can be Thr, Ser, Glu, or Asp
<220> FEATURE:
<221> NAME/KEY: misc_feature
<222> LOCATION: (12)..(12)
<223> OTHER INFORMATION: Xaa can be Asp, Tyr, or Gly
<220> FEATURE:
<221> NAME/KEY: misc_feature
<222> LOCATION: (16)..(16)
<223> OTHER INFORMATION: Xaa can be Glu or His

<400> SEQUENCE: 108

Arg Ser Ser Gln Ser Leu Xaa Xaa Ser Asp Gly Xaa Thr Phe Leu Xaa
1               5                   10                  15

<210> SEQ ID NO 109
<211> LENGTH: 7
<212> TYPE: PRT
<213> ORGANISM: Artificial Sequence
<220> FEATURE:
<223> OTHER INFORMATION: Synthethic Polypeptide
<220> FEATURE:
<221> NAME/KEY: misc_feature
<222> LOCATION: (1)..(1)
<223> OTHER INFORMATION: Xaa can be Glu, Asp, or Ala
```

```
<220> FEATURE:
<221> NAME/KEY: misc_feature
<222> LOCATION: (4)..(4)
<223> OTHER INFORMATION: Xaa can Asn, Ser, Thr, Glu, or His

<400> SEQUENCE: 109

Xaa Val Ser Xaa Arg Phe Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Synthethic Polypeptide
<220> FEATURE:
<221> NAME/KEY: misc_feature
<222> LOCATION: (1)..(1)
<223> OTHER INFORMATION: Xaa can be Phe or Met
<220> FEATURE:
<221> NAME/KEY: misc_feature
<222> LOCATION: (3)..(3)
<223> OTHER INFORMATION: Xaa can be Val or Ala
<220> FEATURE:
<221> NAME/KEY: misc_feature
<222> LOCATION: (5)..(5)
<223> OTHER INFORMATION: Xaa can be His or Tyr
<220> FEATURE:
<221> NAME/KEY: misc_feature
<222> LOCATION: (8)..(8)
<223> OTHER INFORMATION: Xaa can be Met, Leu, or Val
<220> FEATURE:
<221> NAME/KEY: misc_feature
<222> LOCATION: (9)..(9)
<223> OTHER INFORMATION: Xaa can be Thr or Ser

<400> SEQUENCE: 110

Xaa Gln Xaa Thr Xaa Asp Pro Xaa Xaa
1               5

<210> SEQ ID NO 111
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 112
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 112
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 113
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Gln Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

-continued

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Asn His Tyr Thr
305                 310                 315                 320

Gln Lys Ser Leu Ser Leu Ser Pro Gly
                325
```

```
<210> SEQ ID NO 114
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 114
```

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Asn Tyr
                20                  25                  30

Gly Met Asn Trp Ile Arg Gln Ala Pro Gly Lys Gly Leu Glu Trp Ile
                35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240
```

-continued

```
Phe Pro Pro Lys Pro Lys Asp Thr Leu Met Ile Ser Arg Thr Pro Glu
            245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
            275             280             285

Pro Arg Glu Glu Gln Tyr Asn Ser Thr Tyr Arg Val Val Ser Val Leu
        290             295             300

Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
                325             330             335

Ala Lys Gly Gln Pro Arg Glu Pro Gln Val Tyr Thr Leu Pro Pro Ser
            340             345             350

Arg Glu Glu Met Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
        370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly
            435             440
```

```
<210> SEQ ID NO 115
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 115
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Tyr Tyr
            20              25              30

Gly Met Asn Trp Ile Arg Gln Ala Pro Gly Lys Gly Leu Glu Trp Ile
        35              40              45

Gly Met Ile Tyr Tyr Asp Ser Ser Glu Lys His Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Gly Thr Thr Pro Asp Tyr Trp Gly Gln Gly Thr Met Val Thr
            100             105             110

Val Ser Ser Ala Ser Thr Lys Gly Pro Ser Val Phe Pro Leu Ala Pro
            115             120             125

Ser Ser Lys Ser Thr Ser Gly Gly Thr Ala Ala Leu Gly Cys Leu Val
        130             135             140

Lys Asp Tyr Phe Pro Glu Pro Val Thr Val Ser Trp Asn Ser Gly Ala
145             150             155             160
```

```
Leu Thr Ser Gly Val His Thr Phe Pro Ala Val Leu Gln Ser Ser Gly
            165             170             175

Leu Tyr Ser Leu Ser Ser Val Val Thr Val Pro Ser Ser Ser Leu Gly
            180             185             190

Thr Gln Thr Tyr Ile Cys Asn Val Asn His Lys Pro Ser Asn Thr Lys
            195             200             205

Val Asp Lys Lys Val Glu Pro Lys Ser Cys Asp Lys Thr His Thr Cys
        210             215             220

Pro Pro Cys Pro Ala Pro Glu Ala Ala Gly Gly Pro Ser Val Phe Leu
225             230             235             240

Phe Pro Pro Lys Pro Lys Asp Thr Leu Met Ile Ser Arg Thr Pro Glu
            245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
            275             280             285

Pro Arg Glu Glu Gln Tyr Asn Ser Thr Tyr Arg Val Val Ser Val Leu
        290             295             300

Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
            325             330             335

Ala Lys Gly Gln Pro Arg Glu Pro Gln Val Tyr Thr Leu Pro Pro Ser
            340             345             350

Arg Glu Glu Met Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
        370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly
            435             440
```

```
<210> SEQ ID NO 116
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 116
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Asn Tyr
            20              25              30

Gly Met Asn Trp Ile Arg Gln Ala Pro Gly Lys Gly Leu Glu Trp Ile
            35              40              45

Gly Met Ile Tyr Tyr Asp Ser Ser Asp Lys His Tyr Ala Asp Ser Val
        50              55              60

Lys Gly Arg Phe Thr Ile Ser Arg Asp Asn Ser Lys Asn Thr Leu Tyr
65              70              75              80
```

```
Leu Gln Met Asn Ser Leu Arg Ala Glu Asp Thr Ala Val Tyr Tyr Cys
            85                  90                  95

Ala Lys Gly Thr Thr Pro Asp Val Trp Gly Gln Gly Thr Met Val Thr
            100             105             110

Val Ser Ser Ala Ser Thr Lys Gly Pro Ser Val Phe Pro Leu Ala Pro
            115             120             125

Ser Ser Lys Ser Thr Ser Gly Gly Thr Ala Ala Leu Gly Cys Leu Val
    130             135             140

Lys Asp Tyr Phe Pro Glu Pro Val Thr Val Ser Trp Asn Ser Gly Ala
145             150             155             160

Leu Thr Ser Gly Val His Thr Phe Pro Ala Val Leu Gln Ser Ser Gly
            165             170             175

Leu Tyr Ser Leu Ser Ser Val Val Thr Val Pro Ser Ser Ser Leu Gly
            180             185             190

Thr Gln Thr Tyr Ile Cys Asn Val Asn His Lys Pro Ser Asn Thr Lys
            195             200             205

Val Asp Lys Lys Val Glu Pro Lys Ser Cys Asp Lys Thr His Thr Cys
    210             215             220

Pro Pro Cys Pro Ala Pro Glu Ala Ala Gly Gly Pro Ser Val Phe Leu
225             230             235             240

Phe Pro Pro Lys Pro Lys Asp Thr Leu Met Ile Ser Arg Thr Pro Glu
            245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
            275             280             285

Pro Arg Glu Glu Gln Tyr Asn Ser Thr Tyr Arg Val Val Ser Val Leu
    290             295             300

Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
            325             330             335

Ala Lys Gly Gln Pro Arg Glu Pro Gln Val Tyr Thr Leu Pro Pro Ser
            340             345             350

Arg Glu Glu Met Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly
            435             440
```

<210> SEQ ID NO 117
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 117

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

-continued

```
Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 118
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Ala Ala Gly Gly Pro Ser Val Phe Leu
225                 230                 235                 240

Phe Pro Pro Lys Pro Lys Asp Gln Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335
```

```
Ala Lys Gly Gln Pro Arg Glu Pro Gln Val Tyr Thr Leu Pro Pro Ser
            340             345             350

Arg Glu Glu Met Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
        370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Leu His Glu Ala Leu His Asn
            420             425             430

His Tyr Thr Gln Lys Ser Leu Ser Leu Ser Pro Gly
        435             440
```

<210> SEQ ID NO 119
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 119

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Asn Tyr
            20              25              30

Gly Met Asn Trp Val Arg Gln Ala Pro Gly Lys Gly Leu Glu Trp Ile
        35              40              45

Gly Met Ile Tyr Tyr Asp Ser Ser Glu Lys His Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Lys Gly Thr Thr Pro Asp Lys Trp Gly Gln Gly Thr Met Val Thr
            100             105             110

Val Ser Ser Ala Ser Thr Lys Gly Pro Ser Val Phe Pro Leu Ala Pro
            115             120             125

Ser Ser Lys Ser Thr Ser Gly Gly Thr Ala Ala Leu Gly Cys Leu Val
        130             135             140

Lys Asp Tyr Phe Pro Glu Pro Val Thr Val Ser Trp Asn Ser Gly Ala
145             150             155             160

Leu Thr Ser Gly Val His Thr Phe Pro Ala Val Leu Gln Ser Ser Gly
            165             170             175

Leu Tyr Ser Leu Ser Ser Val Val Thr Val Pro Ser Ser Ser Leu Gly
            180             185             190

Thr Gln Thr Tyr Ile Cys Asn Val Asn His Lys Pro Ser Asn Thr Lys
            195             200             205

Val Asp Lys Lys Val Glu Pro Lys Ser Cys Asp Lys Thr His Thr Cys
        210             215             220

Pro Pro Cys Pro Ala Pro Glu Ala Ala Gly Gly Pro Ser Val Phe Leu
225             230             235             240

Phe Pro Pro Lys Pro Lys Asp Thr Leu Met Ile Ser Arg Thr Pro Glu
            245             250             255
```

Val Thr Cys Val Val Val Asp Val Ser His Glu Asp Pro Glu Val Lys
              260                 265                 270

Phe Asn Trp Tyr Val Asp Gly Val Glu Val His Asn Ala Lys Thr Lys
              275                 280                 285

Pro Arg Glu Glu Gln Tyr Asn Ser Thr Tyr Arg Val Val Ser Val Leu
              290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
              325                 330                 335

Ala Lys Gly Gln Pro Arg Glu Pro Gln Val Tyr Thr Leu Pro Pro Ser
              340                 345                 350

Arg Glu Glu Met Thr Lys Asn Gln Val Ser Leu Thr Cys Leu Val Lys
              355                 360                 365

Gly Phe Tyr Pro Ser Asp Ile Ala Val Glu Trp Glu Ser Asn Gly Gln
              370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
              405                 410                 415

Gln Gly Asn Val Phe Ser Cys Ser Val Met His Glu Ala Leu His Asn
              420                 425                 430

His Tyr Thr Gln Lys Ser Leu Ser Leu Ser Pro Gly
              435                 440

<210> SEQ ID NO 120
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 120

Glu Val Gln Leu Val Glu Ser Gly Gly Gly Leu Val Gln Pro Gly Gly
1                 5                 10                  15

Ser Leu Arg Leu Ser Cys Ala Ala Ser Gly Phe Thr Phe Ser Asn Tyr
              20                  25                  30

Gly Met Asn Trp Val Arg Gln Ala Pro Gly Lys Gly Leu Glu Trp Ile
              35                  40                  45

Gly Met Ile Tyr Tyr Asp Ser Ser Glu Lys His Tyr Ala Asp Ser Val
              50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
              85                  90                  95

Ala Lys Gly Ser Thr Pro Asp Tyr Trp Gly Gln Gly Thr Met Val Thr
              100                 105                 110

Val Ser Ser Ala Ser Thr Lys Gly Pro Ser Val Phe Pro Leu Ala Pro
              115                 120                 125

Ser Ser Lys Ser Thr Ser Gly Gly Thr Ala Ala Leu Gly Cys Leu Val
              130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
              165                 170                 175

```
Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

```
<210> SEQ ID NO 121
<211> LENGTH: 14
<212> TYPE: PRT
<213> ORGANISM: Artificial Sequence
<220> FEATURE:
<223> OTHER INFORMATION: Synthetic

<400> SEQUENCE: 121

Ser Ser Pro Met Ala Leu Gly Ala Asn Ala Thr Ala Thr Arg
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Synthetic

<400> SEQUENCE: 122

Thr Ser Ser Pro Met Ala Leu Gly Ala Asn Ala Thr Ala Thr
1               5                   10

<210> SEQ ID NO 123
```

<211> LENGTH: 364
<212> TYPE: PRT
<213> ORGANISM: Artificial Sequence
<220> FEATURE:
<223> OTHER INFORMATION: Synthetic

<400> SEQUENCE: 123

Gln Cys Lys Ile Leu Arg Cys Asn Ala Glu Tyr Val Ser Ser Thr Leu
1               5                   10                  15

Ser Leu Arg Gly Gly Gly Ser Ser Gly Ala Leu Arg Gly Gly Gly Gly
            20                  25                  30

Gly Gly Arg Gly Gly Gly Val Gly Ser Gly Gly Leu Cys Arg Ala Leu
            35                  40                  45

Arg Ser Tyr Ala Leu Cys Thr Arg Arg Thr Ala Arg Thr Cys Arg Gly
        50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Pro Pro Pro Arg Gly
            85                  90                  95

Pro Ala Leu Pro Gly Ala Gly Ser Gly Leu Pro Ala Pro Asp Pro Cys
            100                 105                 110

Asp Tyr Glu Gly Arg Phe Ser Arg Leu His Gly Arg Pro Pro Gly Phe
            115                 120                 125

Leu His Cys Ala Ser Phe Gly Asp Pro His Val Arg Ser Phe His His
        130                 135                 140

His Phe His Thr Cys Arg Val Gln Gly Ala Trp Pro Leu Leu Asp Asn
145                 150                 155                 160

Asp Phe Leu Phe Val Gln Ala Thr Ser Ser Pro Met Ala Leu Gly Ala
            165                 170                 175

Asn Ala Thr Ala Thr Arg Lys Leu Thr Ile Ile Phe Lys Asn Met Gln
            180                 185                 190

Glu Cys Ile Asp Gln Lys Val Tyr Gln Ala Glu Val Asp Asn Leu Pro
            195                 200                 205

Val Ala Phe Glu Asp Gly Ser Ile Asn Gly Gly Asp Arg Pro Gly Gly
        210                 215                 220

Ser Ser Leu Ser Ile Gln Thr Ala Asn Pro Gly Asn His Val Glu Ile
225                 230                 235                 240

Gln Ala Ala Tyr Ile Gly Thr Thr Ile Ile Arg Gln Thr Ala Gly
            245                 250                 255

Gln Leu Ser Phe Ser Ile Lys Val Ala Glu Asp Val Ala Met Ala Phe
            260                 265                 270

Ser Ala Glu Gln Asp Leu Gln Leu Cys Val Gly Gly Cys Pro Pro Ser
        275                 280                 285

Gln Arg Leu Ser Arg Ser Glu Arg Asn Arg Arg Gly Ala Ile Thr Ile
        290                 295                 300

Asp Thr Ala Arg Arg Leu Cys Lys Glu Gly Leu Pro Val Glu Asp Ala
305                 310                 315                 320

Tyr Phe His Ser Cys Val Phe Asp Val Leu Ile Ser Gly Asp Pro Asn
            325                 330                 335

Phe Thr Val Ala Ala Gln Ala Ala Leu Glu Asp Ala Arg Ala Phe Leu
            340                 345                 350

Pro Asp Leu Glu Lys Leu His Leu Phe Pro Ser Asp
        355                 360

<210> SEQ ID NO 124

```
<211> LENGTH: 21
<212> TYPE: PRT
<213> ORGANISM: Artificial Sequence
<220> FEATURE:
<223> OTHER INFORMATION: Synthetic

<400> SEQUENCE: 124

Ser Ser Pro Met Ala Leu Gly Ala Asn Ala Thr Ala Thr Arg Lys Leu
1               5                   10                  15

Thr Ile Ile Phe Lys
            20

<210> SEQ ID NO 125
<211> LENGTH: 30
<212> TYPE: PRT
<213> ORGANISM: Artificial Sequence
<220> FEATURE:
<223> OTHER INFORMATION: Synthetic

<400> SEQUENCE: 125

Asp Asn Asp Phe Leu Phe Val Gln Ala Thr Ser Ser Pro Met Ala Leu
1               5                   10                  15

Gly Ala Asn Ala Thr Thr Arg Lys Leu Thr Ile Ile Phe Lys
            20                  25                  30

<210> SEQ ID NO 126
<211> LENGTH: 21
<212> TYPE: PRT
<213> ORGANISM: Artificial Sequence
<220> FEATURE:
<223> OTHER INFORMATION: Synthetic

<400> SEQUENCE: 126

Gln Leu Cys Val Gly Gly Cys Pro Pro Ser Gln Arg Leu Ser Arg Ser
1               5                   10                  15

Glu Arg Asn Arg Arg
            20

<210> SEQ ID NO 127
<211> LENGTH: 12
<212> TYPE: PRT
<213> ORGANISM: Artificial Sequence
<220> FEATURE:
<223> OTHER INFORMATION: Synthetic

<400> SEQUENCE: 127

Ser Gln Arg Leu Ser Arg Ser Glu Arg Asn Arg Arg
1               5                   10

<210> SEQ ID NO 128
<211> LENGTH: 426
<212> TYPE: PRT
<213> ORGANISM: Homo sapiens

<400> SEQUENCE: 128

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Gly Ser Ser Gly Ala Leu Arg Gly
    50                  55                  60
```

Gly Gly Gly Gly Gly Arg Gly Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
        115                 120                 125

Pro Pro Arg Gly Pro Ala Leu Pro Gly Ala Gly Ser Gly Leu Pro Ala
    130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
    210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
            275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
            325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
            405                 410                 415

Gly Leu Phe Val Leu Trp Leu Cys Ile Gln
            420                 425

<210> SEQ ID NO 129
<211> LENGTH: 25
<212> TYPE: PRT
<213> ORGANISM: Artificial Sequence
<220> FEATURE:
<223> OTHER INFORMATION: Synthetic

<400> SEQUENCE: 129

-continued

```
Asp Thr His Phe Pro Ile Cys Ile Phe Cys Cys Gly Cys Cys His Arg
1               5                   10                  15

Ser Lys Cys Gly Met Cys Cys Lys Thr
            20              25
```

ANTI-HEMOJUVELIN (HJV) ANTIBODIES FOR TREATING ANEMIA OF CHRONIC DISEASE

RELATED APPLICATIONS

This application is a national stage filing under 35 U.S.C. 371 of International Patent Application Serial No. PCT/US2021/032345, filed May 13, 2021, entitled "ANTI-HEMOJUVELIN (HJV) ANTIBODIES FOR TREATING ANEMIA OF CHRONIC DISEASE," which claims the benefit under 35 U.S.C. § 119(e) of U.S. provisional application Ser. No. 63/024,427, filed May 13, 2020, entitled "ANTI-HEMOJUVELIN (HJV) ANTIBODIES FOR TREATING ANEMIA OF CHRONIC DISEASE," 63/035,634, filed Jun. 5, 2020, entitled "ANTI-HEMOJUVELIN (HJV) ANTIBODIES FOR TREATING ANEMIA OF CHRONIC DISEASE," 63/047,844, filed Jul. 2, 2020, entitled "ANTIHEMOJUVELIN (HJV) ANTIBODIES FOR TREATING ANEMIA OF CHRONIC DISEASE," and 63/164,307, filed Mar. 22, 2021, entitled "ANTI-HEMOJU-VELIN (HJV) ANTIBODIES FOR TREATING ANEMIA OF CHRONIC DISEASE," the entire contents of each of which are incorporated herein by reference.

REFERENCE TO A SEQUENCE LISTING SUBMITTED AS A TEXT FILE VIA EFS-WEB

The present application contains a Sequence Listing which has been submitted in ASCII format via EFS-Web and is hereby incorporated by reference in its entirety. Said ASCII copy, created on Nov. 10, 2022, is named D084270002US04-SEQ-EPG and is 165,458 bytes in size.

BACKGROUND

Iron is a key component of oxygen-transporting storage molecules, such as hemoglobin and myoglobin. Iron deficiency results in anemia, while iron overload leads to tissue damage and fibrosis. Hepcidin is a key peptide hormonal regulator of systemic iron homeostasis. It exerts its regulatory function by binding to the cellular iron exporter ferroportin, a transmembrane protein present on hepatocytes, enterocytes in the duodenum, macrophages, and adipocytes. The binding of hepcidin promotes ferroportin degradation, preventing the export of iron from cells and release of iron into the plasma.

SUMMARY

Aspects of the disclosure provide methods for treating high hepcidin disorders. In particular, methods are provided for treating anemia of chronic disease (ACD). ACD is a type of anemia that often arises in chronic conditions that involve inflammation. ACD can impair underlying inflammatory processes associated with chronic conditions and is a significant contributor to negative outcomes. ACD generally arises through mechanisms driven by immune and inflammatory effects that include shortened erythrocyte survival, impaired proliferation of erythroid progenitor cells, as well as abnormalities in iron metabolism. In some embodiments, effects of iron metabolism observed in ACD are associated with hepcidin upregulation by increased inflammatory cytokines, causing macrophage iron sequestration and iron-restricted erythropoiesis. Moreover, in ACD, proinflammatory cytokines that induce hepcidin synthesis, such as IL-6 and oncostatin-M, are typically increased and associated with this iron sequestration, macrophage iron loading, as well as myeloid proliferation and macrophage activation (See, e.g., FIG. 11).

Aspects of the present disclosure relates to effective bioavailability being achieved by subcutaneous administration of an isolated antibody that binds to hemojuvelin (HJV) to a subject having ACD together with beneficially low maximum serum concentrations ($C_{max}$). In some embodiments, subcutaneous administration of an anti-HJV antibody yields comparable pharmacodynamics effects (e.g., decreased circulating hepcidin-25 levels, increased TSAT %, and/or increased serum iron levels) at lower maximum concentration ($C_{max}$) of the anti-HJV antibody compared to intravenous administration of the same antibody. $C_{max}$ is the maximum (or peak) serum concentration that a drug (e.g., an anti-HJV antibody) after the agent/antibody has been administered and before the administration of a second dose. In some embodiments, achieving a low $C_{max}$ within a short period of time (e.g., within 12 hours, within 24 hours) after administration of an anti-HJV antibody minimizes undesirable increases in serum iron response, and/or minimizes chances of off-target effects of the antibody (e.g., binding to RGMa). In some embodiments, blunting $C_{max}$ by subcutaneous administration of an anti-HJV antibody avoids an undesirably sharp increase in serum iron response. In some embodiments, blunting $C_{max}$ by subcutaneous administration of an anti-HJV antibody reduces the off-target effects of the antibody.

Aspects of the disclosure also relates to an isolated antibody that binds to human hemojuvelin (HJV) for use in a method of treating a subject having ACD, in which the subject is administered with the isolated antibody by subcutaneous administration, and wherein the antibody comprises a heavy chain variable region (VH) comprising an amino acid sequence of SEQ ID NO: 38, and a light chain variable region (VL) comprising an amino acid sequence of SEQ ID NO: 39.

Aspects of the disclosure also relates to an isolated antibody that binds to human hemojuvelin (HJV) for use in a method of inhibiting HJV activity in a subject having ACD, in which the subject is administered with the isolated antibody by subcutaneous administration, and wherein the antibody comprises a heavy chain variable region (VH) comprising an amino acid sequence of SEQ ID NO: 38, and a light chain variable region (VL) comprising an amino acid sequence of SEQ ID NO: 39.

In some embodiments, the administration (e.g., intravenous injection or subcutaneous injection) of an anti-HJV antibody reduces circulating hepcidin-25 (e.g., serum or plasma hepcidin-25), which is the active form of hepcidin.

In some aspects, the present disclosure provides a method for reducing hepcidin-25 in a subject having ACD, the method comprising: administering to the subject an effective amount of the isolated antibody that binds to human hemojuvelin (HJV), wherein the antibody comprises: a heavy chain variable region (VH) comprising an amino acid sequence of SEQ ID NO: 38, and a light chain variable region (VL) comprising an amino acid sequence of SEQ ID NO: 39. In some aspects, the present disclosure provides an isolated antibody that binds to hemojuvelin (HJV) for use in a method of reducing hepcidin-25 in a subject having ACD, wherein the antibody comprises: a heavy chain variable region (VH) comprising an amino acid sequence of SEQ ID NO: 38, and a light chain variable region (VL) comprising an amino acid sequence of SEQ ID NO: 39. In some embodiments, the subject is administered via subcutaneous injection. In some embodiments, the administration reduces hepcidin-25 with 4 hours, 6 hours, 8 hours, 12 hours, 28 hours, 24 hours, 2 days, 3 days, 4 days, 5 days, 6 days, 1 week, or two weeks of administration. In some embodiments, the administration reduces hepcidin-25 by at least 30%, least 40%, leash 50%, least 60%, least 70%, least 80%, least 90%, or least 95% of hepcidin-25 compared to the hepcidin-25 level in the subject prior to administration.

ACD is often associated with conditions having chronic immune activation, including, for example, chronic kidney disease, chronic renal failure, cancer (e.g., solid tumors, haematological tumors, such as myeloma), infection (e.g., viral, bacterial, parasitic, fungal), autoimmune disease (e.g., rheumatoid arthritis, systemic lupus erythematosus and related conditions, such as vasculitis, sarcoidosis, and inflammatory bowel disease) and other chronic conditions that involve inflammation, such as diabetes and chronic heart failure. In some embodiments, methods provided herein are useful for treating ACD associated with such conditions.

In some aspects, the present disclosure provides a method of treating a subject having an anemia of chronic disease. In some embodiments, the method comprises administering to the subject an effective amount of an isolated antibody that binds to human hemojuvelin (HJV).

In some embodiments, the antibody comprises: a heavy chain complementary determining region 1 (HC CDR1) set forth as $X_1$YGMN (SEQ ID NO: 105), in which $X_1$ can be N or Y; a heavy chain complementary determining region 2 (HC CDR2) set forth as MIYYDSSX$_2$KHYADSVKG (SEQ ID NO: 106), in which $X_2$ can be E or D; a heavy chain complementary determining region 3 (HC CDR3) set forth as GX$_3$TPDX$_4$ (SEQ ID NO: 107), in which $X_3$ can be T or S, and $X_4$ can be Y, V, or K; and/or a light chain complementary determining region 1 (LC CDR1) set forth as RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H, a light chain complementary determining region 2 (LC CDR2) set forth as X$_9$VSX$_{10}$RFS (SEQ ID NO: 109), in which $X_9$ can be E, D or A, and $X_{10}$ can be N, S, T, E or H, a light chain complementary determining region 3 (LC CDR3) set forth as X$_{11}$QX$_{12}$TX$_{13}$DPX$_{14}$X$_{15}$ (SEQ ID NO:110), in which $X_{11}$ can be F or M, $X_{12}$ can be V or A, $X_{13}$ can be H or Y, $X_{14}$ can be M, L or V, and $X_{15}$ can be T or S.

In some embodiments, the antibody comprises a VH comprising an amino acid sequence at least 85% identical to SEQ ID NO: 38, and/or a VL comprising an amino acid sequence at least 85% identical to SEQ ID NO: 39. In some embodiments, the antibody comprises a VH comprising an amino acid sequence of SEQ ID NO: 38, and a VL comprising an amino acid sequence of SEQ ID NO: 39.

In some embodiments, the antibody is a humanized antibody. In some embodiments, the humanized antibody comprises a humanized VH and/or a humanized VL. In some embodiments, the antibody is selected from the group consisting of a full-length IgG, a Fab fragment, a F(ab') fragment, a F(ab')$_2$ fragment, a scFv, and a Fv. In some embodiments, the antibody is a full-length IgG. In some embodiments, the antibody comprises a heavy chain constant region of the isotype IgG1, IgG2, IgG3, or IgG4. In some embodiments, the antibody further comprises a heavy chain constant region set forth in SEQ ID NOs: 46, 48, 112 or 113. In some embodiments, the antibody further comprises a light chain constant region set forth in SEQ ID NO: 47. In some embodiments, the antibody comprises: (i) a heavy chain comprising an amino acid sequence at least 85% identical to SEQ ID NO: 61 or 117, and/or a light chain comprising an amino acid sequence at least 85% identical to SEQ ID NO: 62; or (ii) a heavy chain comprising an amino acid sequence at least 85% identical to SEQ ID NO: 63 or 118, and/or a light chain comprising an amino acid sequence at least 85% identical to SEQ ID NO: 62. In some embodiments, the antibody comprises a heavy chain comprising an amino acid sequence of SEQ ID NO: 61 or 117, and a light chain comprising an amino acid sequence of SEQ ID NO: 62. In some embodiments, the antibody comprises a heavy chain comprising an amino acid sequence of SEQ ID NO: 63 or 118, and a light chain comprising an amino acid sequence of SEQ ID NO: 62.

In some embodiments, the subject is erythrocyte transfusion-dependent. In some embodiments, the subject is erythrocyte transfusion-independent. In some embodiments, the anemia of chronic disease is an iron-restricted anemia. In some embodiments, the iron-restricted anemia is associated with a functional iron deficiency.

In some embodiments, the anemia of chronic disease is associated with (or caused by) chronic kidney disease.

In some embodiments, the anemia of chronic disease is associated with (or caused by) cancer. In some embodiments, the cancer is a myeloma.

In some embodiments, the anemia of chronic disease is associated with (or caused by) a chronic infection. In some embodiments, the infection is a bacterial, viral, fungal or parasitic infection.

In some embodiments, the anemia of chronic disease is associated with (or caused by) an autoimmune disease. In some embodiments, the anemia of chronic disease is associated with (or caused by) a chronic disease that involves inflammation. In some embodiments, the chronic disease that involves inflammation is inflammatory bowel disease, diabetes, or heart failure.

In some embodiments, the subject is identified prior to treatment as having high hepcidin levels. In some embodiments, the subject is identified as having a functional iron deficiency. In some embodiments, the subject is identified as exhibiting inflammation and/or iron-restricted erythropoiesis.

In some embodiments, the subject is a human.

In some aspects, the present disclosure also provides an isolated antibody that binds to human hemojuvelin (HJV) and compositions comprising the same. In some embodiments, the antibody comprises: a heavy chain complementary determining region 1 (HC CDR1) set forth as X$_1$YGMN (SEQ ID NO: 105), in which $X_1$ can be N or Y; and/or a heavy chain complementary determining region 2 (HC CDR2) set forth as MIYYDSSX$_2$KHYADSVKG (SEQ ID NO: 106), in which $X_2$ can be E or D; and/or a heavy chain complementary determining region 3 (HC CDR3) set forth as GX$_3$TPDX$_4$ (SEQ ID NO. 107), in which $X_3$ can be T or S, and $X_4$ can be Y, V, or K. In some embodiments, the antibody comprises: a light chain complementary determining region 1 (LC CDR1) set forth as RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H; and/or a light chain complementary determining region 2 (LC CDR2) set forth as X$_9$VSX$_{10}$RFS (SEQ ID NO: 109), in which $X_9$ can be E, D or A, and $X_{10}$ can be N, S, T, E or H; and/or a light chain complementary determining region 3 (LC CDR3) set forth as X$_{11}$QX$_{12}$TX$_{13}$DPX$_{14}$X$_{15}$ (EQ ID NO: 110), in which $X_{11}$ can be F or M, $X_{12}$ can be V or A, $X_{13}$ can be H or Y, $X_{14}$ can be M, L or V, and $X_{15}$ can be T or S.

In some aspects, the present disclosure also provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 8. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 4, a LC CDR2 of SEQ ID NO: 5, a LC CDR3 of SEQ ID NO: 6. In some embodiments, the antibody comprises a VH comprising an amino acid sequence at least 85% identical to SEQ ID NO: 7, and/or a VL comprising an amino acid sequence at least 85% identical to SEQ ID NO: 8.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 30. In some embodiments the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 4, a LC CDR2 of SEQ ID NO: 49, a LC CDR3 of SEQ ID NO: 24. In some embodiments, the antibody comprises a VH comprising an amino acid sequence at least 85% identical to SEQ ID NO: 7, and/or a VL comprising an amino acid sequence at least 85% identical to SEQ ID NO: 30.

In some aspects, the present disclosure provides an isolated antibody that binds to hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; (ii) and/or a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 31. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 4, a LC CDR2 of SEQ ID NO: 18, a LC CDR3 of SEQ ID NO: 25. In some embodiments, the antibody comprises a VH comprising an amino acid sequence at least 85% identical to SEQ ID NO: 7, and/or a VL comprising an amino acid sequence at least 85%1 identical to SEQ ID NO: 8.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 32. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 14, a LC CDR2 of SEQ ID NO: 19, a LC CDR3 of SEQ ID NO: 25. In some embodiments, the antibody comprises a VH comprising an amino acid sequence at least 85% identical to SEQ ID NO: 7, and/or a VL comprising an amino acid sequence at least 85% identical to SEQ ID NO: 32.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 7; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 33. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 15, a LC CDR2 of SEQ ID NO: 20, a LC CDR3 of SEQ ID NO: 26. In some embodiments, the antibody comprises a VH comprising an amino acid sequence at least 85% identical to SEQ ID NO: 7, and/or a VL comprising an amino acid sequence at least 85% identical to SEQ ID NO: 33.

In some aspects, the present disclosure provide an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 34; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 35. In some embodiments, the antibody comprises: a HC CDR1 of SEQ ID NO: 9, a HC CDR2 of SEQ ID NO: 2, a HC CDR3 of SEQ ID NO: 3, and/or a LC CDR1 of SEQ ID NO: 16, a LC CDR2 of SEQ ID NO: 21, a LC CDR3 of SEQ ID NO: 27. In some embodiments, the antibody comprises a VH comprising an amino acid sequence at least 85% identical to SEQ ID NO: 34, and/or a VL comprising an amino acid sequence at least 85% identical to SEQ ID NO: 35.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 36; and/or (ii) a light chain complementary determining region 1 (LC CDR1), a light chain complementary determining region 2

(LC CDR2), and a light chain complementary determining region 3 (LC CDR3) of a light chain variable region (VL) comprising the amino acid sequence of SEQ ID NO: 37. In some embodiments, the antibody comprises: a HC CDR1 of SEQ ID NO: 1, a HC CDR2 of SEQ ID NO: 10, a HC CDR3 of SEQ ID NO: 11, and/or a LC CDR1 of SEQ ID NO: 17, a LC CDR2 of SEQ ID NO: 18, a LC CDR3 of SEQ ID NO: 28. In some embodiments, the antibody comprises a VH comprising an amino acid sequence at least 85% identical to SEQ ID NO: 36, and/or a VL comprising an amino acid sequence at least 85% identical to SEQ ID NO: 37.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 38; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 39. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 17, a LC CDR2 of SEQ ID NO: 5, a LC CDR3 of SEQ ID NO: 27. In some embodiments, the antibody comprises a VH comprising an amino acid sequence at least 85% identical to SEQ ID NO: 38, and/or a VL comprising an amino acid sequence at least 85% identical to SEQ ID NO: 39.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 38; and/or (ii) a light chain complementary determining region 1 (LC CDR1), a light chain complementary determining region 2 (LC CDR2), and a light chain complementary determining region 3 (LC CDR3) of a light chain variable region comprising the amino acid sequence of SEQ ID NO: 41. In some embodiments, the antibody comprises: a HC CDR1 of SEQ ID NO: 1, a HC CDR2 of SEQ ID NO: 2, a HC CDR3 of SEQ ID NO: 3, and/or a LC CDR1 of SEQ ID NO: 50, a LC CDR2 of SEQ ID NO: 22, a LC CDR3 of SEQ ID NO: 28. In some embodiments, the antibody comprises a VH comprising an amino acid sequence at least 85% identical to SEQ ID NO: 38, and/or a VL comprising an amino acid sequence at least 85% identical to SEQ ID NO: 41.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 42; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 43. In some embodiments, the antibody comprises: a HC CDR1 of SEQ ID NO: 1, a HC CDR2 of SEQ ID NO: 2, a HC CDR3 of SEQ ID NO: 12, and/or a LC CDR1 of SEQ ID NO: 15, a LC CDR2 of SEQ ID NO: 23, a LC CDR3 of SEQ ID NO: 27. In some embodiments, the antibody comprises a VH comprising an amino acid sequence at least 85% identical to SEQ ID NO: 42, and/or a VL comprising an amino acid sequence at least 85% identical to SEQ ID NO: 43.

In some aspects, the present disclosure provides an isolated antibody that binds to human hemojuvelin (HJV), in which the antibody comprises: (i) a heavy chain complementary determining region 1 (HC CDR1), a heavy chain complementary determining region 2 (HC CDR2), and a heavy chain complementary determining region 3 (HC CDR3) of a heavy chain variable region (VH) comprising the amino acid sequence of SEQ ID NO: 44; and/or (ii) a light chain complementary determining region 1 (LC CDR1), a light chain complementary determining region 2 (LC CDR2), and a light chain complementary determining region 3 (LC CDR3) of a light chain variable region (VL) comprising the amino acid sequence of SEQ ID NO: 45. In some embodiments, the antibody comprises: a HC CDR1 of SEQ ID NO: 1, a HC CDR2 of SEQ ID NO: 2, a HC CDR3 of SEQ ID NO: 13, and/or a LC CDR1 of SEQ ID NO: 16, a LC CDR2 of SEQ ID NO: 21, a LC CDR3 of SEQ ID NO: 29. In some embodiments, the antibody comprises a VH comprising an amino acid sequence at least 85% identical to SEQ ID NO: 44, and/or a VL comprising an amino acid sequence at least 85% identical to SEQ ID NO: 45.

In some aspects, the present disclosure provides an isolated antibody that binds to hemojuvelin (HJV), in which the antibody comprises: a HC CDR1, a HC CDR2, and a HC CDR3, which collectively contains no more than 10 amino acid variations, preferably no more than 8 amino acid variations, more preferably no more than 5 amino acid variations, and more preferably no more than 2 amino acid variation, as compared with the HC CDR1, a HC CDR2, and a HC CDR3 of any one of the antibodies listed in Table 1; and/or wherein the antibody comprises a LC CDR1, a LC CDR2, and a LC CDR3, which collectively contains no more than 10 amino acid variations, preferably no more than 8 amino acids variations, as compared with the a LC CDR1, a LC CDR2, and a LC CDR3 of any one of the antibodies listed in Table 1.

In some embodiments, any of the antibodies provided herein is a humanized antibody. In some embodiments, the humanized antibody comprises a humanized VH and/or a humanized VL. In some embodiments, the antibody is selected from the group consisting of a full-length IgG, a Fab fragment, a F(ab') fragment, a F(ab')2 fragment, a scFv, and a Fv. In some embodiments, the antibody is a full-length IgG. In some embodiments, the antibody comprises a heavy chain constant region of the isotype IgG1, IgG2, IgG3, or IgG4. In some embodiments, the antibody further comprises a heavy chain constant region set forth in SEQ ID NOs: 46, 48, 112 or 113. In some embodiments, the antibody further comprises a light chain constant region set forth in SEQ ID NO: 47. In some embodiments, the antibody comprises: (i) a heavy chain comprising an amino acid sequence at least 85% identical to SEQ ID NO: 51 or 114, and/or a light chain comprising an amino acid sequence at least 85% identical to SEQ ID NOs: 52-56; (ii) a heavy chain comprising an amino acid sequence at least 85% identical to SEQ ID NO: 57 or 115, and/or a light chain comprising an amino acid sequence at least 85% identical to SEQ ID NO: 58; (iii) a heavy chain comprising an amino acid sequence at least 85% identical to SEQ ID NO: 59 or 116, and/or a light chain comprising an amino acid sequence at least 85% identical to SEQ ID NO:

60; (iv) a heavy chain comprising an amino acid sequence at least 85% identical to SEQ ID NO: 61 or 117, and/or a light chain comprising an amino acid sequence at least 85% identical to SEQ ID NO: 62; (v) a heavy chain comprising an amino acid sequence at least 85% identical to SEQ ID NO: 63 or 118, and/or a light chain comprising an amino acid sequence at least 85% identical to SEQ ID NO: 62; (vi) a heavy chain comprising an amino acid sequence at least 85% identical to SEQ ID NO: 61 or 117, and/or a light chain comprising an amino acid sequence at least 85% identical to SEQ ID NO: 65; (vii) a heavy chain comprising an amino acid sequence at least 85% identical to SEQ ID NO: 66 or 119, and/or a light chain comprising an amino acid sequence at least 85% identical to SEQ ID NO: 67; or (viii) a heavy chain comprising an amino acid sequence at least 85% identical to SEQ ID NO: 68 or 120, and/or a light chain comprising an amino acid sequence at least 85% identical to SEQ ID NO: 69.

In some embodiments, the antibody binds HJV with an equilibrium dissociation constant (KD) less than 100 nM. In some embodiments, the antibody binds to HJV with an equilibrium dissociation constant (KD) less than 1 nM.

In some embodiments, the antibody is conjugated to a molecular payload. In some embodiments, the molecular payload is a detectable agent, a diagnostic agent, or a therapeutic agent.

In some aspects, the present disclosure also provides a nucleic acid encoding the isolated antibody described herein.

In some aspects, the present disclosure also provides vector comprising the nucleic acid encoding the antibody described herein. In some embodiments, the vector comprises a nucleic acid sequence of nucleic acid sequences as set forth in Table 3.

In some aspects, the present disclosure also provides a host cell comprising the nucleic acid encoding the isolated antibody described herein of and/or the vectors comprising the same.

In some aspects, the present disclosure also provides a pharmaceutical composition comprising the anti-HJV antibody described herein, and a pharmaceutically acceptable carrier.

In some aspects, the present disclosure also provides a metho for producing an anti-human hemojuvelin (HJV) antibody, the method comprises: (i) culturing the host cell under conditions allowing for expressing of the antibody that binds human hemojuvelin (HJV); and (ii) harvesting the cultured host cell or culture medium for collection of the antibody that binds human hemojuvelin (HJV). In some embodiments, the method comprising purifying the antibody that binds human hemojuvelin (HJV).

In some aspects, the present disclosure also provides an isolated antibody that binds to human hemojuvelin (HJV) produced by expressing in a host cell (i) nucleic acid sequence encoding a heavy chain, in which the nucleic acid sequence is at least 90% identical to SEQ ID NO: 92; and/or (ii) a nucleic acid sequence encoding a light chain, in which the nucleic acid sequence is at least 90% identical to SEQ ID NO: 93. In some aspects, the present disclosure also provides an isolated antibody that binds to human hemojuvelin (HJV) produced by expressing in a host cell (i) a nucleic acid sequence encoding a heavy chain, wherein the nucleic acid sequence is at least 90% identical to SEQ ID NO: 94; and/or (ii) a nucleic acid sequence encoding a light chain, in which the nucleic acid sequence is at least 90% identical to SEQ ID NO: 93. In some embodiments, the host cell is Chinese hamster ovary (CHO) cells, dhfr– CHO cell, human embryonic kidney (HEK)-293 cells, verda reno (VERO) cells, nonsecreting null (NS0) cells, human embryonic retinal (PER.C6) cells, Sp2/0 cells, baby hamster kidney (BHK) cells, Madin-Darby Canine Kidney (MDCK) cells, Madin-Darby Bovine Kidney (MDBK) cells, or monkey kidney CV1 line transformed by SV40 (COS) cells.

In some aspects, the present disclosure provides an isolated antibody that binds to human hemojuvelin (HJV) for use in a method of treating a subject having an anemia of chronic disease, wherein the antibody comprises a heavy chain variable region (VH) comprising an amino acid sequence of SEQ ID NO: 38, and a light chain variable region (VL) comprising an amino acid sequence of SEQ ID NO: 39.

In some aspects, the present disclosure provides an isolated antibody that binds to human hemojuvelin (HJV) for use in inhibiting iron sequestration in a subject having anemia of chronic disease, wherein the antibody comprises a heavy chain variable region (VH) comprising an amino acid sequence of SEQ ID NO: 38, and a light chain variable region (VL) comprising an amino acid sequence of SEQ ID NO: 39.

In some embodiments, the anemia results from hepcidin synthesis that is induced by pro-inflammatory cytokines, and wherein the administration of the antibody reduces the anemia.

In some embodiments, the pro-inflammatory cytokines comprise interleukin-6 (IL-6).

The foregoing and other aspects, implementations, acts, functionalities, features and embodiments of the present teachings can be more fully understood from the following description in conjunction with the accompanying drawings.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIG. 1A shows a schematic process of generation of the anti-hemojuvelin antibody, humanization, and affinity maturation.

FIG. 2A shows the general principle of HJV BMP reporter assay. FIG. 2B shows the effect of anti-HJV antibodies in inhibiting RGMc BMP signaling. FIG. 2C shows the effect of anti-HJV antibodies in inhibiting RGMa BMP signaling.

FIG. 4A shows the structure of hHA-008. FIG. 4B shows the structure of hHA-008-QL. FIG. 4C shows a comparison in antibody structure between hHA-008 and hHA-008-QL.

FIG. 6A shows maximal effect of hHA-008 measured by TSAT % occurred between 4-8 days post treatment. FIG. 6B shows hHA-008 reached maximum effect as measured by TSAT % about 1-4 days after injection in female cynos. FIG. 6C shows hHA-008 reached maximum effect as measured by TSAT % about 1-4 days after injection in male cynos, but one of the males did not respond to hHA-008 treatment.

FIG. 7A shows the maximum TSAT % increase occurred 1-4 days after injection ($T_{max}$=1-4 days), and one of the animals tested had a drastic decline of TSAT around day 34. FIG. 7B shows plasma hepcidin-25 concentration changes over time after hHA-008 injection. FIG. 7C shows plasma hHA-008 concentration changes over time after hHA-008 injection. FIGS. 7D-7F show that hHA-008 had robust PK/PD correlation of PK (plasma antibody concentration) to TSAT % and plasma hepcidin-25 concentration. The results of each tested Cyno are shown in FIG. 7D (Cyno 1), FIG. 7E (Cyno 2), and FIG. 7F (Cyno 3).

FIG. 8A shows TSAT % and hHA008 concentrations after animals were treated with either 0 (vehicle control) or 0.6 mpk hHA-008. FIG. 8B shows TSAT % and hHA-008 concentrations after animals were treated with either 0 (vehicle control) or 3 mpk hHA-008. FIG. 8C shows TSAT % and hHA-008 concentrations after animals were treated with either 0 (vehicle control) or 60 mpk hHA-008.

FIG. 9A shows TSAT % changes over time in Cynos post treatment of hHA-008 or hHA-008-QL. FIG. 9A shows TSAT % changes over time in Cynos post treatment of hHA-008 or hHA-008-QL. FIG. 9B shows plasma concentration of the antibodies over time in Cynos post treatment of hHA-008 or hHA-008-QL. FIG. 9C shows a time course of decline of plasma concentration of hHA-008 and hHA-008-QL.

FIG. 10A shows binding of FcRn of hHA-008 and hHA-008-QL at pH 6.0. FIG. 10B shows binding of FcRn of hHA-008 and hHA-008-QL at pH 7.4. X axis: Time. Y Axis: Response.

FIG. 15 shows the interaction of 3720-RG-050 and hHA-008. A 3720-RG-050 PDB structure was generated by homology using Swiss Model software. 3720-RG-050 amino acids 170-183 (SSPMALGANATATR (SEQ ID NO: 121)) are shown in A, B, C, D, E: ribbon/surface representation of front view (A); back view (B), side view 1 (C), side view 2 (D) and top view (E). F, G, H, I, J: ribbon representation of front view (F); back view (G), side view 1 (H), side view 2 (I) and top view (J).

FIG. 17 shows the interaction 3720-RG-050/hHA-008-QL. A 3720-RG-050 PDB structure was generated by homology using Swiss Model software. 372-RG-050 amino acids 169-182 (TSSPMALGANATAT (SEQ ID NO: 122)) and 289-29 (SQR) are shown in A, B, C, D, E: ribbon/surface representation of front view (A); back view (B), side view 1 (C), side view 2 (D) and top view (E). F, G, H, I, J: ribbon representation of front view (F); back view (G), side view 1 (H), side view 2 (I) and top view (J).

FIG. 20A shows serum concentration-time profiles became indistinguishable between SC injection and IV injection 4 days after administration. FIGS. 20B-20D show the return of serum iron to baseline levels was consistent with the decline in hHA-008 serum concentrations after 0.3 mpk, 0.6 mpk and 1 mpk injection of hHA-008 either by subcutaneous injection or intravenous injection.

DETAILED DESCRIPTION

Figure 1A:
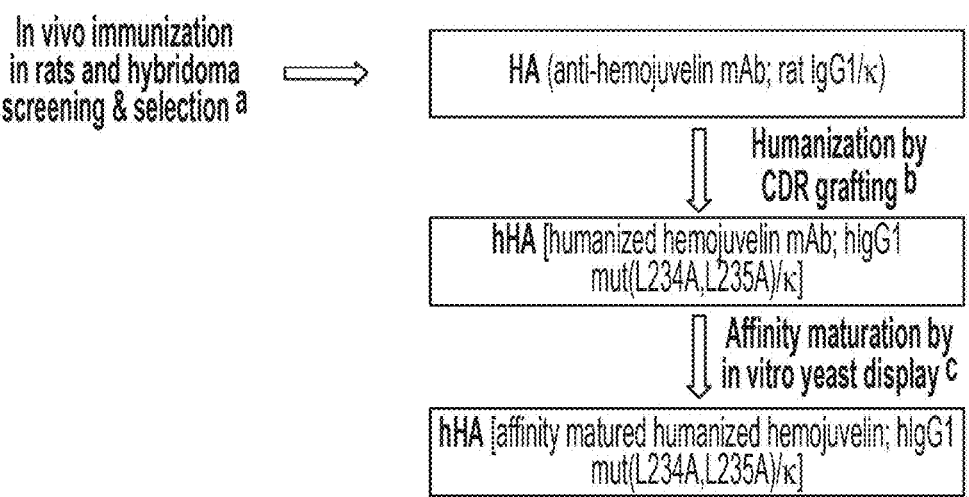
FIGS. 1A-IG are graphs showing generation and characterization of anti-HJV antibodies.
Figure 1B:
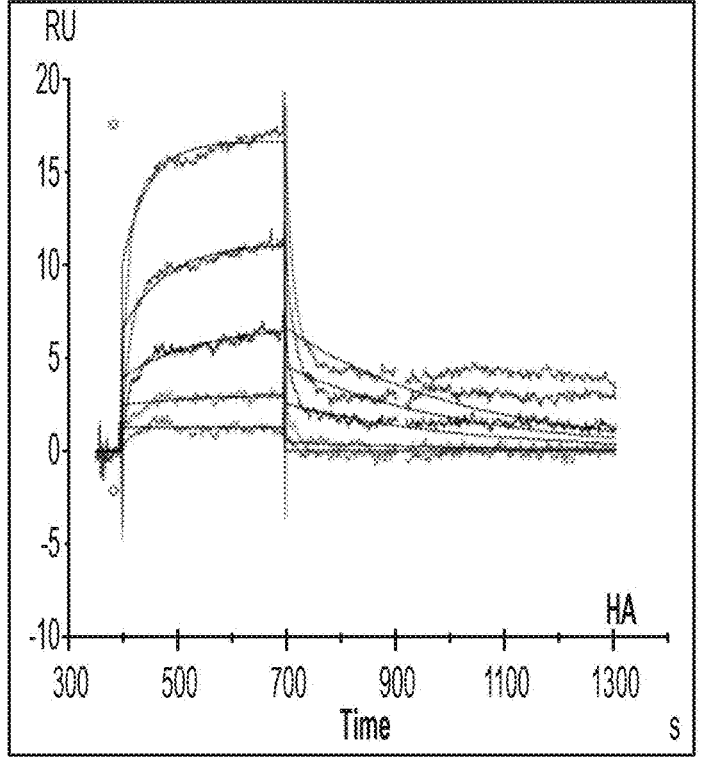
FIGS. 1B-1G shows the sensorgrams by BIAcore analysis of antibodies HA, hHA-004, hHA-008, hHA-009 and hHA-011.
Figure 1C:
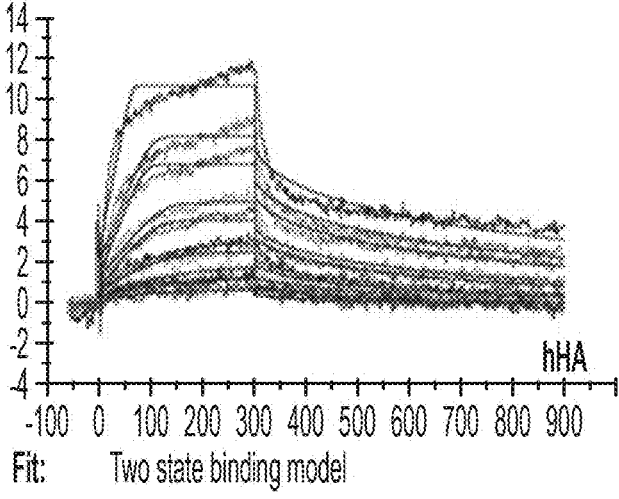
Figure 1D:
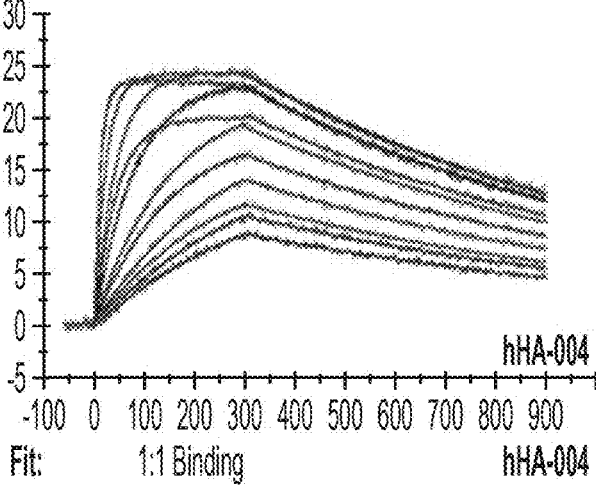
Figure 1E:
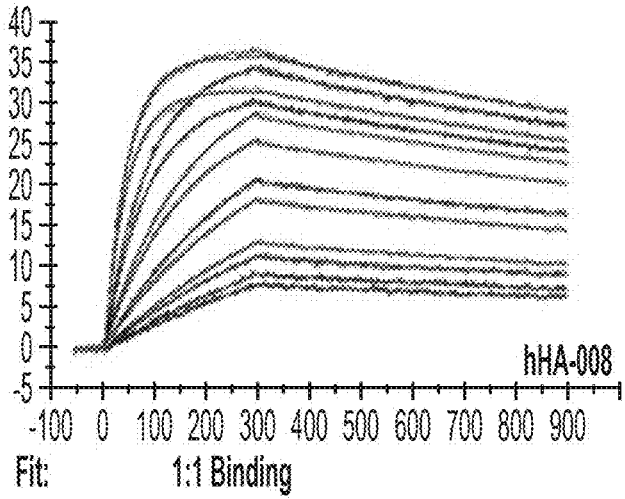
Figure 1F:
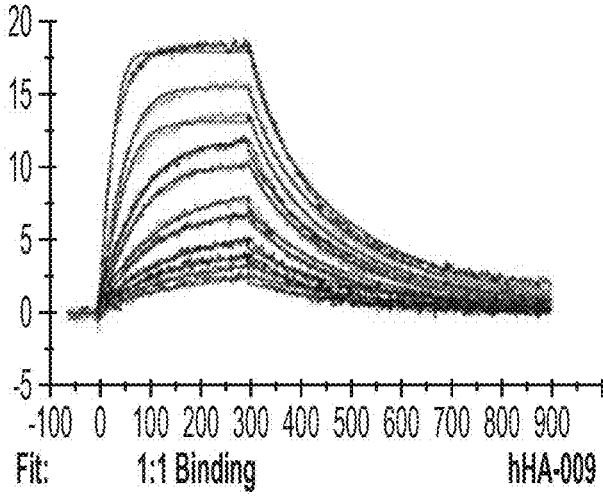
Figure 1G:
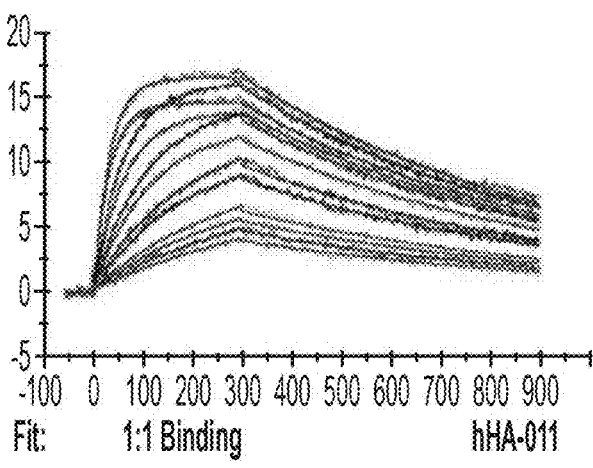

According to some aspects, the disclosure provides hepcidin antagonists for targeting hepcidin that are effective for inhibiting hepcidin function and/or reducing hepcidin expression, particularly for modulating iron homeostasis for the treatment of anemias of chronic disease (ACD) and/or one or more symptoms or complications thereof. Accordingly, in related aspects, the disclosure provides compositions and methods for treating ACD, which may be associated with chronic kidney disease, cancer, chronic infection, autoimmune disease, or other chronic inflammatory conditions as disclosed herein.

Certain aspects of this disclosure relate to an observation that hemojuvelin (HJV) is a regulator of hepcidin synthesis and that loss of hemojuvelin function may be associated with iron overload. For example, in some embodiments, homozygous HJV knockdown animals fail to amplify hepcidin synthesis in response to IL-6 and are unable to mount an effective hypoferremic response to acute inflammation. Accordingly, in some embodiments, methods provided herein involve administering to a subject in need thereof a hepcidin antagonist, which may be a hemojuvelin antagonist, in an amount effective to treat a high-hepcidin disorder. In some embodiments, the hemojuvelin antagonist is an anti-hemojuvelin antibody. In some embodiments, the anti-hemojuvelin antibody binds RGMc as its primary mode of action (as compared with RGMa and RGMb). Accordingly, in some embodiments, the anti-hemojuvelin antibody preferentially binds RGMc versus RGMa and/or RGMb. In some embodiments, the anti-hemojuvelin antibody binds RGMc with an equilibrium dissociation constant (KD) less than one hundred nanomolar (nM) (KD<100 nM). However, in some embodiments, the anti-hemojuvelin antibody binds RGMc with a similar affinity as RGMa and/or RGMb.

The foregoing and other aspects, implementations, acts, functionalities, features and embodiments of the present teachings can be more fully understood from the following description in conjunction with the accompanying drawings.

I. Definitions

Administering: As used herein, the terms "administering" or "administration" means to provide a complex to a subject in a manner that is physiologic ally and/or pharmacologically useful (e.g., to treat a condition in the subject).

Anemia of Chronic Disease: As used herein, the term "anemia of chronic disease" (ACD) refers to a haematological disorder arising in the context of an illness or condition that elicits an active immune/inflammatory response resulting in a deficiency in the ability of blood to transport oxygen. Chronic conditions (e.g., lasting 3 months or longer) can give rise to a low level of iron in the blood, despite normal or even increased levels of iron stores in macrophages and hepatocytes. In this context, inflammation may prevent the use of stored iron to product sufficient healthy red blood cells, leading to anemia. In some embodiments, ACD is the result of a deficiency in red blood cells, a deficiency in hem globin, and/or a deficiency in total blood volume. In some embodiments, ACD is associated with an alteration of iron metabolism and diversion of body iron (e.g., via macrophage sequestration), haemophagocytosis, reduction in erythropoiesis, and/or diminished response to erythropoietin stimulation. In some embodiments, ACD may be associated with or characterized by one or more of the following: impaired production of erythropoietin (EPO), blunted marrow erythroid response to EPO, iron-restricted erythropoiesis, and a diminished pool of EPO-responsive cells in combination with an associated chronic condition associated with inflammation. Accordingly, in some embodiments, low serum iron levels can provide diagnostic indicia of the presence of ACD in a subject when observed in the presence of an underlying chronic condition or disease. In some embodiments, ACD is an iron-restricted anemia, which may be characterized by a functional iron deficiency, which may present in a subject as a result of iron accumulation in tissue macrophages. Conditions associated with ACD include diseases which share features of immune activation. Examples of conditions associated with ACD include, without limitation, chronic kidney disease, cancer (e.g., a myeloma), infection (e.g., viral, bacterial, parasitic, or fungal), malignancies (e.g., hematological or solid tumors), autoimmune disease (e.g., rheumatoid arthritis, lupus, vasculitis, sarcoidosis), renal disease (e.g., chronic renal failure), cardia disease, and chronic disease that involves inflammation (e.g., inflammatory bowel disease, diabetes, heart failure).

Affinity Matured Antibody: "Affinity Matured Antibody" is used herein to refer to an antibody with one or more alterations in one or more CDRs, which result in an improvement in the affinity (i.e. KD, kd or ka) of the antibody for a target antigen compared to a parent antibody, which does not possess the alteration(s). Exempla affinity matured antibodies will have nanomolar or even picomolar affinities for the target antigen. A variety of procedures for producing affinity matured antibodies are known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

Antibody: As used herein, the term "antibody" refers to a polypeptide that includes at least one immunoglobulin variable domain or at least one antigenic determinant, e.g., paratope that specifically binds to an antigen. In some embodiments, a antibody is a full-length antibody. In some embodiments, an antibody is a chimeric antibody. In some embodiments, an antibody is a humanized antibody. However, in some embodiments, an antibody is a Fab fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as $V_H$), and/or a light (L) chain variable region (abbreviated herein as $V_L$). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha ($\alpha$), delta ($\Delta$), epsilon ($\varepsilon$), gamma ($\gamma$) or mu ($\mu$) heavy chain. In some embodiments, the heavy chain of an antibody described herein can comprise a human alpha ($\alpha$), delta ($\Delta$), epsilon ($\varepsilon$), gamma ($\gamma$) or mu ($\mu$) heavy chain. In a particular embodiment, an antibody described herein comprises a human gamma 1 CH1, CH2, and/or CH3 domain. In some embodiments, the amino acid sequence of the $V_H$ domain comprises the amino acid sequence of a human gamma ($\gamma$) heavy chain constant region, such as any known in the art. Non-limiting examples of human constant region sequences have been described in the art, e.g. see U.S. Pat. No. 5,693,780 and Kabat E A et al., (1991) supra. In some embodiments, the $V_H$ domain comprises an amino acid sequence that is at least 70%, 75%, 80%, 85% 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the strepta-vidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

Approximately: As used herein, the term "approximately" or "about," as applied to one or more values of interest, refers to a value that is similar to a state reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

CDR: As used herein, the term "CDR" refers to the complementarity determining region within antibody vari-able sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR, FR2, CDR2, FR3, CDR3, FR4. The extent of the framework region and CDRs can be precisely identified using method-ology known in the art, for example, by the Kabat definition, the IMGT definition, the Chothia definition, the AbM defi-nition, and/or the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information System® http://www.img-t.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). ee also hgmp.mrc.ac.uk and bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

Generally, there are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and 3 where the "L" and the "H" designates the light chain and the heavy chains regions, respectively. These regions may be referred to as Chothia CDRs, which have boundaries that overlap with Kabat CDRs. Other boundaries defining CDRs over-lapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although pre-ferred embodiments use Kabat or Chothia defined CDRs.

CDR-grafted antibody: The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complemen-tary" refers to the capacity for precise pairing between two nucleotides or two sets of nucleotides. In particular, comple-mentary is a term that characterizes an extent of hydrogen bond pairing that brings about binding between two nucleo-tides or two sets of nucleotides. For example, if a base at one position of an oligonucleotide is capable of hydrogen bond-ing with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroin-dole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the elative charge or size characteristics of the protein in which the amino acid substitution is made. Variants can be prepared according to methods for altering polypeptide sequence know to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Cross-reactive: As used herein and in the context of a targeting agent (e.g., antibody), the term "cross-reactive," refers to a property of the agent be ng capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human hemojuvelin and non-human primate hemojuvelin) is capable of binding to the human antigen and non-huma primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

Effective Amount: As used herein, "an effective amount" refers to the amount of each active agent (e.g., hepcidin antagonist, anti-HJV antibody) required to confer therapeutic effect on the subject, either alone or in combination with one or more other active agents. In some embodiments, the therapeutic effect is reduced hepcidin level or activity, increased level of transferrin saturation (TSAT %), decreased level of circulating transferrin level, and/or alleviated disease conditions (e.g., reduced anemia).

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Hemojuvelin (HJV): As used herein, the term "hemojuvelin (HJV)" (also known as repulsive guidance molecule C (RGMc) or hemochromatosis type 2 protein (HFE2)) refers to a membrane-bound and soluble form protein that regulates hepcidin production through the BMP/SMAD signaling pathway. The HFE2 gene encodes two known classes of GPI-anchored and glycosylated HJV molecules, which are targeted to the membrane and undergo distinct fates. HJV exists in multiple isoforms, including two soluble is forms and two membrane-associated isoforms. In some embodiments, a predominant membrane-associated isoform is a disulfide-linked two-chain form composed of N- and C-terminal fragments. In some embodiments, a full-length single-chain isoform associates with the membrane, but is released from the cell surface and accumulates in extracellular fluid. In some embodiments, HJV may be of human (NCBI Gene ID 148738), non-human primate (e.g., NCBI Gene ID 698805), or rodent (e.g., NCBI Gene ID 69585 or NCBI Gene ID 310681) origin. In addition to HJV (RGMc), the repulsive guidance molecule family includes repulsive guidance molecule A (RGMa) and repulsive guidance molecule B (RGMb). RGMa and RGMb are expressed in the central nervous system during development and are thought to be involved in controlling axonal patterning and neuronal survival, while HJV is produced in the liver and in cardiac and skeletal muscle.

Hepcidin: As used herein, a "hepcidin" refers to an iron-regulating peptide hormone primarily made in the liver that is encoded by the HAMP gene. In some embodiments, hepcidin controls the delivery of iron to blood plasma from intestinal cells absorbing iron, from erythrocyte-recycling macrophages, and from iron-storing hepatocytes. In some embodiments, hepcidin inhibits iron transport by binding to the iron export channel ferroportin which is located on the basolateral surface of gut enterocyte and the plasma membrane of reticuloendothelial cells (macrophages). In some embodiments, inhibiting ferroportin prevents iron from being exported and the iron is sequestered in the cells. In some embodiments, by inhibiting ferroportin, hepcidin prevents enterocytes from allowing iron into the hepatic portal system, thereby reducing dietary iron absorption. Hepcidin expression involves multiple aspects, including, for example, transcription of the HAMP gene, translation of the transcribed mRNA, and the posttranslational processing of the hepcidin precursor into the bioactive hepcidin-25 peptide (DTHFPICIFCCGCCHRSKCGMCCKT (SEQ ID NO: 129)). In some embodiments, hepcidin expression is modulated via the hemojuvelin-induced BMP signaling pathway. In some embodiments, hepcidin expression is modulated via the IL-6-JAK-STAT signaling pathway.

HJV-induced BMP signaling: As used herein, the term "HJV-induced BMP signaling" refers to signaling through BMP receptors that is induced by Hemojuvelin (HJV), which is a membrane bound co-receptor for bone morphogenetic protein (BMP) signaling. As discussed in Xia Y, et al., 1i Hemojuvelin regulates hepcidin expression via a selective subset of BMP ligands and receptors independently of neogenin, Blood. 2008 May 15; 111(10): 5195-5204, in hepatocytes, HJV-induced BMP signaling positively regulates hepcidin mRNA expression. In some embodiments, HJV binds to BMP2, BMP4, BMP5, or BMP6 to induce BMP signaling, e.g., to positively regulate hepcidin levels in hepatocytes. In some embodiments, cleavage of HJV by matripatase-2 reduces the amount of cell surface HJV available to participate in BMP signaling. In some embodiments, induction of BMP signaling by HJV is independent of neogenin. However, in some embodiments, neogenin facilitates induction of BMP signaling by HJV, as discussed in Zhao et al, *Neogenin Facilitates the Induction of Hepcidin*

*Expression by Hemojuvelin in the Liver*, J Biol Chem. 2016 Jun. 3; 291(23): 12322-12335. In some embodiments, BMP6 is responsible for iron-dependent activation of the Smad signaling. In some embodiments, BMP6 is secreted from liver sinusoidal endothelial cells and binds to a BMP receptor (BMPR) on hepatocytes and thereby activates the SMAD signaling cascade. In such embodiments, HJV serves as a co-receptor for such BMP6, e.g., to positively regulate hepcidin levels in hepatocytes. In some embodiments, BMPs transduce signals by binding to one or a combination of type I and II serine/threonine kinase receptors. BMP type II receptors include BMPRII, ActRIIA, and ActRIIB. BMP type I receptors include ALK3, ALK6, and ALK2. In some embodiments, upon ligand binding, constitutively active type II receptors phosphorylate type I receptors, and type I receptors then phosphorylate intracellular receptor-activated Smads (R-Smads), namely Smad 1, Smad 5 and/or Smad 8. In such embodiments, activated R-Smads complex with the common partner Smad4 and translocate to the nucleus to regulate gene transcription, e.g., induction of hepcidin expression.

Hepcidin Antagonist: As used herein, a "hepcidin antagonist" refers to an agent that reduces hepcidin expression and/or hepcidin activity (directly or indirectly). In some embodiments, a hepcidin antagonist reduces hepcidin-25 levels and/or activity (directly or indirectly). In some embodiments, a hepcidin antagonist inhibits hepcidin-induced ferroportin degradation. Accordingly, in some embodiments, a hepcidin antagonist targets hepcidin function indirectly through the hepcidin stimulatory pathway to decrease hepcidin expression. In some embodiments, a hepcidin antagonist targets hepcidin function directly, e.g., by binding the hepcidin peptide to sequester free hepcidin or by binding ferroportin to inhibit the hepcidin-ferroportin binding interaction, thereby decreasing hepcidin-induced ferroportin degradation. In some embodiments, a hepcidin antagonist is a ferroportin inhibitor that disrupts ferroportin-hepcidin interactions, such as, for example, as disclosed in Ross S L, et al., *Identification of Antibody and Small Molecule Antagonists of Ferroportin-Hepcidin Interaction.* Front Pharmacol. 2017 Nov. 21; 8:838; Fung E., et al., High Throughput Screening of Small Molecules Identifies Hepcidin Antagonists. Molecular Pharmacology March 2013, 83 (3) 681-690; and Angeliki Katsarou and Kostas Pantopoulos, Hepcidin Therapeutics. Pharmaceuticals (Basel). 2018 December; 11(4): 127, the relevant contents of each of which are incorporated herein by reference.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the $V_H$ and/or $V_L$ sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-hemojuvelin antibodies and antigen binding portions are provided. Such antibodies may be generated by obtaining murine anti-hemojuvelin monoclonal antibodies using traditional hybridoma technology followed by humanization using in vitro genetic engineering, such as those disclose in Kasaian et al PCT publication No. WO 2005/123126 A2.

Isolated antibody: An "isolated antibody", as used herein, is intended to refer to an antibody that is substantially free of other antibodies having different antigenic specificities (e.g., an isolated antibody that specifically binds hemojuvelin is substantially free of antibodies that specifically bind antigens other than hemojuvelin). An isolated antibody that specifically binds hemojuvelin may, however, have cross-reactivity to other antigens, such as other repulsive guidance molecule (RGM) proteins (e.g., RGMa and/or RGMb). Moreover, an isolated antibody may be substantially free of other cellular material and/or chemicals.

JAK-STAT signaling: As used herein, the term "JAK-STAT signaling" refers to signaling through cellular receptors that recruits a Janus Kinase (JAK), such as, for example, Janus Kinase 1 (JAK1) or Janus Kinase 2 (JAK2), to activate a transcription factor signal transducer and activator of transcription (STAT), such as, for example, STAT3. In some embodiments, as discussed in Maliken, B D, et al., *The Hepcidin Circuits Act: Balancing Iron and Inflammation*, Hepatology. 2011 May; 53(5): 1764-1766, JAK-STAT signaling involves binding of the cytokine interleukin-6 (IL-6) to its cognate cellular receptor, which then recruits Janus Kinase 2 (JAK2) to phosphorylate STAT3. In some embodiments, STAT3 is then (following JAK2 activation/phosphorylation) translocated into the nucleus. In some embodiments, activated STAT3 then induces hepcidin transcription, e.g., by binding to the STAT3 binding motif in the hepcidin promoter region. Thus, in some embodiments, hepcidin expression is induced via JAK-STAT signaling during inflammation through activation STAT3 by IL-6.

Kabat numbering: The terms "Kabat numbering", "Kabat definitions and "Kabat labeling" are used interchangeably herein. These terms, which are recognized in the art, refer to a system of numbering amino acid residues which are more variable i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDI 2, and amino acid positions 89 to 97 for CDR3.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, aptamers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O- methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however such recombinant human antibodies are subjected to in vitro mutagenesis (or, when an animal transgenic for human Ig sequences is used, in-vivo somatic mutagenesis) and thus the amino acid sequences of the $V_H$ and $V_L$ regions of the recombinant antibodies are sequences that, while derived from and related to human germline $V_H$ and VL sequences, may not naturally exist within the human antibody germline repertoire in vivo. One embodiment of the disclosure provides fully human antibodies capable of binding human hemojuvelin which can be generated using techniques well known in the art, such as, but not limited to, using human Ig phage libraries such as those disclosed in Jermutus et al., PCT publication No. WO 2005/007699 A2.

Selective: As used herein, the term "selective" or "selectively" refers to the ability of a molecule to produce an effect in relation to its target molecule compared to a reference molecule. For example, a molecule that selectively inhibits its target molecule means that this molecule is capable of inhibiting its target molecule with a degree that is distinguishable from a reference molecule in an inhibition assay or other inhibitory context. For example, with respect to an inhibitor, the term, "selectively inhibits", refers to the ability of the inhibitor to inhibit its target molecule with a degree that is distinguishable from a reference molecule that is not substantially inhibited in an inhibition assay, e.g., to an extent that permit selective inhibition of the target molecule, as described herein. For example, the half maximal inhibitory concentration (IC50) for the target molecule and/or the reference molecule can be tested in a kinase potency assay as described in Asshoff, M. et al., Momelotinib inhibits ACVR1/ALK2, decreases hepcidin production, and ameliorates anemia of chronic disease in rodents. Blood. 2017 Mar. 30; 129(13): 1823-1830 (e.g., Kinase potency assay by Carna Biosciences). In this assay, inhibitor solution (e.g., solution containing the selective inhibitor to be tested)/ kinase substrate is mixed with target molecule solution (e.g., ALK2) or reference molecule solution (e.g., JAK1 or JAK2), and incubated under room temperature for 1 hour.

Once the reaction is terminated, the signal produced by enzymatic activity on the substrate can be measured. The half maximal inhibitor concentration for the target molecule and the reference molecule can be calculated. In some embodiments, a molecule described herein selectively binds to a target molecule. In some embodiments, a molecule described herein selectively inhibits to a target molecule. In some embodiments, a molecule described herein selectively antagonizes to a target molecule. In some embodiments, a molecule described herein selectively neutralizes to a target molecule.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to hemojuvelin.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having ACD and/or one or more conditions which are associated with, or may give rise to, ACD and/or a functional iron deficiency.

Treatment: As used herein, the term "treating" or "treatment" refers to the application or administration of a composition including one or more active agents (e.g., anti-HJV antibodies) to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder. Alleviating a target disease/disorder includes delaying or preventing the development or progression of the disease, or reducing disease severity.

II. Anti-Hemojuvelin (HJV) Antibodies

In some embodiments, the hemojuvelin antagonist binds to on: or more proteins of the repulsive guidance molecule (RGM) family, including RGMa, RGMb, and RGMc (HJV). In some embodiments, the hemojuvelin antagonist selectively binds hemojuvelin (RGMc) over RGMa and RGMb. In some embodiments, the hemojuvelin antagonist is an antisense oligonucleotide that reduces expression of hemojuvelin (see, e.g., U.S. Pat. No. 7,534,764; U.S. Patent Publication No. US 2014/127325; and International Publication No. WO 2016/180784, which are incorporated herein by reference). In some embodiments, the hemojuvelin antagonist is a small molecule compound that inhibits hemojuvelin, e.g., by competitive binding and/or chemical modification of hemojuvelin.

In some embodiments, the hemojuvelin antagonist is an antibody (e.g., HA001-HA012) specific for hemojuvelin and/or one or more proteins of the RGM protein family (e.g., RGMa, RGMb). Appropriate antibodies specific for hemojuvelin and/or one or more RGM proteins that may be useful in certain methods provided herein are provided for example, in U.S. Pat. Nos. 10,118,958; and 8,507,435; U.S. Patent Publication Nos. US 2013/330343; US 2015/166672; and US 2017/029499; and International Publication Nos. WO 2015/171691; and WO 2018/009624, which are incorporated herein by reference.

Provided herein, in some aspects, are antibodies that bind to human hemojuvelin (HJV) with high specificity and affinity. In some embodiments, the anti-HJV antibody described herein specifically binds to any extracellular epitope of a HJV or an epitope that becomes exposed to an antibody. In some embodiments, anti-HJV antibodies provided herein bind specifically to HJV from human, non-human primates, mou e, rat, etc. In some embodiments, anti-HJV antibodies provided herein bind to human HJV. In some embodiments, the anti-HJV antibody described herein binds to an amino acid segment of a human or non-human primate HJV.

In some embodiments, the anti-HJV antibody described herein specifically binds to an epitope on human HJV. Human HJV is a 426 amino acid protein with a predicted N-terminal signal peptide of 31 amino acids and a C-terminal GPI-attachment signal of 45 amino acids. An exemplary human HJV amino acid sequence is set fort in SEQ ID NO: 128:

(SEQ ID NO: 128)
MGEPGQSPSPRSSHGSPPTLSTLTLLLLLCGHAHSQCKILRCNAEYVSS

TLSLRGGGSSGALRGGGGGGRGGGVGSGGLCRALRSYALCTRRTARTCR

GDLAFHSAVHGIEDLMIQHNCSRQGPTAPPPPRGPALPGAGSGLPAPDP

CDYEGRFSRLHGRPPGFLHCASFGDPHVRSFHHHFHTCRVQGAWPLLDN

DFLFVQATSSPMALGANATATRKLTIIFKNMQECIDQKVYQAEVDNLPV

AFEDGSINGGDRPGGSSLSIQTANPGNHVEIQAAYIGTTIIIRQTAGQL

SFSIKVAEDVAMAFSAEQDLQLCVGGCPPSQRLSRSERNRRGAITIDTA

RRLCKEGLPVEDAYFHSCVFDVLISGDPNFTVAAQAALEDARAFLPDLE

KLHLFPSDAGVPLSSATLLAPLLSGLFVLWLCIQ

In some embodiments, the anti-HJV antibody described herein may bind to a fragment of a human HJV. The fragment of HJV may be between about 5 and about 425 amino acids, between about 10 and about 400 amino acids, between about 50 and about 350 amino acids, between about 100 and about 300 amino acids, between about 150 and about 250 amino acids, between about 200 and about 300 amino acids, or between about 75 and about 150 amino acids in length. The fragment may comprise a contiguous number of amino acids from RGMc. An exemplary amino acid of a HJV fragment is set forth in SEQ ID NO: 123:

(SEQ ID NO: 123)
QCKILRCNAEYVSSTLSLRGGGSSGALRGGGGGGRGGGVGSGGLCRALR

SYALCTRRTARTCRGDLAFHSAVHGIEDLMIQHNCSRQGPTAPPPPRGP

ALPGAGSGLPAPDPCDYEGRFSRLHGRPPGFLHCASFGDPHVRSFHHHF

-continued
HTCRVQGAWPLLDNDFLFVQATSSPMALGANATATRKLTIIFKNMQECI

DQKVYQAEVDNLPVAFEDGSINGGDRPGGSSLSIQTANPGNHVEIQAAY

IGTTIIIRQTAGQLSFSIKVAEDVAMAFSAEQDLQLCVGGCPPSQRLSR

SERNRRGAITIDTARRLCKEGLPVEDAYFHSCVFDVLISGDPNFTVAAQ

AALEDARAFLPDLEKLHLFPSD

In some embodiments, the anti-HJV antibody described herein binds to different epitopes within a human HJV or a human HJV fragment.

In some embodiments, the anti-HJV antibody interacts with an epitope within amino acids 160-190 of SEQ ID NO: 123. In some embodiments, the anti-HJV antibody interacts with an epitope having an amino acid sequence of amino acids 170-183 of SEQ ID NO: 123. In some embodiments, the anti-HJV antibody interacts with an epitope having the amino acid sequence of SSPMALGANATATR (SEQ ID NO: 121). In some embodiments, the anti-HJV antibody interacts with different segments within SSPMALGANA-TATR (SEQ ID NO: 121). In some embodiments, the anti-HJV antibody interacts with amino acids 170-171, amino acids 171-180, amino acids 180-182, and amino acids 182-183 of SEQ ID NO: 123. In some embodiments, the antibody interacts with amino acids 170 (S), 171(S), 180 (T), 182 (T) and 183 (R) of SEQ ID NO: 123. In some embodiments, hHA-008 interacts with the epitope SSPMALGA-NATATR (SEQ ID NO: 121). In some embodiments, hHA-008 interacts with amino acids 170 (S), 171(S), 180 (T), 182 (T) and 183 (R of SEQ ID NO: 123.

In some embodiments, the anti-HJV antibody interacts with epitope within amino acids 160-190 of SEQ ID NO: 123 and/or amino acids 280-310 of SEQ ID NO: 123. In some embodiments, the anti-HJV antibody interacts with an epitope within amino acids 169-182 of SEQ ID NO: 123 and/or amino acids 289-300 of SEQ ID NO: 123. In some embodiments, the anti-HJV antibody interacts with an epitope within amino acids 169-182 of SEQ ID NO: 123 and amino acids 289-300 of SEQ ID NO: 123. In some embodiments, the anti-HJV antibody interacts with an epitope having the amino acid sequence of TSSPMALGANATAT (SEQ ID NO: 122) and amino acid sequence SQRLSRSERNRR (SEQ ID NO: 127). In some embodiments, the anti-HJV antibody interacts with different segments within TSSPMALGANATAT (SEQ ID NO: 122) and SQRLSRSERNRR (SEQ ID NO: 127). In some embodiments, the anti-HJV antibody interacts with amino acids 169-171, amino acids 171-180, and amino acids 180-182 of SEQ ID NO: 123, and amino acids 289-293, amino acids 293-294, amino acids 294-295, amino acids 295-297 and amino acids 297-300 of SEQ ID NO: 123. In some embodiments, the antibody interacts with amino acids 169 (T), 170 (S), 171(S), 180 (T), 182 (T), 289 (S), 293 (S), 294 (R), 295(S), 297(R), and 300 (R) of SEQ ID NO: 123. In some embodiments, hHA-008-QL interacts with different segments within TSSPMALGANATAT (SEQ ID NO: 122) and SQRLSRSERNRR (SEQ ID NO: 127). In some embodiments, hHA-008-QL interacts with amino acids 169 (T), 170 (S), 171(S), 180 (T), 182 (T), 289 (S), 293 (S), 294 (R), 295(S), 297(R); an 300 (R) of SEQ ID NO: 123.

In some embodiments, the anti-HJV antibodies described herein are affinity matured clones. In some embodiments, an anti-HJV antibody specifically binds a HJV (e.g., a human or non-human primate HJV) with binding affinity (e.g., as indicated by $K_D$) of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. For example, the anti-HJV antibodies of the present disclosure can bind to a hemojuvelin protein (e.g., human hemojuvelin) with an affinity between 5 pM and 500 nM, e.g., between 50 pM and 100 nM, e.g., between 500 pM and 50 nM. The disclosure also includes antibodies that compete with any of the antibodies described herein for binding to a hemojuvelin protein (e.g., human hemojuvelin) and that have an affinity of 100 nM or lower (e.g., 80 nM or lower, 50 nM or lower, 20 nM or lower, 10 nM or lower, 500 pM or lower, 50 pM or lower, or 5 pM or lower). The affinity and binding kinetics of the anti-HJV antibody can be tested using any suitable method including but not limited to biosensor technology (e.g., OCTET or BIACORE). In some embodiments, the anti-HJV antibodies described herein binds to HJV with a $K_D$ of sub-nanomolar range. In some embodiments, the anti-HJV antibodies described herein selectively binds to RGMc, but not RGMa or RGMb.

Binding affinity (or binding specificity) can be determined by a variety of methods including equilibrium dialysis, equilibrium binding, gel filtration, ELISA, surface plasmon resonance (SPR), florescent activated cell sorting (FACS) or spectroscopy (e.g., using a fluorescence assay). Exemplary conditions for evaluating binding affinity are in HBS-P buffer (10 mM HEPES pH7.4, 150 mM NaCl, 0.005% (v/v) surfactant P20) and PBS buffer (10 mM P04-3, 137 mM NaCl, and 2.7 mM KCl). These techniques can be used to measure the concentration of bound proteins as a function of target protein concentration. The concentration of bound protein ([Bound]) is generally related to the concentration of free target protein ([Free]) by the following equation:

$$[\text{Bound}]=[\text{Free}]/(Kd+[\text{Free}])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The heavy chain (HC) and light chain (LC) sequences, heavy chain variable domain (VH) and light chain variable domain (VL), CDR sequences, and heavy chain and light chain constant region sequences of non-limiting examples of anti-HJV antibodies are provided in Table 1.

TABLE 1

| Examples of anti-HJV antibodies (CDRs according to the Kabat definition) | | | |
|---|---|---|---|
| humanized Hemojuvelin Antagonist (HA) Antibody | | Sequences | SEQ ID NO |
| hHA-001 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLETSDGDTFLE | 4 |
| | LC CDR2 | EVSTRFS | 5 |
| | LC CDR3 | FQVTHDPMT | 6 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLETSDGDTFLEW FQQRPGQSPRLLIYEVSTRFSGVPDRFSGSGSGTDFTLKI SRVEAEDVGVYYCFQVTHDPMTFGQGTKLEIK | 8 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLETSDGDTFLEW FQQRPGQSPRLLIYEVSTRFSGVPDRFSGSGSGTDFTLKI SRVEAEDVGVYYCFQVTHDPMTFGQGTKLEIKRTVAAPSV FIFPPSDEQLKSGTASVVCLLNNFYPREAKVQKVDNALQ SGNSQESVTEQDSKDSTYSLSSTLTLSKADYEKHKVYACE VTHQGLSSPVTKSFNRGEC | 52 |
| hHA-002 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLETSDGDTFLE | 4 |
| | LC CDR2 | EVSSRFS | 49 |
| | LC CDR3 | MQVTHDPLT | 24 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLETSDGDTFLEW FQQRPGQSPRLLIYEVSSRFSGVPDRFSGSGSGTDFTLKI SRVEAEDVGVYYCMQVTHDPLTFGQGTKLEIK | 30 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK | 114 |

TABLE 1-continued

| | | | |
|---|---|---|---|

Examples of anti-HJV antibodies (CDRs according to the Kabat definition)

| humanized Hemojuvelin Antagonist (HA) Antibody | | Sequences | SEQ ID NO |
|---|---|---|---|
| | Light Chain | VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG DVVLTQSPLSLPVTLGQPASISCRSSQSLETSDGDTFLEW FQQRPGQSPRLLIYEVSSRFSGVPDRFSGSGSGTDFTLKI SRVEAEDVGVYYCMQVTHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 53 |
| hHA-003 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLETSDGDTFLE | 4 |
| | LC CDR2 | EVSNRFS | 18 |
| | LC CDR3 | FQVTHDPVT | 25 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLETSDGDTFLEW FQQRPGQSPRLLIYEVSNRFSGVPDRFSGSGSGTDFTLKI SRVEAEDVGVYYCFQVTHDPVTFGQGTKLEIK | 31 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLETSDGDTFLEW FQQRPGQSPRLLIYEVSNRFSGVPDRFSGSGSGTDFTLKI SRVEAEDVGVYYCFQVTHDPVTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 54 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| hHA-004 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLESSDGDTFLE | 14 |
| | LC CDR2 | DVSTRFS | 19 |
| | LC CDR3 | FQVTHDPVT | 25 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |
| | VL | DVVLTQSPLSLPVTLGQPASISCRSSQSLESSDGDTFLEW FQQRPGQSPRLLIYDVSTRFSGVPDRFSGSGSGTDFTLKI SRVEAEDVGVYYCFQVTHDPVTFGQGTKLEIK | 32 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̲FNW YVDGVEVHNAKTK̲PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̲FNW YVDGVEVHNAKTK̲PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain at C-terminal of heavy chain) (with or without the lysine residue | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTK̲PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTK̲PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 114 |
| | Light Chain | DVVLTQSPLSLPVTLGQPASISCRSSQSLESSDGDTFLEW FQQRPGQSPRLLIYDVSTRFSGVPDRFSGSGSGTDFTLKI SRVEAEDVGVYYCFQVTHDPVTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 55 |
| hHA-005 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLEESDGYTFLE | 15 |
| | LC CDR2 | DVSERFS | 20 |
| | LC CDR3 | FQATYDPLT | 26 |
| | VH | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSS | 7 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| | VL | DVVLTQSPLSLPVTLGQPASISCRSSQSLEESDGYTFLEW FQQRPGQSPRLLIYDVSERFSGVPDRFSGSGSGTDFTLKI SRVEAEDVGVYYCFQATYDPLTFGQGTKLEIK | 33 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̲FNW YVDGVEVHNAKT̲K̲PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVM̲HEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̲FNW YVDGVEVHNAKT̲K̲PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVM̲HEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain at C-terminal of heavy chain) (with or without the lysine residue | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̲FNWYVDGV EVHNAKT̲K̲PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVM̲HEALHNHYTQKSLS LSPGK | 51 |
| | | EVQLVESGGGLVQPGGSLRLSCAASGFTFSNYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̲FNWYVDGV EVHNAKT̲K̲PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVM̲HEALHNHYTQKSLS LSPG | 114 |
| | Light Chain | DVVLTQSPLSLPVTLGQPASISCRSSQSLEESDGYTFLEW FQQRPGQSPRLLIYDVSERFSGVPDRFSGSGSGTDFTLKI SRVEAEDVGVYYCFQATYDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 56 |
| hHA-006 | HC CDR1 | YYGMN | 9 |
| | HC CDR2 | MIYYDSSEKHYADSVKG | 2 |
| | HC CDR3 | GTTPDY | 3 |
| | LC CDR1 | RSSQSLEDSDGGTFLE | 16 |
| | LC CDR2 | DVSSRFS | 21 |
| | LC CDR3 | FQATHDPLT | 27 |
| | VH | EVQLVESGGGLVQPGGSLRLSCAASGFTFSYYGMNWIRQA PGKGLEWIGMIYYDSSEKHYADSVKGRFTISRDNSKNTLY LQMNSLRAEDTAVYYCAKGTTPDYWGQGTMVTVSS | 34 |
| | VL | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLTFGQGTKLEIK | 35 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̲FNW YVDGVEVHNAKT̲K̲PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVM̲HEALHNHYT | 46 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| | | QKSLSLSPGK ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSYYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 57 |
| | | EVQLVESGGGLVQPGGSLRLSCAASGFTFSYYGMNWIRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 115 |
| | Light Chain | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 58 |
| hHA-007 | HC CDR1 | NYGMN | 1 |
| | HC CDR2 | MIYYDSSDKHYADSVKG | 10 |
| | HC CDR3 | GTTPDV | 11 |
| | LC CDR1 | RSSQSLEESDGYTFLH | 17 |
| | LC CDR2 | EVSNRFS | 18 |
| | LC CDR3 | FQATHDPVT | 28 |
| | VH | EVQLVESGGGLVQPGGSLRLSCAASGFTFSNYGMNWIRQA PGKGLEWIGMIYYDSSDKHYADSVKGRFTISRDNSKNTLY LQMNSLRAEDTAVYYCAKGTTPDVWGQGTMVTVSS | 36 |
| | VL | DVVLTQSPLSLPVTLGQPASISCRSSQSLEESDGYTFLHW FQQRPGQSPRLLIYEVSNRFSGVPDRFSGSGSGTDFTLKI SRVEAEDVGVYYCFQATHDPVTFGQGTKLEIK | 37 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWIRQA PGKGLEWIGMIYYDSSDKHYADSVKGRFTISRDNSKNTLY LQMNSLRAEDTAVYYCAKGTTPDVWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | 59 |
| | | EVQLVESGGGLVQPGGSLRLSCAASGFTFSNYGMNWIRQA PGKGLEWIGMIYYDSSDKHYADSVKGRFTISRDNSKNTLY LQMNSLRAEDTAVYYCAKGTTPDVWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 116 |
| | Light Chain | DVVLTQSPLSLPVTLGQPASISCRSSQSLEESDGYTFLHW FQQRPGQSPRLLIYEVSNRFSGVPDRFSGSGSGTDFTLKI SRVEAEDVGVYYCFQATHDPVTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 60 |
| hHA-008 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLEESDGYTFLH | 17 |
| | LC CDR2 | EVSTRFS | 5 |
| | LC CDR3 | FQATHDPLT | 27 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSS | 38 |
| | VL | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIK | 39 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPG | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK | 61 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| | | VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK | |
| | | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPG | 117 |
| | Light Chain | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 62 |
| hHA-008-QL | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLEESDGYTFLH | 17 |
| | LC CDR2 | EVSTRFS | 5 |
| | LC CDR3 | FQATHDPLT | 27 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSS | 38 |
| | VL | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIK | 39 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDQLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVLHEALHNHYT QKSLSLSPGK | 48 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDQLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVLHEALHNHYT QKSLSLSPG | 113 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDQLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVLHEALHNHYTQKSLS LSPGK | 63 |
| | | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDQLMISRTPEVTCVVVDVSHEDPEVKFNWYVDGV | 118 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| | | EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSV<u>L</u>HEALHNHYTQKSLS LSPG | |
| | Light Chain | DVVLTQSPLSLPVTLGQPASISCRSSQSLEESDGYTFLHW FQQRPGQSPRLLIYEVSTRFSGVPDRFSGSGSGTDFTLKI SRVEAEDVGVYYCFQATHDPLTFGQGTKLEIKRTVAAPSV FIFPPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 62 |
| hHA-009 | HC CDR1 | NYGMN | 1 |
| | HC CDR2 | MIYYDSSEKHYADSVKG | 2 |
| | HC CDR3 | GTTPDY | 3 |
| | LC CDR1 | RSSQSLADSDGDTFLH | 50 |
| | LC CDR2 | AVSHRFS | 22 |
| | LC CDR3 | FQATHDPVT | 28 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSS | 38 |
| | VL | DVVLTQSPLSLPVTLGQPASISCRSSQSLADSDGDTFLHW FQQRPGQSPRLLIYAVSHRFSGVPDRFSGSGSGTDFTLKI SRVEAEDVGVYYCFQATHDPVTFGQGTKLEIK | 41 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSV<u>M</u>HEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSV<u>M</u>HEALHNHYT QKSLSLSPG | 112 |
| | LC Constant Region | RTVAAPSVFIFPPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSV<u>M</u>HEALHNHYTQKSLS LSPGK | 61 |
| | | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSV<u>M</u>HEALHNHYTQKSLS LSPG | 117 |
| | Light Chain | DVVLTQSPLSLPVTLGQPASISCRSSQSLADSDGDTFLHW FQQRPGQSPRLLIYAVSHRFSGVPDRFSGSGSGTDFTLKI SRVEAEDVGVYYCFQATHDPVTFGQGTKLEIKRTVAAPSV FIFPPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 65 |

TABLE 1-continued

Examples of anti-HJV antibodies (CDRs according to the Kabat definition)

| humanized Hemojuvelin Antagonist (HA) Antibody | | Sequences | SEQ ID NO |
|---|---|---|---|
| hHA-010 | HC CDR1 | NYGMN | 1 |
| | HC CDR2 | MIYYDSSEKHYADSVKG | 2 |
| | HC CDR3 | GTTPDK | 12 |
| | LC CDR1 | RSSQSLEESDGYTFLE | 15 |
| | LC CDR2 | EVSHRFS | 23 |
| | LC CDR3 | FQATHDPLT | 27 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDKWGQGTMVTVSS | 42 |
| | VL | DVVLTQSPLSLPVTLGQPASISCRSSQSLEESDGYTFLEW FQQRPGQSPRLLIYEVSHRFSGVPDRFSGSGSGTDFTLKI SRVEAEDVGVYYCFQATHDPLTFGQGTKLEIK | 43 |
| | HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKD<u>T</u>LMISRTPEVTCVVVDVSHEDPEVK<u>F</u>NW YVDGVEVHNAKT<u>K</u>PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSV<u>M</u>HEALHNHYT QKSLSLSPGK | 46 |
| | | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKD<u>T</u>LMISRTPEVTCVVVDVSHEDPEVK<u>F</u>NW YVDGVEVHNAKT<u>K</u>PREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSV<u>M</u>HEALHNHYT QKSLSLSPG<u></u> | 112 |
| | LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| | Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDKWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKD<u>T</u>LMISRTPEVTCVVVDVSHEDPEVK<u>F</u>NWYVDGV EVHNAKT<u>K</u>PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSV<u>M</u>HEALHNHYTQKSLS LSPGK | 66 |
| | | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGTTPDKWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKD<u>T</u>LMISRTPEVTCVVVDVSHEDPEVK<u>F</u>NWYVDGV EVHNAKT<u>K</u>PREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSV<u>M</u>HEALHNHYTQKSLS LSPG<u></u> | 119 |
| | Light Chain | DVVLTQSPLSLPVTLGQPASISCRSSQSLEESDGYTFLEW FQQRPGQSPRLLIYEVSHRFSGVPDRFSGSGSGTDFTLKI SRVEAEDVGVYYCFQATHDPLTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 67 |
| hHA-011 | HC CDR1 | NYGMN | 1 |
| | HC CDR2 | MIYYDSSEKHYADSVKG | 2 |
| | HC CDR3 | GSTPDY | 13 |
| | LC CDR1 | RSSQSLEDSDGGTFLE | 16 |
| | LC CDR2 | DVSSRFS | 21 |
| | LC CDR3 | FQATHDPLS | 29 |
| | VH | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGSTPDYWGQGTMVTVSS | 44 |

TABLE 1-continued

Examples of anti-HJV antibodies (CDRs according to the Kabat definition)

| humanized Hemojuvelin Antagonist (HA) Antibody | Sequences | SEQ ID NO |
|---|---|---|
| VL | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLSFGQGTKLEIK | 45 |
| HC Constant Region (with or without the lysine residue at C-terminal of heavy chain constant region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVK̲FNW YVDGVEVHNAKT̲KPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVM̲HEALHNHYT QKSLSLSPGK | 46 |
| | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDT̲LMISRTPEVTCVVVDVSHEDPEVK̲FNW YVDGVEVHNAKT̲KPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVM̲HEALHNHYT QKSLSLSPG | 112 |
| LC Constant Region | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC | 47 |
| Heavy Chain (with or without the lysine residue at C-terminal of heavy chain) | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGSTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̲FNWYVDGV EVHNAKT̲KPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVM̲HEALHNHYTQKSLS LSPGK | 68 |
| | EVQLVESGGGLVQPGGSLRLSCAASGFTFSNYGMNWVRQA PGKGLEWIGMIYYDSSEKHYADSVKGRFTISRDNSKNTLY LQMNSLRAEDTAVYYCAKGSTPDYWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVK̲FNWYVDGV EVHNAKT̲KPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVM̲HEALHNHYTQKSLS LSPG | 120 |
| Light Chain | DVVLTQSPLSLPVTLGQPASISCRSSQSLEDSDGGTFLEW FQQRPGQSPRLLIYDVSSRFSGVPDRFSGSGSGTDFTLKI SRVEAEDVGVYYCFQATHDPLSFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC | 69 |

In some embodiments, the N-terminal of the heavy chain of the anti-HJV antibody described herein is glutamic acid (E). In some embodiments, the glutamic acid can cyclize spontaneously to pyroglutamic acid by post-translational modification. Spontaneous cyclization of glutamic acid to pyroglutamic acid has been previously described, e.g., Chelius et al., Formation of Pyroglutamic Acid From N-terminal Glutamic Acid in Immunoglobulin Gamma Antibodies, Anal Chem. 2006; 78(7):2370-2376. In some embodiments, the N-terminal of the heavy chain of the anti-HJV antibody described herein is a pyroglutamic acid. In some embodiments, the anti-HJV antibodies having N-terminal pyroglutamic acid are impurities in the population of anti-HJV antibodies (e.g., less than 5%, less than 4%, less than 3%, less than 2%, less than 1%, less than 0.5%, less than 0.1%, less than 0.05%, or less than 0.01%) in the population of anti-HJV antibody. In some embodiments, the population of the anti-HJV antibodies comprises a mixture of anti-HJV antibodies having glutamic acid or pyroglutamic acid at the N-terminal of the heavy chain.

In some embodiments, the anti-HJV antibodies of the present disclosure comprises one or more of the HC CDRs (e.g., HC CDR1, HC CDR2, or HC CDR3) amino acid sequences from any one of the anti-HJV antibodies selected from Table 1. In some embodiments, the anti-HJV antibodies of the present disclosure comprise the HC CDR1, HC CDR2, and HC CDR3 as provided for any one of the antibodies elected from Table 1. In some embodiments, the anti-HJV antibodies of the present disclosure comprises one or more of the LC CDRs (e.g., LC CDR1, LC CDR2, or LC CDR3) amino acid sequences from any one of the anti-HJV antibodies selected from Table 1. In some embodiments, the anti-HJV antibodies of the present disclosure comprise the LC CDR1, LC CDR2, and LC CDR3 as provided for any one of the anti-HJV antibodies selected from Table 1.

In some embodiments, the anti-HJV antibodies of the present disclosure comprises the HC CDR1, HC CDR2, HC CDR3, LC CDR1, LC CDR2, and LC CDR3 as provided for any one of the anti-HJV antibodies selected from Table 1. In some embodiments, antibody heavy and light chain CDR3 domains may play a particularly important role in the binding specificity/affinity of an antibody for an antigen. Accordingly, the anti-HJV antibodies of the disclosure may include at least the heavy and/or light chain CDR3s of any one of the anti-HJV antibodies selected from Table 1.

In some embodiments, the isolated anti-HJV antibody comprises a heavy chain variable region that comprises a heavy chain CDR1 (HC CDR1), a heavy chain CDR2 (HC CDR2), and a heavy chain CDR3 (HC CDR3).

In some embodiments, following the Kabat definition, the HC CDR1 may comprise the amino acid sequence of $X_1$YGMN (SEQ ID NO: 105), in which $X_1$ can be N or Y. Alternatively or in addition, the HC CDR2 may comprise the amino acid sequence of MIYYDSSX$_2$KHYADSVKG (SEQ ID NO: 106), in which $X_2$ can be E or D. Alternatively or in addition, the HC CDR3 may comprise the amino acid sequence of GX$_3$TPDX$_4$ (SEQ ID NO: 107), in which $X_3$ can be T or S, and $X_4$ can be Y, V, or K.

In some embodiments, following the Kabat definition, the anti-HJV antibody may comprise a light chain variable region that comprises a light chain CDR (LC CDR1), a light chain CDR2 (LC CDR2), and a light chain CDR3 (LC CDR3). In some embodiments, the LC CDR1 may comprise the amino acid sequence of RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H. Alternatively or in addition, the LC CDR2 may comprise the amino acid sequence of X$_9$VSX$_{10}$RFS (SEQ ID NO: 109), in which $X_9$ can be E, D or A, and $X_{10}$ can be N, S, T, E or H. Alternatively or in addition, the LC CDR3 may comprise the amino acid sequence of X$_1$QX$_{12}$TX$_{13}$DPX$_{14}$X$_{15}$ (SEQ ID NO: 110), in which $X_{11}$ can be F or M, $X_{12}$ can be V or A, $X_{13}$ can be H or Y, $X_{14}$ can be M, L or V, and $X_{15}$ can be T or S.

Also within the scope of the present disclosure are functional variants of any of the exemplary anti-HJV antibodies as disclosed herein. A functional variant may contain one or more amino acid residue variations in the $V_H$ and/or $V_L$, or in one or more of the HC CDRs and/or one or more of the LC CDRs as relative to the reference antibody, while retaining substantially similar binding and biological activities (e.g., substantially similar binding affinity, binding specificity, inhibitory activity, anti-inflammatory activity, or a combination thereof) as the reference antibody.

In some embodiments, any of the anti-HJV antibodies of the disclosure have one or more CDRs (e.g., HC CDR or LC CDR) sequences substantially similar to any of the HC CDR1, HC CDR2, HC CDR3, LC CDR1, LC CDR2, and/or LC CDR3 sequences from one of the anti-HJV antibodies selected from Table 1. In some embodiments, the position of one or more CDRs along the VH (e.g., HC CDR1, HC CDR2, or HC CDR3) and/or VL (e.g., LC CDR1, LC CDR2, or LC CDR3) region of an antibody described herein can vary by one, two, three, four, five, or six amino acid positions so long as immunospecific binding to hemojuvelin (e.g., human hemojuvelin) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or C-terminal boundary of the CDR by one, two, three, four, five, or six amino acids, relative to the CDR position of any one of the antibodies described herein, so long as immunospecific binding to hemojuvelin (e.g., human hemojuvelin) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., HC CDR1, HC CDR2, or HC CDR3) and/or VL (e.g., LC CDR1, LC CDR2, or LC CDR3) region of an antibody described herein can vary (e.g., be shorter or longer) by one, two, three, four, five, or more amino acids, so long as immunospecific binding to hemojuvelin (e.g., human hemojuvelin) is maintained (e.g., substantially maintained, for example, at least 50%, at least 60%, at least 70%, at least 80%, at least 90%, at least 95% of the binding of the original antibody from which it is derived).

Accordingly, in some embodiments, a HC CDR1, HC CDR2, C CDR3, LC CDR1, LC CDR2, and/or LC CDR3 described herein may be one, two, three, four, five or more amino acids shorter than one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived) In some embodiments, a HC CDR1, HC CDR2, HC CDR3, LC CDR1, LC CDR2, and/or LC CDR3 described herein may be one, two, three, four, five or more amino acids longer than one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, the amino portion of HC CDR1, HC CDR2, HC CDR3, LC CDR1, LC CDR2, and/or LC CDR3 described herein can be extended by one, two, three, four, five or more amino acids compared to one or ore of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, it least 70%, at least 80%, at least 90%, at least 95% relative to the binding of the original antibody from which it is derived). In some embodiments, the carboxy portion of a HC CDR1, IC CDR2, HC CDR3, LC CDR1, LC CDR2, and/or LC CDR3 described herein can be extended by one, two, three, four, five or more amino acids compared to one or more of the CDRs described herein (e.g., GDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, the amino portion of a HC CDR1, HC CDR2, HC CDR3, LC CDR1, LC CDR2, and/or LC CDR3 described herein can be shorter ed by one, two, three, four, five or more amino acids compared to one or more of the CDRs described herein (e.g., CDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a HC CDR1, HC CDR2, HC CDR3, LC CDR1, LC CDR2, and/or LC CDR3 described herein can be shortened by one, two three, four, five or more amino acids compared to one or more of the CDRs described herein (e.g., GDRS from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to hemojuvelin (e.g., human hemojuvelin) is maintained, for example, using binding assays and conditions described in the art.

In some examples, any of the anti-HJV antibodies of the disclosure have one or more CDR (e.g., HC CDR or LC CDR) sequences substantially similar to any one of the anti-HJV antibodies selected from Table 1. For example, the antibodies may include one or more CDR sequence(s) from any of the anti-HJV antibodies selected from Table 1 containing up to 5, 4, 3, 2, or 1 amino acid residue variations as compared to the corresponding CDR region in any one of the CDRs provided herein (e.g., CDRs from any of the anti-HJV antibodies selected from Table 1) so long as immunospecific binding to hemojuvelin (e.g., human hemojuvelin) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a hemoju- velin protein (e.g., a human hemojuvelin protein), for example, as determined based on a crystal structure. Some aspects of the disclosure provide anti-HJV antibodies that comprise one or more of the heavy chain variable (VH) and/or light chain variable (VL) domains provided herein. In some embodiments, any of the VH domains provided herein include one or more of the HC CDR sequences (e.g. HC CDR1, HC CDR2, and HC CDR3) provided herein, for example, any of the CDR-H sequences provided in any one of the anti-HJV selected from Table 1. In some embodi- ments, any of the VL domains provided herein include one or more of the CDR-L sequences (e.g., LC CDR1, LC CDR2, and LC CDR3) provided herein, for example, any of the LC CDR sequences provided in any one of the anti-HJV antibodies selected from Table 1.

In some embodiments, the anti-HJV antibodies of the disclosure include any antibody that includes a heavy chain variable domain and/or a light chain variable domain of any one of the anti-HJV antibodies selected from Table 1, and variants thereof. In some embodiments, anti-HJV antibodies of the disclosure include any antibody that includes the heavy chain variable and light chain variable pairs of any anti-HJV antibodies selected from Table 1.

Aspects of the disclosure provide anti-HJV antibodies having a heavy chain variable (VH) and/or a light chain variable (VL) domain amino acid sequence homologous to any of those described herein. In some embodiments, the anti-HJV antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any one of the anti-HJV antibodies selected from Table 1. In some embodiments, the homolo- gous heavy chain variable and/or light chain variable amino acid sequences do not vary within any of the CDR sequences provided herein. For example, in some embodiments, the degree of sequence variation (e.g., 5%, 80%, 85%, 90%, 95%, 98%, or 99%) may occur within a heavy chain variable and/or a light chain variable sequence excluding any of the CDR sequences provided herein. In some embodiments, any of the anti-HJV antibodies provided herein comprise a heavy chain variable sequence and a light chain variable sequence that comprises a framework sequence that is at least 75%, 80%, 85%, 90%, 95%, 98%, or 99% identical to the frame- work sequence of any anti-HJV antibodies selected from Table 1.

In some embodiments, the anti-HJV antibody of the present disclosure is a humanized antibody (e.g., a human- ized variant containing one or more CDRs of Table 1). In some embodiments, the anti-HJV antibody of the present disclosure comprises a HC CDR1, a HC CDR2, a HC CDR3, a LC CDR1, a LC CDR2, and a LC CDR3 that are the same as the HC CDR1, HC CDR2, HC CDR3, LC CDR1, LC CDR2, and LC CDR3 shown in Table 1, and comprises a humanized heavy chain variable region and/or a humanized light chain variable region.

Humanized antibodies are human immunoglobulins (re- cipient antibody) in which residues from a complementary determining region (CDR) of the recipient are replaced by residues from a CDR of a non-human species (donor anti- body) such as mouse, rat, or rabbit having the desired specificity, affinity, and capacity. In some embodiments, Fv framework region (FR) residues of the human immuno- globulin are replaced by corresponding non-human residues. Furthermore, the humanized antibody may comprise resi- dues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or sub- stantially all of the FR regions are those of a human immunoglobulin consensus sequence. The humanized anti- body optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by graft- ing the CDRs (e.g., as shown in Table 1) into the human variable domains (e.g., IGKV1-NL1*01 and IGHV1-3*01 human variable domain). In some embodiments, the anti- HJV antibody of the present disclosure is a humanized variant comprising one or more amino acid substitutions (e.g., in the VH framework region) as compared with any one of the VHs listed in Table 1, and/or one or more amino acid substitutions (e.g., in the VL framework region) as compared with any one of the VLs listed in Table 1.

In some embodiments, the anti-HJV antibody of the present disclosure is a humanized antibody comprising a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH of any of the anti-HJV antibodies listed in Table 1. Alternatively or in addition, the anti-HJV antibody of the present disclosure is a humanized antibody comprising a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL of any one of the anti-HJV antibodies listed in Table 1.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of light chain variable domain having the amino acid sequence of SEQ ID NO: 8.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 4, a LC CDR2 having the amino acid sequence of SEQ ID NO: 5, and a LC CDR3 having the amino acid sequence of SEQ ID NO: 6.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 4, LC CDR2 having the amino acid sequence of SEQ ID NO: 5, and LC CDR3 having the amino acid sequence of SEQ ID NO: 6.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 4, LC CDR2 having the amino acid sequence of SEQ ID NO: 5, and LC CDR3 having the amino acid sequence of SEQ ID NO: 6.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 4; a LC CDR2 having no more than 3 amino acid variations (e.g., no more than 3, 2, or 1 amino acid variation) as compared with the LC CDR2 having the amino acid sequence of SEQ ID NO: 5; and/or a LC CDR3 having no more than 3 amino acid variations (e.g., no more than 3, 2, or 1 amino acid variation) as compared with the LC CDR3 having the amino acid sequence of SEQ ID NO: 6.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 8.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 8.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99% identical to the VL as set forth in SEQ ID NO: 8.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of light chain variable domain having the amino acid sequence of SEQ ID NO: 30.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 4, a LC CDR2 having the amino acid sequence of SEQ ID NO: 49, and a LC CDR3 having the amino acid sequence of SEQ ID NO: 24.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 4, LC CDR2 having the amino acid sequence of SEQ ID NO: 49, and LC CDR3 having the amino acid sequence of SEQ ID NO: 24.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99% identical to the to the LC CDR1 having the amino acid sequence of SEQ ID NO: 4, LC CDR2 having the amino acid sequence of SEQ ID NO: 49, and LC CDR3 having the amino acid sequence of SEQ ID NO: 24.

In some embodiments, the anti-HJV antibody of the present disclosure comprises: a HC CDR1 having no more than 3 amino acid variations (e.g., no more an 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 4; a LC CDR2 having no more than 3 amino acid variations (e.g., no more than 3, 2, or 1 amino acid variation) as comp ed with the LC CDR2 having the amino acid sequence of SEQ ID NO: 49; and/or a LC CDR3 having no more than 3 amino acid variations (e.g., no more than 3, 2, or 1 amino acid variation) as compared with the LC CDR3 having the amino acid sequence of SEQ ID NO: 24.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 30.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 30.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 30.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of a light chain variable domain having the amino acid sequence of SEQ ID NO: 31.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 4, a LC CDR2 having the amino acid sequence of SEQ ID NO: 18, and a LC CDR3 having the amino acid sequence of SEQ ID NO: 25.

In some embodiments, anti-HJV antibody of the present disclosure comprises a HC CDR1, a HC CDR2, and a HC CDR3, which collectively contains no ore than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 4, LC CDR2 having the amino acid sequence of SEQ ID NO: 18, and LC CDR3 having the amino acid sequence of SEQ ID NO: 25.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99% identical to the to the LC CDR1 having the amino acid sequence of SEQ ID NO: 4, LC CDR2 having the amino acid sequence of SEQ ID NO: 18, and LC CDR3 having the amino acid sequence of SEQ ID NO: 25.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 4; a LC CDR2 having no more than 3 amino acid variations (e.g., no more than 3, 2, or 1 amino acid variation) as compared with the LC CDR2 having the amino acid sequence of SEQ ID NO: 18; and/or a LC CDR3 having no more than 3 amino acid variations (e.g., no more than 3, 2, or 1 amino acid variation) as compared with the LC CDR3 having the amino acid sequence of SEQ ID NO: 25

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 31

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 31

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 31.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of a light chain variable domain having the amino acid sequence of SEQ ID NO: 32.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 14, a LC CDR2 having the amino acid sequence of SEQ ID NO: 19, and a LC CDR3 having the amino acid sequence of SEQ ID NO: 25.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 14, LC CDR2 having the amino acid sequence of SEQ ID NO: 19, and LC CDR3 having the amino acid sequence of SEQ ID NO: 25.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 14, LC CDR2 having the amino acid sequence of SEQ ID NO: 19, and LC CDR3 having the amino acid sequence of SEQ ID NO: 25.

In some embodiments, the anti-HJV antibody of the present disclosure comprises: a HC CDR1 having no more than 3 amino acid variations (e.g., no more tan 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 14; a LC CDR2 having no more than 3 amino acid variations (e.g., no more than 3, 2, or 1 amino acid variation) as compared with the LC CDR2 having the amino acid sequence of SEQ ID NO: 19; and/or a LC CDR3 having no more than 3 amino acid variations (e.g., no more than 3, 2, or 1 amino acid variation) as compared with the LC CDR3 having the amino acid sequence of SEQ ID NO: 25.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 32.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 32.

In some embodiments, the anti-HJV antibody of the present disclosure comprises a VH comprising an amino acid sequence that is at least 80% (e.g., 80%, 5%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99% identical to the VL as set forth in SEQ ID NO: 32.

In some embodiments, the anti-HJV antibody of the present disclosure comprises a HC CDR1, HC CDR2 and HC CDR3 of a heavy chain variable domain having the amino acid sequence of SEQ ID NO: 7. Alternatively or in addition, the anti-HJV antibody of the present disclosure comprises a LC CDR1, LC CDR2 and LC CDR3 of light chain variable domain having the amino acid sequence of SEQ ID NO: 33.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 15, a LC CDR2 having the amino acid sequence of SEQ ID NO: 20, and a LC CDR3 having the amino acid sequence of SEQ ID NO: 26.

In some embodiments, anti-HJV antibody of the present disclosure comprises a HC CDR1, a HC CDR2, and a HC CDR3, which collectively contains no ore than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 15, LC CDR2 having the amino acid sequence of SEQ ID NO: 20, and LC CDR3 having the amino acid sequence of SEQ ID NO: 26.

In some embodiments, the anti-HJV antibody of the present disclosure comprises a HC CDR1, a HC CDR2, and a HC CDR3 that collectively are at least 83% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 15, LC CDR2 having the amino acid sequence of SEQ ID NO: 20, and LC CDR3 having the amino acid sequence of SEQ ID NO: 26.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation)

as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 15; a LC CDR2 having no more than 3 amino acid variations (e.g., no more than 3, 2, or 1 amino acid variation) as compared with the LC CDR2 having the amino acid sequence of SEQ ID NO: 20; and/or a LC CDR3 having no more than 3 amino acid variations (e.g., no more than 3, 2, or 1 amino acid variation) as compared with the LC CDR3 having the amino acid sequence of SEQ ID NO: 26.

In some embodiments, the anti-HJV antibody of the present disclosure comprises a VH comprising the amino acid sequence of SEQ ID NO: 7. Alternatively or in addition, the anti-HJV antibody of the present disclosure comprises a VL comprising the amino acid sequence of SEQ ID NO: 33.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 7. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 33.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 7. Alternatively or in addition, the anti-HJV antibody of the present disclosure comprises a VL comprising an amino acid sequence that is at least 80% (e.g., 80%, 85%, 90%, 95%, 98%, or 99% identical to the VL as set forth in SEQ ID NO: 33.

In some embodiments, the anti-HJV antibody of the present disclosure comprises a HC CDR1, HC CDR2 and HC CDR3 of a heavy chain variable domain having the amino acid sequence of SEQ ID NO: 34. Alternatively or in addition, the anti-HJV antibody of the present disclosure comprises a LC CDR1, LC CDR2 and LC CDR3 of light chain variable domain having the amino acid sequence of SEQ ID NO: 35.

In some embodiments, according to the Kabat definition system, the anti-HJV antibody of the present disclosure comprises a HC CDR1 having the amino acid sequence of SEQ ID NO: 9, a HC CDR2 having the amino acid sequence of SEQ ID NO: 2, a HC CDR3 having the amino acid sequence of SEQ ID NO: 3, a LC CDR1 having the amino acid sequence of SEQ ID NO: 16, a LC CDR2 having the amino acid sequence of SEQ ID NO: 21, and a LC CDR3 having the amino acid sequence of SEQ ID NO: 27.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 9, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 16, LC CDR2 having the amino acid sequence of SEQ ID NO: 21, and LC CDR3 having the amino acid sequence of SEQ ID NO: 27.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 9, HC CDR2 having the amino acid sequence of SEQ ID NO: 2 and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 16, LC CDR2 having the amino acid sequence of SEQ ID NO: 21, and LC CDR3 having the amino acid sequence of SEQ ID NO: 27.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 9; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 16; a LC CDR2 having no more than 3 amino acid variations (e.g., no more than 3, 2, or 1 amino acid variation) as compared with the LC CDR2 having the amino acid sequence of SEQ ID NO: 21; and/or a LC CDR3 having no more than 3 amino acid variations (e.g., no more than 3, 2, or 1 amino acid variation) as compared with the LC CDR3 having the amino acid sequence of SEQ ID NO: 27.

In some embodiments, the anti-HJV antibody of the present disclosure comprises a VH comprising the amino acid sequence of SEQ ID NO: 34. Alternatively or in addition, the anti-HJV antibody of the present disclosure comprises a VL comprising the amino acid sequence of SEQ ID NO: 35.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 34. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 35.

In some embodiments, the anti-HJV antibody of the present disclosure comprises a VH comprising an amino acid sequence that is at least 80% (e.g., 80%, 35%, 90%, 95%, 98%, or 99%) identical to the VH as set forth in SEQ ID NO: 34. Alternatively or in addition, the anti-HJV antibody of the present disclosure comprises a VL comprising an amino acid sequence that is at least 80% (e.g., 80%, 85%, 90%, 95%, 9%, or 99%) identical to the VL as set forth in SEQ ID NO: 35.

In some embodiments, the anti-HJV antibody of the present disclosure comprises a HC CDR1, HC CDR2 and HC CDR3 of a heavy chain variable domain having the amino acid sequence of SEQ ID NO: 36. Alternatively or in addition, the anti-HJV antibody of the present disclosure comprises a LC CDR1, LC CDR2 and LC CDR3 of a light chain variable domain having the amino acid sequence of SEQ ID NO: 37.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 10, a HC CDR3 having the amino acid sequence of SEQ ID NO: 11, a LC CDR1 having the amino acid sequence of SEQ ID NO: 17, a LC CDR2 having the amino acid sequence of SEQ ID NO: 18, and a LC CDR3 having the amino acid sequence of SEQ ID NO: 28.

In some embodiments, anti-HJV antibody of the present disclosure comprises a HC CDR1, a HC CDR2, and a HC CDR3, which collectively contains no pore than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 10, and HC CDR3 having the amino acid sequence of SEQ ID NO: 11. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 17, LC CDR2 having the amino acid sequence of SEQ ID NO: 18, and LC CDR3 having the amino acid sequence of SEQ ID NO: 28.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 10, and HC CDR3 having the amino acid sequence of SEQ ID NO: 11. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 17, LC CDR2 having the amino acid sequence of SEQ ID NO: 18, and LC CDR3 having the amino acid sequence of SEQ ID NO: 28.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., 10 more than 3, 2, or 1 amino acid variation) as compared with the HC CDR2 having the amino acid sequence of SEQ ID NO: 10; and/or a HC CDR3 having no more than 3 amino acid variations (e.g., no more than 3, 2, or 1 amino acid variation) as compared with the HC CDR3 having the amino acid sequence of SEQ ID NO: 11. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 17; a LC CDR2 having no more than 3 amino acid variations (e.g., no more than 3, 2, or 1 amino acid variation) as compared with the LC CDR2 having the amino acid sequence of SEQ ID NO: 18; and/or a LC CDR3 having no more than 3 amino acid variations (e.g., no more than 3, 2, or 1 amino acid variation) as compared with the LC CDR3 having the amino acid sequence of SEQ ID NO: 28.

In some embodiments, the anti-HJV antibody of the present disclosure comprises a VH comprising the amino acid sequence of SEQ ID NO: 36. Alternatively or in addition, the anti-HJV antibody of the present disclosure comprises a VL comprising the amino acid sequence of SEQ ID NO: 37.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 36. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 37.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 36. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 37.

In some embodiments, the anti-HJV antibody of the present disclosure comprises a HC CDR1, HC CDR2 and HC CDR3 of a heavy chain variable domain having the amino acid sequence of SEQ ID NO: 38. Alternatively or in addition, the anti-HJV antibody of the present disclosure comprises a LC CDR1, LC CDR2 and LC CDR3 of a light chain variable domain having the amino acid sequence of SEQ ID NO: 39.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 17, a LC CDR2 having the amino acid sequence of SEQ ID NO: 5, and a LC CDR3 having the amino acid sequence of SEQ ID NO: 27.

In some embodiments, anti-HJV antibody of the present disclosure comprises a HC CDR1, a HG CDR2, and a HC CDR3, which collectively contains no wore than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 17, LC CDR2 having the amino acid sequence of SEQ ID NO: 5, and LC CDR3 having the amino acid sequence of SEQ ID NO: 27.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 17, LC CDR2 having the amino acid sequence of SEQ ID NO: 5, and LC CDR3 having the amino acid sequence of SEQ ID NO: 27.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., po more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 17; a LC CDR2 having no more than 3 amino acid variations (e.g., no more than 3, 2, or 1 amino acid variation) as compared with the LC CDR2 having the amino acid sequence of SEQ ID NO: 5; and/or a LC CDR3 having no more than 3 amino acid variations (e.g., no more than 3, 2, or 1 amino acid variation) as compared with the LC CDR3 having the amino acid sequence of SEQ ID NO: 27.

In some embodiments, the anti-HJV antibody of the present disclosure comprises a VH comprising the amino acid sequence of SEQ ID NO: 38. Alternatively or in addition, the anti-HJV antibody of the present disclosure comprises a VL comprising the amino acid sequence of SEQ ID NO: 39.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 38. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 39.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 38. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 39.

In some embodiments, the anti-HJV antibody of the present disclosure comprises a HC CDR1, HC CDR2 and HC CDR3 of a heavy chain variable domain having the amino acid sequence of SEQ ID NO: 38. Alternatively or in addition, the anti-HJV antibody of the present disclosure comprises a LC CDR1, LC CDR2 and LC CDR3 of light chain variable domain having the amino acid sequence of SEQ ID NO: 41.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 3, a LC CDR1 having the amino acid sequence of SEQ ID NO: 50, a LC CDR2 having the amino acid sequence of SEQ ID NO: 22, and a LC CDR3 having the amino acid sequence of SEQ ID NO: 28.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 3. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 50, LC CDR2 having the amino acid sequence of SEQ ID NO: 22, and LC CDR3 having the amino acid sequence of SEQ ID NO: 28.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 3. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 50, LC CDR2 having the amino acid sequence of SEQ ID NO: 22, and LC CDR3 having the amino acid sequence of SEQ ID NO: 28.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 3. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 50; a LC CDR2 having no more than 3 amino acid variations (e.g., no more than 3, 2, or 1 amino acid variation) as compared with the LC CDR2 having the amino acid sequence of SEQ ID NO: 22; and/or a LC CDR3 having no more than 3 amino acid variations (e.g., no more than 3, 2, or 1 amino acid variation) as compared with the LC CDR3 having the amino acid sequence of SEQ ID NO: 28.

In some embodiments, the anti-HJV antibody of the present disclosure comprises a VH comprising the amino acid sequence of SEQ ID NO: 38. Alternatively or in addition, the anti-HJV antibody of the present disclosure comprises a VL comprising the amino acid sequence of SEQ ID NO: 41.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 38. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 41.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 38. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 41.

In some embodiments, the anti-HJV antibody of the present disclosure comprises a HC CDR1, HC CDR2 and HC CDR3 of a heavy chain variable domain having the amino acid sequence of SEQ ID NO: 42. Alternatively or in addition, the anti-HJV antibody of the present disclosure comprises a LC CDR1, LC CDR2 and LC CDR3 of a light chain variable domain having the amino acid sequence of SEQ ID NO: 43.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 12, a LC CDR1 having the amino acid sequence of SEQ ID NO: 15, a LC CDR2 having the amino acid sequence of SEQ ID NO: 23, and a LC CDR3 having the amino acid sequence of SEQ ID NO: 2.

In some embodiments, anti-HJV antibody of the present disclosure comprises a HC CDR1, a HC CDR2, and a HC CDR3, which collectively contains no more than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 12. "Collectively," as used anywhere in the present disclosure, means that the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 15, LC CDR2 having the amino acid sequence of SEQ ID NO: 23, and LC CDR3 having the amino acid sequence of SEQ ID NO: 27.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 12. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 15, LC CDR2 having the amino acid sequence of SEQ ID NO: 23, and LC CDR3 having the amino acid sequence of SEQ ID NO: 27.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 12. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 15; a LC CDR2 having no more than 3 amino acid variations (e.g., no more than 3, 2, or 1 amino acid variation) as compared with the LC CDR2 having the amino acid sequence of SEQ ID NO: 23; and/or a LC CDR3 having no more than 3 amino acid variations (e.g., no more than 3, 2, or 1 amino acid variation) as compared with the LC CDR3 having the amino acid sequence of SEQ ID NO: 27.

In some embodiments, the anti-HJV antibody of the present disclosure comprises a VH comprising the amino acid sequence of SEQ ID NO: 42. Alternatively or in addition, the anti-HJV antibody of the present disclosure comprises a VL comprising the amino acid sequence of SEQ ID NO: 43.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 42. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 43.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 42. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 43.

In some embodiments, the anti-HJV antibody of the present disclosure comprises a HC CDR1, HC CDR2 and HC CDR3 of a heavy chain variable domain having the amino acid sequence of SEQ ID NO: 44. Alternatively or in addition, the anti-HJV antibody of the present disclosure comprises a LC CDR1, LC CDR2 and LC CDR3 of light chain variable domain having the amino acid sequence of SEQ ID NO: 45.

In some embodiments, according to the Kabat definition system, the anti-HJV antibody of the present disclosure comprises a HC CDR1 having the amino acid sequence of SEQ ID NO: 1, a HC CDR2 having the amino acid sequence of SEQ ID NO: 2, a HC CDR3 having the amino acid sequence of SEQ ID NO: 13, a LC CDR1 having the amino acid sequence of SEQ ID NO: 16, a LC CDR2 having the amino acid sequence of SEQ ID NO: 21, and a LC CDR3 having the amino acid sequence of SEQ ID NO: 29.

In some embodiments, anti-HJV antibody of the present disclosure comprises a HC CDR1, a HC CDR2, and a HC CDR3, which collectively contains no ore than 5 amino acid variations (e.g., no more than 5, 4, 3, 2, or 1 amino acid variation) as compared with the HC CDR1 having the amino acid sequence of SEQ ID NO: 1, HC CDR2 having the amino acid sequence of SEQ ID NO: 2, and HC CDR3 having the amino acid sequence of SEQ ID NO: 13. "Collectively," as used anywhere in the present disclosure, means at the total number of amino acid variations in all of the three heavy chain CDRs is within the defined range. Alternatively or in addition, the anti-HJV antibody of the present disclosure comprises a LC CDR1, a LC CDR2, and a LC CDR3, which collectively contains no more than 5 amino acid variations (e.g., no more than 5, 4, 3, 2 or 1 amino acid variation) as compared with the LC CDR1 having the amino acid sequence of SEQ ID NO: 16, LC CDR2 having the amino acid sequence of SEQ ID NO: 21, and LC CDR3 having the amino acid sequence of SEQ ID NO: 29.

In some embodiments, the anti-HJV antibody of the present disclosure comprises a HC CDR1, a HC CDR2, and a HC CDR3 that collectively are at least 80% (e.g., 80%, 85%, 90%, 95%, 98%, or 99%) identical to the HC CDR1 having the amino acid sequence of SEQ ID NO: 1, HC CDR2 having the amino acid sequence of SEQ ID NO: 2, and HC CDR3 having the amino acid sequence of SEQ ID NO: 13. Alternatively or in addition, the anti-HJV antibody of the present disclosure comprises a LC CDR1, a LC CDR2, and a LC CDR3 that collectively are at least 80% (e.g., 80%, 85%, 90%, 95%, 98%, or 99%) identical to the to the LC CDR1 having the amino acid sequence of SEQ ID NO: 16, LC CDR2 having the amino acid sequence of SEQ ID NO: 21, and LC CDR3 having the amino acid sequence of SEQ ID NO: 29.

In some embodiments, the anti-HJV antibody of the present disclosure comprises: a HC CDR1 having no more than 3 amino acid variations (e.g., no more than 3, 2, or 1 amino acid variation) as compared with the HC CDR1 having the amino acid sequence of SEQ ID NO: 1; a HC CDR2 having no more than 3 amino acid variations (e.g., no more than 3, 2, or 1 amino acid variation) as compared with the HC CDR2 having the amino acid sequence of SEQ ID NO: 2; and/or a HC CDR3 having no more than 3 amino acid variations (e.g., no more than 3, 2, or 1 amino acid variation) as compared with the HC CDR3 having the amino acid sequence of SEQ ID NO: 13. Alternatively or in addition, the anti-HJV antibody of the present disclosure comprises: a LC CDR1 having no more than 3 amino acid variations (e.g., no more than 3, 2, or 1 amino acid variation) as compared with the LC CDR1 having the amino acid sequence of SEQ ID NO: 16; a LC CDR2 having no more than 3 amino acid variations (e.g., no more than 3, 2, or 1 amino acid variation) as compared with the LC CDR2 having the amino acid sequence of SEQ ID NO: 21; and/or a LC CDR3 having no more than 3 amino acid variations (e.g., no more than 3, 2, or 1 amino acid variation) as compared with the LC CDR3 having the amino acid sequence of SEQ ID NO: 29.

In some embodiments, the anti-HJV antibody of the present disclosure comprises a VH comprising the amino acid sequence of SEQ ID NO: 44. Alternatively or in addition, the anti-HJV antibody of the present disclosure comprises a VL comprising the amino acid sequence of SEQ ID NO: 45.

In some embodiments, the anti-HJV antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 44. Alternatively or in addition, the anti-HJV antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or amino acid variation) as compared with the VL as set forth in SEQ ID NO: 45.

In some embodiments, the anti-HJV antibody of the present disclosure comprises a VH comprising an amino acid sequence that is at least 80% (e.g., 80%, 85%, 90%, 95%, 98%, or 99%) identical to the VH as set forth in SEQ ID NO: 44. Alternatively or in addition, the anti-HJV antibody of the present disclosure comprises a VL comprising an amino acid sequence that is at least 80% (e.g., 80%, 85%, 90%, 95%, 98%, or 99%) identical to the VL as set forth in SEQ ID NO: 45.

The CDRs of an antibody may have different amino acid sequences when different definition systems are used (e.g., the IMGT definition, the Kabat definition, or the Chothia definition). A definition system annotates each amino acid in a given antibody sequence (e.g., VH or VL sequence) with a number, and numbers corresponding to the heavy chain and light chain CDRs are provided in Table 2. The CDRs listed in Table 1 are defined in accordance with the Kabat definition. One skilled in the art is able to derive the CDR sequences using the different numbering systems for the anti-HJV antibodies provided in Table 1.

TABLE 2

| | CDR Definitions | | |
| --- | --- | --- | --- |
| | IMGT[1] | Kabat[2] | Chothia[3] |
| HC CDR1 | 27-38 | 31-35 | 26-32 |
| HC CDR2 | 56-65 | 50-65 | 53-55 |
| HC CDR3 | 105-116/117 | 95-102 | 96-101 |
| LC CDR1 | 27-38 | 24-34 | 26-32 |
| LC CDR2 | 56-65 | 50-56 | 50-52 |
| LC CDR3 | 105-116/117 | 89-97 | 91-96 |

[1]IMGT ®, the international ImMunoGeneTics information system ®, imgt.org, Lefranc, M.-P. et al., Nucleic Acids Res., 27:209-212 (1999)
[2] Kabat et al. (1991) Sequences of Proteins of Immunological Interest, Fifth Edition, U.S. Department of Health and Human Services, NIH Publication No. 91-3242
[3]Chothia et al., J. Mol. Biol. 196:901-917 (1987))

In some embodiments, the anti-HJV antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-HJV antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-HJV antibody of the present disclosure comprises a VL domain and/or VH domain of any one of the anti-HJV antibodies selected from Table 1, and comprises a constant region comprising the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra. An example of a human IgG1 constant region is given below:

```
                                        (SEQ ID NO: 103)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

In some embodiments, the heavy chain of any of the anti-HJV antibodies described herein comprises a mutant human IgG1 constant region. For example, the introduction of LALA mutations (a mutant derived from mAb b12 that has been mutated to replace the lower hinge residues Leu234 Leu235 with Ala234 and Ala235) in the CH2 domain of human IgG1 is known to reduce Fcg receptor binding (Bruhns, P., et al. (2009) and Xu, D. et al. (2000)). The mutant human IgG1 constant region is provided below (mutations bonded and underlined):

```
                                         (SEQ ID NO: 46)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV
```

-continued

EPKSCDKTHTCPPCPAPEAAGGPSVFLFPPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

In some embodiments, the heavy chain of any of the anti-HJV antibodies described herein further comprises mutations in human IgG1 constant region. For example, the introduction of T250Q and M248L substitutions. In some embodiments, such substitution may affect FcRn binding and serum half-life (WO2005047307 and WO2013063110). An exemplary IgG1 constant region comprising the LALA mutation and the QL mutation is provided below (mutations bonded and underlined):

(SEQ ID NO: 48)

ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPEAAGGPSVFLFPPPKPKDQLMISRIPEVTCVVV

DVSHEDPEVKENWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVLHEALHNHYTQKSLSLSPGK

In some embodiments, during the production of the antibodies, particularly with Chinese Hamster Ovary Cells (CHO cells), it can be appreciated that the lysine at the C-terminus of the heavy chain is cleaved. Accordingly, a human IgG1 constant region within a secreted antibody can be:

(SEQ ID NO: 111)

ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG

In some embodiments, a mutant human IgG1 comprising the LALA mutations in a secreted antibody can be:

(SEQ ID NO: 112)

ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPEAAGGPSVFLFPPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

-continued

VSLTCLVKGFYPSDIAVEWESNGQPENNYKTTPPVLDSDGSFFLYSKLT

VDKSRWQQGNVFSCSVMHEALHNHYTQKSLSLSPG

In some embodiments, a mutant human IgG1 comprising the ALA mutations and the QL mutations can be:

(SEQ ID NO: 113)

ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPEAAGGPSVFLFPPPKPKDQLMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKL

TVDKSRWQQGNVFSCSVLHEALHNHYTQKSLSLSPG

In some embodiments, the light chain of any of the anti-HJV antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

(SEQ ID NO: 47)

RTVAAPSVFIFPPSDEQLKSGTASVVCLLNNFYPREAKVQWKVDNAL
QSGNSQESVTEQDSKDSTYSLSSTLTLSKADYEKHKVYACEVTHQGL
SSPVTKSFNRGEC

Other antibody heavy and light chain constant regions are well known in the art, e.g., those provided in the IMGT database (www.imgt.org) or at www.vbase2.org/vbstat.php., both of which are incorporated by reference herein.

In some embodiments, the anti-HJV antibody described herein comprises a heavy chain comprising any one of the VH as listed in Table 1 or any variants thereof and a heavy chain constant region that is at least 80%, at least 85%, at least 90%, at east 95%, or at least 99% identical to SEQ ID NO: 46, SEQ ID NO: 48, SEQ ID NO: 112, or SEQ ID NO: 113. In some embodiments, the anti-HJV antibody described herein comprises a heavy chain comprising any one of the VH as listed in Table 1 or any variants thereof and a heavy chain constant region that contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with SEQ ID NO: 46, SEQ ID NO: 48, SEQ ID NO: 112, or EQ ID NO: 113. In some embodiments, the anti-HJV antibody-described herein comprises a heavy chain comprising any one of the VH as listed in Table 1 or any variants thereof and a heavy chain constant region as set forth in SEQ ID NO: 46. In some embodiments, the anti-HJV antibody described herein comprises heavy chain comprising any one of the VH as listed in Table 1 or any variants thereof and a heavy chain constant region as set forth in SEQ ID NO: 48. In some embodiments, the anti-HJV antibody described herein comprises heavy chain comprising any one of the VH as listed in Table 1 or any variants thereof and a heavy chain constant region as set forth in SEQ ID NO: 112. In some embodiments, the anti-HJV antibody described herein comprises heavy chain comprising any one of the VH as listed in Table 1 or any variants thereof and a heavy chain constant region as set forth in SEQ ID NO: 113.

In some embodiments, the anti-HJV antibody described herein comprises a light chain comprising any one of the VL as listed in Table 1 or any variants thereof and a light chain constant region that is at least 80%, at least 85%, at least 90%, at least 95%, or at least 99% identical to SEQ ID NO: 47. In some embodiments, the anti-HJV antibody described herein comprises a light chain comprising any one of the VL as listed in Table 1 or any variants thereof and a light chain constant region contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with SEQ ID NO: 47. In some embodiments, the anti-HJV antibody described herein comprises a light chain comprising any one of the VL as listed in Table 1 or any variants thereof and a light chain constant region set forth in SEQ ID NO: 47.

Examples of IgG heavy chain and light chain amino acid sequences of the anti-HJV antibodies described are provided in Table 1 above.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51, 57, 59, 61, 63, 66, 68, 114, 115, 116, 117, 118, 119 or 120. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 13, 2, or 1 amino acid variation) as compared with the light chain as set forth in any one of SEQ ID NOs: 52, 53, 54, 55, 56, 58, 60, 62, 65, 67 or 69. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51, 57, 59, 61, 63, 66, 68, 114, 115, 116, 117, 118, 119 or 120. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 52, 53, 54, 55, 56, 58, 60, 62, 65, 67 or 69. In some embodiments, the anti-HJV antibody described herein comprises a heavy chain comprising the amino acid sequence of any one of SEQ ID NOs: 51, 57, 59, 61, 63, 66, 68, 114, 115, 116, 117, 118, 119 or 120. Alternatively or in addition, the anti-HJV antibody described herein comprises a light chain comprising the amino acid sequence of any one of SEQ ID NOs: 52, 53, 54, 55, 56, 58, 60, 62, 65, 67 or 69.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid varia ion) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 52. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 52. In some embodiments, the anti- HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 52.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 53. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 53. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 53.

In some embodiments, the anti-HJV antibody of the present disclosure comprises a heavy chain containing no more than 20 amino acid variations (e.g., no ore than 20, 19, 18, 17, 16, 15, 14, 13, 12, 11, 10, 9, 8, 7, 6, 5, 4, 3, 2, or 1 amino acid varia ion) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 54. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 54. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 54.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 51 or 114. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 55. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 55. In some embodiments, the anti-HJV antibody described herein comprises a heavy chain comprising the amino acid sequence of any one of SEQ ID NOs: 51 or 114. Alternatively or in addition, the anti-HJV antibody described herein comprises a light chain comprising the amino acid sequence of any one of SEQ ID NOs: 55.

In some embodiments, the anti-HJV antibody of the present disclosure comprises a heavy chain containing no more than 20 amino acid variations (e.g., no ore than 20, 19, 18, 17, 16, 15, 14, 13, 12, 11, 10, 9, 8, 7, 6, 5, 4, 3, 2, or 1 amino acid varia ion) as compared with the heavy chain as set forth in any one of SEQ ID NOs: 51 or 114. Alternatively or in addition, the anti-HJV antibody of the present disclo- sure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 56. In some embodiments, the anti- HJV antibody described herein comprises a heavy chain comprising an amino acid sequence that is at least 80% (e.g., 80%, 85%, 90%, 95%, 98%, or 99%) identical to any one of SEQ ID N s: 51 or 114. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 56. In some embodiments, the anti-HJV antibody described herein comprises a heavy chain com- prising the amino acid sequence of any one of SEQ ID NOs: 51 or 114. Alternatively or in addition, the anti-HJV anti- body described herein comprises a light chain comprising the amino acid sequence of any one of SEQ ID NOs: 56.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 57 or 115. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 58. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 57 or 115. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 58. In some embodiments, the anti- HJV antibody described herein comprises a heavy chain comprising the amino acid sequence of any one of SEQ ID NOs: 57 or 115. Alternatively or in addition, the anti-HJV antibody described herein comprises a light chain compris- ing the amino acid sequence of any one of SEQ ID NOs: 58.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 59 or 116. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 60. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 59 or 116. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 60. In some embodiments, the anti- HJV antibody described herein comprises a heavy chain comprising the amino acid sequence of any one of SEQ ID NOs: 59 or 116. Alternatively or in addition, the anti-HJV antibody described herein comprises a light chain compris- ing the amino acid sequence of any one of SEQ ID NOs: 60.

In some embodiments, the anti-HJV antibody of the present disclosure comprises a heavy chain containing no more than 20 amino acid variations (e.g., no ore than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 61 or 117. Alternatively or in addition, the anti-HJV antibody of the present disclo- sure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 62. In some embodiments, the anti- HJV antibody described herein comprises a heavy chain comprising an amino acid sequence that is at least 80% (e.g., 80%, 85%, 90%, 95%, 98%, or 99%) identical to any one of SEQ ID NOs: 61 or 117. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 62. In some embodiments, the anti-HJV antibody described herein comprises a heavy chain com- prising the amino acid sequence of any one of SEQ ID NOs: 61 or 117. Alternatively or in addition, the anti-HJV anti- body described herein comprises a light chain comprising the amino acid sequence of any one of SEQ ID NOs: 62.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 63 or 118. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 62. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 63 or 118. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 62. In some embodiments, the anti- HJV antibody described herein comprises a heavy chain comprising the amino acid sequence of any one of SEQ ID NOs: 63 or 118. Alternatively or in addition, the anti-HJV antibody described herein comprises a light chain comprising the amino acid sequence of any one of SEQ ID NOs: 62.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 61 or 117. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 65. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 61 or 117. Alternatively or in addition, the anti-HJV antibody described herein comprises a light chain comprising an amino acid sequence that is at least 80% (e.g., 80%, 85% 90%, 95%, 98%, or 99%) identical to any one of SEQ ID NOs: 65. In some embodiments, the anti-HJV antibody described herein comprises a heavy chain comprising the amino acid sequence of any one of SEQ ID NOs: 61 or 117. Alternatively or in addition, the anti-HJV antibody described herein comprises a light chain comprising the amino acid sequence of any one of SEQ ID NOs: 65.

In some embodiments, the anti-HJV antibody of the present disclosure comprises a heavy chain containing no more than 20 amino acid variations (e.g., no ore than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 66 or 119. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 67. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 66 or 119. Alternatively or in addition, the anti-HJV antibody described herein comprises a light chain comprising an amino acid sequence that is at least 80% (e.g., 80%, 85%, 90%, 95%, 98%, or 99%) identical to any one of SEQ ID NOs: 67. In some embodiments, the anti-HJV antibody described herein comprises a heavy chain comprising the amino acid sequence of any one of SEQ ID NOs: 66 or 119. Alternatively or in addition, the anti-HJV antibody described herein comprises a light chain comprising the amino acid sequence of any one of SEQ ID NOs: 67.

In some embodiments, the anti-HJV antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 68 or 120. Alternatively or in addition, the anti-HJV antibody of the present disclosure comprises a light chain containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in any one of SEQ ID NOs: 69. In some embodiments, the anti-HJV antibody described herein comprises a heavy chain comprising an amino acid sequence that is at least 80% (e.g., 80%, 85%, 90%, 95%, 98%, or 99%) identical to any one of SEQ ID NOs: 68 or 120. Alternatively or in addition, the anti-HJV antibody described herein comprises a light chain comprising an amino acid sequence that is at least 80% (e.g., 80%, 85% 90%, 95%, 98%, or 99%) identical to any one of SEQ ID NOs: 69. In some embodiments, the anti-HJV antibody described herein comprises a heavy chain comprising the amino acid sequence of any one of SEQ ID NOs: 68 or 120. Alternatively or in addition, the anti-HJV antibody described herein comprises a light chain comprising the amino acid sequence of any one of SEQ ID NOs: 69.

The anti-HJV antibodies described herein can be in any antibody form, including, but not limited to, intact (i.e., full-length) antibodies, antigen-binding fragments thereof (such as Fab, F(ab'), F(ab')2, Fv), single chain antibodies, bi-specific antibodies, or nanobodies. In some embodiments, the anti-HJV antibody described herein is a scFv. In some embodiments, the anti-HJV antibody described herein is a scFv-Fab (e.g., scFv fused to a portion of a constant region).

In some embodiments, conservative mutations can be introduced into antibody sequences (e.g., CDRs or framework sequences) at positions where the residues are not likely to be involved in interacting with a target antigen (e.g., hemojuvelin), for example, as determined based on a crystal structure. In some embodiments, one, two or more mutations (e.g., amino acid substitutions) are introduced into the Fc region of an anti-HJV antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutation (i.e., substitutions, insertions or deletions) are introduced into an IgG constant domain, or FcRn-binding fragment thereof (preferably an Fe or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-HJV antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-HJV antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of an anti-HJV antibody described herein can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcγ receptor. This approach is described further in International Publication No. WO 00/42072.

In some embodiments, the heavy and/or light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind hemojuvelin, such that the variant, CDR-grafted, chimeric, humanized, or composite antibody has at least 50%, at least 60%, at least 70%, at least 80%, at least 90%, at least 95% or more binding to hemojuvelin relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

In some embodiments, any one of the anti-HJV antibodies described herein may comprise a signal peptide in the heavy and/or light chain sequence (e.g., a N-terminal signal peptide). In some embodiments, the anti-HJV antibody described herein comprises any one of the VH and VL sequences, any one of the IgG heavy chain and light chain sequences, or any one of the F(ab') heavy chain and light chain sequences described herein, and further comprises a signal peptide (e.g., a N-terminal signal peptide). In some embodiments, the signal peptide comprises the amino acid sequence of MEFGLSWLFLVAILKGVQC (SEQ ID NO: 104).

III. Preparation of the Anti-HJV Antibodies

Antibodies capable of binding hemojuvelin as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., HJV) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies re known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, CA) and HuMAb-Mouse® and TC Mouse™ from Medarex, Inc. (Princeton, NJ) or H2L2 mice from Harbour Antibodies BV (Holland). In another alternative, antibodies may be made recombinantly by phage display or yeast technology. See, for example, U.S. Pat. Nos. 5,565,332; 5,580,717; 5,733, 743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, human HEK293 cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Alternatively, techniques described for the production of single chain antibodies (U.S. Pat. Nos. 4,946,778 and 4,704, 692) can be adapted to produce a phage or yeast scFv library and scFv clones specific to HJV can be identified from the library following routine procedures. Positive clones can be subjected to further screening to identify those that has high HJV binding affinity.

Antibodies obtained following a method known in the art and described herein can be characterized using methods well known in the art. For example, on method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In one example, epitope mapping can be accomplished use H/D-Ex (hydrogen deuterium exchange) coupled with proteolysis and mass spectrometry. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. Alternatively, competition assays can be performed using other antibodies known to bind to the same antigen to determine whether an antibody binds to the same epitope as the other antibodies. Competition assays are well known to those of skill in the art.

In some examples, an anti-HJV antibody is prepared by recombinant technology as exemplified below. Nucleic acids encoding the heavy and light chain of an anti-HJV antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV promoter, and the herpes simplex tk virus promoter.

Regulatable promoters can also be used. Such regulatable promoters include those using the lac repressor from *E. coli* as a transcription modulator to regulate transcription from lac operator bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-555115 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad, among others.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551(1992)] combined the tetracycline repressor (tetR) with the transcription activator (VP 16) to create a tetR-mammalian cell transcription activator fusion protein, tTa (tetR-VP 16), with the tetO bearing minimal promoter derived from the human cytomegalovirus (hCMV) promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells trans-activator or repressor fusion protein, which in some instances can be toxic to cells (Gossen 5 et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art. Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies (e.g., the nucleic acid coding sequence listed in Table 3) may be introduced into suitable host cells for producing the antibodies. Non-limiting examples of the host cells include Chinese hamster ovary (CHO) cells, dhfr– CHO cell, human embryonic kidney (HEK)-293 cells, verda reno (VERO) cells, nonsecreting null (NS0) cells, human embryonic retinal (PER.C6) cells, Sp2/0 cells, baby hamster kidney (BHK) cells, Madin-Darby Canine Kidney (MDCK) cells, Madin-Darby Bovine Kidney (MDBK) cells, and monkey kidney CV1 line transformed by SV40 (COS) cells. In some embodiments, the host cell expressing the anti-HJV antibodies are CHO cells. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody. In some embodiments, the host cell comprises the nucleic acid encoding the heavy chain of the anti-HJV antibody. In some embodiments, the host cell comprises the nucleic acid encoding the light chain of the anti-HJV antibody. In some embodiments, the host cell comprises the nucleic acid encoding the heavy chain and the nucleic acid encoding the light chain.

In some embodiments, methods for preparing an antibody described herein involve a recombinant expression vector that encodes both the heavy chain and the light chain of an anti-HJV antibody, as also described herein. The recombinant expression vector can be introduced into a suitable host cell (e.g., a dhfr– CHO cell) by a conventional method, e.g., calcium phosphate mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-HJV antibody and the other encoding the light chain of the anti-HJV antibody. Both of the two recombinant expression vectors can be introduced into a suitable host cell (e.g., dhfr– CHO cell) by a conventional method, e.g., calcium phosphate-mediated transfection.

Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-HJV antibody as described herein (e.g., as provided in Table 3), vectors (e.g., expression vectors) containing such; and host cells comprising the vectors are within the scope of the present disclosure.

TABLE 3

| Nucleic acids Sequences encoding the VH/VL of anti-HJV antibodies listed in Table 1 | | | |
| --- | --- | --- | --- |
| humanized HA Antibody | | Nucleic Acid Sequences | SEQ ID NO |
| hHA-001 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGC | 70 |
| | VL | GACGTAGTACTGACCCAAAGCCCCCTTTCTCTCCCAGTAACCCTCGGACA ACCAGCCTCAATTTCATGCAGATCATCACAATCACTTGAGACGAGCGACG GAGACACTTTTCTTGAGTGGTTCCAACAAAGACCCGGACAAAGCCCACGC CTGCTTATTTACGAGGTATCAACGAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTTCAAGTCACCCACGACCCC ATGACGTTCGGACAAGGAACTAAGCTCGAAATCAAA | 72 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG | 71 |

TABLE 3-continued

Nucleic acids Sequences encoding the VH/VL of anti-HJV antibodies
listed in Table 1

| humanized HA Antibody | | Nucleic Acid Sequences | SEQ ID NO |
|---|---|---|---|
| | | AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | |
| Light Chain | | GACGTAGTACTGACCCAAAGCCCCCTTTCTCTCCCAGTAACCCTCGGACA<br>ACCAGCCTCAATTTCATGCAGATCATCACAATCACTTGAGACGAGCGACG<br>GAGACACTTTTCTTGAGTGGTTCCAACAAAGACCCGGACAAAGCCCACGC<br>CTGCTTATTTACGAGGTATCAACGAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTTTTCAAGTCACCCACGACCCC<br>ATGACGTTCGGACAAGGAACTAAGCTCGAAATCAAAAGAACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGTTGA | 73 |
| hHA-002 | VH | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAATTGGATTAGACAAGCGCCCGGAAAAGGATTGGAATGGATAGGAATG<br>ATATACTACGATAGCTCAGAAAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGAACA<br>ACACCAGATTATTGGGGTCAAGGACAATGGTAACCGTGTCAAGC | 70 |
| | VL | GACGTAGTACTGACCCAAAGCCCCCTTTCTCTCCCAGTAACCCTCGGACA<br>ACCAGCCTCAATTTCATGCAGATCATCACAATCACTTGAGACGAGCGACG<br>GAGACACTTTTCTTGAGTGGTTCCAACAAAGACCCGGACAAAGCCCACGC<br>CTGCTTATTTACGAGGTATCAAGCAGATTCTCAGGAGTTCCAGACAGATT<br>TTCAGGCAGCGGATCCGGCACAGACTTCACCCTTAAAATTAGCAGAGTAG<br>AAGCAGAAGATGTAGGAGTGTATTATTGTATGCAAGTCACCCACGACCCC<br>CTGACCTTCGGACAAGGAACTAAGCTCGAAATCAAA | 74 |
| | Heavy Chain | GAAGTACAGTTGGTAGAAAGCGGCGGAGGACTTGTGCAGCCAGGTGGATC<br>TCTCAGACTTTCATGTGCCGCAAGCGGTTTTACTTTTAGTAACTATGGAA<br>TGAATTGGATTAGACAAGCGCCCGGAAAAGGATTGGAATGGATAGGAATG<br>ATATACTACGATAGCTCAGAAAAACATTATGCCGACTCAGTTAAAGGAAG<br>ATTTACAATATCAAGAGACAATAGCAAAAACACACTTTATCTTCAAATGA<br>ATTCACTGCGAGCCGAGGATACAGCAGTCTATTATTGCGCAAAAGGAACA<br>ACACCAGATTATTGGGGTCAAGGACAATGGTAACCGTGTCAAGCGCGTC<br>GACCAAGGGCCCATCGGTCTTCCCCCTGGCACCCTCCTCCAAGAGCACCT<br>CTGGGGGCACAGCGGCCCTGGGCTGCCTGGTCAAGGACTACTTCCCCGAA<br>CCGGTGACGGTGTCGTGGAACTCAGGCGCCCTGACCAGCGGCGTGCACAC<br>CTTCCCGGCTGTCCTACAGTCCTCAGGACTCTACTCCCTCAGCAGCGTGG<br>TGACCGTGCCCTCCAGCAGCTTGGGCACCCAGACCTACATCTGCAACGTG<br>AATCACAAGCCCAGCAACACCAAGGTGGACAAGAAAGTTGAGCCCAAATC<br>TTGTGACAAAACTCACACATGCCCACCGTGCCCAGCACCTGAAGCCGCGG<br>GGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGA<br>AGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTA<br>CAAGTGCAAGGTCTCCAACAAAGCCCTCCCAGCCCCCATCGAGAAAACCA<br>TCTCCAAAGCCAAAGGGCAGCCCCGAGAACCACAGGTGTACACCCTGCCC<br>CCATCCCGCGAGGAGATGACCAAGAACCAGGTCAGCCTGACCTGCCTGGT<br>CAAAGGCTTCTATCCCAGCGACATCGCCGTGGAGTGGGAGAGCAATGGGC<br>AGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACT<br>ACACGCAGAAGAGCCTCTCCCTGTCTCCGGGTAAATGA | 71 |
| | Light Chain | GACGTAGTACTGACCCAAAGCCCCCTTTCTCTCCCAGTAACCCTCGGACA<br>ACCAGCCTCAATTTCATGCAGATCATCACAATCACTTGAGACGAGCGACG<br>GAGACACTTTTCTTGAGTGGTTCCAACAAAGACCCGGACAAAGCCCACGC | 75 |

TABLE 3-continued

| | | Nucleic acids Sequences encoding the VH/VL of anti-HJV antibodies listed in Table 1 | |
|---|---|---|---|
| humanized HA Antibody | | Nucleic Acid Sequences | SEQ ID NO |
| | | CTGCTTATTTACGAGGTATCAAGCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTATGCAAGTCACCCACGACCCC CTGACCTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAACACAAAGTCTACGCCTGCGAA GTCACCCATCAGGGCCTGAGCTCGCCCGTCACAAAGAGCTTCAACAGGGG AGAGTGTTGA | |
| hHA-003 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGC | 70 |
| | VL | GACGTAGTACTGACCCAAAGCCCCCTTTCTCTCCCAGTAACCCTCGGACA ACCAGCCTCAATTTCATGCAGATCATCACAATCACTTGAGACCAGCGACG GAGATACTTTTCTTGAGTGGTTCCAACAAAGACCCGGACAAAGCCCACGC CTGCTTATTTACGAGGTATCAAACAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGTCACCCACGACCCC GTCACGTTCGGACAAGGAACTAAGCTCGAAATCAAA | 76 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 71 |
| | Light Chain | GACGTAGTACTGACCCAAAGCCCCCTTTCTCTCCCAGTAACCCTCGGACA ACCAGCCTCAATTTCATGCAGATCATCACAATCACTTGAGACCAGCGACG GAGATACTTTTCTTGAGTGGTTCCAACAAAGACCCGGACAAAGCCCACGC CTGCTTATTTACGAGGTATCAAACAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGTCACCCACGACCCC GTCACGTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAACACAAAGTCTACGCCTGCGAA GTCACCCATCAGGGCCTGAGCTCGCCCGTCACAAAGAGCTTCAACAGGGG AGAGTGTTGA | 77 |
| hHA-004 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG | 70 |

TABLE 3-continued

| | | | |
|---|---|---|---|
| Nucleic acids Sequences encoding the VH/VL of anti-HJV antibodies listed in Table 1 | | | |
| humanized HA Antibody | | Nucleic Acid Sequences | SEQ ID NO |
| | VL | ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGC GACGTAGTACTGACCCAAAGCCCCCTTTCTCTCCCAGTAACCCTCGGACA ACCAGCCTCAATTTCATGCAGATCATCACAATCACTTGAGTCCAGCGACG GAGACACTTTTCTTGAGTGGTTCCAACAAAGACCCGGACAAAGCCCACGC CTGCTTATTTACGATGTATCAACTAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTTCAAGTCACCCATGACCCC GTGACCTTCGGCAAGGAACTAAGCTCGAAATCAAA | 78 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 71 |
| | Light Chain | GACGTAGTACTGACCCAAAGCCCCCTTTCTCTCCCAGTAACCCTCGGACA ACCAGCCTCAATTTCATGCAGATCATCACAATCACTTGAGTCCAGCGACG GAGACACTTTTCTTGAGTGGTTCCAACAAAGACCCGGACAAAGCCCACGC CTGCTTATTTACGATGTATCAACTAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTTCAAGTCACCCATGACCCC GTGACCTTCGGCAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 79 |
| hHA-005 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGC | 70 |
| | VL | GACGTAGTACTGACCCAAAGCCCCCTTTCTCTCCCAGTAACCCTCGGACA ACCAGCCTCAATTTCATGCAGATCATCACAATCACTTGAGGAAAGCGACG GATACACTTTTCTTGAATGGTTCCAACAAAGACCCGGACAAAGCCCACGC CTGCTTATTTACGATGTATCAGAAAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTTCCAAGCGACCTACGACCCC CTCACCTTCGGACAAGGAACTAAGCTCGAAATCAAA | 80 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAATTGGATTAGACAAGCGCCCGGAAAAGGATTGGAATGGATAGGAATG ATATACTACGATAGCTCAGAAAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGAACA ACACCAGATTATTGGGGTCAAGGAACAATGGTAACCGTGTCAAGCGCGTC GACCAAGGGCCCATCGGTCTTCCCCCTGGCACCCTCCTCCAAGAGCACCT | 71 |

TABLE 3-continued

Nucleic acids Sequences encoding the VH/VL of anti-HJV antibodies
listed in Table 1

| humanized HA Antibody | | Nucleic Acid Sequences | SEQ ID NO |
|---|---|---|---|
| | | CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | |
| Light Chain | | GACGTAGTACTGACCCAAAGCCCCCTTTCTCTCCCAGTAACCCTCGGACA ACCAGCCTCAATTTCATGCAGATCATCACAATCACTTGAGGAAAGCGACG GATACACTTTTCTTGAATGGTTCCAACAAAGACCCGGACAAAGCCCACGC CTGCTTATTTACGATGTATCAGAAAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCGACCTACGACCCC CTCACCTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 81 |
| hHA-006 | VH | GAAGTACAGTTGGTAGAAAGCGGCGGAGGACTTGTGCAGCCAGGTGGATC TCTCAGACTTTCATGTGCCGCAAGCGGTTTTACTTTTAGTTACTATGGAA TGAACTGGATTAGACAAGCGCCCGGAAAAGGATTGGAATGGATAGGCATG ATATACTACGACAGCTCGGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGGACG ACGCCCGATTACTGGGGTCAAGGAACAATGGTAACCGTGTCAAGC | 82 |
| | VL | GACGTAGTACTGACCCAAAGCCCCCTTTCTCTCCCAGTAACCCTCGGACA ACCAGCCTCAATTTCATGCAGATCATCACAATCACTTGAGGACAGCGACG GAGGAACTTTTCTTGAGTGGTTCCAACAAAGACCCGGACAAAGCCCACGC CTGCTTATTTACGACGTATCAAGCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTTCAAGCGACCCACGACCCC CTGACGTTCGGACAAGGAACTAAGCTCGAAATCAAA | 83 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTTACTATGGAA TGAACTGGATTAGACAAGCGCCCGGAAAAGGATTGGAATGGATAGGCATG ATATACTACGACAGCTCGGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGGACG ACGCCCGATTACTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC | 84 |

TABLE 3-continued

Nucleic acids Sequences encoding the VH/VL of anti-HJV antibodies
listed in Table 1

| humanized HA Antibody | | Nucleic Acid Sequences | SEQ ID NO |
|---|---|---|---|
| | Light Chain | AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA GACGTAGTACTGACCCAAAGCCCCCTTTCTCTCCCAGTAACCCTCGGACA ACCAGCCTCAATTTCATGCAGATCATCACAATCACTTGAGGACAGCGACG GAGGAACTTTTCTTGAGTGGTTCCAACAAAGACCCGGACAAAGCCCACGC CTGCTTATTTACGACGTATCAAGCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTTCAAGCGACCCACGACCCC CTGACGTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 85 |
| hHA-007 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGATAAGACAAGCGCCCGGAAAAGGATTGGAATGGATAGGCATG ATATACTACGACAGCTCGGACAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGGACG ACGCCGGATGTATGGGGTCAAGGAACAATGGTAACCGTGTCAAGC | 86 |
| | VL | GACGTAGTACTGACCCAAAGCCCCCTTTCTCTCCCAGTAACCCTCGGACA ACCAGCCTCAATTTCATGCAGATCATCACAATCACTTGAAGAGAGCGACG GATACACTTTTCTTCATTGGTTCCAACAAAGACCCGGACAAAGCCCACGC CTGCTTATTTACGAGGTATCAAACAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCACGACCCC GTGACGTTCGGACAAGGAACTAAGCTCGAAATCAAA | 87 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGATAAGACAAGCGCCCGGAAAAGGATTGGAATGGATAGGCATG ATATACTACGACAGCTCGGACAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGGACG ACGCCGGATGTATGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 88 |
| | Light Chain | GACGTAGTACTGACCCAAAGCCCCCTTTCTCTCCCAGTAACCCTCGGACA ACCAGCCTCAATTTCATGCAGATCATCACAATCACTTGAAGAGAGCGACG GATACACTTTTCTTCATTGGTTCCAACAAAGACCCGGACAAAGCCCACGC CTGCTTATTTACGAGGTATCAAACAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCACGACCCC GTGACGTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 89 |

TABLE 3-continued

Nucleic acids Sequences encoding the VH/VL of anti-HJV antibodies
listed in Table 1

| humanized HA Antibody | | Nucleic Acid Sequences | SEQ ID NO |
|---|---|---|---|
| hHA-008 | VH | GAAGTACAGTTGGTAGAAAGCGGCGGAGGACTTGTGCAACCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG ATATATTACGACAGCTCGGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGGACC ACCCCCGATTACTGGGGTCAAGGAACAATGGTAACCGTGTCAAGC | 90 |
| | VL | GACGTAGTACTGACCCAAAGCCCCCTTTCTCTCCCAGTAACCCTCGGACA ACCAGCCTCAATTTCATGCAGATCATCACAATCACTTGAAGAAAGCGACG GATACACTTTTCTTCACTGGTTCCAACAAAGACCCGGACAAAGCCCACGC CTGCTTATTTACGAGGTATCAACCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCACGACCCC CTGACCTTCGGACAAGGAACTAAGCTCGAAATCAAA | 91 |
| | Heavy Chain | GAAGTACAGTTGGTAGAAAGCGGCGGAGGACTTGTGCAACCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG ATATATTACGACAGCTCGGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGGACC ACCCCCGATTACTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 92 |
| | Light Chain | GACGTAGTACTGACCCAAAGCCCCCTTTCTCTCCCAGTAACCCTCGGACA ACCAGCCTCAATTTCATGCAGATCATCACAATCACTTGAAGAAAGCGACG GATACACTTTTCTTCACTGGTTCCAACAAAGACCCGGACAAAGCCCACGC CTGCTTATTTACGAGGTATCAACCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCACGACCCC CTGACCTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 93 |
| hHA-008-QL | VH | GAAGTACAGTTGGTAGAAAGCGGCGGAGGACTTGTGCAACCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG ATATATTACGACAGCTCGGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGGACC ACCCCCGATTACTGGGGTCAAGGAACAATGGTAACCGTGTCAAGC | 90 |
| | VL | GACGTAGTACTGACCCAAAGCCCCCTTTCTCTCCCAGTAACCCTCGGACA ACCAGCCTCAATTTCATGCAGATCATCACAATCACTTGAAGAAAGCGACG GATACACTTTTCTTCACTGGTTCCAACAAAGACCCGGACAAAGCCCACGC CTGCTTATTTACGAGGTATCAACCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCACGACCCC CTGACCTTCGGACAAGGAACTAAGCTCGAAATCAAA | 91 |
| | Heavy Chain | GAAGTACAGTTGGTAGAAAGCGGCGGAGGACTTGTGCAACCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG | 94 |

TABLE 3-continued

Nucleic acids Sequences encoding the VH/VL of anti-HJV antibodies
listed in Table 1

| humanized HA Antibody | | Nucleic Acid Sequences | SEQ ID NO |
|---|---|---|---|
| | | ATATATTACGACAGCTCGGAGAAACATTATGCCGACTCAGTTAAAGGAAG | |
| | | ATTTACAATATCAAGAGACAATAGCAAAAACACACTTTATCTTCAAATGA | |
| | | ATTCACTGCGAGCCGAGGATACAGCAGTCTATTATTGCGCAAAAGGGACC | |
| | | ACCCCCGATTACTGGGGTCAAGGAACAATGGTAACCGTGTCAAGCGCGTC | |
| | | GACCAAGGGCCCATCGGTCTTCCCCCTGGCACCCTCCTCCAAGAGCACCT | |
| | | CTGGGGGCACAGCGGCCCTGGGCTGCCTGGTCAAGGACTACTTCCCCGAA | |
| | | CCGGTGACGGTGTCGTGGAACTCAGGCGCCCTGACCAGCGGCGTGCACAC | |
| | | CTTCCCGGCTGTCCTACAGTCCTCAGGACTCTACTCCCTCAGCAGCGTGG | |
| | | TGACCGTGCCCTCCAGCAGCTTGGGCACCCAGACCTACATCTGCAACGTG | |
| | | AATCACAAGCCCAGCAACACCAAGGTGGACAAGAAAGTTGAGCCCAAATC | |
| | | TTGTGACAAAACTCACACATGCCCACCGTGCCCAGCACCTGAAGCCGCGG | |
| | | GGGGACCGTCAGTCTTCCTCTTCCCCCCAAAACCCAAGGACCAACTCATG | |
| | | ATCTCCCGGACCCCTGAGGTCACATGCGTGGTGGTGGACGTGAGCCACGA | |
| | | AGACCCTGAGGTCAAGTTCAACTGGTACGTGGACGGCGTGGAGGTGCATA | |
| | | ATGCCAAGACAAAGCCGCGGGAGGAGCAGTACAACAGCACGTACCGTGTG | |
| | | GTCAGCGTCCTCACCGTCCTGCACCAGGACTGGCTGAATGGCAAGGAGTA | |
| | | CAAGTGCAAGGTCTCCAACAAAGCCCTCCCAGCCCCCATCGAGAAAACCA | |
| | | TCTCCAAAGCCAAAGGGCAGCCCCGAGAACCACAGGTGTACACCCTGCCC | |
| | | CCATCCCGCGAGGAGATGACCAAGAACCAGGTCAGCCTGACCTGCCTGGT | |
| | | CAAAGGCTTCTATCCCAGCGACATCGCCGTGGAGTGGGAGAGCAATGGGC | |
| | | AGCCGGAGAACAACTACAAGACCACGCCTCCCGTGCTGGACTCCGACGGC | |
| | | TCCTTCTTCCTCTACAGCAAGCTCACCGTGGACAAGAGCAGGTGGCAGCA | |
| | | GGGGAACGTCTTCTCATGCTCCGTGCTGCATGAGGCTCTGCACAACCACT | |
| | | ACACGCAGAAGAGCCTCTCCCTGTCTCCGGGTAAATGA | |
| | Light Chain | GACGTAGTACTGACCCAAAGCCCCCTTTCTCTCCCAGTAACCCTCGGACA | 93 |
| | | ACCAGCCTCAATTTCATGCAGATCATCACAATCACTTGAAGAAAGCGACG | |
| | | GATACACTTTTCTTCACTGGTTCCAACAAAGACCCGGACAAAGCCCACGC | |
| | | CTGCTTATTTACGAGGTATCAACCAGATTCTCAGGAGTTCCAGACAGATT | |
| | | TTCAGGCAGCGGATCCGGCACAGACTTCACCCTTAAAATTAGCAGAGTAG | |
| | | AAGCAGAAGATGTAGGAGTGTATTATTGTTTCCAAGCCACCCACGACCCC | |
| | | CTGACCTTCGGACAAGGAACTAAGCTCGAAATCAAAAGAACGGTGGCTGC | |
| | | ACCATCTGTCTTCATCTTCCCGCCATCTGATGAGCAGTTGAAATCTGGAA | |
| | | CTGCCTCTGTTGTGTGCCTGCTGAATAACTTCTATCCCAGAGAGGCCAAA | |
| | | GTACAGTGGAAGGTGGATAACGCCCTCCAATCGGGTAACTCCCAGGAGAG | |
| | | TGTCACAGAGCAGGACAGCAAGGACAGCACCTACAGCCTCAGCAGCACCC | |
| | | TGACGCTGAGCAAAGCAGACTACGAGAACACAAAGTCTACGCCTGCGAA | |
| | | GTCACCCATCAGGGCCTGAGCTCGCCCGTCACAAAGAGCTTCAACAGGGG | |
| | | AGAGTGTTGA | |
| hHA-009 | VH | GAAGTACAGTTGGTAGAAAGCGGCGGAGGACTTGTGCAACCAGGTGGATC | 90 |
| | | TCTCAGACTTTCATGTGCCGCAAGCGGTTTTACTTTTAGTAACTATGGAA | |
| | | TGAACTGGGTTAGACAAGCGCCCGGAAAAGGATTGGAATGGATAGGCATG | |
| | | ATATATTACGACAGCTCGGAGAAACATTATGCCGACTCAGTTAAAGGAAG | |
| | | ATTTACAATATCAAGAGACAATAGCAAAAACACACTTTATCTTCAAATGA | |
| | | ATTCACTGCGAGCCGAGGATACAGCAGTCTATTATTGCGCAAAAGGGACC | |
| | | ACCCCCGATTACTGGGGTCAAGGAACAATGGTAACCGTGTCAAGC | |
| | VL | GACGTAGTACTGACCCAAAGCCCCCTTTCTCTCCCAGTAACCCTCGGACA | 95 |
| | | ACCAGCCTCAATTTCATGCAGATCATCACAATCACTTGCGGACAGCGACG | |
| | | GAGATACTTTTCTTCACTGGTTCCAACAAAGACCCGGACAAAGCCCACGC | |
| | | CTGCTTATTTACGCGGTATCACACAGATTCTCAGGAGTTCCAGACAGATT | |
| | | TTCAGGCAGCGGATCCGGCACAGACTTCACCCTTAAAATTAGCAGAGTAG | |
| | | AAGCAGAAGATGTAGGAGTGTATTATTGTTTCCAAGCCACCCATGACCCC | |
| | | GTCACGTTCGGACAAGGAACTAAGCTCGAAATCAAA | |
| | Heavy Chain | GAAGTACAGTTGGTAGAAAGCGGCGGAGGACTTGTGCAACCAGGTGGATC | 92 |
| | | TCTCAGACTTTCATGTGCCGCAAGCGGTTTTACTTTTAGTAACTATGGAA | |
| | | TGAACTGGGTTAGACAAGCGCCCGGAAAAGGATTGGAATGGATAGGCATG | |
| | | ATATATTACGACAGCTCGGAGAAACATTATGCCGACTCAGTTAAAGGAAG | |
| | | ATTTACAATATCAAGAGACAATAGCAAAAACACACTTTATCTTCAAATGA | |
| | | ATTCACTGCGAGCCGAGGATACAGCAGTCTATTATTGCGCAAAAGGGACC | |
| | | ACCCCCGATTACTGGGGTCAAGGAACAATGGTAACCGTGTCAAGCGCGTC | |
| | | GACCAAGGGCCCATCGGTCTTCCCCCTGGCACCCTCCTCCAAGAGCACCT | |
| | | CTGGGGGCACAGCGGCCCTGGGCTGCCTGGTCAAGGACTACTTCCCCGAA | |
| | | CCGGTGACGGTGTCGTGGAACTCAGGCGCCCTGACCAGCGGCGTGCACAC | |
| | | CTTCCCGGCTGTCCTACAGTCCTCAGGACTCTACTCCCTCAGCAGCGTGG | |
| | | TGACCGTGCCCTCCAGCAGCTTGGGCACCCAGACCTACATCTGCAACGTG | |
| | | AATCACAAGCCCAGCAACACCAAGGTGGACAAGAAAGTTGAGCCCAAATC | |
| | | TTGTGACAAAACTCACACATGCCCACCGTGCCCAGCACCTGAAGCCGCGG | |
| | | GGGGACCGTCAGTCTTCCTCTTCCCCCCAAAACCCAAGGACACCCTCATG | |
| | | ATCTCCCGGACCCCTGAGGTCACATGCGTGGTGGTGGACGGCGTGGAGGTGCATA | |
| | | AGACCCTGAGGTCAAGTTCAACTGGTACGTGGACGGCGTGGAGGTGCATA | |
| | | ATGCCAAGACAAAGCCGCGGGAGGAGCAGTACAACAGCACGTACCGTGTG | |
| | | GTCAGCGTCCTCACCGTCCTGCACCAGGACTGGCTGAATGGCAAGGAGTA | |
| | | CAAGTGCAAGGTCTCCAACAAAGCCCTCCCAGCCCCCATCGAGAAAACCA | |
| | | TCTCCAAAGCCAAAGGGCAGCCCCGAGAACCACAGGTGTACACCCTGCCC | |

TABLE 3-continued

Nucleic acids Sequences encoding the VH/VL of anti-HJV antibodies
listed in Table 1

| humanized HA Antibody | | Nucleic Acid Sequences | SEQ ID NO |
|---|---|---|---|
| | Light Chain | CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | |
| | Light Chain | GACGTAGTACTGACCCAAAGCCCCCTTTCTCTCCCAGTAACCCTCGGACA ACCAGCCTCAATTTCATGCAGATCATCACAATCACTTGCGGACAGCGACG GAGATACTTTTCTTCACTGGTTCCAACAAAGACCCGGACAAAGCCCACGC CTGCTTATTTACGCGGTATCACACAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCATGACCCC GTCACGTTCGGACAAGGAACTAAGCTCGAAATCAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 96 |
| hHA-010 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG ATATACTACGACAGCTCCGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGCACG ACGCCCGATAAATGGGGTCAAGGAACAATGGTAACCGTGTCAAGC | 97 |
| | VL | GACGTAGTACTGACCCAAAGCCCCCTTTCTCTCCCAGTAACCCTCGGACA ACCAGCCTCAATTTCATGCAGATCATCACAATCACTTGAGGAGAGCGACG GATACACTTTTCTTGAGTGGTTCCAACAAAGACCCGGACAAAGCCCACGC CTGCTTATTTACGAGGTATCACATAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCGACCCACGACCCC CTGACGTTCGGACAAGGAACTAAGCTCGAAATCAAA | 98 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGCATG ATATACTACGACAGCTCCGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGCACG ACGCCCGATAAATGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 99 |
| | Light Chain | GACGTAGTACTGACCCAAAGCCCCCTTTCTCTCCCAGTAACCCTCGGACA ACCAGCCTCAATTTCATGCAGATCATCACAATCACTTGAGGAGAGCGACG GATACACTTTTCTTGAGTGGTTCCAACAAAGACCCGGACAAAGCCCACGC CTGCTTATTTACGAGGTATCACATAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCGACCCACGACCCC CTGACGTTCGGACAAGGAACTAAGCTCGAAATCAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA | 100 |

TABLE 3-continued

Nucleic acids Sequences encoding the VH/VL of anti-HJV antibodies
listed in Table 1

| humanized HA Antibody | | Nucleic Acid Sequences | SEQ ID NO |
|---|---|---|---|
| | | GTCACCCATCAGGGCCTGAGCTCGCCCGTCACAAAGAGCTTCAACAGGGG AGAGTGTTGA | |
| hHA-011 | VH | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGAATG ATATACTACGACAGCTCCGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGCTCG ACCCCCGATTACTGGGGTCAAGGAACAATGGTAACCGTGTCAAGC | 101 |
| | VL | GACGTAGTACTGACCCAAAGCCCCCTTTCTCTCCCAGTAACCCTCGGACA ACCAGCCTCAATTTCATGCAGATCATCACAATCACTTGAGGACAGCGACG GAGGCACTTTTCTTGAGTGGTTCCAACAAAGACCCGGACAAAGCCCACGC CTGCTTATTTACGACGTATCAAGCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCACGACCCC CTCAGCTTCGGACAAGGAACTAAGCTCGAAATCAAA | 102 |
| | Heavy Chain | GAAGTACAGTTGGTAGAAAGCGGCGGAGGACTTGTGCAGCCAGGTGGATC TCTCAGACTTTCATGTGCCGCAAGCGGTTTTACTTTTAGTAACTATGGAA TGAACTGGGTTAGACAAGCGCCCGGAAAAGGATTGGAATGGATAGGAATG ATATACTACGACAGCTCCGAGAAACATTATGCCGACTCAGTTAAAGGAAG ATTTACAATATCAAGAGACAATAGCAAAAACACACTTTATCTTCAAATGA ATTCACTGCGAGCCGAGGATACAGCAGTCTATTATTGCGCAAAAGGCTCG ACCCCCGATTACTGGGGTCAAGGAACAATGGTAACCGTGTCAAGCGCGTC GACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAA CCGGTGACGGTGTCGTGGAACTCAGGCGCCCTGACCAGCGGCGTGCACAC CTTCCCGGCTGTCCTACAGTCCTCAGGACTCTACTCCCTCAGCAGCGTGG TGACCGTGCCCTCCAGCAGCTTGGGCACCCAGACCTACATCTGCAACGTG AATCACAAGCCCAGCAACACCAAGGTGGACAAGAAAGTTGAGCCCAAATC TTGTGACAAAACTCACACATGCCCACCGTGCCCAGCACCTGAAGCCGCGG GGGGACCGTCAGTCTTCCTCTTCCCCCCAAAACCCAAGGACACCCTCATG ATCTCCCGGACCCCTGAGGTCACATGCGTGGTGGTGGACGTGAGCCACGA AGACCCTGAGGTCAAGTTCAACTGGTACGTGGACGGCGTGGAGGTGCATA ATGCCAAGACAAAGCCGCGGGAGGAGCAGTACAACAGCACGTACCGTGTG GTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCA TCTCCAAAGCCAAAGGGCAGCCCCGAGAACCACAGGTGTACACCCTGCCC CCATCCCGCGAGGAGATGACCAAGAACCAGGTCAGCCTGACCTGCCTGGT CAAAGGCTTCTATCCCAGCGACATCGCCGTGGAGTGGGAGAGCAATGGGC AGCCGGAGAACAACTACAAGACCACGCCTCCCGTGCTGGACTCCGACGGC TCCTTCTTCCTCTACAGCAAGCTCACCGTGGACAAGAGCAGGTGGCAGCA GGGGAACGTCTTCTCATGCTCCGTGATGCATGAGGCTCTGCACAACCACT ACACGCAGAAGAGCCTCTCCCTGTCTCCGGGTAAATGA | 40 |
| | Light Chain | GACGTAGTACTGACCCAAAGCCCCCTTTCTCTCCCAGTAACCCTCGGACA ACCAGCCTCAATTTCATGCAGATCATCACAATCACTTGAGGACAGCGACG GAGGCACTTTTCTTGAGTGGTTCCAACAAAGACCCGGACAAAGCCCACGC CTGCTTATTTACGACGTATCAAGCAGATTCTCAGGAGTTCCAGACAGATT TTCAGGCAGCGGATCCGGCACAGACTTCACCCTTAAAATTAGCAGAGTAG AAGCAGAAGATGTAGGAGTGTATTATTGTTTCCAAGCCACCCACGACCCC CTCAGCTTCGGACAAGGAACTAAGCTCGAAATCAAAAGAACGGTGGCTGC ACCATCTGTCTTCATCTTCCCGCCATCTGATGAGCAGTTGAAATCTGGAA CTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAG TGTCACAGAGCAGGACAGCAAGGACAGCACCTACAGCCTCAGCAGCACCC TGACGCTGAGCAAAGCAGACTACGAGAAACACAAAGTCTACGCCTGCGAA GTCACCCATCAGGGCCTGAGCTCGCCCGTCACAAAGAGCTTCAACAGGGG AGAGTGTTGA | 64 |

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 75.

In some embodiments, the anti-HJV described herein is produced by expressing (i) a nucleic acid at least 60% (e.g., 60%, 65%, 70%, 75%, 80%, 85%, 909, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 77.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 79.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 71, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 81.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 84, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 85.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 88, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 89.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 92, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 93.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 94, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 93.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 92, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 96.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 99, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 100.

In some embodiments, the anti-HJV described herein is produced by expressing (i) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 40, and/or (ii) a nucleic acid at least 60% (e.g., 60%, 65%, 70%, 75%, 80%, 85%, 90%, 91%, 92%, 93%, 94%, 95%, 96%, 97%, 98%, 99%, or 100%) identical to SEQ ID NO: 64.

In some embodiments, the anti-HJV antibodies described herein can be used for delivering a molecular payload to a target cell or a target tissue (e.g., a cell or tissue that expresses HJV). Accordingly, the anti-HJV antibody described herein can be linked to a molecular payload. The complexes described herein may be used in various applications, e.g., diagnostic or therapeutic applications.

In some embodiments, the complex described herein is used to modulate the activity or function of at least one gene, protein, and/or nucleic acid. In some embodiments, the molecular payload is responsible for the modulation of a gene, protein, and/or nucleic acids. A molecular payload may be a small molecule, protein, nucleic acid, oligonucleotide, or any molecular entity capable of modulating the activity or function of a gene, protein, and/or nucleic acid in a cell. In some embodiments, a molecular payload is an oligonucleotide that targets a disease-associated repeat in muscle cells.

IV. Pharmaceutical Composition

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The anti-HJV antibody containing pharmaceutical composition disclosed herein may further comprise a suitable buffer agent. A buffer agent is a weak acid or base used to maintain the pH of a solution near a chosen value after the addition of another acid or base. In some examples, the buffer agent disclosed herein can be a buffer agent capable of maintaining physiological pH despite changes in carbon dioxide concentration (produced by cellular respiration). Exemplary buffer agents include, but are not limited to a HEPES (4-(2-hydroxyethyl)-1-piperazineethanesulfonic acid) buffer, Dulbecco's phosphate-buffered saline (DPBS) buffer, or Phosphate-buffered Saline (PBS) buffer. Such buffers may comprise disodium hydrogen phosphate and sodium chloride, or potassium dihydrogen phosphate and potassium chloride.

In some embodiments, the buffer agent in the pharmaceutical composition described herein may maintain a pH value of about 5-8. For example, the pH of the pharmaceutical composition can be about 7.1, 7.2, 7.3, 7.4, 7.5, 7.6, 7.7, 7.8, 7.9, or 8.0. In other examples, the pharmaceutical composition may have a pH value lower than 7, for example, about 7, 6.8, 6.5, 6.3, 6, 5.8, 5.5, 5.3, or 5.

The pharmaceutical composition described herein comprises one or more suitable salts. A salt is an ionic compound that can be formed by the neutralization reaction of an acid and a base. (Skoog, D. A; West, D. M.; Holler, J. F.; Crouch, S. R. (2004) "chapters 14-16". Fundamentals of Analytical Chemistry (8th ed.)). Salts are composed of related numbers of cations (positively charged ions) and anions (negative ions) so that the product is electrically neutral (without a net charge).

In some embodiments, the pharmaceutical compositions can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). In some embodiments, the pharmaceutical composition can be formulated for intravenous injection. In some embodiments, the pharmaceutical composition can be formulated for subcutaneous injection.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous or subcutaneous solution bag or vial having a stopper pierceable by a hypodermic injection needle.

V. Methods of Use

Aspects of the disclosure relate to compositions and methods for treating ACD and/or one or more conditions arising as a result of ACD in a subject.

In some aspects, the disclosure relates to compositions and methods for treating ACD in a subject. In some embodiments, a subject to be treated in accordance with the disclosure may be identified based on an appropriate diagnostic methodology, as described, for example, in Cullis, J O, *Diagnosis and management of anaemia of chronic disease: current status* British Journal of Haematology, Volume 154, Issue 3, August 2011 pages 289-300; and Madua A J and Ughasoro M D, *Anaemia of Chronic Disease: An In-Depth Review* Med Princ Pract. 2017 January; 26(1): 1-9, the contents of each of which are incorporated herein by reference. Typically, diagnosis involves an evaluation of signs and symptoms of the underlying chronic condition combined with an assessment of indicia of anemia and/or defects in iron metabolism, including, for example, through an analysis of complete blood count (CBC), serum iron, ferritin, transferrin, reticulocyte count, and other markers. In some embodiments, ACD may be present in subjects having microcytic or normocytic anemia who also have chronic conditions such as an infection, autoimmune disease, chronic kidney disease or cancer, e.g., myeloma.

In some embodiments, a subject in need of treatment in accordance with the disclosure may be identified based on a reduced EPO production. For example, under normal physiological conditions, levels of EPO are inversely correlated with hemoglobin levels and tissue oxygenation, but in chronic inflammatory conditions the EPO response is blunted, leading to inadequate levels of EPO for the degree of anemia, and this is thought to be mediated via inflammatory cytokines such as IL-1 and tumor necrosis factor-α (TNF-α). Accordingly, in some embodiments, a blunted EPO response may be diagnostic of ACD in a subject.

In some embodiments, a subject in need of treatment in accordance with the disclosure may be identified based on a reduced erythroid responsiveness. For example, ACD may be characterized by a reduced proliferation and differentiation of erythroid progenitor cells. It has been shown that macrophages from patients with ACD suppress colony formation in vitro due to inhibitory effects of inflammatory cytokines (e.g., interferon-γ) on growth of erythroid burst-forming units (BFU-E) and erythroid colony-forming units (CFU-E), and that this effect could be overcome by addition of high concentrations of EPO to the culture systems. It has also been shown that bone marrow cultures from patients with active rheumatoid arthritis showed defective growth when compared to normal controls, and that there was an inverse correlation between colony growth and levels of TNF-α in the culture supernatant. Moreover, these effects were reversed both in vitro and in vivo following treatment with infliximab, an antibody against TNF-α. Accordingly, in some embodiments, a reduced erythroid responsiveness in a subject can be identified using these or similar such assays for evaluating erythroid responsiveness.

In some embodiments, a subject in need of treatment in accordance with the disclosure may be identified based on an anemic state that is mild to moderate and/or normochromic and normocytic (although anemia may become microcytic as disease progresses). In some embodiments, a subject is identified based on a low reticulocyte count, which may be indicative of the hypoproliferative nature of ACD in the subject. Inflammation in a subject may be inferred from other features of the blood count, such as neutrophilia, monocytosis or thrombocytosis, and through measurement of non-specific inflammatory markers, such as C-reactive protein (CRP) or erythrocyte sedimentation rate (ESR).

In some embodiments, a subject in need of treatment in accordance with the disclosure may be identified based on the presence or absence of iron-deficiency anemia (IDA) in the subject. In some embodiments, a subject is identified by exclusion of IDA in the subject, although ACD and IDA can co-exist. Typically, serum iron and transferrin saturation are both decreased in ACD and iron deficiency, indicating limited iron supply to the erythron, but transferrin levels are increased in IDA, whereas in ACD they are normal or decreased. Accordingly, in some embodiments, the subject is identified by an assessment of iron stores in a biological sample of the subject, e.g., using a Perl's stain ed bone marrow aspirate.

In some embodiments, a subject is identified by determining level of growth differentiation factor 15 (GDF15) in the subject. GDF15 is an erythropoiesis-derived hormone that is markedly increased in β-thalassemia and congenital dyserythropoietic anemia, and inhibits hepcidin expression, contributing to the iron overload seen in these anemias. Levels of GDF15 have been studied in patients with ACD, ACD/IDA and IDA. Subjects with both ACD and ACD/IDA showed significantly higher levels of GDF15 than patients with IDA, and GDF15 concentrations correlated with interleukin-1β, suggesting that inflammation induces GDF15 expression. Accordingly, in some embodiments, the subject is identified based on an increased level of GDF15 (e.g., increased as compared to a subject known to have IDA or a healthy subject).

In some embodiments, a subject is identified by determining a ratio of serum transferrin receptor (sTFR) to ferritin. The measurement of sTFR, the truncated fragment of the membrane receptor, has been described as an indicator for differentiating between ACD and IDA in a subject. The transferrin receptor is found on virtually all ells in the body, but is present at high levels on erythroid progenitors. sTFR levels increase in IDA as the availability of iron for erythropoiesis decreases, whereas in ACD levels may not differ from steady state because transferrin receptor expression is negatively affected by inflammatory cytokines. The ratio of sTFR to the log of the serum ferritin may be used in the diagnosis of ACD in a subject, and in some cases may be used for differentiating ACD from IDA. A ratio of less than 1 makes ACD likely, whereas ratios of greater than 2 suggest that iron stores are deficient, with or without ACD.

In some embodiments, anemia of chronic diseases (ACD) is caused by ineffective erythropoiesis due to various chronic conditions (e.g., cancer, inflammation, chronic kidney diseases, autoimmune diseases, etc) and deficiencies in iron metabolism, increased destruction of red blood cell due to splenomegaly, increased plasma volume, abnormal pro-inflammatory environment, or a combination thereof.

In some embodiments, ACD is associated with abnormal iron metabolism. In some embodiments, the abnormal iron metabolism in ACD patients is functional iron deficiency (FID). FID represents a state of iron-restricted erythropoiesis characterized by an imbalance between iron demand and serum iron that is readily available for effective erythropoiesis. In FID, even when the body has adequate or increased systemic iron stores, iron is sequestered and not available for erythropoiesis. In some embodiments, FID is caused by an increase of hepcidin relative to the iron store levels. In some embodiments, increased hepcidin expression is caused by upregulation of pro-inflammatory cytokines.

In ACD, pro-inflammatory cytokines that induce hepcidin synthesis, such as IL-6 and oncostatin-M, are typically increased and associated with iron sequestration, macrophage iron loading, as well as myeloid proliferation and macrophage activation. These increased hepcidin levels may lead to anemia.

In some embodiments, the pro-inflammatory cytokine is IL-6. Normal range of IL-6 (e.g., in subjects without disease) is equal or less than 1.8 pg/ml. In some embodiments, the subject has a higher-than-normal serum IL-6 levels, e.g., greater than 1.8 pg/ml.

In some embodiments, the present disclosure provides a method of treating a subject having ACD. In some embodiments, the subject has anemia resulting from hepcidin synthesis that is induced by pro-inflammatory cytokines. In some embodiments, the pro-inflammatory cytokine that increases hepcidin synthesis is IL-6. In some embodiments, administration of the anti-HJV antibody to the subject reduces hepcidin synthesis induced by IL-6. In some embodiments, the administration of the anti-HJV antibody ameliorates FID associated with increased hepcidin synthesis induced by proinflammatory cytokines (e.g., IL-6). In some embodiments, a subject in need of treatment in accordance with the disclosure may be identified using red cell indices. For example, the reticulocyte hemoglobin content (CHr) and the percentage hypochromic red cells (% HYPO) can provide information about iron supply to the erythron, and may be useful in guiding the management of ACD. CHr is a measure of hemoglobin in the most recently formed erythrocytes, while the % HYPO indicates the percentage of cells with hemoglobin content of <280 g/l. The former gives a relatively acute evaluation of recent bone marrow activity (e.g., 48 hours), whereas the latter gives a time-averaged picture (e.g., 20-120 days). Similar indices can be reported by the Sysmex XE-2100 analyser (Sysmex, Mundelein, IL, USA), which derives RET-Y (equivalent to CHr) and RBC-Y (equivalent to HYPO %). CHr has been shown to be a useful tool in the detection of early iron deficiency, as well as in monitoring early response to iron therapy.

In some aspects, the disclosure relates to compositions and methods for treating ACD. The ACD may be characterized as a mild to moderate anemia or a severe anemia in accordance with appropriate diagnostic threshold parameters. For example, in some embodiments, the ACD is characterized based on a level of hemoglobin (Hgb), wherein the severity of the anemia increases with decreasing levels of Hgb. In some embodiments, mild to moderate anemia is associated with Hgb levels of at least 8 g/dL and less than the lower limit of normal (e.g., between about 8 and about 14 g/dL, between about 8 and about 12 g/dL, between about 8 and about 10 g/dL, between about 10 and about 14 g/dL, or between about 10 and about 12 g/dL). In some embodiments, severe anemia is associated with Hgb levels of about 8 g/dL or lower (e.g., between about 2 and about 8 g/dL, between about 4 and about 8 g/dL, or between about 6 and about 8 g/dL). In some embodiments, severe anemia is associated with erythrocyte-transfusion dependence. In some embodiments, severe anemia is associated with erythrocyte-transfusion independence resulting from a therapeutic intervention (e.g., therapeutic reversal of a transfusion dependent state), where a subject is dependent upon ongoing therapeutic treatment to maintain transfusion independence.

In some aspects, the disclosure provides compositions and methods for treating a subject that is known to have, or is suspected of having, a hematologic disorder characterized by low systemic iron levels. In some embodiments, the subject has ACD and/or one or more conditions which may give rise to ACD, as described elsewhere herein. In some embodiments, the subject is erythrocyte-transfusion dependent. In some embodiments, the subject is erythrocyte-transfusion independent.

Determination of whether an amount of the antibody (e.g., anti-HJV antibody) achieved the therapeutic effect would be evident to one of skill in the art based on the teachings provided herein. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. The particular dosage regimen, i.e., dose, timing and repetition, used in the method described herein will depend on the particular subject and that subject's medical history, as discussed herein.

Empirical considerations, such as the time to maximum effect half-life, and/or time above a specific concentration generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Other reasons for dose-adjusting include differences in pharmacokinetics or pharmacodynamic response driven by sex, age, individual response, polymorphisms on the antibody target and/or receptors involved in antibody clearance. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In some embodiments, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Dosing frequencies may vary in accordance with the claimed methods. In some embodiments, a composition may be administered once. In some embodiments, a composition will be administered on multiple occasions. In some embodiments, dosing frequency is every week, every 2 weeks, every 3 weeks, every 4 weeks, every 5 weeks, every 6 weeks, every 7 weeks, every 8 weeks, every 9 weeks, or every 10 weeks; or once every month, every 2 months, or every 3 months, or longer. In some embodiments, a composition will be administered daily, biweekly, weekly, bimonthly, monthly, or at any time interval that provide suitable (e.g., maximal) efficacy while minimizing safety risks to the subject. Generally, the efficacy and the treatment and safety risks may be monitored throughout the course of treatment.

Figure 7A:
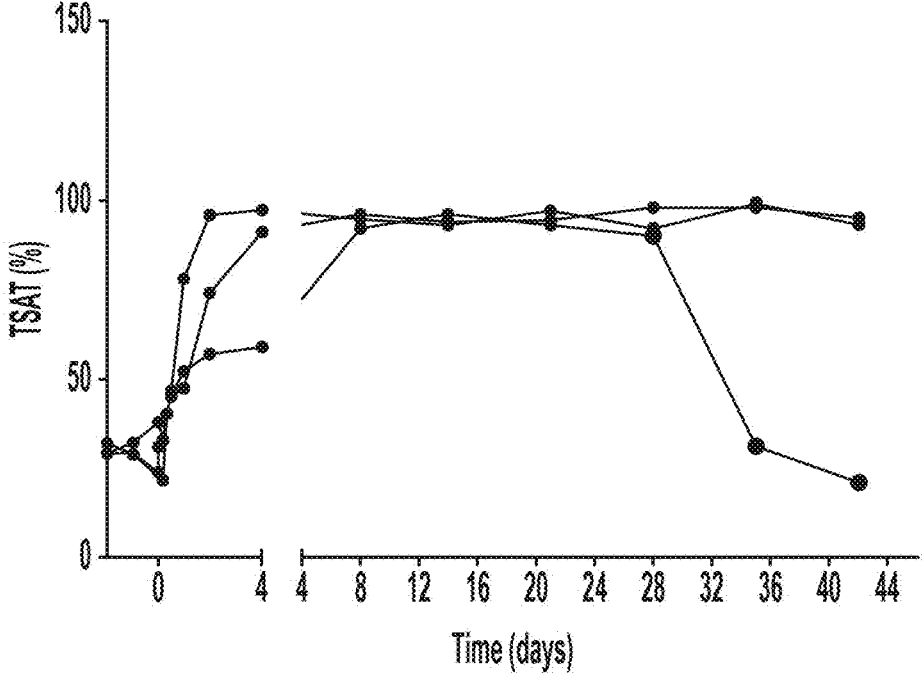
FIGS. 7A-7F shows PK/PD correlation in Cynos with single dose of 6 mpk.

In some embodiments, administration of anti-HJV antibody results in a decrease in hepcidin (e.g., circulating hepcidin-25 levels) concentration and/or increase serum TSAT % (see, e.g., FIGS. 7D-7E), and in some embodiments, these effects persist for a period of time (e.g., one month or more). Accordingly, in some embodiments, timing and frequency of administration of anti-HJV antibody can be determined by monitoring one or more biomarkers, e.g., measurable criteria to assess iron availability or flag possible iron overload. For example, in some embodiments, anti-HJV antibody is administered intermittently or in accordance with the level of a particular biomarker such as hepcidin (e.g., circulating hepcidin-25 levels) levels, circulating transferrin level, or transferrin saturation percentage (TSAT %). In some embodiments, a biomarker level can be used to determine whether a subject is a candidate for treatment. However, in some embodiments, a biomarker may be used to determine whether to continue treatment or to resume a treatment or to halt a treatment, e.g., halt treatment with an anti-HJV antibody.

For example, in some embodiments, a subject may be considered as not being candidate for treatment if TSAT % of the subject is at or above 70%, at or above 75%, at or above 80%, at or above 85%, at or above 90%, or at or above 95%. In some cases, if TSAT % of the subject is at or above 70%, at or above 75%, at or above 80%, at or above 85%, at or above 90%, or at or above 95%. An ongoing treatment with an anti-HJV antibody may be stopped or temporarily stopped, e.g., to prevent iron overload. In other embodiments, administration of an anti-HJV antibody may be performed when a TSA % of a subject is at or below 95%, at or below 90%, at or below 80%, at or below 70%, at or below 65%, at or below 60%, at or below 55%, at or below 50%, at or below 45%, at or below 40%, at or below 35%, or at or below 30%. Thus, in some embodiments, TSAT % of a subject can be monitored, e.g., continuously or periodically, while a patient is receiving a treatment or under care of a treating physician, e.g., for anemia, to prevent iron overload or otherwise to assess whether further treatments are appropriate. It should be appreciated, however, that other suitable markers may be monitored to determine dosage and dosage frequency (including, for example, ferritin levels, serum iron levels, creatinine levels, etc.) in accordance with the methods provided herein In some embodiments, a subject may be administered a composition provided herein (e.g., an anti-HJV antibody) at one or more intervals during a set period of time. In some cases, periods of time during which a subject is administered a composition at one or more intervals may be separated by periods of time in which the subject is not administered the composition. In some embodiments, the relative durations of respective periods of time may depend on the subject's response to treatment or severity of disease or both and/or may be determined based on the judgment of a treating physician. For example, in some embodiments, during the course of a year a subject may be administered a composition weekly, biweekly or monthly for two months and then the administration is stopped for ten months. In some embodiments, during the course of a year a subject may be administered a composition weekly, biweekly or monthly for three months and then the administration is stopped for nine months. In some embodiments, during the course of a year a subject may be administered a composition weekly, biweekly or monthly for four months and then the administration is stopped for eight months. In some embodiments, during the course of a year a subject may be administered a composition weekly, biweekly or monthly for five months and then the administration is stopped for seven months. In some embodiments, during the course of a year a subject may be administered a composition weekly, biweekly or monthly for six months and then the administration is stopped for six months. In some embodiments, during the course of a year a subject may be administered a composition weekly, biweekly or monthly for seven months and then the administration is stopped for five months. In some embodiments, during the course of a year a subject may be administered a composition weekly, biweekly or monthly for eight months and then the administration is stopped for four months. In some embodiments, during the course of a year a subject may be administered a composition weekly, biweekly or monthly for nine months and then the administration is stopped for three months. In some embodiments, during the course of a year a subject may be administered a composition weekly, biweekly or monthly for ten months and then the administration is stopped for two months. In some embodiments, during the course of a year a subject may be administered a composition weekly, biweekly or monthly for two months on, two months off; or for three months on, three months off; or for four months on, four months off.

Generally, for administration of any of the antibodies described herein, a dose may be about 0.01 mg/kg, 0.05 mg/kg. 0.1 mg/kg, 0.2 mg/kg, 0.3 mg/kg, 0.4 mg/kg, 0.5 mg/kg, 0.6 mg/kg, 1 mg/kg, 2 mg/kg, 3 mg/kg, 4 mg/kg, 5 mg/kg, 6 mg/kg, 7 g/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg or 100 mg/kg.

In some embodiments, the dosage the anti-HJV antibody is up to 0.01 mg/kg, up to 0.05 mg/kg. up to 0.1 mg/kg, up to 0.2 mg/kg, up to 0.3 mg/kg, up to 0.4 mg/kg, up to 0.5 mg/kg, up to 0.6 mg/kg, up to 1 mg/kg, mg/kg, up to 2 mg/kg, up to 3 mg/kg, up to 4 mg/kg, up to 5 g/kg, up to 6 mg/kg, up to 7 mg/kg, up to 8 mg/kg, up to 9 mg/kg, up to 10 mg/kg, up to 20 mg/kg, up to 30 mg/kg, up to 40 mg/kg, up to 50 mg/kg, up to 60 g/kg, up to 70 mg/kg, 80 mg/kg, up to 90 mg/kg, up to 100 mg/kg or more.

However, in some embodiments, the dose of the anti-HJV antibody can be in a range of 0.01 mg/kg to 100 mg/kg, 0.01 mg/kg to 10 mg/kg, 0.5 mg/kg to 15 mg/kg, 1 mg/kg to 15 mg/kg, 5 mg/kg to 25 mg/kg, 10 mg/kg to 30 mg/kg, 20 mg/kg to 40 mg/kg, 30 mg/kg to 50 mg/kg, 40 mg/kg to 60 mg/kg, 50 mg/kg to 75 mg/kg, or 50 mg/kg to 100 mg/kg In some embodiments, the antibodies described herein are administered to a subject in need of the treatment at an amount sufficient to inhibit the activity of the target antigen (e.g., an amount sufficient to inhibit HJV-induced BMP signaling) by at least 20% (e.g., 30%, 40%, 50%, 60%, 70%, 80%, 90% or greater) in vivo. In other embodiments, the antibody is administered in an amount effective in reducing the activity level of a target antigen by at least 20% (e.g., 30%, 40%, 50%, 60%, 70%, 80%, 90% or greater).

In some embodiments, an antibody can be administered parenterally. For example, a parenterally administered composition may be administered by subcutaneous, intracutaneous, intravenous, intraperitoneal, intratumor, intramuscular, intraarticular, intraarterial, or infusion techniques. In addition, it can be administered to the subject via injectable depot routes of administration such as using 1-, 3-, or 6-month depot injectable or biodegradable materials and methods.

In some embodiments, an antibody (e.g., an anti-HJV antibody) is administered intravenously. In some embodiments, an antibody (e.g., an anti-HJV antibody) is administered subcutaneously. In some embodiments, subcutaneous administration of an ani-HJV antibody results in similar bioavailability compared to intravenous administration of the same antibody at the same dose.

In some embodiments, subcutaneous administration of the anti-HJV antibody yields comparable pharmacodynamics effects (e.g., decreased circulating hepcidin-25 levels, increased TSAT %, and/or increased serum iron levels) at lower maximum concentrations ($C_{max}$) of the anti-HJV antibody compared to intravenous administration of the same antibody. $C_{max}$ is the maximum (or peak) serum concentration that a drug (e.g., an anti-HJV antibody) after the drug has been administered and before the administration of a second dose. In some embodiments, achieving a low $C_{max}$ within a short period of time (e.g., within 12 hours, within 24 hours, etc) after administration of an anti-HJV antibody minimizes undesirable increases in serum iron response, and/or minimizes chances of off-target effects of the antibody (e.g., binding to RGMa). In some embodiments, blunting $C_{max}$ by subcutaneous administration of an anti-HJV antibody avoids an undesirably sharp increase in serum iron response. In some embodiments, blunting $C_{max}$ by subcutaneous administration of an anti-HJV antibody reduces the off-target effects of the antibody. In some embodiments, the $C_{max}$ reached by subcutaneous administration is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the $C_{max}$ reached by intravenous administration of an anti-HJV antibody.

For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline. Ringer's solution or other suitable excipients. Other injectable compositions may contain various carriers such as vegetable oils, dimethylactamide, dimethyformamide, ethyl lactate, ethyl carbonate, is propyl myristate, ethanol, and polyols (glycerol, propylene glycol, liquid polyethylene glycol, and the like). In some cases, preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents. Treatment efficacy for a target disease/disorder can be assessed by methods well-known in the art.

The anti-HJV antibody and treatment methods involving such as described in the present disclosure may be utilized in combination with other types of therapy for the target disease or disorder disclosed herein. In this context, an antibody composition and a therapeutic agent may be given either simultaneously or sequentially. Examples include chemotherapy, immune therapy (e.g. therapies involving other hepcidin antagonists), surgery, radiation, gene therapy, and so forth, or anti-infection therapy. Such therapies can be administered simultaneously or sequentially (in any order) with the treatment according to the present disclosure.

For example, the combination therapy can include the anti-HJV antibody and pharmaceutical composition described herein, co-formulated with and/or co-administered with, at least one additional therapeutic agent. Such combination therapies may advantageously utilize lower dosages of the administered therapeutic a ents, thus preventing possible toxicities or complications associated with the various monotherapies. Moreover, the additional therapeutic agents disclosed herein may act on pathways in addition to or distinct from the hepcidin/BMP pathway, and thus may enhance and/or synergize with the effects of the anti-HJV antibodies.

Accordingly, in some embodiments, a subject in need of treatment in accordance with the disclosure has previously received therapeutic intervention for a hematologic disorder. In some embodiments, the subject has previously undergone surgical procedure for treating one or more hematologic disorders. In some embodiments, the subject has previously undergone a splenectomy. In some embodiments, the subject has previously received a therapeutic agent for treating one or more hematologic disorders.

In some embodiments, a subject has previously received an erythropoietin stimulating agent. In some embodiments, the erythropoietin stimulating agent is selected from the group consisting of danazol, prednisone, thalidomide, lenalidomide, and pomalidomide.

In some embodiments, a subject has previously received a JAK-STAT pathway inhibitor. In some embodiments, the JAK-STAT pathway inhibitor is a JAK inhibitor or a STAT inhibitor. In some embodiments, the JAK inhibitor is selective for one or both of subtypes JAK1 and JAK2 (e.g., a JAK1/2 inhibitor). In some embodiments, the STAT inhibitor is a STAT3 inhibitor. In some embodiments, the JAK1/2 or STAT3 inhibitor is selected from the group consisting of ruxolitinib, fedratinib, momelotinib, pacritinib, INCB039110, AG490, and PpYLKTK.

In some embodiments, a subject has previously received a growth factor ligand trap. In some embodiments, the growth factor ligand trap is a transforming growth factor beta (TGF-β) ligand trap. In some embodiments, the TGF-β ligand trap is sotatercept or luspatercept. In some embodiments, a subject has previously received an anti-fibrotic agent. In some embodiments, the anti-fibrotic agent is PRM-151.

In some embodiments, a subject in need of treatment in accordance with the disclosure continues to receive a therapeutic treatment for a hematologic disorder. The disclosure therefore provides, in some aspects, compositions and methods for treating ACD and/or one or more conditions arising as a result of ACD by administering to a subject in need thereof a hepcidin antagonist (e.g., anti-HJV antibody) in combination with one or more therapeutic treatments for a hematologic disorder.

In some embodiments, a subject is administered a hemojuvelin antagonist (e.g., anti-HJV antibodies and compositions thereof) in combination with an erythropoietin stimulating agent. In some embodiments, the erythropoietin stimulating agent is selected from the group consisting of danazol, prednisone, thalidomide, lenalidomide, and pomalidomide.

In some embodiments, a subject is administered a hemojuvelin antagonist (e.g., anti-HJV antibodies and compositions thereof) in combination with a JAK-STAT pathway inhibitor. In some embodiments, the JAK-STAT pathway inhibitor is a JAK inhibitor or a STAT inhibitor. In some embodiments, the JAK inhibitor is selective for one or both of subtypes JAK1 and JAK2 (e.g., a JAK1/2 inhibitor). In some embodiments, the STAT inhibitor is a STAT3 inhibitor. In some embodiments, the JAK1/2 or STAT3 inhibitor is selected from the group consisting of ruxolitinib, fedratinib, momelotinib, pacritinib, INCB039110, AG490, and PpYLKTK. In some embodiments, a subject is administered a hemojuvelin antagonist (e.g., anti-HJV antibodies and compositions thereof) in combination with ruxolitinib.

In some embodiments, the hemojuvelin antagonist (e.g., anti-HJV antibodies and compositions thereof) reduces the extent to which a subject exhibits an anemic response to the JAK-STAT pathway inhibitor. For example, in some embodiments, a subject treated with a JAK-STAT pathway inhibitor as a monotherapy may be characterized as having a deficiency in the ability of blood to transport oxygen as compared to the subject's pretreatment state, a deficiency in red blood cells as compared to the subject's pretreatment state, a deficiency in hemoglobin as compared to the subject's pretreatment state, an/or a deficiency in total blood volume as compared to the subject's pretreatment state. Accordingly, in some embodiments, the hemojuvelin antagonist (e.g., anti-HJV antibody) reduces the extent to which a subject exhibits an anemic response to a JAK-STAT pathway inhibitor selected from the group consisting of ruxolitinib, fedratinib, momelotinib, pacritinib, INCB039110, AG490, and PpYLKTK. In some embodiments, the hemojuvelin antagonist (e.g., anti-HJV antibodies and compositions thereof) reduces the extent to which a subject exhibits an anemic response to ruxolitinib administration.

In some embodiments, a subject is administered a hemojuvelin antagonist (e.g., anti-HJV antibodies and compositions thereof) in combination with a growth factor ligand trap. In some embodiments, the growth factor ligand trap is a transforming growth factor beta (TGF-β) ligand trap. In some embodiments, the TGF-β ligand trap is sotatercept or luspatercept. In some embodiments, a subject is administered a hemojuvelin antagonist (e.g., anti-HJV antibodies and compositions thereof) in combination with an anti-fibrotic agent. In some embodiments, the anti-fibrotic agent is PRM-151.

Successful treatment of a subject in accordance with the disclosure may be determined by methods known in the art or by a skilled practitioner. In some embodiments, hepcidin antagonist (e.g., anti-HJV antibodies and compositions thereof) treatment is evaluated based on hepcidin (e.g., circulating hepcidin-25 levels) levels in a subject. For example, in some embodiments, baseline hepcidin (e.g., circulating hepcidin-25 levels) levels in a subject are determined (e.g., before treatment with a hepcidin antagonist (e.g., anti-HJV antibodies and compositions thereof) or otherwise in absence of hepcidin antagonist (e.g., anti-HJV antibodies and compositions thereof) treatment at the time of determining) and compared to post-treatment hepcidin (e.g., circulating hepcidin-25 levels) levels in the subject. In some embodiments, a subject is successfully treated where a hepcidin antagonist (e.g., anti-HJV antibodies and compositions thereof) decreases hepcidin (e.g., circulating hepcidin-25 levels) levels in the subject by between about 1 ng/mL and about 300 ng/mL. In some embodiments, the hepcidin antagonist (e.g., anti-HJV antibodies and compositions thereof) decreases hepcidin (e.g., circulating hepcidin-25 levels) levels in a subject by between about 1 ng/mL and about 200 ng/mL, between about 1 ng/mL and about 100 ng/mL, between about 1 ng/mL and about 50 ng/mL, between about 1 ng/mL and about 10 ng/mL, between about 10 ng/mL and about 100 ng/mL, or between about 10 ng/mL and about 50 ng/mL. In some embodiments, the present disclosure provides a method for reducing hepcidin (e.g., circulating hepcidin-25 levels) in a subject having ACD. In some embodiments, the administration reduces hepcidin-25 within 4 hours, 6 ours, 8 hours, 12 hours, 28 hours, 24 hours, 2 days, 3 days, 4 days, 5 days, 6 days, 1 week, or two weeks of administration. In some embodiments, the administration reduces hepcidin (e.g., circulating hepcidin-25 levels) by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of hepcidin (e.g., circulating hepcidin-25 levels) compared to the hepcidin (e.g., circulating hepcidin-25 levels) level in the subject prior to administration.

In some embodiments, hepcidin antagonist (e.g., anti-HJV antibodies and compositions thereof) treatment is evaluated based on serum ferritin levels in a subject. For example, in some embodiments, baseline serum ferritin levels in a subject are determined (e.g., before treatment with a hepcidin antagonist (e.g., anti-HJV antibodies and compositions thereof) or otherwise in absence of hepcidin antagonist (e.g., anti-HJV antibodies and compositions thereof) treatment at the time of determining) and compared to post-treatment serum ferritin levels in the subject. In some embodiments, a subject is successfully treated where a hepcidin antagonist (e.g., anti-HJV antibodies and composition thereof) decreases serum ferritin levels in the subject by between about 1 ng/mL and about 200 ng/mL. In some embodiments, the hepcidin antagonist (e.g., anti-HJV antibodies and compositions thereof) decreases serum ferritin levels in a subject by between about 1 ng/mL and about 100 ng/mL, between about 1 ng/mL and about 50 ng/mL, between about 1 ng/mL and about 25 ng/mL, between about 1 ng/mL and about 10 ng/mL, between about 10 ng/mL and about 100 ng/mL, or between about 10 ng/mL and about 50 ng/mL.

In some embodiments, hepcidin antagonist (e.g., anti-HJV antibodies and compositions thereof) treatment is evaluated based on serum hemoglobin levels in a subject. For example, in some embodiments, baseline serum hemoglobin levels in a subject are determined (e.g., before treatment with a hepcidin antagonist (e.g., anti-HJV antibodies and compositions thereof) or otherwise in absence of hepcidin antagonist (e.g., anti-HJV antibodies and compositions thereof) treatment at the time of determining) and compared to post-treatment serum hemoglobin levels in the subject. In some embodiments, a subject is successfully treated where a hepcidin antagonist (e.g., anti-HJV antibodies and compositions thereof) decreases serum hemoglobin levels in the subject by between about 0.01 g/dL and about 5 g/dL. In some embodiments, the hepcidin antagonist (e.g., anti-HJV antibodies and compositions thereof) decreases serum ferritin levels in a subject by between about 0.01 g/dL and about 1 g/dL, between about 0.1 g/dL and about 5 g/dL, between about 1 g/dL and about 5 g/dL, between about 0.01 g/dL and about 0.1 g/dL, between about 0.5 g/dL and about 2.5 g/dL, or between about 0.1 g/dL and about 1 g/dL.

VI. Kits for Therapeutic and Diagnostic Applications

The present disclosure also provides kits for the therapeutic or diagnostic applications as disclosed herein. Such kits can include one or more containers comprising an anti-HJV antibody, e.g., any of those described herein.

In some embodiments, the kit can comprise instructions for use in accordance with any of the methods described herein. The included instructions can comprise a description of administration of the anti-HJV antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-HJV antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder. Instructions nay be provided for practicing any of the methods described herein.

The kits of this invention are in suitable packaging. Suitable packaging includes, but is not limited to, vials, bottles, jars, flexible packaging (e.g., sealed Mylar or plastic bags), and the like.

Also contemplated are packages for use in combination with a specific device, such as an infusion device, such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-HJV antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Also provided herein are kits for use in detecting hemojuvelin in a sample. Such a kit may comprise any of the anti-HJV antibodies described herein. In some instances, the anti-HJV antibody can be conjugated with a detectable label as those described herein. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

Alternatively or in addition, the kit may comprise a secondary antibody capable of binding to anti-HJV antibody. The kit may further comprise instruction for using the anti-HJV antibody for detecting hemojuvelin.

EXAMPLES

Example 1: Anti-HJV Antibodies Generation and Characterization

From rats immunized with human hemojuvelin, hybridoma clones capable of binding to human hemojuvelin were identified. The anti-hemojuvelin monoclonal antibodies (mAb with rat IgG1/κ) were humanized by CDR grafting (hHA antibodies with hIgG1 constant region carrying the L234A, L235A mutations). Affinity matured anti-HJV (e.g., HA-001 to HA-011) in vitro yeast display assay. A general process for generation of humanized affinity matured anti-HJV antibodies is illustrated in FIG. 1A.

Binding affinities of the anti-HJV antibodies to soluble human RGMa, Rat RGMa and human RGMc were measured by BIAcore analysis. Table 4 shows the affinity of the anti-hemojuvelin antibodies to human RGMa. Table 5 shows the affinity of the anti-hemojuvelin antibodies to rat RGMa. Table 6 shows the affinity of the anti-hemojuvelin antibodies to human RGMc.

TABLE 4

Binding Affinity (by BIAcore) of anti-HJV antibodies to Human RGMa

| Ab Name | $K_a$ (1/MS) | $K_d$ (1/s) | KD (M) |
|---|---|---|---|
| hHA-001 | 1.8E+06 | 6.7E−05 | 3.8E−11 |
| hHA-002 | 1.4E+06 | 5.0E−05 | 3.7E−11 |
| hHA-003 | 1.1E+06 | 1.4E−04 | 1.2E−10 |
| hHA-004 | 1.4E+06 | 2.2E−05 | 1.5E−11 |
| hHA-005 | 1.9E+06 | 2.5E−04 | 1.3E−10 |
| hHA-006 | 1.2E+06 | 1.4E−04 | 1.2E−10 |
| hHA-007 | 5.9E+05 | 8.9E−05 | 1.5E−10 |
| hHA-008 | 8.7E+05 | 2.7E−05 | 3.1E−11 |
| hHA-009 | 8.6E+05 | 4.0E−04 | 4.7E−10 |
| hHA-010 | 8.5E+05 | 1.0E−04 | 1.2E−10 |
| hHA-011 | 9.3E+05 | 9.9E−05 | 1.1E−10 |
| hHA | 6.0E+06 | 2.2E−03 | 3.7E−09 |
| HA | 1.2E+06 | 2.9E−03 | 2.4E−09 |

TABLE 5

Binding Affinity (by BIAcore) of anti-HJV antibodies to rat RGMa

| Ab Name | $K_a$ (1/MS) | $K_d$ (1/s) | KD (M) |
|---|---|---|---|
| hHA-001 | 1.2E+06 | 3.6E−05 | 3.1E−11 |
| hHA-002 | 1.0E+06 | 5.5E−05 | 5.3E−11 |

TABLE 5-continued

Binding Affinity (by BIAcore) of anti-HJV antibodies to rat RGMa

| Ab Name | $K_a$ (1/MS) | $K_d$ (1/s) | KD (M) |
|---|---|---|---|
| hHA-003 | 8.7E+05 | 3.1E−05 | 3.6E−11 |
| hHA-004 | 1.1E+06 | <1e−6 | <9.4e−13 |
| hHA-005 | 1.4E+06 | 2.1E−04 | 1.5E−10 |
| hHA-006 | 9.4E+05 | 3.0E−05 | 3.2E−11 |
| hHA-007 | 5.1E+05 | <1e−6 | <2.0e−12 |
| hHA-008 | 6.6E+05 | <1e−6 | <1.5e−12 |
| hHA-009 | 6.8E+05 | 2.1E−04 | 3.1E−10 |
| hHA-010 | 6.6E+05 | 2.6E−05 | 3.9E−11 |
| hHA-011 | 7.0E+05 | 5.2E−05 | 7.4E−11 |
| hHA | 8.3E+05 | 1.7E−03 | 2.1E−09 |
| HA | 8.3E+05 | 2.5E−03 | 3.0E−09 |

TABLE 6

Binding Affinity (by BIAcore) of anti-HJV antibodies to Human RGMc

| Ab Name | $K_a$ (1/MS) | $K_d$ (1/s) | KD (M) |
|---|---|---|---|
| hHA-001 | 1.08E+07 | 1.65E−03 | 1.6E−10 |
| hHA-002 | 7.65E+06 | 1.70E−03 | 2.25E−10 |
| hHA-003 | 8.10E+06 | 2.40E−03 | 3E−10 |

TABLE 6-continued

Binding Affinity (by BIAcore) of anti-HJV antibodies to Human RGMc

| Ab Name | $K_a$ (1/MS) | $K_d$ (1/s) | KD (M) |
|---|---|---|---|
| hHA-004 | 7.85E+06 | 1.04E−03 | 1.3E−10 |
| hHA-005 | 4.15E+07 | 1.36E−02 | 3.2E−10 |
| hHA-006 | 6.65E+06 | 2.55E−03 | 3.85E−10 |
| hHA-007 | 5.05E+06 | 2.15E−03 | 4.25E−10 |
| hHA-008 | 3.95E+06 | 3.90E−04 | 1.05E−10 |
| hHA-009 | 1.55E+07 | 1.07E−02 | 7.1E−10 |
| hHA-010 | 9.90E+06 | 4.40E−03 | 4.45E−10 |
| hHA-011 | 5.05E+06 | 1.40E−03 | 2.85E−10 |
| hHA | 8.3E+05 | | 2.1E−08 |

Within these antibodies, at lease hHA-004, hHA-008, hHA-009 and hHA-011 showed strong binding to human RGMc, and were selected for further testing. Sensorgrams by BIAcore analysis of antibodies HA, hHA-004, hHA-008, hHA-009 and hHA-011 are shown in FIGS. 1B-1G. hHA-008 was further tested for its binding affinity to human RGMa, Cyno RGMa, Rat RGMa, human RGMc, Cyno RGMc, Rat RGMc, and human RGMb, and the respective binding affinity is shown in Table 7. hHA-008 showed high affinity binding to human RGMa and RGMc with strong cross-reactivity to cyno and rodent species.

TABLE 7

Binding affinities of hHA-008 to human RGMa, Cyno RGMa, Rat RGMa, human RGMc, Cyno RGMc, Rat RGMc, and Human RGMb.

| RGM antigen | hHA-008 | | | hHA | | |
|---|---|---|---|---|---|---|
| in solution | ka (1/Ms) | kd (1/s) | KD (M) | ka (1/Ms) | kd (1/s) | KD (M) |
| Human RGMa | 4.9E+05 | 3.6E−05 | 7.4E−11 | 2.7E+05 | 2.3E−03 | 8.3E−09 |
| Cyno RGMa | 5.5E+05 | 3.5E−04 | 6.4E−10 | 2.1E+05 | 6.6E−04 | 3.1E−09 |
| Rat RGMa | 3.1E+05 | 3.6E−05 | 1.2E−10 | 2.3E+05 | 2.1E−03 | 9.1E−09 |
| Human RGMc | 2.5E+06 | 2.9E−04 | 1.2E−10 | 1.4E+06 | n/a | 4.0E−08* |
| cyno RGMc | 2.6E+06 | 3.1E−04 | 1.2E−10 | 1.8E+06 | n/a | 3.2E−08* |
| Rat RGMc | 1.4E+06 | 3.2E−04 | 2.3E−10 | | | 6.6E−08** |
| Human RGMb | no significant binding | | | no significant binding | | |

*Data for the hHA with human and cyno RGMc was fitted to a two-state model. $K_{a1}$ represents the Ab Ag association in a two-state binding model

**Data for the hHA with Rat RGMc was fitted to a steady state affinity model

Figure 2A:
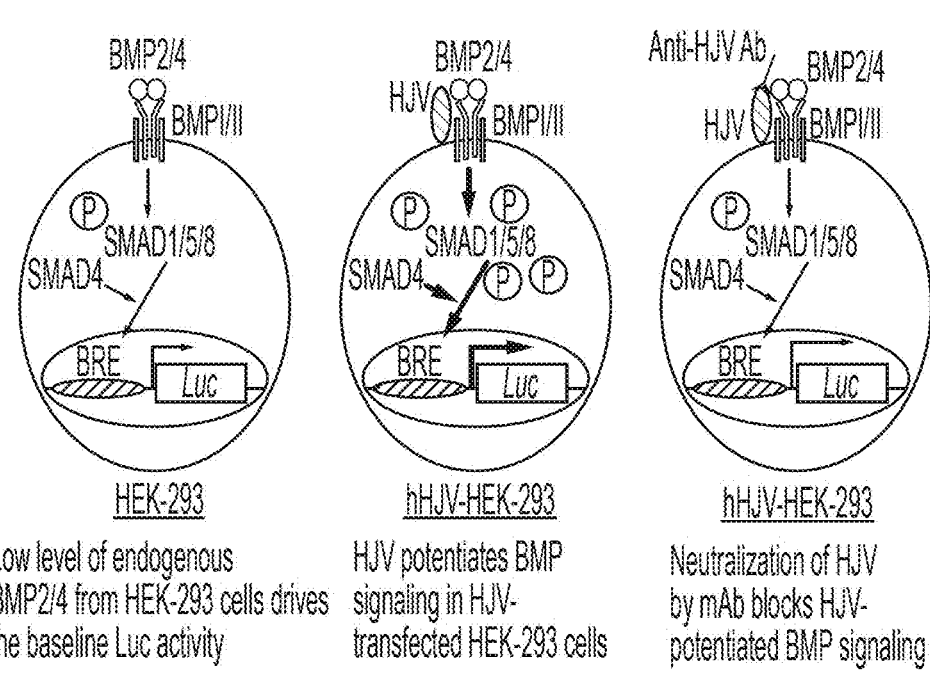
FIGS. 2A-2C are graphs showing the BMP reporter gene assay for anti-HJV antibodies.

The RGMc (HJV) BMP reporter gene assay was used for screening and characterization potency of anti-HJV antibodies in blocking membrane-bound RGMc induced BMP/Smad1/5/8 signaling. The assay is directly related to the mechanism of action of the anti-HJV mAbs in inhibiting RGMc/BMP/Smad1/5/8 signaling pathway that is responsible for induction of iron hormone hepcidin gene expression. The principle of HJV BMP reporter assay is illustrated in FIG. 2A.

The BRE-Luc reporter gene vector initially described by Korchynskyi and Dijke (J. Biol. Chem. 2002; 277:4883c) was used to transiently transfect porcine kidney epithelial cell line LLC-PK1 with or without co-transfection of an RGMa expression vector by Babbit et al (J. Biol. Chem. 2005; 280:29820) to determine if RGMa expression modulates BMP signaling. In BRE-Luc transiently transfected cells, RGMa was demonstrated to enhance BMP signaling through the Smad1/5/8 signaling pathway, consistent with a role for RGMa as a BMP co-receptor. All RGM members (RGMa, RGMb, and RGMc) act as BMP co-receptor and enhance BMP signaling. The BRE-Luc reporter vector was constructed and established the RGM BMP reporter gene assay in HEK293 cells. Human RGMc expression vector used in the assay was pcDNA-hRGMc.

HEK293 cells were cultured in growth media (base media DMEM (Invitrogen catalog #11965-092) containing 10% fetal bovine serum (Gibco #10438-026) and 1% sodium pyruvate (Invitrogen, catalog #11360-070)). To prepare cells for transfection, $9 \times 10^6$ cells HEK293 cells were plated in 10 cm dishes and incubated at 37° C., 5% $CO_2$ for 6 hours. The cells were then transfected using PolyJet (µL): DNA (µg) ratio of 2:1, specifically 20 µl PolyJet (SignaGen, cat #SL100688) with 5 µg pGL[luc2P/BRE/Hygro] DNA (Abbvie) and 5 µg pcDNA-hRGMc (Abbvie) for 16 hours at 37° C., 5% $CO_2$. The media was replaced with fresh HEK293 growth media for 6 hours. The cells were then trypsinized with TrpLE (ThermoFisher, cat #12605010), counted, and plated in 96-well white assay plates (Thermo Scientific Nunclon delta F96, cat #136102) at $1 \times 10^5$ cells per well. The cells were treated with anti-RGMc mAb, anti-BMP2/4 mAb (R&D Systems, cat #MAB3552) (as a positive control), or an isotype control mAb for 16 hours at 37° C., 5% $CO_2$.

Figure 2B:
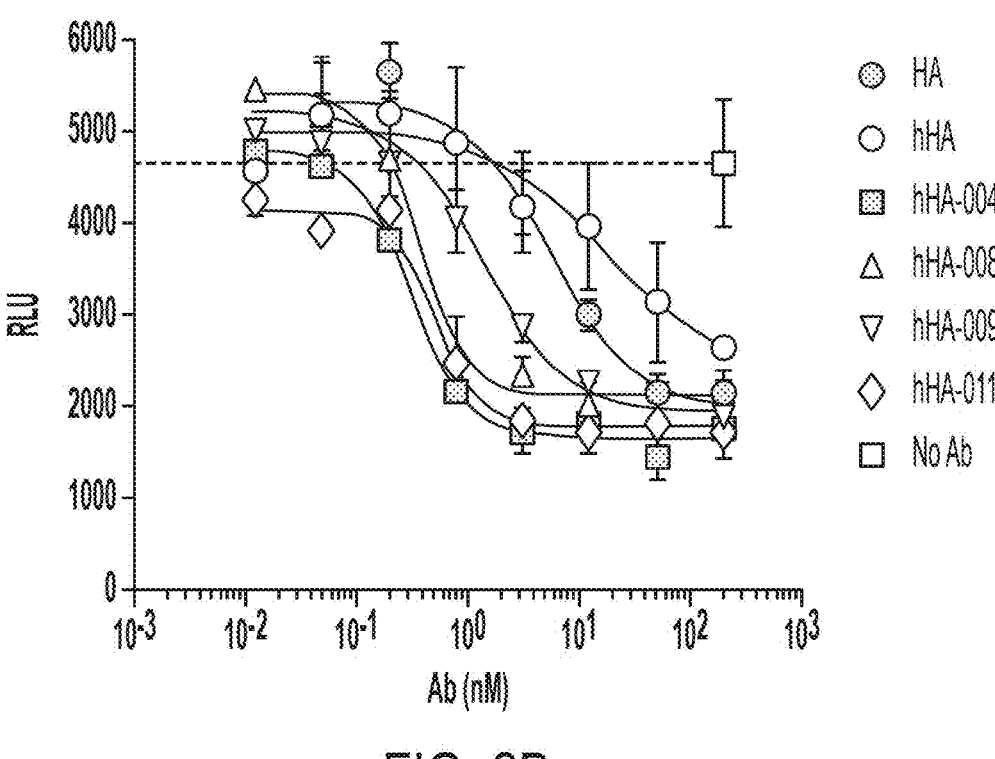

Luciferase activity was detected using the One-Glo Luciferase kit (Promega, cat #E6120) and measurement on a TopCount luminescence counter. The results showed that anti-HJV antibodies dose-dependently inhibit RGMc potentiated BMP signaling (FIG. 2B). The IC50 (nM) of each of the antibodies tested in inhibiting RGMc signaling in BMP reporter assay are shown in Table 8.

TABLE 8

| IC50 of the anti-HJV antibodies in BMP reporter assay for RGMc. | | | | | | |
|---|---|---|---|---|---|---|
| | HA | hHA | hHA-004 | hHA-008 | hHA-009 | hHA-011 |
| IC50 (nM) | 5.713 | 17.08 | 0.3124 | 0.3772 | 1.362 | 0.0554 |

Figure 2C:
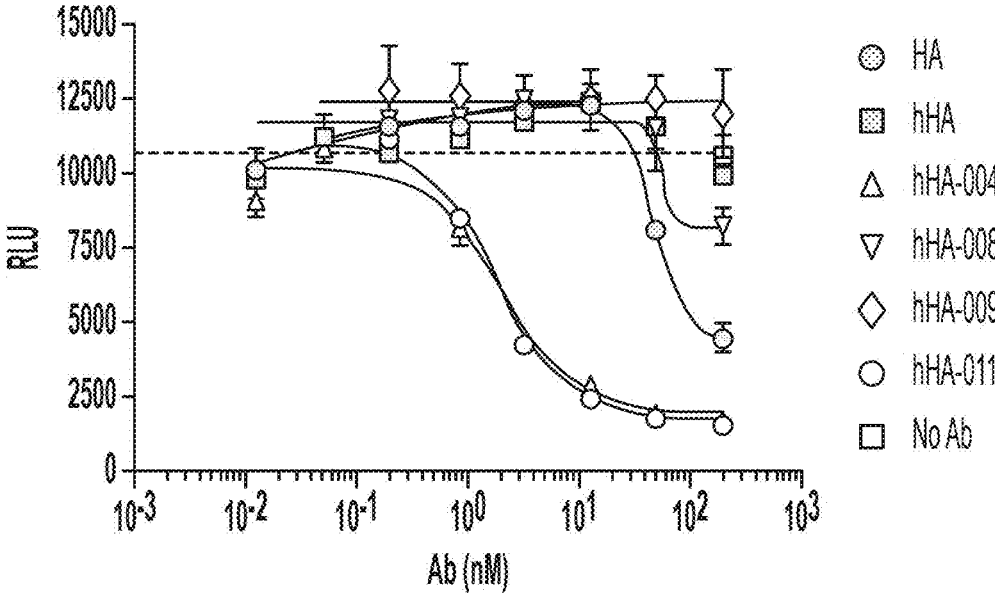

Further, the anti-HJV antibodies were tested for their ability to inhibit RGMa signaling in BMP reporter assays. The hHA-004 and hHA-011 showed potent inhibition on membrane-bound human RGMa in RGMa BMP reporter gene assay, whereas hHA-008 and hHA-009 showed no to minimal inhibition on RGMa activity. The hHA antibody showed no inhibition to membrane bound RGMa. The rat mAb HA showed inhibition on RGMa but to much less extent as compared to hHA-004 and hHA-011. FIG. 2C. The IC50 (nM) of each of the antibodies tested in inhibiting RGMa signaling in BMP reporter assay are shown in Table 9.

TABLE 9

| IC50 of the anti-HJV antibodies in BMP reporter assay for RGMa | | | | | |
|---|---|---|---|---|---|
| | HA | hHA-004 | hHA-008 | hHA-009 | hHA-011 |
| IC50 (nM) | 47.63 | 2.014 | −56.54 | N/A | 1.657 |

The above data showed that the potency of the anti-HJV antibodies in neutralizing membrane RGMc in BMP reporter assay correlates with binding affinity on soluble RGMc. A summary of the anti-HJV antibody binding affinity to soluble human RGMc, and their capability to inhibit membrane bound RGMc and RGMa signaling are shown in Table 10.

TABLE 10

| Anti-HJV antibody binding affinity to soluble human RGMc, and their capability to inhibit membrane bound RGMc and RGMa signaling. | | | | | |
|---|---|---|---|---|---|
| | Binding Affinity (BIAcore) on soluble hRGMc | | | Potency on membrane hRGMc (RGMc/BMP reporter assay) | Potency on membrane hRGMa (RGMa/BMP reporter assay) |
| IgG | Ka (1/MS) | Kd (1/s) | $K_D$ (M) | $IC_{50}$ (nM) | $IC_{50}$ (nM) |
| hHA-004 | 7.85E+06 | 1.04E−03 | 1.30E−10 | 0.31 | 2 |
| hHA-008 | 3.95E+06 | 3.90E−04 | 1.05E−10 | 0.37 | Minimal inhibition |
| hHA-009 | 1.55E+07 | 1.07E−02 | 7.10E−10 | 1.36 | No inhibition |
| hHA-011 | 5.05E+06 | 1.40E−03 | 2.85E−10 | 0.52 | 1.7 |
| hHA | 8.3E+05 ($k_{a1}$)* | n/a | 2.9E−08 | 17 | No inhibition |
| HA | 3.40E+06 | 5.00E−03 | 1.60E−10 | 5.7 | 48 |

Figure 3:
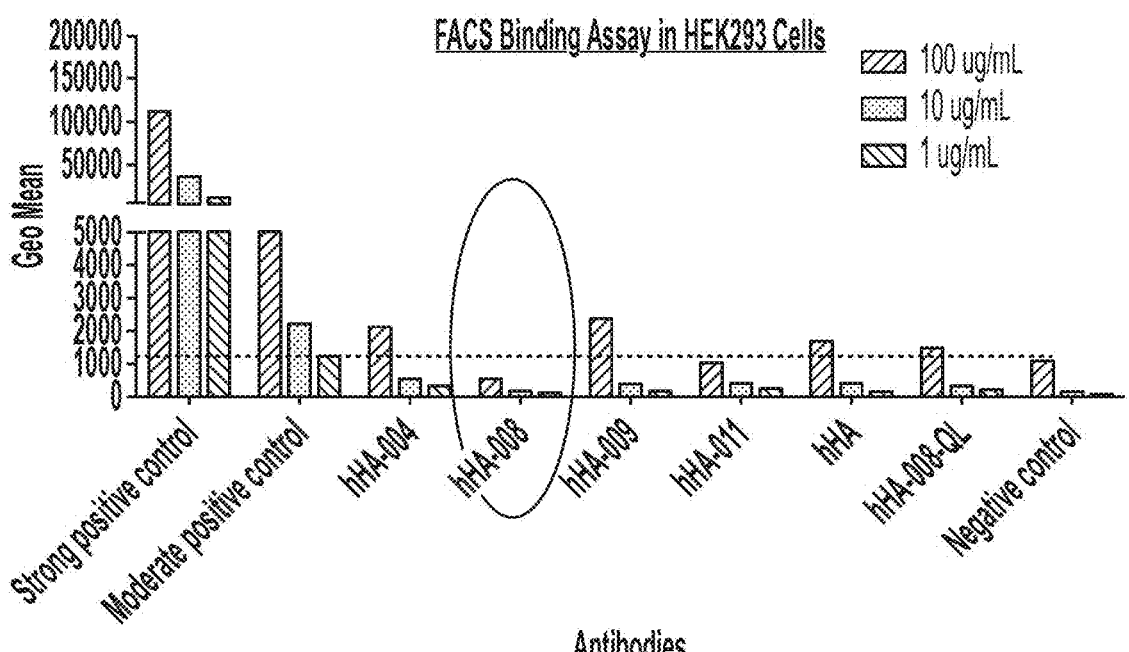
FIG. 3 is a graph showing anti-HJV antibodies non-specific binding to HEK293 cells. Bars from left to right in each group: 100 µg/ml, 10 µg/ml, and 1 µg/ml.

The antibodies, including hHA, hHA-004, hHA-008, hHA-008-QL, hHA-009, and hHA-011 were tested for non-specific cell binding to HEK293 cells by FACS analysis. The data showed hHA and its hHA-008, hHA-008-QL and hHA-011 showed no to minimal non-specific cell binding on HEK293 cells at conc. up to 100 ug/ml. hHA-004 and hHA-009 showed some non-specific cell binding at higher concentrations, but to a much less extent compared to positive control IgGs (FIG. 3).

Figure 4A:
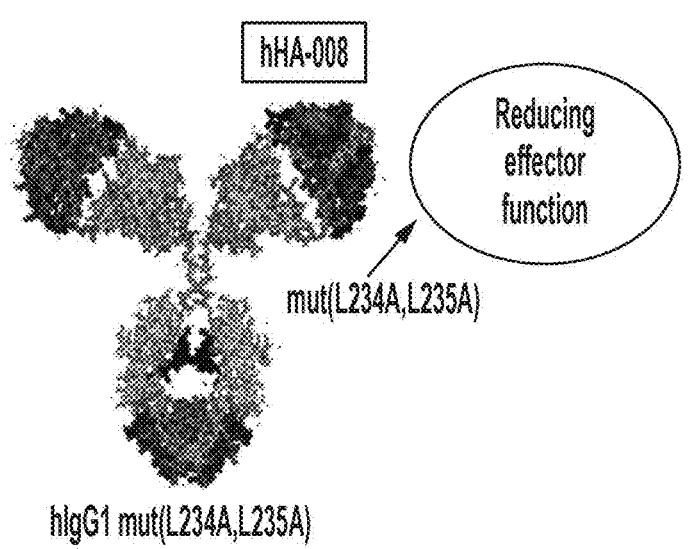
FIGS. 4A-4C are schematic illustrations showing the structure and designs of hHA-008 and hHA-008-QL.
Figure 4B:
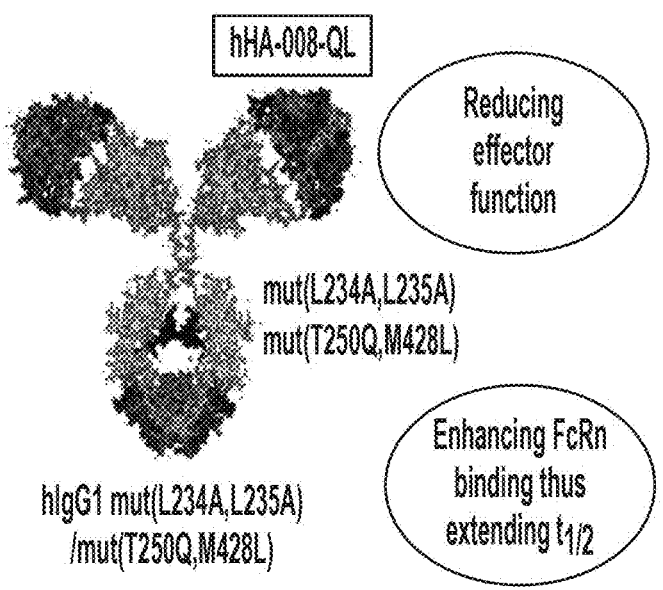
Figure 4C:
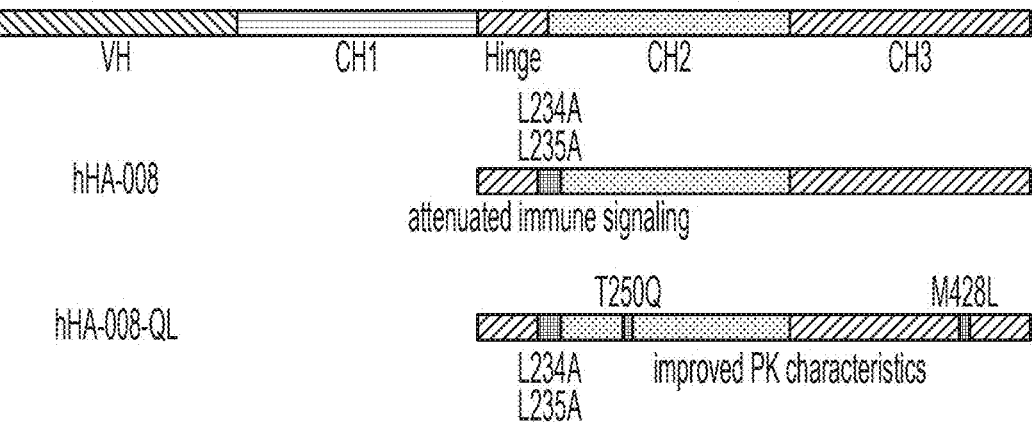

Example 2: Generation of hHA-008-QL hHA-008-QL was developed to prolong IgG serum half-line ($t_{1/2}$). Previous studies have shown that neonatal Fc receptor (FcRn) protects IgG from catabolism, thereby increasing IgG serum half-life. Accordingly, the Fc portion of hHA-008-QL was engineered to have T250Q and M428L mutations (QL mutations) such that it has enhanced binding to FcRn. FIGS. 4A and 4B illustrates the structure of hHA-008 and hHA-008-QL respectively. A further illustration of hHA-008 and hHA-008-QL is shown in FIG. 4C.

First, hHA-008-QL was tested for its RGMa and RGMc binding capabilities, and the data showed that hHA-008-QL had binding affinities to RGMa and RGMc comparable to that of hHA-008 (Table 11)

TABLE 11

| hHA-008-QL and hHA-008 binding affinities to RGMa and RGMc | | | | | | |
|---|---|---|---|---|---|---|
| | huRGMa | | | huRGMc | | |
| IgG | ka (1/Ms) | kd (1/s) | KD (M) | ka (1/Ms) | kd (1/s) | KD (M) |
| hHA-008-QL (hIgG1mut(LALA)/QL/k) | 4.3E+05 | 3.3E−05 | 7.7E−11 | 2.7E+06 | 3.3E−04 | 1.2E−10 |
| hHA-008 (hIgG1mut(LALA)/k) | 5.4E+05 | 4.2E−05 | 7.8E−11 | 3.0E+06 | 3.2E−04 | 1.1E−10 |

Figure 5:
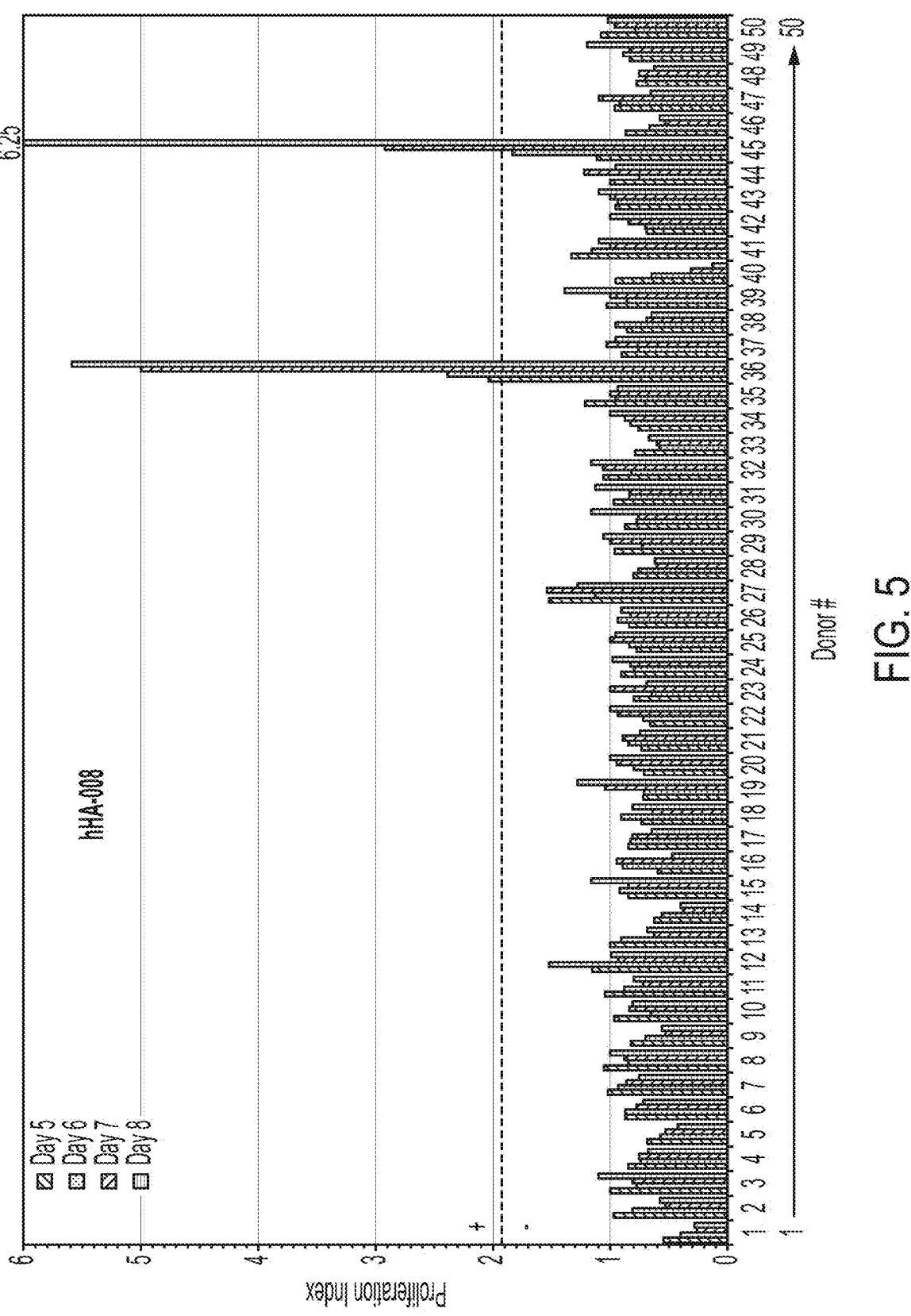
FIG. 5 is a graph showing the CD4+ T cell response peripheral blood mononuclear cells (PBMCs) challenged with hHA-008 or hHA-008-QL.
Figure 5:
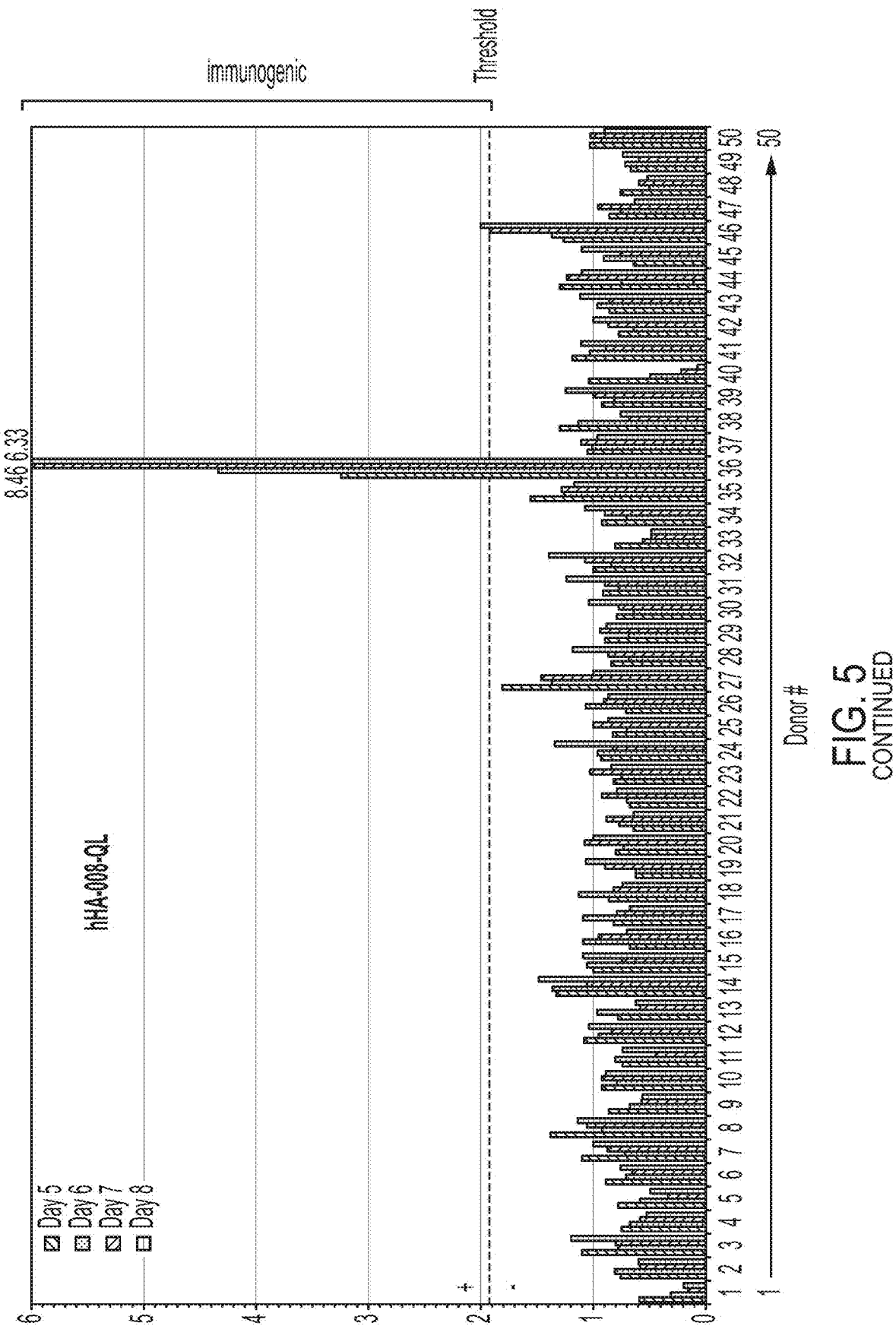

Example 3: Immunogenicity Studies of hHA-008 and hHA-008-QL hHA-008 and hHA-008-QL were tested for their immunogenicity using peripheral blood mononuclear cells (PBMCs) from 50 donors (representing all major HLA-DR and HLA-DQ haplotypes) challenged with hHA-008 or hHA-008-QL in a CD4+ T cell response assay. The results showed only 4% of the 50 donors (2/50) showed a T ell response suggesting that both antibodies have low risk of immunogenicity. In this assay, Herceptin were used as negative control, to which 8% of the donors had a T cell response. Bydureon and keyhole limpet haemocyanin (KLH) were used as positive control. 32% of the donors showed T cell response to Bydureon and 100% donor had a T cell response to KLH. FIG. 5 showed T cell response in 50 donors for hHA-008 and hHA-008-QL.

Further, FcγR binding was tested for hHA-008 and hHA-008-QL as another parameter for immunogenicity. The control group, wild-type irrelevant IgG1 had significant binding to both the high and low affinity Fc gamma receptors. As expected, the binding of the wild-type irrelevant IgG4 is significantly lower than that of wild-type irrelevant IgG1. Binding to the high affinity and low affinity receptors is significantly reduced for both hHA-008 and hHA-008-QL compared to wild-type IgG1, suggesting low immunogenicity for both antibodies.

Figure 6A:
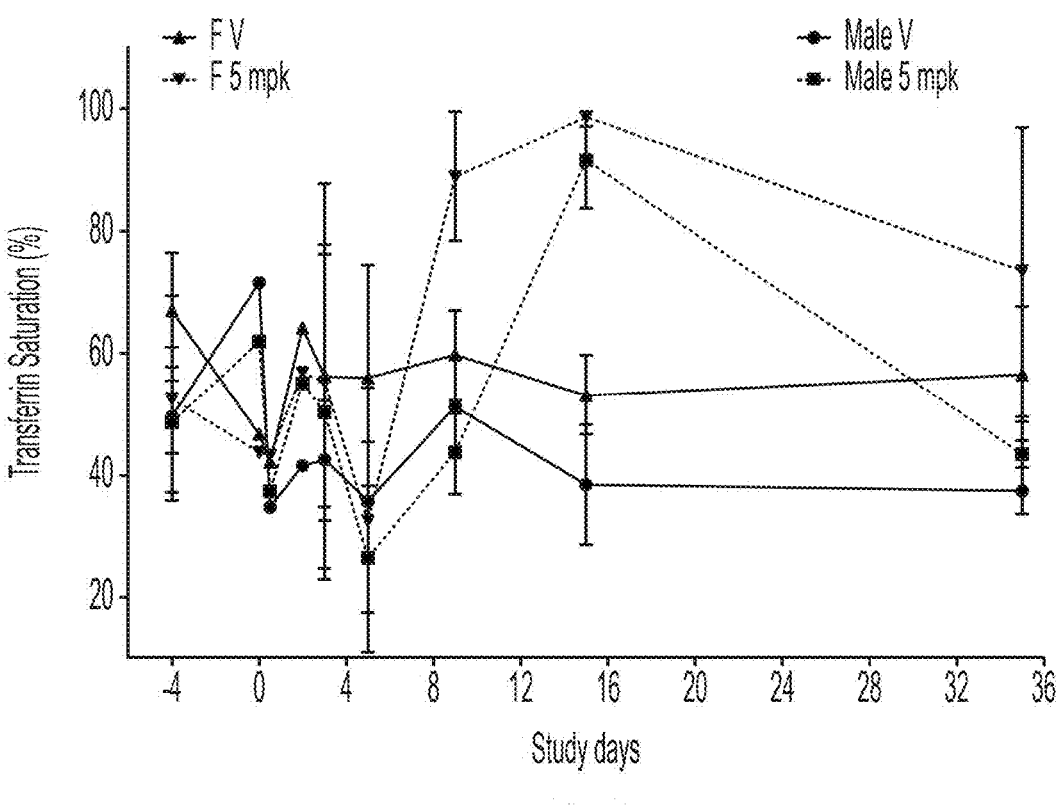
FIGS. 6A-6C are graphs showing PK/PD analysis of hHA-008 in rats.

Example 4: Pharmacokinetics/Pharmacodynamics (PK/PD) Modeling of hHA-008 and hHA-008-QL In an initial study for PK/PD of hHA-008, male rats were treated with a single dose of hHA-008 at 5 mg per kilogram of body weight (mpk) by intravenous injection. Transferrin saturation (TSAT %; determined as the percentage of serum iron over serum total iron binding capacity) were tested over time. The data showed that maximal effect of increased TSAT occurred between 4-8 days post treatment (FIG. 6A).

Figure 6B:
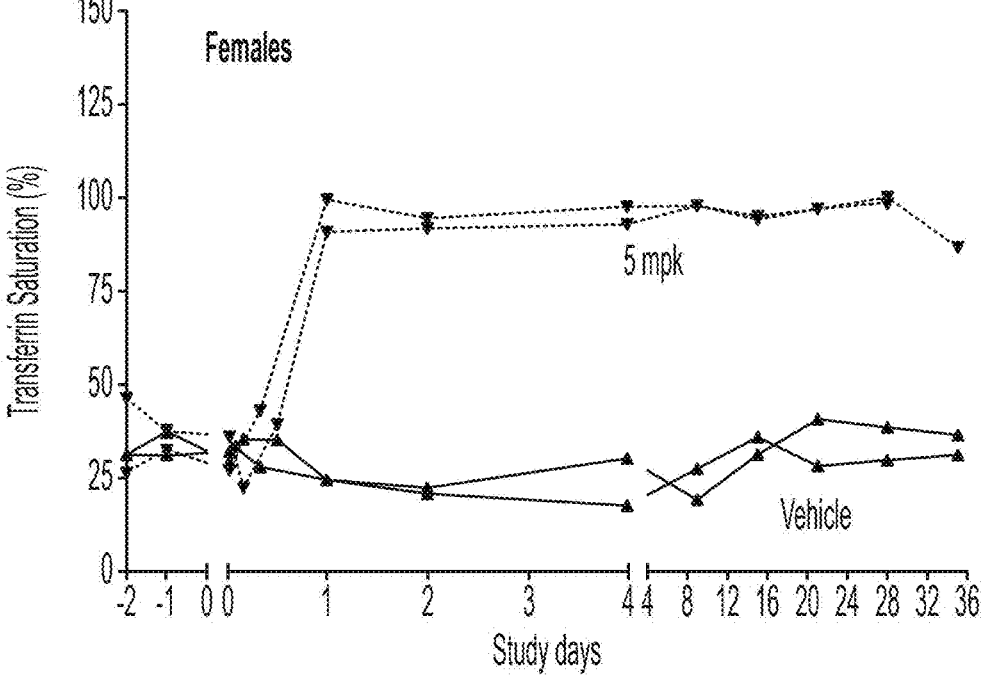
Figure 6C:
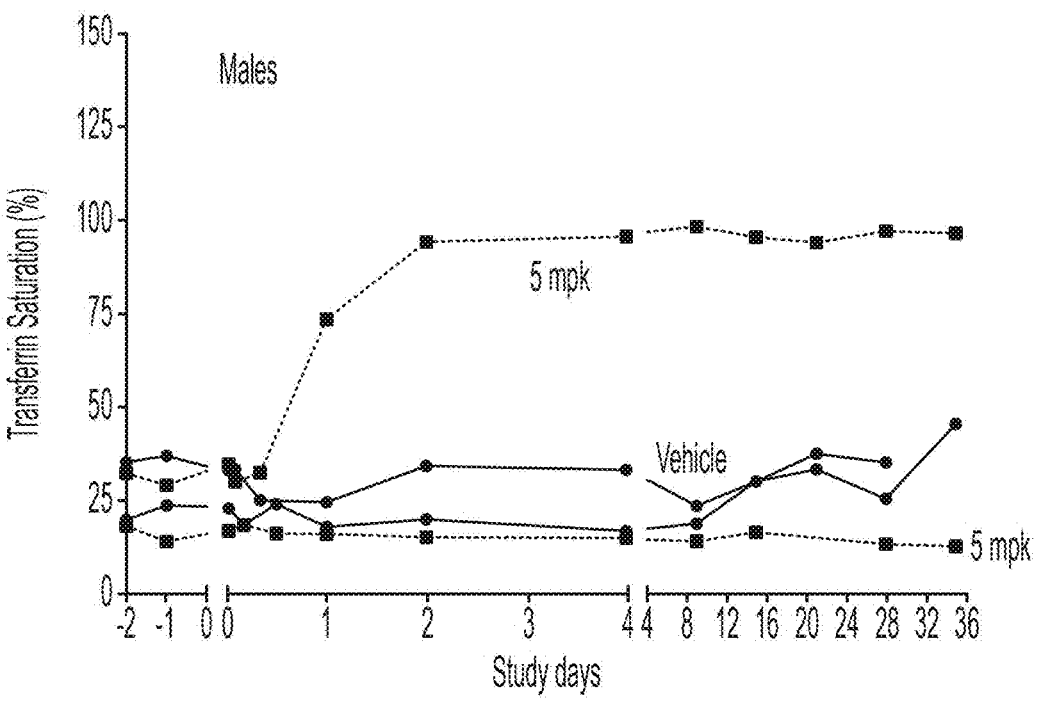

Further, a similar study was conducted in non-human primate Cynomolgus macaque (cyno). Both female (n=2) and male (n=2) cynos received a single dose of hHA-008 at 5 mg per kilogram of body weight (mpk) by intravenous injection. Transferrin saturation (TSAT %) were tested over time. Both female cynos showed maximum effect of increased TSAT % about 1-4 days after injection (FIG. 6B). One of the males showed the same effect, while the other one didn't respond to hHA-008 treatment (FIG. 6C). It as subsequently determined by examining the hematological profile of this male, that the lack of response was the result of this cyno having plasma Hepcidin-25 level that was below the limit of detection (below 2 ng/mL). Further, before the injection, this male cyno had a lower baseline TSAT % and serum iron level than other cynos in the group: two days before the injection, it had a baseline TSAT % level at 18% and a serum iron level at 77 μg/dL; one day before the injection, it had a baseline TSAT % level at 14% and a serum iron level at 61 μg/dL. The low baseline TSAT % and serum iron levels, in combination with the low Hepcidin-25 levels, was indicative that this male cyno had absolute iron deficiency instead of functional iron deficiency.

Further studies examining the effects of hHA-008 administration in more than 70 cynos revealed that animals having normal baseline serum iron levels (e.g., in the range of 80 μg/dL to 180 μg/dL) and hepcidin-25 levels greater than 2 ng/mL were responsive to hHA-008 treatment in that they exhibited pronounced increase in TSAT % levels shortly after injection (e.g., within 1-2 days post treatment) in response to reduced hepcidin-25 expression.

Figure 7B:
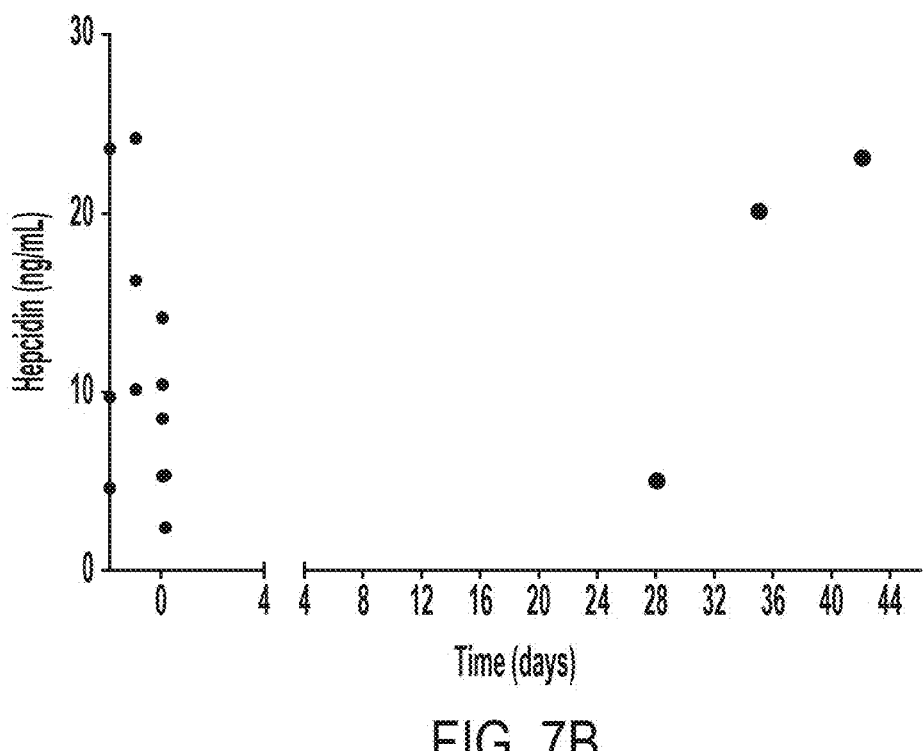
Figure 7C:
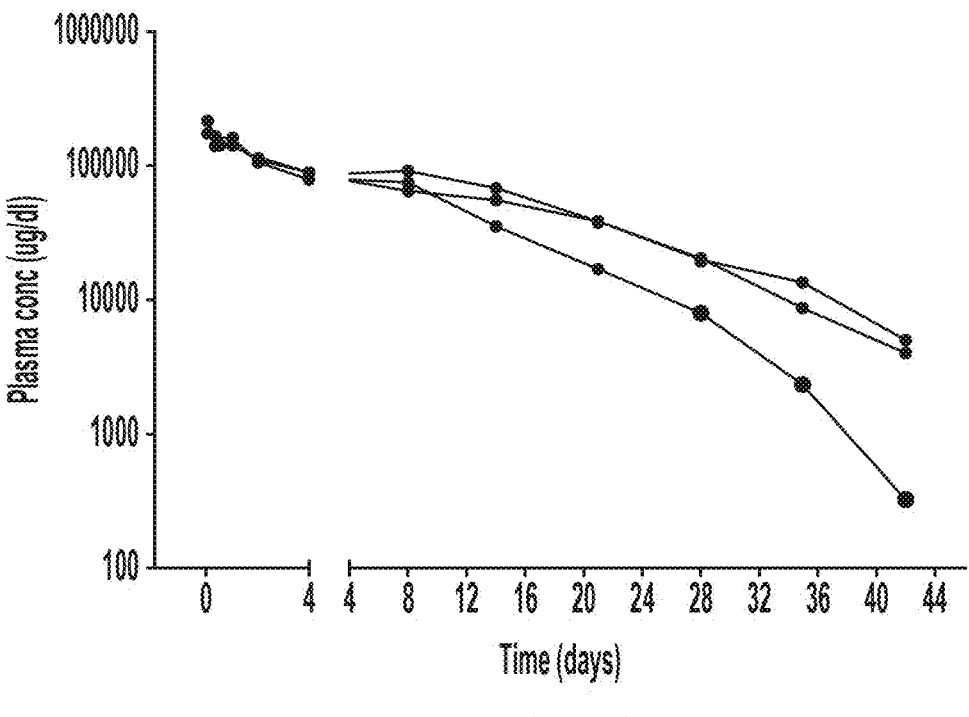

Additional experiments were conducted in cynos. Single dose of 6 mpk of hHA-008 were administered to three cynos via intravenous injection, and TSAT % (determined as serum iron over total iron binding capacity), plasma hepcidin-25 concentration, and plasma hHA-008 concentrations were tested for each animal and time point. Similarly, the data showed that the maximum effect of increased TSAT % occurred 1-4 days after injection ($T_{max}$=1-4 days), which was consistent with the increase of hHA-008 concentrations. One of the animals had a drastic decline of TSAT % around day 34 (FIG. 7A), which was consistent with the declining of plasma hHA-008 concentration around that time. Plasma hepcidin-25 concentration correlated inversely with the concentrations of hHA-008, in that hepcidin-25 was undetectable after antibody injection, and for the animal which had the drastic decline of TSAT %, hepcidin-25 level increased around the same time (FIG. 7B). In this cyno, hHA-008 had a plasma $t_{1/2}$ of about 5 days. The animal showed decline of TSAT % and increased hepcidin-25 levels at approximately day 34, which correlated well with the decrease of hHA-008 from plasma (FIG. 7C). $T_{1/2}$ of ~7 days in Cyno supports≥one/month dosing frequency in human.

Figure 7D:
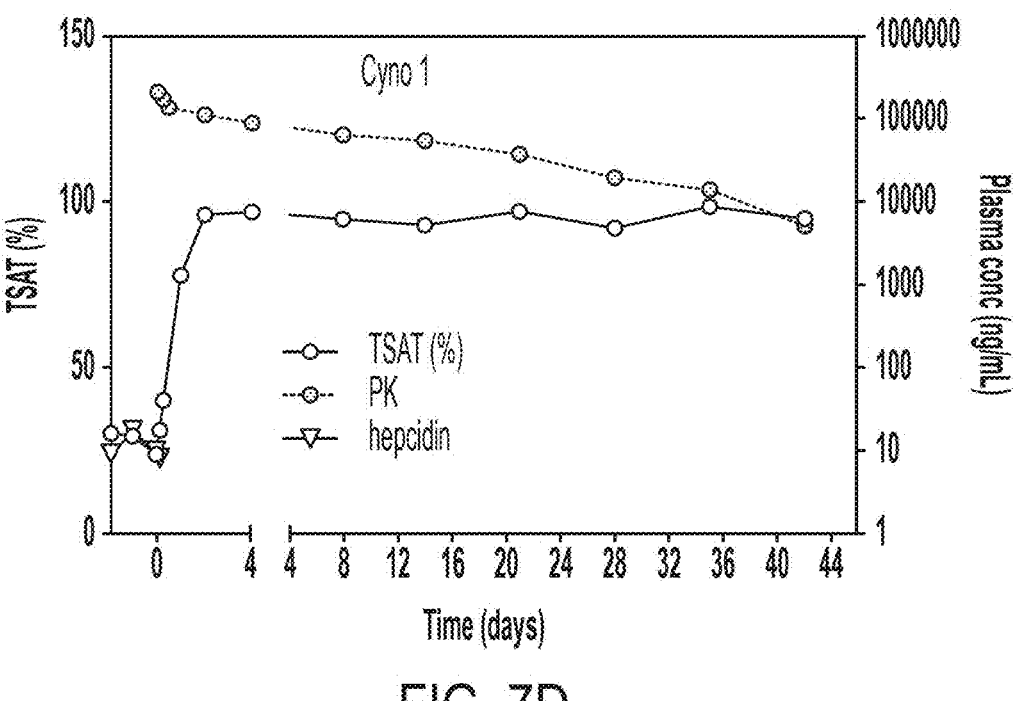
Figure 7E:
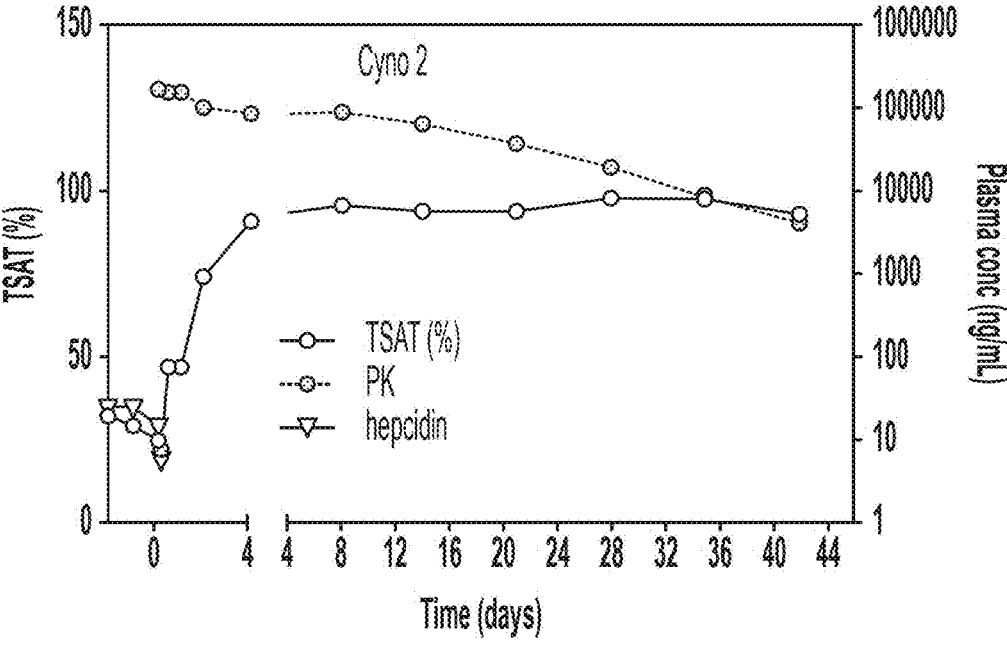
Figure 7F:
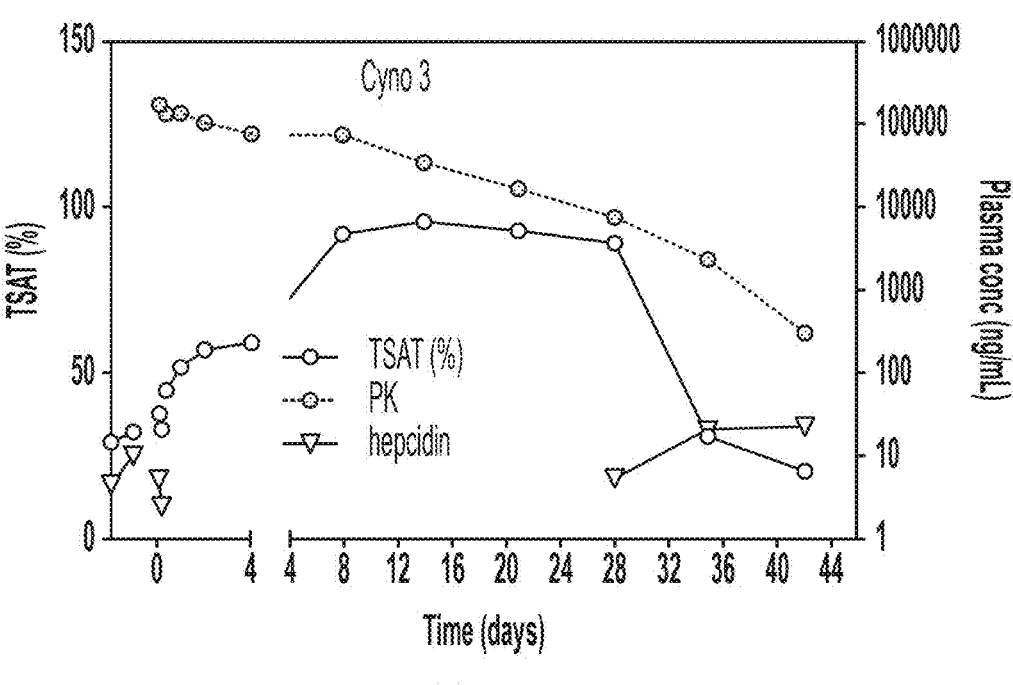
Figure 8A:
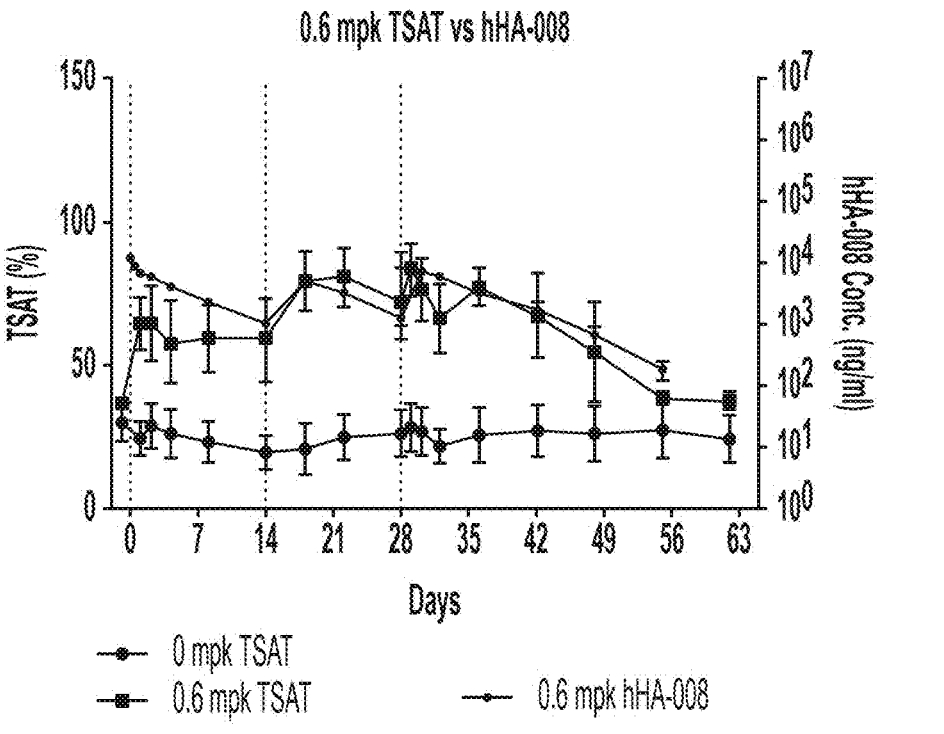
FIGS. 8A-8C show that hHA-008 antibody modulates TSAT % in a dose-dependent manner.
Figure 8B:
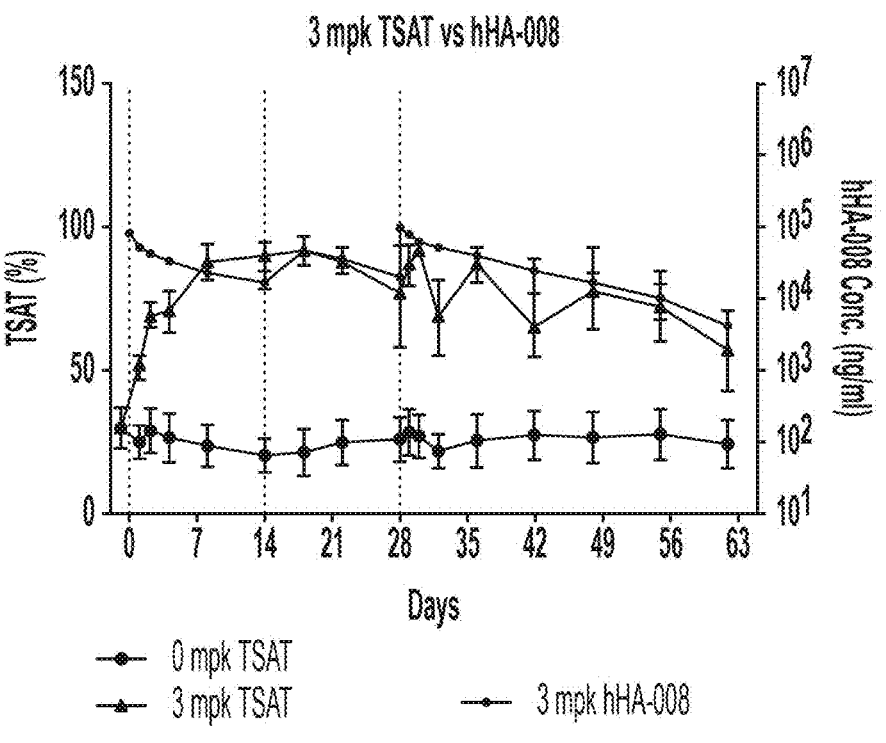
Figure 8C:
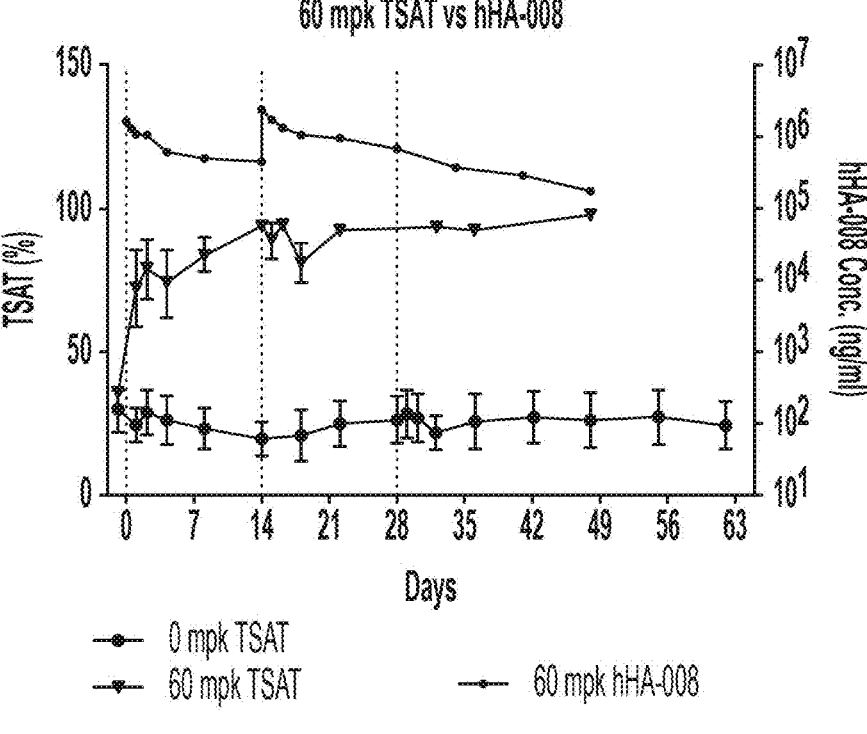

Moreover, hHA-008 had showed robust PK/PD correlation of PK (plasma antibody concentration) to TSAT % and plasma hepcidin-25 concentrations. The results of each tested Cyno are shown in FIG. 7D (Cyno 1), FIG. 7E (Cyno 2), and FIG. 7F (Cyno 3). hHA-008 showed a $t_{1/2}$ of 10.3 days in Cyno 1, $t_{1/2}$ of 8.8 days in Cyno 2, and $t_{1/2}$ of 5.1 days in Cyno 3. Hepcidin-25 level drops to undetectable (<2 ng/ml) after hHA-008 treatment. Interestingly, return of hepcidin-25 level to circulation was well correlated with the $t_{1/2}$ of hHA-008 in Cyno 3 (FIG. 7F).

hHA-008 antibody modulates TSAT % in a dose-dependent manner. Multiple dose studies were conducted in Cynos. The cynos (n=4 per dose level with 2 males and 2 females) were treated with either 0 (vehicle control), 0.6 mpk hHA-008, 3 mpk hHA-008, or 60 mpk hHA-008. The resulting concentrations of hHA-008 and the corresponding TSAT % response are presented in FIG. 8A, FIG. 8B and FIG. 8C for the 0.6, 3 and 60 mpk treatments respectively, all plotted vs the vehicle control. Cynos were dosed every 4 days. Dotted lines represent dose day. TSAT % increased after dosing, and the percent modulation was consistent with the dose levels: at 0.6 mpk, TSAT reached ~60%, and at 3 mpk and 60 mpk, TSAT % was saturated, indicating that hHA-008 modulates TSAT % in a dose dependent manner. Further, after the first dose at 0.6 mpk, TSAT % levels were maintained at ~60%, while at higher dose levels, TSAT % reached 100%, suggesting that TSAT can be modulated by selection of appropriate dose-level/regimen (FIGS. 8A-8C).

Example 5: HHA-008-QL Confers Longer Serum Half-Life and Takes Longer Time to Reach Maximal Effect Compared to hHA-008

Figure 9A:
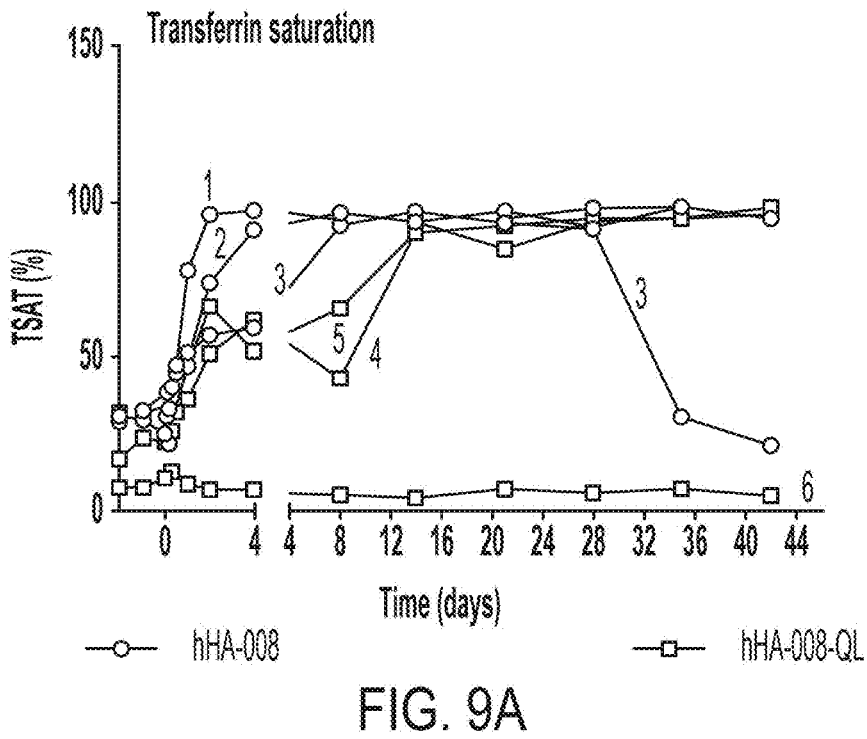
FIGS. 9A-9C are graphs showing the PK/PD comparison between hHA-008 and hHA-008-QL.
Figure 9B:
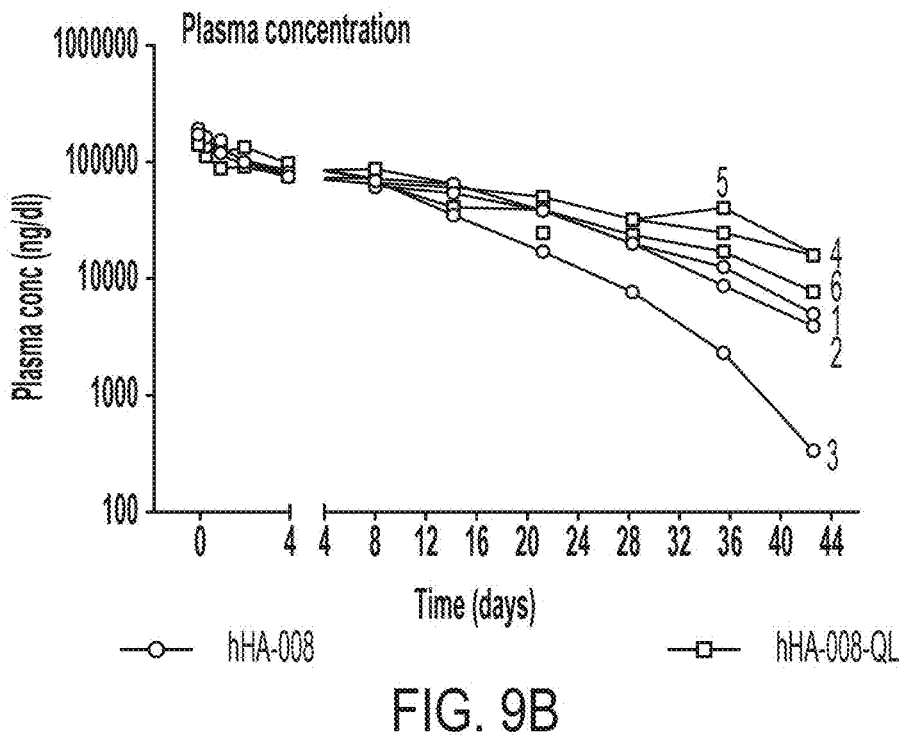
Figure 9C:
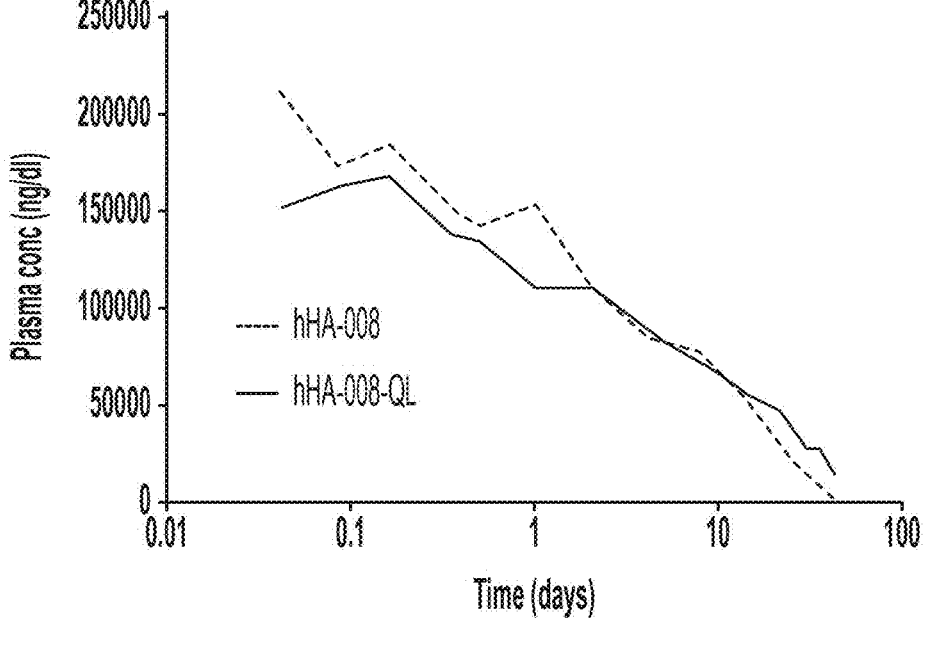

This study was designed to administer hHA-008 or hHA-008-QL at 6 mpk intravenously to Cynos (n=3). Samples were collected from each animal at 48 and 24 hr prior to treatment, and at 0, 0.04, 0.08, 0.167, 0.333, 0.5, 1, 2, 4, 8, 14, 21, 28, 35 and 42 days after treatment. TSAT % and plasma hepcidin-25 level were measured in each sample. The data showed that hHA-008 took shorter time to reach maximal effect ($T_{max}$) of increased TSAT % as compared to hHA-008-QL (FIG. 9A). Note that there was a non-responder in animals treated with hHA-008-QL. As discussed above, the non-responder had low hepcidin-25 levels and low serum iron at base line prior to antibody treatment. On the other hand, hHA-008-QL had longer serum half-life ($T\frac{1}{2}$=12.1 days) compared to hHA-008 ($T\frac{1}{2}$=6.76 days) (FIG. 9B). Plasma concentrations of both antibodies were measured over time, as shown in FIG. 9C. Peak plasma concentrations were determined. A summary of the data between hHA-008 and hHA-008-QL are shown in Table 12.

TABLE 12

| hHA-008 v. hHA-008-QL | | | |
| --- | --- | --- | --- |
| Parameter | Units | hHA-008 | hHA-008-QL |
| $C_{max}$ | µg/mL | 211.15 | 168.4 |
| $T_{max}$ | days | 0.083 | 2 |
| $T\frac{1}{2}$ | days | 6.76 | 12.1 |

Figure 10A:
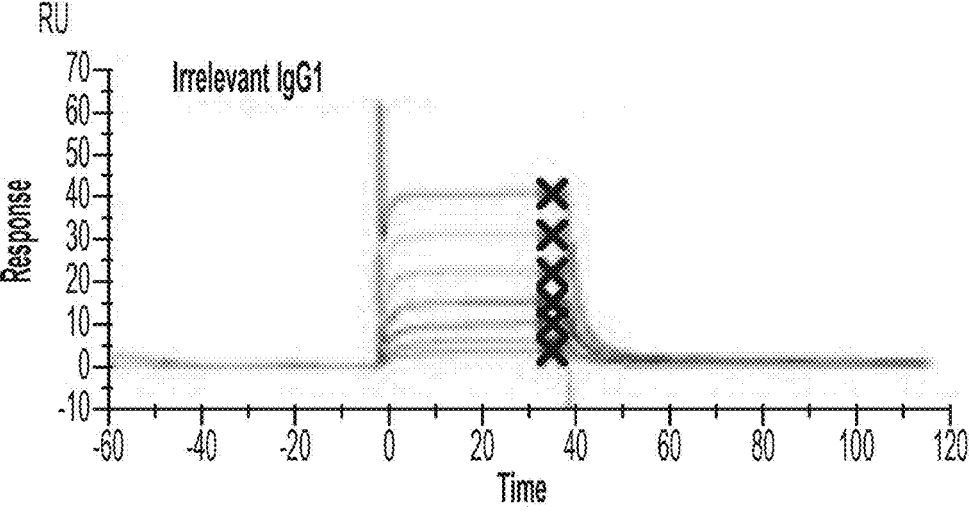
FIGS. 10A-10B are graphs showing binding of FcRn of hHA-008 and hHA-008-QL at pH 6.0 or 7.4.
Figure 10A:
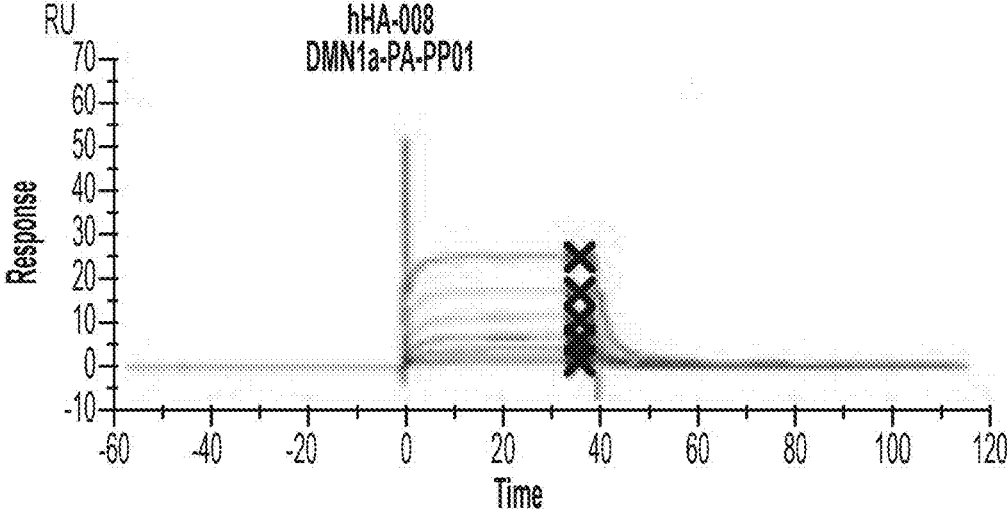
Figure 10A:
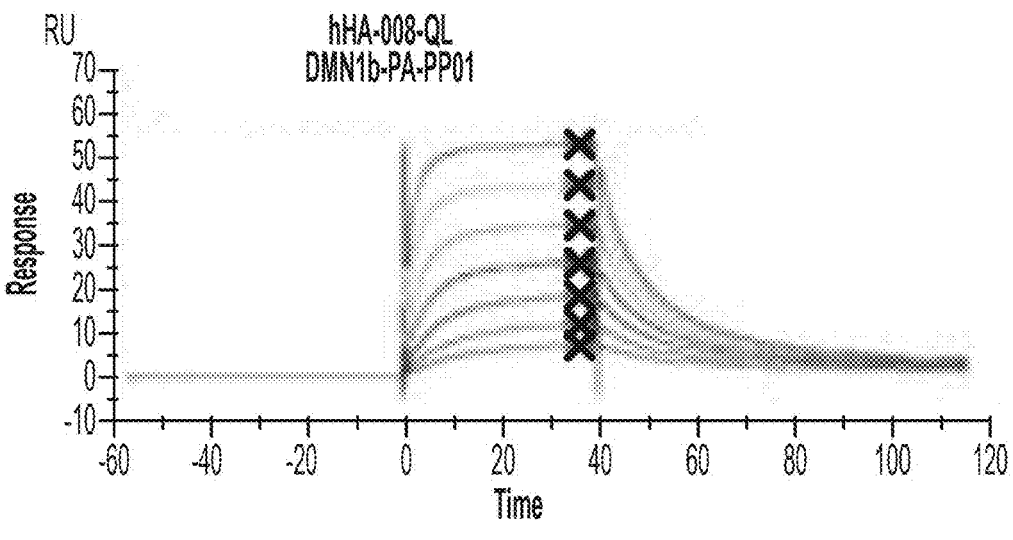
Figure 10A:
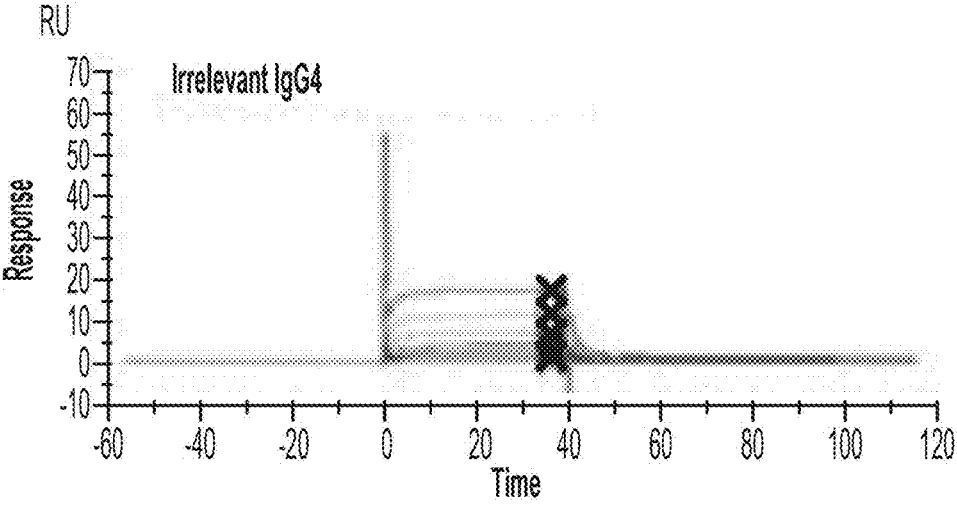
Figure 10A:
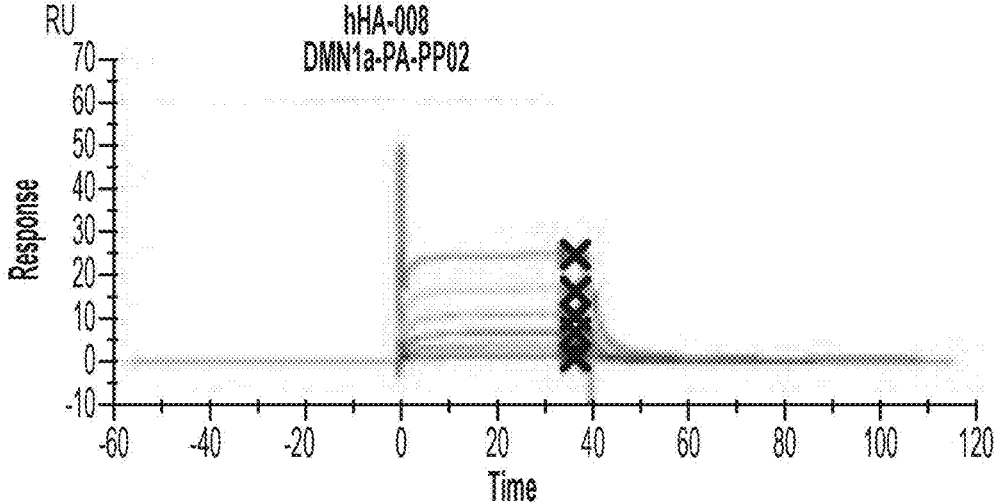
Figure 10A:
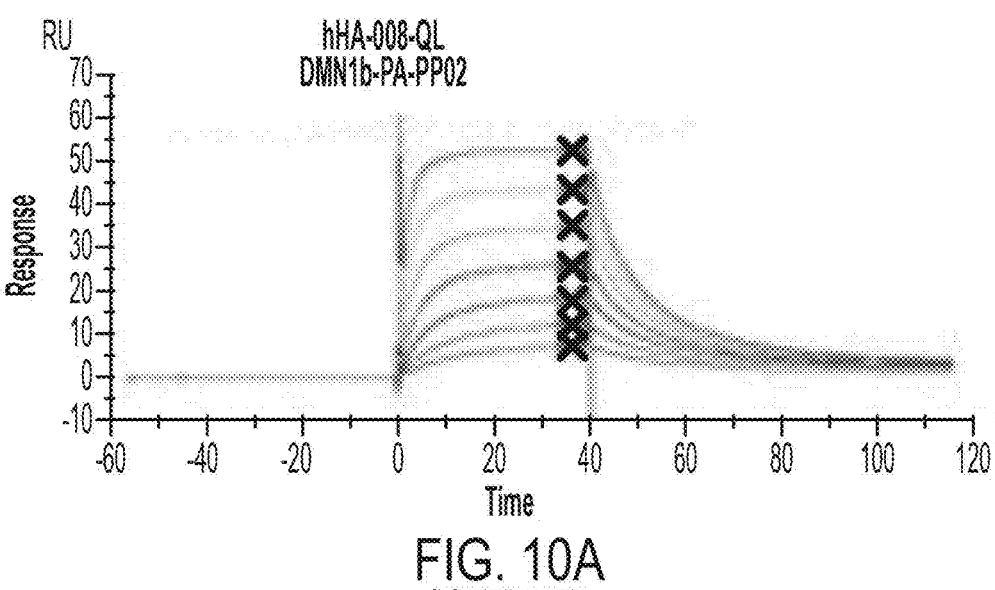
Figure 10B:
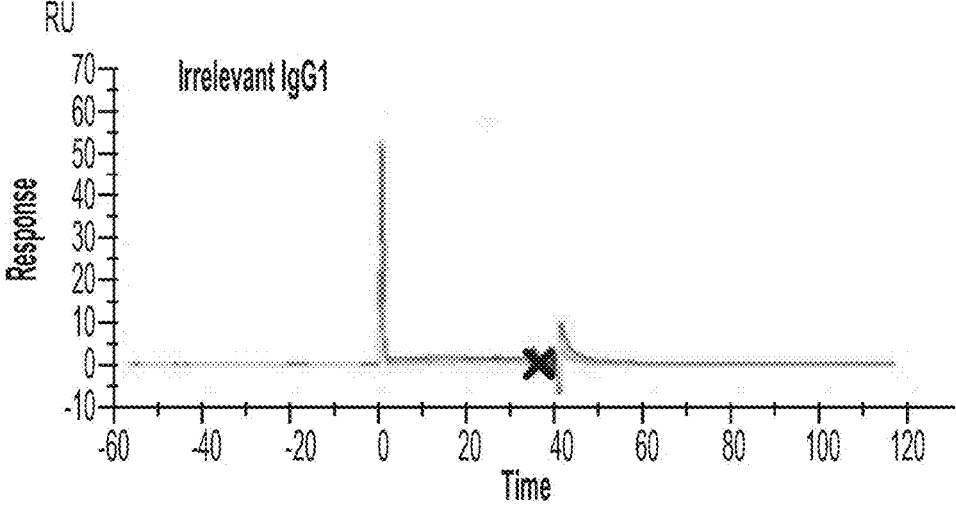
Figure 10B:
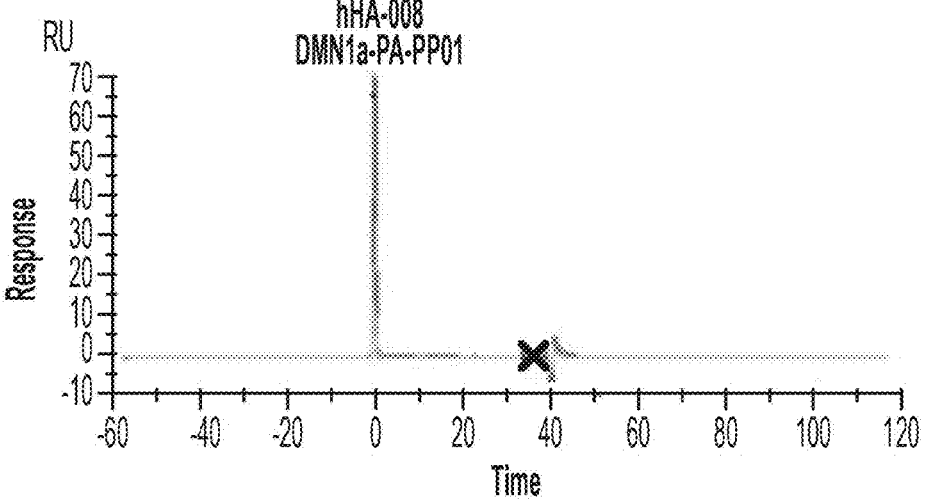
Figure 10B:
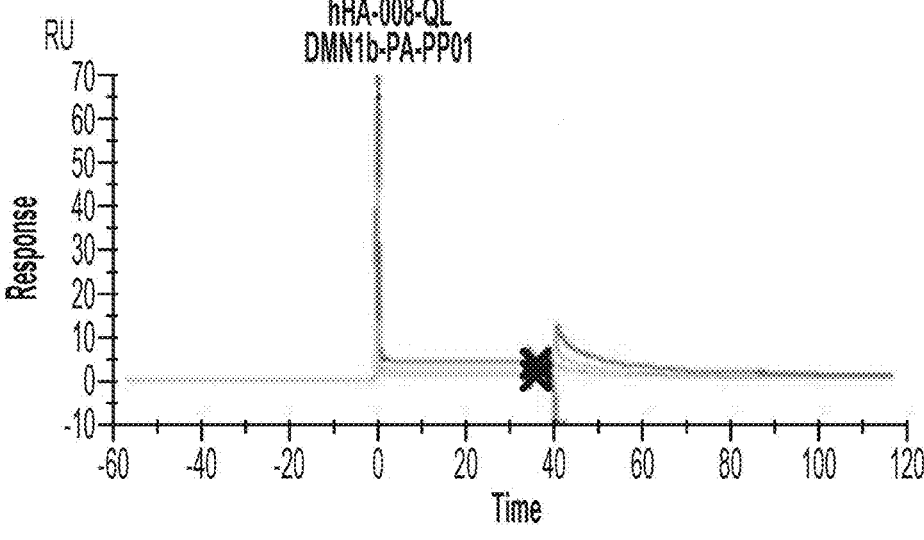
Figure 10B:
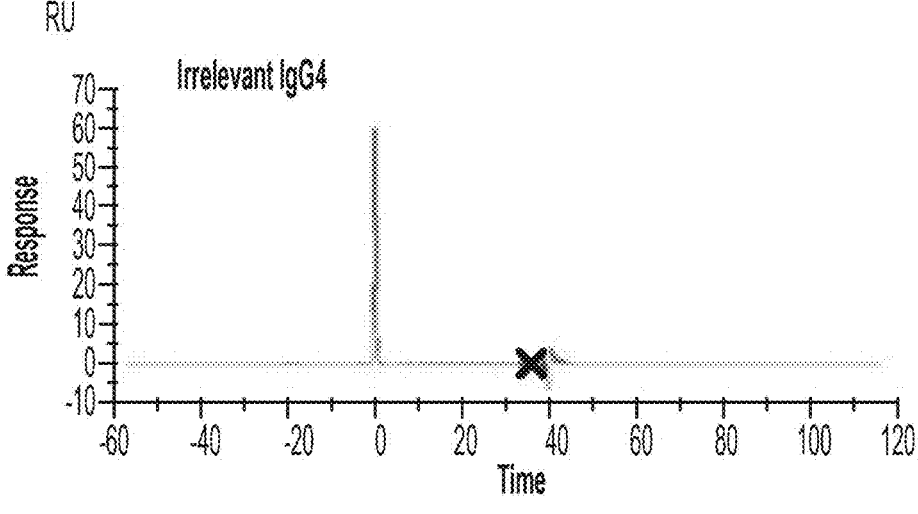
Figure 10B:
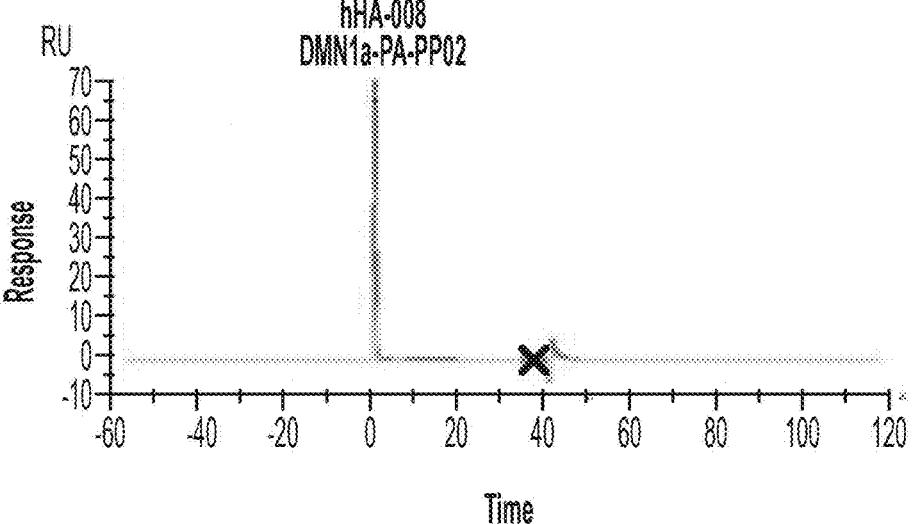
Figure 10B:
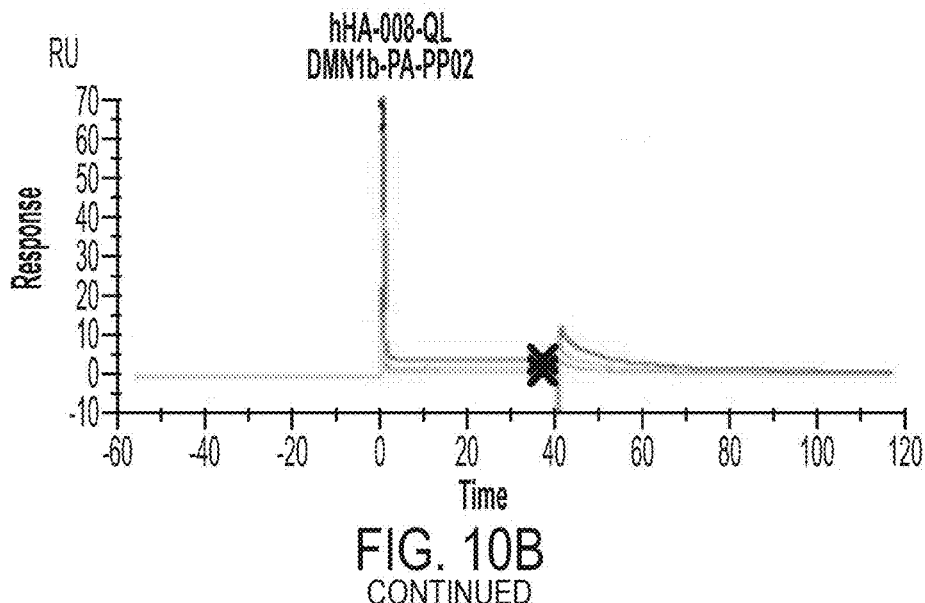

To investigate whether the longer serum life for hHA-008-QL was attributed to higher affinity to FcRn, both antibodies were analyzed for binding to FcRn at pH 6.0 and pH 7.4 using BIAcore. Non-specific IgG1 and IgG4 were used as controls. The dissociation constant (KD) of each of the antibody and the controls to FcRn at pH 6.0 and 7.4 were shown in Table 13, and the response curve were shown in FIGS. 10A-10B. No binding was observed of neither antibodies at pH 7.4 (FIG. 10B).

TABLE 13

| KD for FcRn at pH 6.0 and pH 7.4 | | |
| --- | --- | --- |
| | KD (M) at pH 6.0 | KD (M) at pH 7.4 |
| IgG1 | 1.64E-06 | no binding |
| IgG4 | 3.64E-06 | no binding |
| hHA-008 | 2.95E-06 | no binding |
| hHA-008 | 2.96E-06 | no binding |
| hHA-008-QL | 9.00E-07 | no binding |
| hHA-008-QL | 8.82E-07 | no binding |

The mutations L247A and L248A (Kabat) (L234A and L235A, EU Numbering) do not appear to significantly affect FcRn binding. The overall affinity and response (RMax) for binding of FcRn at pH 6.0 is increased for hHA-008-QL compared to hHA-008, suggesting that the QL mutation confers the longer $t\frac{1}{2}$ via the binding to the receptor.

Figure 11:
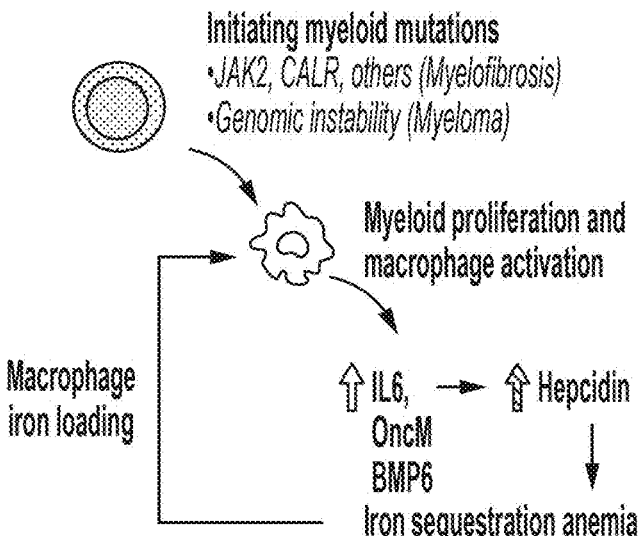
FIG. 11 depicts a myeloproliferation cycle characteristic certain high hepcidin disorders.
Figure 12:
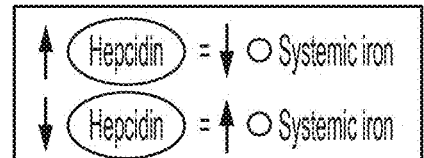
FIG. 12 depicts the hepcidin stimulatory pathway and the physiological regulation of iron homeostasis by hepcidin.
Figure 12:
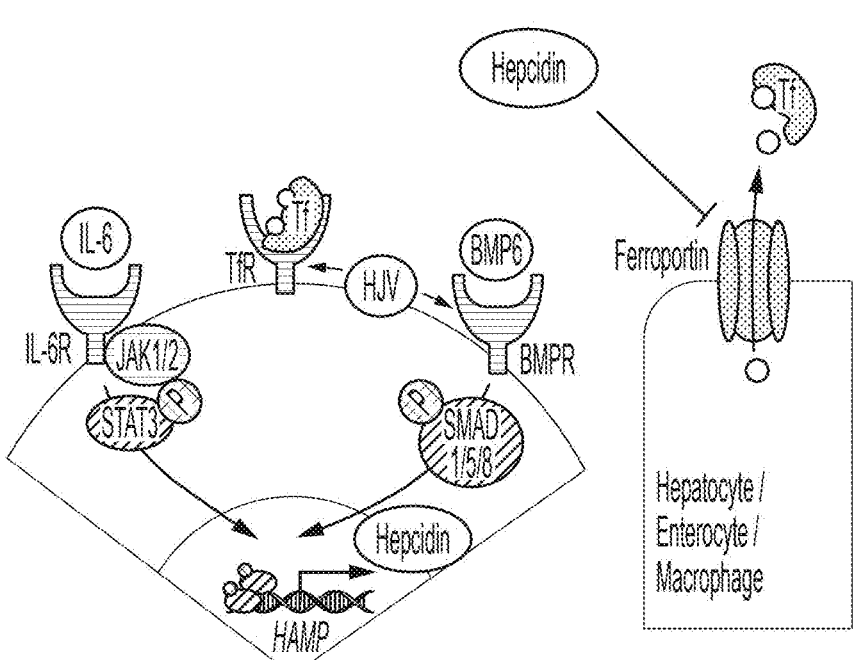
Figure 13:
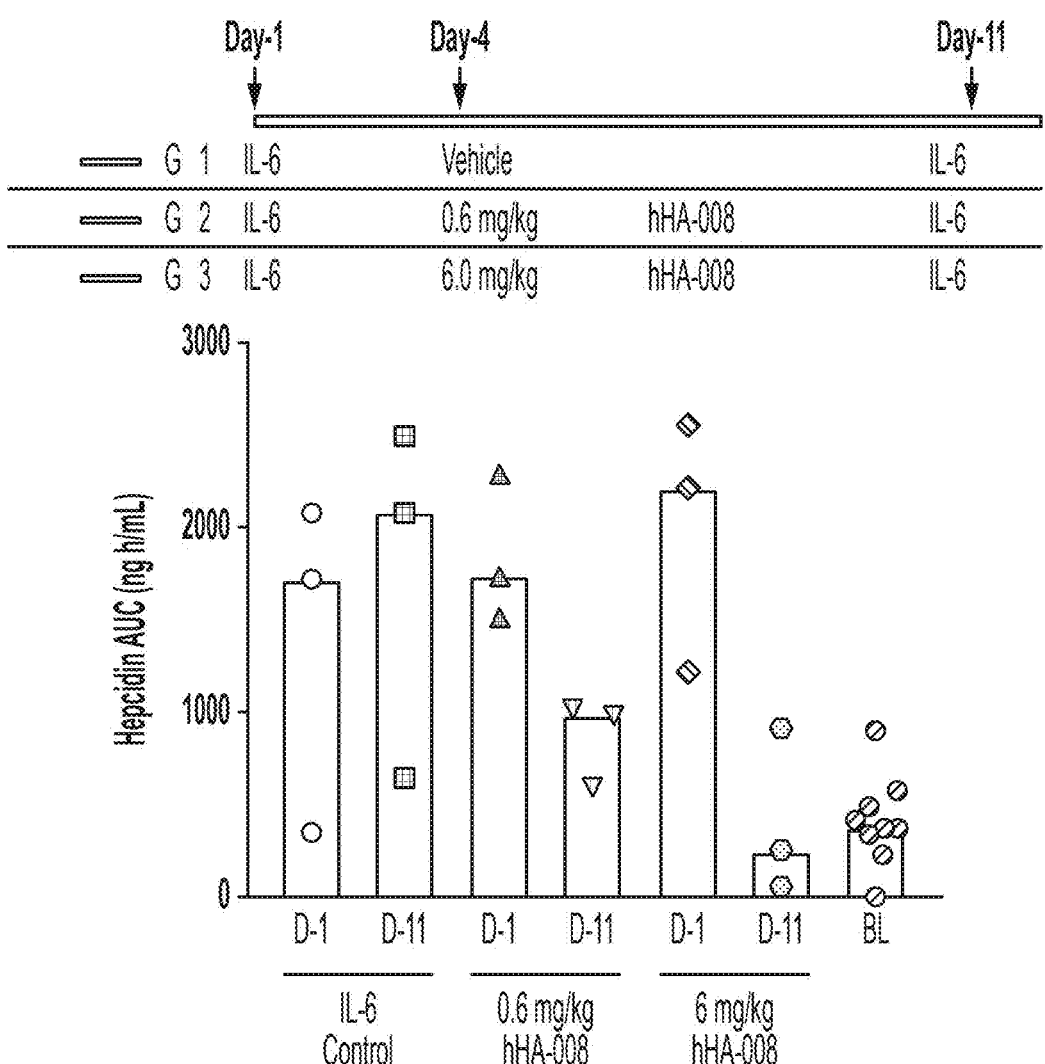
FIG. 13 is a graph showing that IL-6 induces hepcidin expression in Cynos, and hHA-008 treatment prevents inflammation-induced (IL 6) hepcidin-25 increase in a dose-dependent manner.

Example 6: hHA-008 Decreases IL-6 Induced Hepcidin-25 Expression in Non-human Primates As depict in FIG. 11, in iron sequestration anemia, pro-inflammatory cytokines that induce hepcidin synthesis, such as IL-6 and oncostatin-M, are typically increased and associated with iron sequestration, macrophage iron loading, as well as myeloid proliferation and macrophage activation. To test whether IL-6 indeed increases hepcidin expression and whether anti-HJV antibody is capable of inhibiting hepcidin expression induced by IL-6 in non-human primates, cynos were challenged with IL-6 on day 1, and divided into three groups. On day 4, cynos in Group 1 received vehicle control, cynos in Group 2 received hHA-008 antibody at 0.6 mg/kg, and cynos in Group 3 received hHA-008 antibody at 6.0 mg/kg. On day 11, cynos in all three groups were challenged with IL-6 again, and plasma hepcidin-25 in all cynos was measured. As shown in FIG. 13, IL-6 challenge increased plasma hepcidin-25 concentrations on Day 1, compared to pre-challenge baseline (BL) in all three groups of cynos. After the second IL-6 challenge on Day 11, cynos in group 1 showed an increase in plasma hepcidin-25 similar to that observed on Day 1. However, for cynos in groups 2 (0.6 mg/kg hHA-008) and 3 (6 mg/kg hHA-008), the presence hHA-008 prevented the IL-6 induced increase in plasma hepcidin-25 on Day 11 in a dose-dependent manner. That is, hHA-008 was effective in preventing inflammation-induced (IL 6) hepcidin increase in a dose-dependent manner in cynos. These results suggest that anti-HJV antibody are capable of inhibiting hepcidin expression induced by the IL-6 signaling pathway.

Example 7: Epitope Mapping

Epitope mapping was performed on hHA-008 and hHA-008-QL, using 3720-RG-050 (Hemojuvelin (HJV) fragment, SEQ ID NO: 123).

Before epitope mapping, High-Mass MALDI mass spectrometry and chemical cross-linking was used to confirm no non-covalent aggregates of hHA-008 and hHA-008-QL and multimers of the 3720-RG-050 were detected in sample preparation.

In order to determine the epitopes of hHA-008 and hHA-008-QL on 3720-RG-050 with high resolution, 3720-RG-050/hHA-008 and 3720-RG-050/hHA-08-QL complexes were incubated with deuterated cross-linkers and subjected to multi-enzymatic cleavage. After enrichment of the cross-linked peptides, the samples were analyzed by high resolution mass spectrometry (nLC-LTQ-Orbitrap MS) and the data generated were analyzed using XQuest and Stavrox software.

3720-RG-050/hHA-008 (HJV Fragment/hHA-008)

After Trypsin, Chymotrypsin, ASP-N, Elastase and Thermolysin proteolysis of the protein complex 3720-RG-050/hHA-008 with deuterated d0d12, the nLC-orbitrap MS/MS analysis detected 8 cross-linked peptides between 3720-RG-050 and hHA008.

The sequences and positions of cross-links are presented in Table 14 below.

TABLE 14

Cross-linked peptides detected between 3720-RG-050 and hHA-008.
hHA-008 - Chymotrypsin and Thermolysin results in interlink between hHA-008
complementarity determining regions and 3720-RG-050

| Enzyme | hHA-008 HC/hHA-008 LC | 3720-RG-050 | Amino Acid Residues of hHA-008 HC/hHA-008 LC | Amino acid Residues of 3720-RG-050 | nAA1 | nAA2 | Identified on StavroX |
|---|---|---|---|---|---|---|---|
| Chymotrypsin | hHA-008_HC (SEQ ID NO: 38) | SEQ ID NO: 123 | 48-53 | 166-189 | 52 | 170 | YES |
| Chymotrypsin | hHA-008_LC (SEQ ID NO: 39) | SEQ ID NO: 123 | 95-101 | 165-185 | 97 | 170 | YES |
| Chymotrypsin | hHA-008_LC (SEQ ID NO: 39) | SEQ ID NO: 123 | 95-101 | 165-185 | 98 | 171 | YES |
| Chymotrypsin | hHA-008_LC (SEQ ID NO: 39) | SEQ ID NO: 123 | 95-101 | 165-185 | 98 | 180 | YES |
| Chymotrypsin | hHA-008_LC (SEQ ID NO: 39) | SEQ ID NO: 123 | 95-101 | 165-185 | 98 | 182 | YES |
| Thermolysin | hHA-008_HC (SEQ ID NO: 38) | SEQ ID NO: 123 | 50-60 | 177-184 | 53 | 182 | YES |
| Chymotrypsin | hHA-008_LC (SEQ ID NO: 39) | SEQ ID NO: 123 | 95-101 | 165-185 | 98 | 183 | YES |
| Thermolysin | hHA-008_HC (SEQ ID NO: 38) | SEQ ID NO: 123 | 51-63 | 181-186 | 58 | 183 | YES |

Figures 14, 15A, 15B, 15C, 15D, 15E, 15F, 15G, 15H, 15I, 15J:
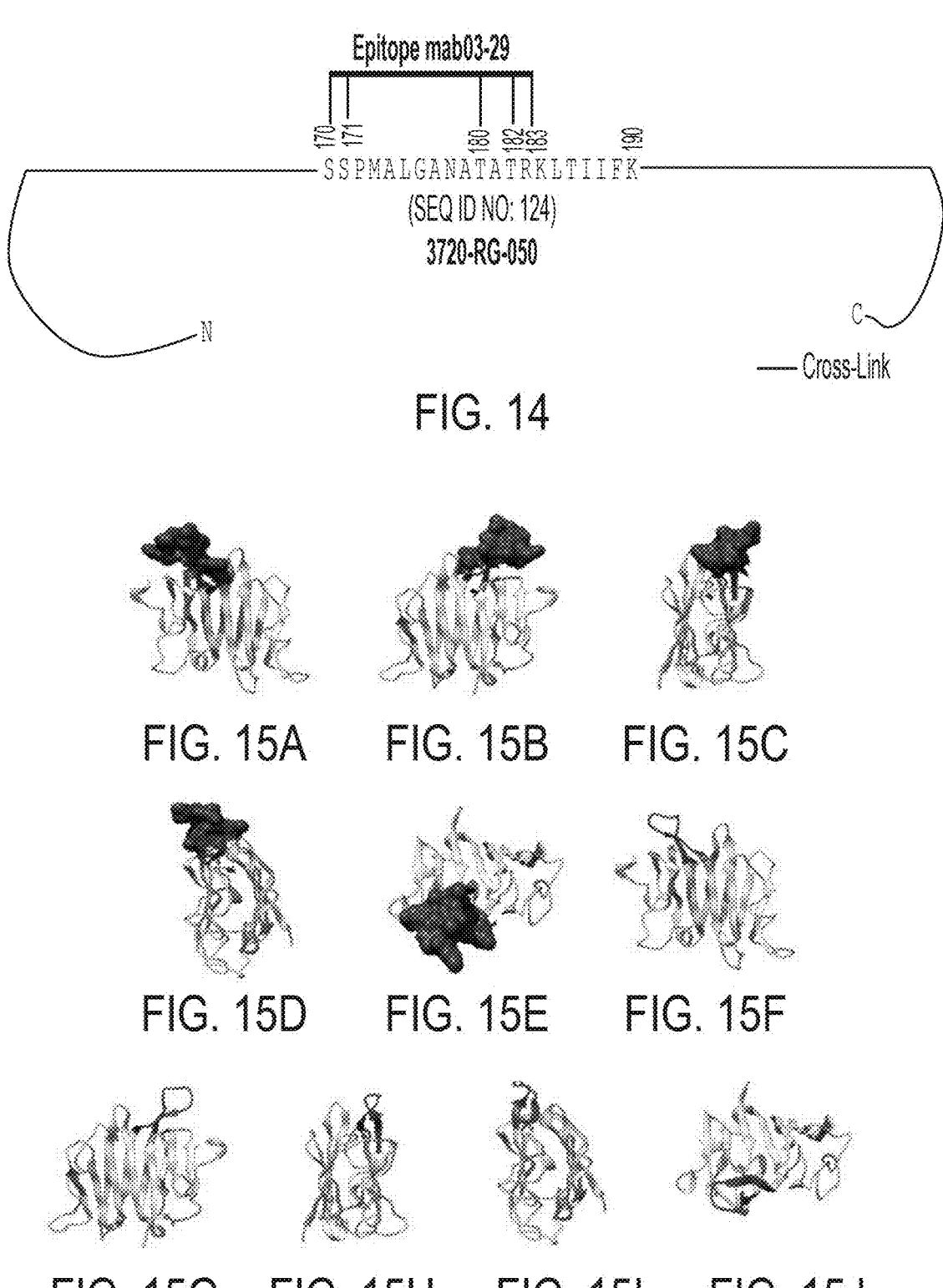
FIG. 14 shows hHA-008 interacts with amino acids 170-183 (SSPMALGANATATR (SEQ ID NO: 121)) on 3720-RG-050. The interaction happens on amino acids 170, 171, 180, 182, 183 on 3720-RG-050.

Using chemical cross-linking, High-Mass MALDI mass spectrometry and nLC-Orbitrap mass spectrometry, molecular interface between 3720-RG-050 and hHA-008 was characterized. FIG. 14 shows hHA-008 interacts with amino acids 170-183 (SSPMALGANATATR (SEQ ID NO: 121)) on 3720-RG-050. The inter action happens on amino acids 170, 171, 180, 182, 183 on 3720-RG-050. FIG. 15 shows the interaction of 3720-RG-050 and hHA-008. A 3720-RG-050 PDB structure was generated by homology using Swiss Model software. 3720-RG-050 amino acids 170-183 (SSP-MALGANATATR (SEQ ID NO: 121)) of 3720-RG-050 sequence are shown in FIG. 15: ribbon/surface representa-tion of front view (A); back view (B), side view 1 (C), side view 2 (D) and top view (E). F, G, H, I, J: ribbon representation of front view (F); back view (G), side view 1 (H), side view 2 (I) and top view (J).

3720-RG-050/hHA-008-QL(HJV Fragment/hHA-008-QL)

After Trypsin, Chymotrypsin, ASP-N, Elastase and Thermolysin proteolysis of the protein complex 3720-RG-050/hHA-008-QL with deuterated d0d12, the nLC-orbitrap MS/MS analysis detected 16 cross-linked peptides between 3720-RG-050 and hHA-008-QL.

The sequences and positions of cross-links are presented in Table 15 below.

TABLE 15

Cross-linked peptides detected between 3720-RG-050 and HA-008-QL.
hHA-008-QL- Trypsin, Chymotrypsin, AspN, Elastase and Thermolysin results Interlink between
hHA-008-QLcomplementarity determining regions and 3720-RG-050

| Enzyme | hHA-008-QL HC/ hHA-008-QL LC | 3720-RG-050 | Amino Acid Residues of hHA-008-QL HC/ hHA-008-QL LC | Amino acid Residues of 3720-RG-050 | nAA1 | nAA2 | Identified on StavroX |
|---|---|---|---|---|---|---|---|
| Chymotrypsin | hHA-008-QL_LC (SEQ ID NO: 39) | SEQ ID NO: 123 | 95-101 | 165-185 | 97 | 169 | YES |
| Chymotrypsin | hHA-008-QL _LC (SEQ ID NO: 39) | SEQ ID NO: 123 | 95-101 | 165-185 | 98 | 169 | YES |
| Chymotrypsin | hHA-008-QL _LC (SEQ ID NO: 39) | SEQ ID NO: 123 | 95-101 | 165-185 | 98 | 171 | YES |
| Chymotrypsin | hHA-008-QL _LC (SEQ ID NO: 39) | SEQ ID NO: 123 | 95-101 | 165-185 | 98 | 180 | YES |
| Chymotrypsin | hHA-008-QL _LC (SEQ ID NO: 39) | SEQ ID NO: 123 | 53-67 | 176-185 | 59 | 180 | YES |
| Chymotrypsin | hHA-008-QL _LC (SEQ ID NO: 39) | SEQ ID NO: 123 | 53-67 | 176-185 | 61 | 180 | YES |
| Chymotrypsin | hHA-008-QL _LC (SEQ ID NO: 39) | SEQ ID NO: 123 | 95-101 | 165-185 | 98 | 182 | YES |
| Chymotrypsin | hHA-008-QL _HC (SEQ ID NO: 38) | SEQ ID NO: 123 | 96-104 | 280-292 | 100 | 289 | YES |
| Thermolysin | hHA-008-QL _HC (SEQ ID NO: 38) | SEQ ID NO: 123 | 29-44 | 283-302 | 32 | 293 | YES |
| Elastase | hHA-008-QL _HC (SEQ ID NO: 38) | SEQ ID NO: 123 | 31-42 | 290-295 | 32 | 294 | YES |
| Thermolysin | hHA-008-QL _HC (SEQ ID NO: 38) | SEQ ID NO: 123 | 29-44 | 283-302 | 32 | 295 | YES |
| Trypsin | hHA-008-QL _HC (SEQ ID NO: 38) | SEQ ID NO: 123 | 39-58 | 292-299 | 52 | 295 | YES |
| Trypsin | hHA-008-QL HC (SEQ ID NO: 38) | SEQ ID NO: 123 | 20-43 | 295-300 | 32 | 297 | YES |
| Thermolysin | hHA-008-QL _HC (SEQ ID NO: 38) | SEQ ID NO: 123 | 29-44 | 283-302 | 30 | 300 | YES |
| Elastase | hHA-008-QL _HC (SEQ ID NO: 38) | SEQ ID NO: 123 | 31-42 | 294-302 | 32 | 300 | YES |
| Elastase | hHA-008-QL _HC (SEQ ID NO: 38) | SEQ ID NO: 123 | 31-42 | 294-302 | 38 | 300 | YES |

Figures 16, 17A, 17B, 17C, 17D, 17E, 17F, 17G, 17H, 17I, 17J:
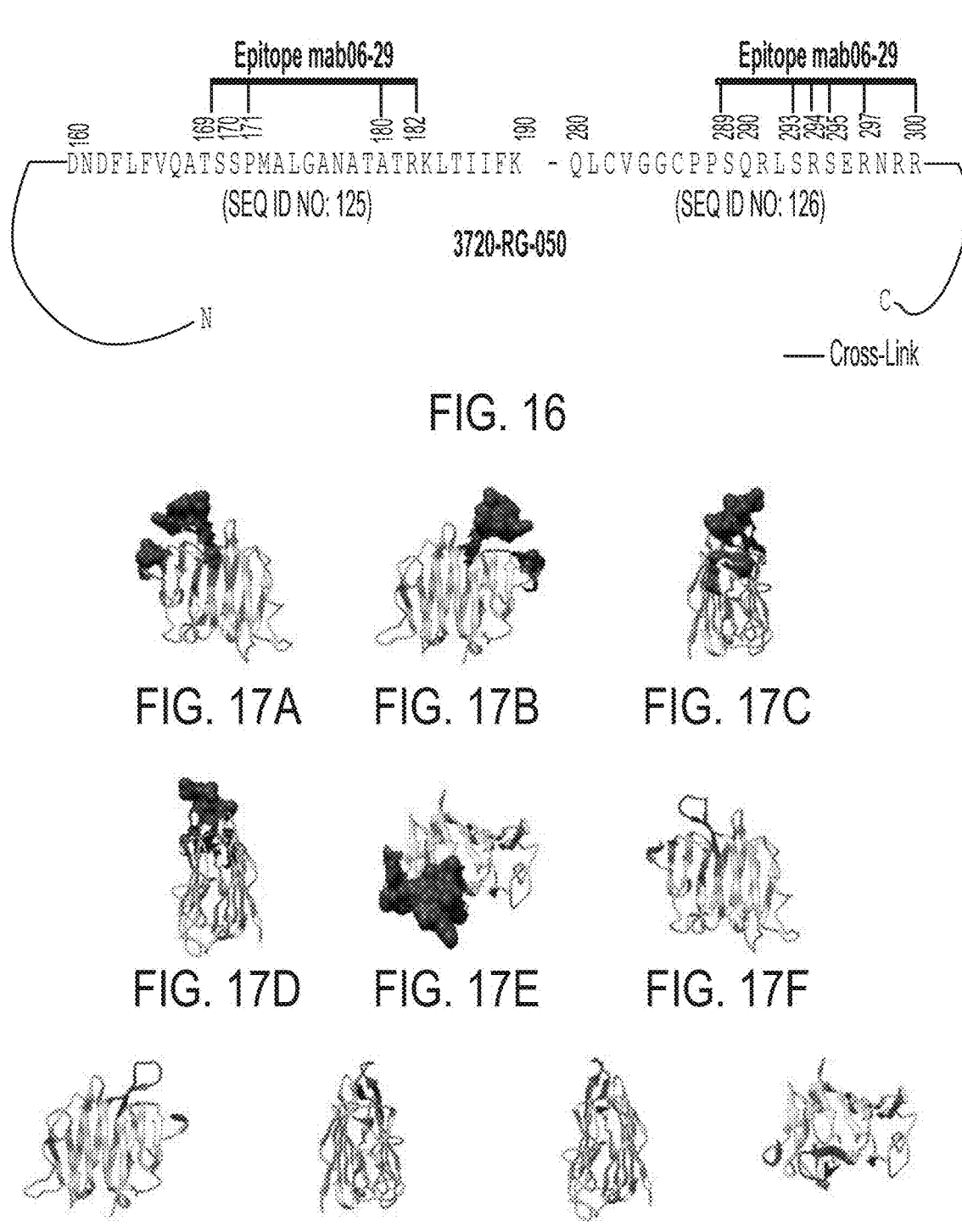
FIG. 16 shows hHA-008-QL interacts with amino acids 169-182 (TSSPMALGANATAT (SEQ ID NO: 122)) and 289-300 (SQRLSRSERNRR (SEQ ID NO: 127)) of 3720-RG-050. The interaction happens on amino acids 169, 171, 180, 182; 289, 293, 294, 295, 297, 300 on 3720-RG-050.

Using chemical cross-linking, High-Mass MALDI mass spectrometry and nLC-Orbitrap mass spectrometry, molecular interface between 3720-RG-05C and hHA-008-QL was characterized. FIG. 16 shows hHA-008-QL interacts with amino a ids 169-182 (TSSPMALGANATAT (SEQ ID NO: 122)) and 289-300 (SQRLSRSERNRR (SEQ ID NO: 127)) of 3720-RG-050. The interaction happens on amino acids 169, 171, 180, 182; 289, 293, 294, 295, 297, 300 on 3720-RG-050. FIG. 17 shows the interaction 3720-RG-050/hHA-008-QL. A 3720-RG-050 PDB structure was generated by homology using Swiss Model software. 3720-RG-050 amino acids 169-182 (TSSPMALGANATAT (SEQ ID NO: 122) and 289-291 (SQR) are shown as FIG. 17: ribbon/surface representation of front view (A); back view (B), side view 1 (C), side view 2 (D) and top view (E). F, G, H, I, J: ribbon representation of front view (F); back view (G), side view 1 (H), side view 2 (I) and top view (j).

Example 8: hHA-008-QL Decreases Circulating Transferrin Level

Circulating transferrin level can be used as an indicator of the iron level in the body along with other markers (e.g., total iron binding capacity, serum ferritin level, etc.). Circulating transferrin is an iron-transport protein that reflects both protein and iron status. Transferrin increases with iron deficiency and decreases when iron status improves (see, e.g., Litchford et al., NUTRITIONAL ISSUES IN THE PATIENT WITH DIABETES AND FOOT ULCERS, Levin and O'Neal's The Diabetic Foot (Seventh Edition), 2008; Ogun et al., Biochemistry, Transferrin, Treasure Island (FL): StatPearls Publishing; 2021 January).

To test whether circulating transferrin level decreases after hHA-008-QL treatment, baseline transferrin level was established for each health Cynomolgus macaque (cynos) in the experiment 11 days before hHA-008-QL dosing on Day 1. Cynos were dosed with 0 mg/kg, 3 mg/kg, 30 mg/kg or 160 mg/kg of hHA-008-QL on day 1, day 15 and day 29 (n=5 in each group). Blood from each cyno was collected 96 hours, 192 hours, and 336 hours after the dosing on day 1; 48 hours, 96 hours, 192 hours, and 336 hours after the dosing on day 15; and 48 hours after the dosing on day 29. Note that blood for the 336-hour timepoint after day 1 dosing was collected 2 hours before the day 15 dosing, and blood for the 336-hour time point after day 15 dosing was collect 2 hours before the day 29 dosing. Transferrin levels were measured in all samples for each cyno, and was compared to its own baseline to calculate the percent change at each time point. The data in Table 16 show that treatment of hHA-008-QL reduced circulating transferrin levels compared to the baseline level.

129     130

TABLE 16

Circulating transferrin levels and changes over baseline in cynos treated with hHA-008-QL.

| Day(s) Relative to Start Date | Males 0 mg/kg/dose | 3 mg/kg/dose | 30 mg/kg/dose | 160 mg/kg/dose | Females 0 mg/kg/dose | 3 mg/kg/dose | 30 mg/kg/dose | 160 mg/kg/dose |
|---|---|---|---|---|---|---|---|---|
| Transferrin Day-11 (mg/dL; Baseline) | 241.96 ± 14.74 | 227.82 ± 22.69 | 239.14 ± 18.75 | 227.58 ± 10.21 | 241.96 ± 14.74 | 227.82 ± 22.69 | 239.14 ± 18.75 | 227.58 ± 10.21 |
| Transferrin Day 1, 96 h (mg/dL) | 259.28 ± 10.46 | 223.74 ± 20.49 ** | 226.74 ± 13.64 ** | 217.74 ± 9.88 ** | 259.28 ± 10.46 | 223.74 ± 20.49 ** | 226.74 ± 13.64 ** | 217.74 ± 9.88 ** |
| Day 1, 96 h tCtrl | — | 0.86 | 0.87 | 0.84 | — | 0.86 | 0.87 | 0.84 |
| Transferrin Day 1, 192 h (mg/dL) | 263.06 ± 19.77 | 224.92 ± 21.07 ** | 226.62 ± 11.34 ** | 221.64 ± 10.96 ** | 263.06 ± 19.77 | 224.92 ± 21.70 ** | 226.62 ± 11.34 ** | 221.64 ± 10.96 ** |
| Day 1, 192 h tCtrl | — | 0.86 | 0.86 | 0.84 | — | 0.86 | 0.86 | 0.84 |
| Transferrin Day 1, 336 h (mg/dL) | 260.68 ± 20.70 | 223.36 ± 24.75 * | 228.82 ± 8.80 | 225.72 ± 8.08 * | 260.68 ± 20.70 | 223.36 ± 24.75 * | 228.82 ± 8.80 | 225.72 ± 8.08 * |
| Day 1, 336 h tCtrl | — | 0.86 | 0.88 | 0.87 | — | 0.86 | 0.88 | 0.87 |
| Transferrin Day 15, 48 h (mg/dL) | 259.76 ± 18.52 | 218.06 ± 28.28 * | 225.86 ± 10.73 | 221.78 ± 9.85 * | 259.76 ± 18.52 | 218.06 ± 28.28 * | 225.86 ± 10.73 | 221.78 ± 9.85 * |
| Day 15, 48 h tCtrl | — | 0.84 | 0.87 | 0.85 | — | 0.84 | 0.87 | 0.85 |
| Transferrin Day 15, 96 h (mg/dL) | 253.88 ± 19.14 | 211.48 ± 22.48 ** | 219.52 ± 11.17 * | 209.26 ± 10.27 ** | 253.88 ± 19.14 | 211.48 ± 22.48 ** | 219.52 ± 11.17 * | 209.26 ± 10.27 ** |
| Day 15, 96 h tCtrl | — | 0.83 | 0.86 | 0.82 | — | 0.83 | 0.86 | 0.82 |
| Transferrin Day 15, 192 h (mg/dL) | 254.78 ± 24.23 | 215.88 ± 27.37 | 219.92 ± 10.13 | 211.30 ± 8.73 * | 254.78 ± 24.23 | 215.88 ± 27.37 | 219.92 ± 10.13 | 211.30 ± 8.73 * |
| Day 15, 192 h tCtrl | — | 0.85 | 0.86 | 0.83 | — | 0.85 | 0.86 | 0.83 |
| Transferrin Day 15, 336 h (mg/dL) | 268.04 ± 24.56 | 222.58 ± 26.20 ** | 235.52 ± 16.40 | 231.42 ± 11.07 * | 268.04 ± 24.56 | 222.58 ± 26.20 ** | 235.52 ± 16.40 | 231.42 ± 11.07 * |
| Day 15, 336 h tCtrl | — | 0.83 | 0.88 | 0.86 | — | 0.83 | 0.88 | 0.86 |
| Transferrin Day 29, 48 h (mg/dL) | 236.04 ± 14.11 | 198.48 ± 19.87 ** | 209.30 ± 14.41 * | 198.12 ± 10.25 ** | 236.04 ± 14.11 | 198.48 ± 19.87 ** | 209.30 ± 14.41 * | 198.12 ± 10.25 ** |
| Day 29, 48 h tCtrl | — | 0.84 | 0.89 | 0.84 | — | 0.84 | 0.89 | 0.84 |
| Transferrin Day 29, 96 h (mg/dL) | 252.24 ± 12.39 | 209.24 ± 24.21 ** | 225.80 ± 225.80 | 209.90 ± 8.04 ** | 252.24 ± 12.39 | 209.24 ± 24.21 ** | 225.80 ± 15.43 ** | 209.90 ± 8.04 ** |
| Day 29, 96 h tCtrl | — | 0.83 | 0.90 | 0.83 | — | 0.83 | 0.90 | 0.83 |

Anova & Dunnett: * = p ≤ 0.05;
** = p ≤ 0.01

Figure 18:
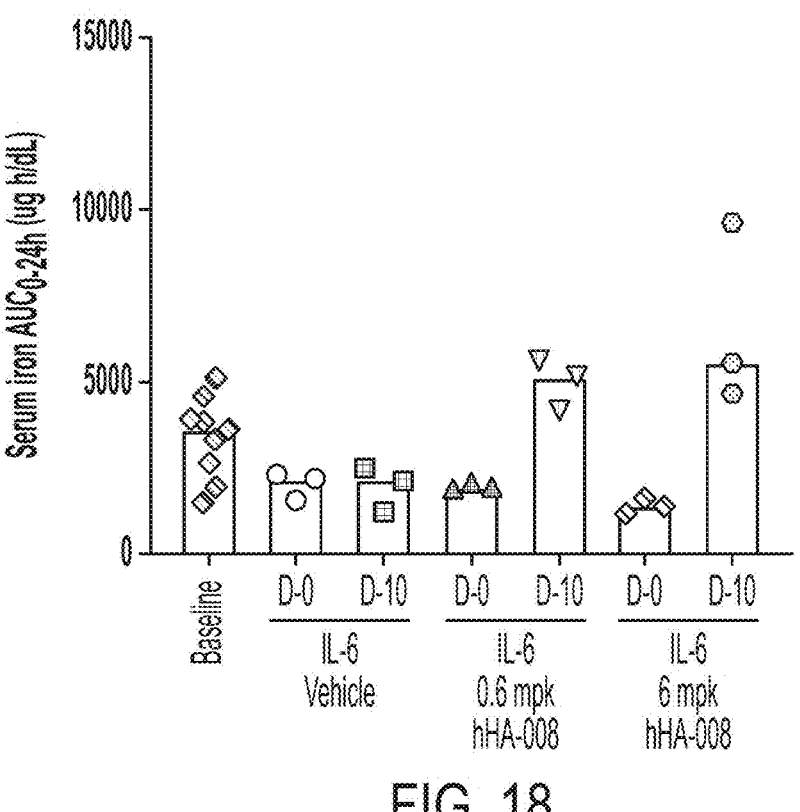
FIG. 18 shows that hHA-008 was effective in preventing IL-6-induced serum iron suppression in a dose-dependent manner in cynomolgus monkeys.

Example 9: hHA-008 Prevents Inflammation-Induced (IL-6) Iron Suppression in Cynomolgus Macaque Prevention of iron suppression by hHA-008 following IL-6 challenge was investigated in this study. On Day 0, three groups of cynos (N=3/group) were challenged with $6 \times 10^4$ international units (IU) IL-6/kg subcutaneously. On Day 3 each group of 3 animals received 0 (vehicle), 0.6 or 6 mg/kg of hHA-008 intravenously, respectively. On Day 10 all groups received a second challenge of $6 \times 10^4$ IU IL-6/kg subcutaneously. Blood was collected from all cynos to evaluate serum iron level at 48 hours and 24 hours prior to each IL-6 challenge, and 2, 4, 8 and 24 hours after each IL-6 dose. The average baseline value of the samples taken 48 and 24 hours prior to each IL-6 dose were used as D0 value. The results showed that hHA-008 was effective in preventing IL-6-induced serum iron suppression in a dose-dependent manner in cynomolgus monkeys (FIG. 18).

Example 10: Subcutaneous Injection of hHA-008 in Sprague-Dawley Rats

Sprague-Dawley Rats (6 females and 6 males) were injected with hHA-008 subcutaneously at 6 mg/kg (mpk). pharmacokinetics (SC PK) and pharmacodynamics (SC PD) were evaluated 35 days after dosing. Serum mean pharmacokinetic parameters (e.g., Cmax, Tmax, t½, and $AUC_{0\text{-}inf}$) were shown in Table 17:

TABLE 17

Serum Mean Pharmacokinetic (PK) Parameters of hHA-008
Following a Single SC Administration in Sprague-Dawley Rats

| Dose (mg/kg) | $C_{MAX}$ (µg/mL) (mean ± SD) | $T_{MAX}$ (DAYS) (mean ± SD) | $T_{1/2}$ (DAYS) (mean ± SD) | $AUC_{0\text{-}INF}$ (HR*MG/ML) (mean ± SD) |
|---|---|---|---|---|
| 6 | 37.6 ± 6.02 | 3.8 ± 0.6 | 4.3 ± 1.4 | 13,357 ± 1,437.4 |

Bioavailability of hHA-008 after subcutaneous adminis-tration was similar to bioavailability of hHA-008 after intravenous administration at 6 mg/kg, as evidenced by that subcutaneous injection bioavailability (SC bioavailability) of hHA-008 as about 84.7% of intravenous injection bio-availability of hHA-008 (IV bioavailability) (SC bioavailability=SC $DN\_AUC_{0\text{-}inf}$/IV $DN\_AUC_{0\text{-}inf}$×100; DN: Dose normalized). Further, the time to reach maximum concentration ($C_{max}$) was 3.6-4 days after SC administration with a much lower Cmax as compared to the Cmax after IV administration.

Figure 19:
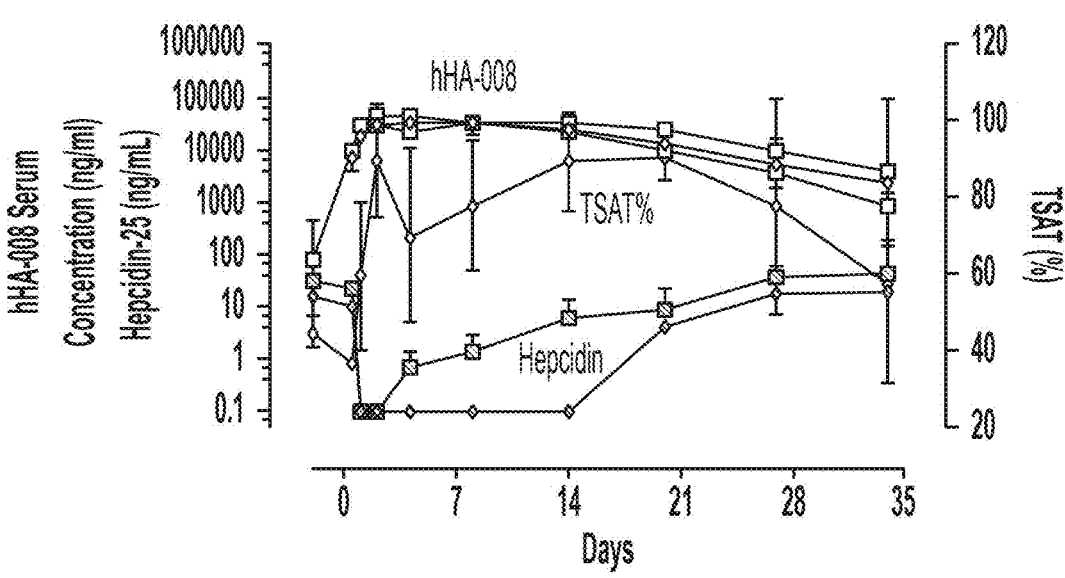
FIG. 19 shows that decline in PD response (e.g., Hepcidin-25 concentration and TSAT %) was consistent with the decrease of hHA-008 serum concentration (FIG. 19) after subcutaneous administration of hHA-008 to Sprague-Dawley Rats.

At similar dose level, the PD response between the IV or SC was indistinguishable: serum hHA-008 concentration became saturated 1-2 days after dosing, remained elevated through at least 21 days and the decline in PD response (e.g., Hepcidin-25 concentration and TSAT %) was consistent with the decrease of hHA-008 serum concentration (FIG. 19).

Example 11. Subcutaneous Dose Administration in Cynomolgus Monkeys

PK/PD of subcutaneous hHA-008 treatment were also evaluated in Cynomolgus (cynos). Cynos were injected with hHA-008 subcutaneously at 0.3 mpk, 0.6 mpk, 1 mpk and 6 mpk.

In the 6 mpk dosing group, 2 male and 1 female cynos received a single subcutaneous injection of hHA-008 at, and blood samples were collected for 61 days. Cynos received IV injection of hHA-008 at 6 mpk were used for comparison.

In the 0.3 mpk, 0.6 mpk, and 1.0 mpk groups, each group included 3 male cynos that received a single subcutaneous injection of hHA-008. Blood samples were collected for 27 days. Cynos received the same dose of hHA-008 by IV were used for comparison for each group.

Figure 20A:
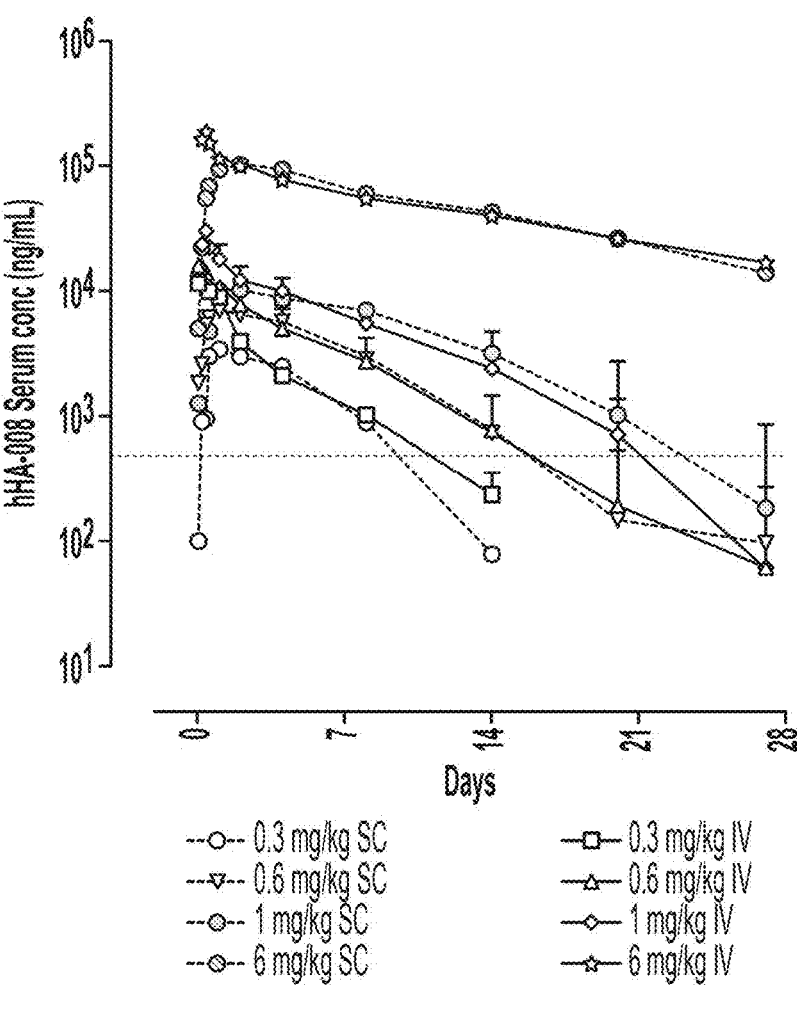
FIGS. 20A-20D show PK/PD analysis in cynomolgus monkeys after subcutaneous administration of hHA-008.

After SC administration of hHA-008 in cynomolgus mon-keys bioavailability was high and increased with dose levels (55.0% at 0.3 mpk, 81.9% at 0.6 mpk, 89.5% at 1 mpk and 100% at 6 mg/kg), when compared to animals injected at the same doses via IV. Tmax was reached rapidly after dosing in a dose dependent manner (1.33 to 2.67 days). Table 18 shows serum mean Pharmacokinetic (PK) parameters of hHA-008 following a single SC administration in cynos. hHA-008 serum concentration-time profiles became indis-tinguishable between SC injection and IV injection 4 days after administration (FIG. 20A).

TABLE 18

Serum Mean Pharmacokinetic (PK) Parameters of hHA-008
Following a Single SC Administration in Cynos

| Dose (mg/kg) | $C_{max}$ (µg/mL) (mean ± SD) | $T_{max}$ (day) (mean ± SD) | $t_{1/2}$ (day) (mean ± SD) | $AUC_{0\text{-}inf}$* (hr*µg/mL) (mean ± SD) | Bioavailability compared to IV |
|---|---|---|---|---|---|
| 0.3 | 3.21 ± 0.72 | 1.33 ± 0.58 | 1.69 ± 0.18 | 496.5 ± 81.29 | 55% |
| 0.6 | 7.2 ± 0.48 | 1.33 ± 0.58 | 2.82 ± 0.2 | 1417 ± 234 | 81.9% |
| 1 | 10.5 ± 1.76 | 2 ± 0 | 3.3 ± 1.43 | 2942 ± 300 | 89.5% |
| 6 | 102 ± 15.4 | 2.67 ± 1.15 | 7.95 ± 1.68 | 34439 ± 2,528 | 100% |

*extrapolation from $AUC_{0\text{-}last}$ was less than 3%.

Figure 20B:
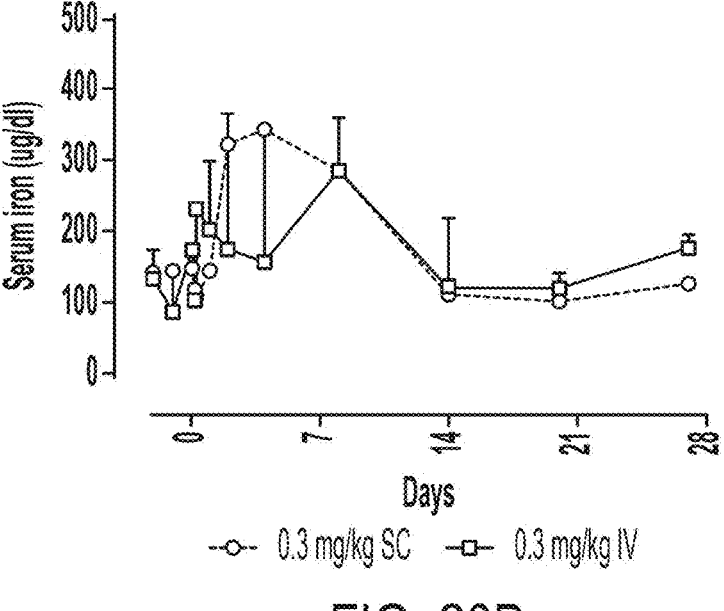
Figure 20C:
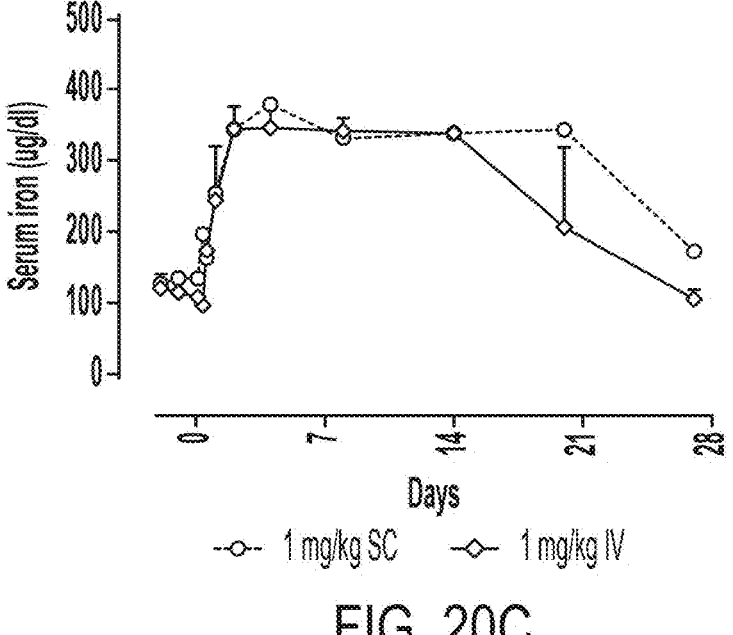
Figure 20D:
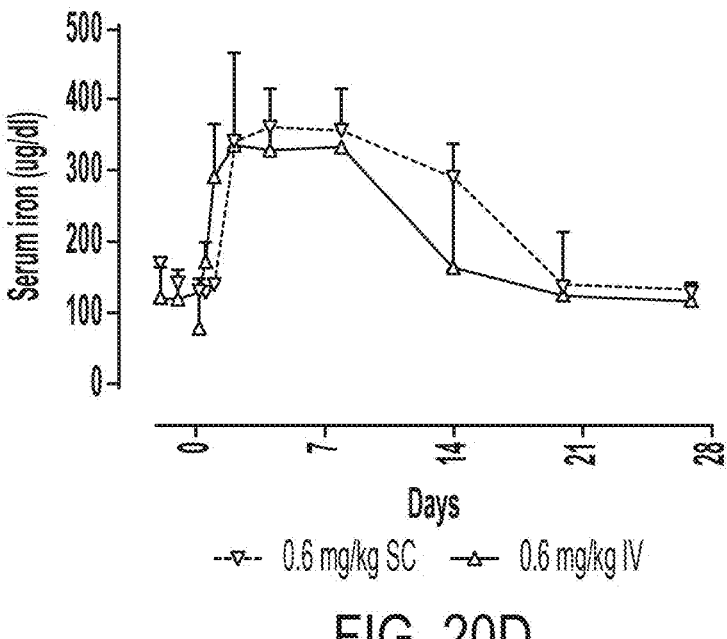

The PD response after SC dose was variable between animals, relatively proportional to the dose-level, and similar to the PD response observed after IV dosing at 0.1 mpk, 0.6 mpk, and 1.0 mpk. For all animals, the PD response was functionally maximal (TSAT>80% and hepcidin-25<LOQ) between 1-2 days after dosing. The return of the PD markers (e.g., serum iron) to baseline levels was consistent with the decline in hHA-008 serum concentrations (FIGS. 20B-20D). At 6 mpk, serum iron concentrations in both SC injected group and IV injected group were too saturated to reflect the change (data not shown).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also set forth as follows.

1. A method of treating a subject having an anemia of chronic disease, the method comprising: administering to the subject an effective amount of an isolated antibody that binds to human hemojuvelin (HJV), wherein the antibody comprises: a heavy chain complementary determining region 1 (HC CDR1) set forth as $X_1$YGMN (SEQ ID NO: 105), in which $X_j$ can be N or Y; a heavy chain complementary determining region 2 (HC CDR2) set forth as MIYYDSSX$_2$KHYADSVKG (SEQ ID NO: 106), in which $X_2$ can be E or D; a heavy chain complementary determining region 3 (HC CDR3) set forth as GX$_3$TPDX$_4$ (SEQ ID NO: 107), in which $X_3$ can be T or S, and $X_4$ can be Y, V, or K; and/or a light chain complementary determining region 1 (LC CDR1) set forth as RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H, a light chain complementary determining region 2 (LC CDR2) set forth as X$_9$VSX$_{10}$RFS (SEQ ID NO: 109), in which $X_9$ can be E, D or A, and $X_{10}$ can be N, S, T, E or H, a light chain complementary determining region 3 (LC CDR3) set forth as X$_{11}$QX$_{12}$TX$_{13}$DPX$_{14}$X$_{15}$ (SEQ ID NO: 110), in which $X_{11}$ can be F or, $X_{12}$ can be V or A, $X_{13}$ can be H or Y, $X_{14}$ can be M, L or V, and $X_{15}$ can be T or S.

2. A method of inhibiting iron sequestration in a subject having anemia of chronic disease, the method comprising administering to the subject an effective amount of the isolated antibody that binds to human hemojuvelin (HJV), wherein the antibody comprises: a heavy chain complementary determining region 1 (HC CDR1) set forth as $X_1$YGMN (SEQ ID NO: 105), in which $X_1$ can be N or Y; a heavy chain complementary determining region 2 (HC CDR2) set forth as MIYYDSSX$_2$KHYADSVKG (SEQ ID NO: 106), in which $X_2$ can be E or D; a heavy chain complementary determining region 3 (HC CDR3) set forth as GX$_3$TPDX$_4$ (SEQ ID NO: 107), in which $X_3$ can be T or S, and $X_4$ can be Y, V, or K; and/or a light chain complementary determining region 1 (C CDR1) set forth as RSSQSLX$_5$X$_6$SDGX$_7$TFLX$_8$ (SEQ ID NO: 108), in which $X_5$ can be A or E, $X_6$ can be T, S, E, or D, $X_7$ can be D, Y, or G, and $X_8$ can be E or H, a light chain complementary determining region 2 (LC CDR2) set forth as X$_9$VSX$_{10}$RFS (SEQ ID NO: 109), in which $X_9$ can be E, D or A, and $X_{10}$ can be N, S, T, E or H, a light chain complementary determining region 3 (LC CDR3) set forth as X$_{11}$QX$_{12}$TX$_{13}$DPX$_{14}$X$_{15}$ (SEQ ID NO: 110), in which $X_{11}$ can be F or M, $X_{12}$ can be V or A, $X_{13}$ can be H or Y, $X_{14}$ can be M, L or V, and $X_{15}$ can be T or S.

3. The method of embodiment 1 or embodiment 2, wherein the antibody comprises a VH comprising an amino acid sequence at least 85% identical to SEQ ID NO: 38, and/or a VL comprising an amino acid sequence at least 85% identical to SEQ ID NO: 39.

4. The method of embodiment 3, wherein the antibody comprises a VH comprising an amino acid sequence of SEQ ID NO: 38, and a VL comprising an amino acid sequence of SEQ ID NO: 39.

5. The method of any one of embodiments 1-4, wherein the antibody is a humanized antibody.

6. The method of embodiment 5, wherein the humanized antibody comprises a humanized VH and/or a humanized VL.

7. The method of any one of embodiments 1-6, wherein the antibody is selected from the group consisting of a full-length IgG, a Fab fragment, a F(ab') fragment, a F(ab')2 fragment, a scFv, and a Fv.

8. The method of embodiment 7, wherein the antibody is a full-length IgG.

9. The method of embodiment 8, wherein the antibody comprises a heavy chain constant region of the isotype IgG1, IgG2, IgG3, or IgG4.

10. The method of embodiment 9, wherein the antibody further comprises a heavy chain constant region set forth in SEQ ID NO: 46 or SEQ ID NO: 48.

11. The method of embodiment 10, wherein the antibody further comprises a light chain constant region set forth in SEQ ID NO: 47.

12. The method of any one of embodiments 1-11, wherein the antibody comprises: (i) a heavy chain comprising an amino acid sequence at least 85% identical to SEQ ID NO: 61, and/or a light chain comprising an amino acid sequence at least 85% identical to SEQ ID NO: 62; or (ii) a heavy chain comprising an amino acid sequence at least 85% identical to SEQ ID NO: 63, and/or a light chain comprising an amino acid sequence at least 85% identical to SEQ ID NO: 62.

13. The method of embodiment 12, wherein the antibody comprises a heavy chain comprising an amino acid sequence of SEQ ID NO: 61, and a light chain comprising an amino acid sequence of SEQ ID NO: 62.

14. The method of embodiment 12 wherein the antibody comprises a heavy chain comprising an amino acid sequence of SEQ ID NO: 63, and a light chain comprising an amino acid sequence of SEQ ID NO: 62.

15. The method of any one of embodiments 1-14, wherein the subject is erythrocyte transfusion-dependent.

16. The method of any one of embodiments 1-14, wherein the subject is erythrocyte transfusion-independent.

17. The method of any one of embodiments 1-14, wherein the anemia of chronic disease is an iron-restricted anemia.

18. The method of embodiment 17, wherein the iron-restricted anemia is associated with a functional iron deficiency.

19. The method of any one of embodiments 1-24, wherein the anemia of chronic disease is associated with (or caused by) chronic kidney disease.

20. The method of any one of embodiments 1-14, wherein the anemia of chronic disease is associated with (or caused by) cancer.

21. The method of embodiment 20, wherein the cancer is a myeloma.

22 The method of any one of embodiments 1-14, wherein the anemia of chronic disease is associated with (or caused by) a chronic infection.

23. The method of embodiment 22, wherein the infection is a bacterial, viral, fungal or parasitic infection.

24. The method of any one of embodiments 1-15, wherein the anemia of chronic disease is associated with (or caused by) an autoimmune disease.

25. The method of any one of embodiments 1-15, wherein the anemia of chronic disease is associated with (or caused by) a chronic disease that involves inflammation.

26. The method of embodiment 25, wherein the chronic disease that involves inflammation is inflammatory bowel disease, diabetes, or heart failure.

27. The method of any one of embodiments 1-26, wherein the subject is identified prior to the treatment as having high hepcidin levels.

28. The method of any one of embodiments 1-27, wherein the subject is identified as having a functional iron deficiency.

29. The method of any one of embodiments 1-28, wherein the subject is identified as exhibiting inflammation and/or iron-restricted erythropoiesis.

30. The method of any one of embodiments 1-29, wherein the subject is a human.

31. The method of any one of embodiments 1-30, wherein the anti-hemojuvelin antibody binds to hemojuvelin with a KD value that is at least 10-fold less than the KD value for binding of the anti-hemojuvelin antibody to RGMa.

32. The method of embodiment 29, wherein the anti-hemojuvelin antibody binds to hemojuvelin with a KD value that is at least 100-fold less than the KD value for binding of the anti-hemojuvelin antibody to RGMa.

33. The method of any one of embodiments 31 or 32, wherein the KD value for hemojuvelin is less than $100 \times 10^{-9}$ M.

34. An isolated antibody that binds to human hemojuvelin (HJV), wherein the antibody comprises a VH comprising an amino acid sequence at least 85% identical to SEQ ID NO: 38, and/or a VL comprising an amino acid sequence at least 85% identical to SEQ ID NO: 39.

35. The isolated antibody of embodiment 30, wherein the antibody comprises a VH comprising an amino acid sequence of SEQ ID NO: 38, and a VL comprising an amino acid sequence of SEQ ID NO: 39.

36. The isolated antibody of embodiment 34 or embodiment 35, wherein the antibody is a humanized antibody.

37. The isolated antibody of embodiment 36, wherein the humanized antibody comprises a humanized VH and/or a humanized VL.

38. The isolated antibody of any one of embodiments 34-37, wherein the antibody is selected from the group consisting of a full-length IgG, a Fab fragment, a F(ab') fragment, a F(ab')2 fragment, a scFv, and a Fv.

39. The isolated antibody of embodiment 38, wherein the antibody is a full-length IgG.

40. The isolated antibody of embodiment 39, wherein the antibody comprises a heavy chain constant region of the isotype IgG1, IgG2, IgG3, or IgG4.

41. The isolated antibody of embodiment 40, wherein the antibody further comprises a heavy chain constant region set forth in SEQ ID NOs: 46, 48, 112 or 113.

42. The isolated antibody of embodiment 41, wherein the antibody further comprises a light chain constant region set forth in SEQ ID NO: 47.

43. The isolated antibody of any one of embodiments 34-42, wherein the antibody comprises: (i) a heavy chain comprising an amino acid sequence at least 85% identical to SEQ ID NOs: 61 or 117, and/or a light chain comprising an amino acid sequence at least 85% identical to SEQ ID NO: 62; or (ii) a heavy chain comprising an amino acid sequence at least 85% identical to SEQ ID NOs: 63 or 118, and/or a light chain comprising an amino acid sequence at least 85% identical to SEQ ID NO: 62.

44. The isolated antibody of embodiment 43, wherein the antibody comprises a heavy chain comprising an amino acid sequence of SEQ ID NOs: 61 or 117, and a light chain comprising an amino acid sequence of SEQ ID NO: 62.

45. The isolated antibody of embodiment 43, wherein the antibody comprises a heavy chain comprising an amino acid sequence of SEQ ID NOs: 63 or 118, and a light chain comprising an amino acid sequence of SEQ ID NO: 62.

46. An isolated antibody that binds to human hemojuvelin (HJV) produced by expressing in a host cell: (i) a nucleic acid sequence encoding a heavy chain, wherein the nucleic acid sequence is at least 90% identical to SEQ ID NO: 92; and/or (ii) a nucleic acid sequence encoding a light chain, wherein the nucleic acid sequence is at least 90% identical to SEQ ID NO: 93.

47. An isolated antibody that binds to human hemojuvelin (HJV) produced by expressing in a host cell: (i) a nucleic acid sequence encoding a heavy chain, wherein the nucleic acid sequence is at least 90% identical to SEQ ID NO: 94; and/or (ii) a nucleic acid sequence encoding a light chain, wherein the nucleic acid sequence is at least 90% identical to SEQ ID NO: 93.

48. The isolated antibody of embodiments 46 or 47, wherein the host cell is Chinese hamster ovary (CHO) cells, dhfr– CHO cell, human embryonic kidney (HEK)-293 cells, verda reno (VERO) cells, nonsecreting null (NS0) cells, human embryonic retinal (PER.C6) cells, Sp2/0 cells, baby hamster kidney (BHK) cells, Madin-Darby Canine Kidney (MDCK) cells, Madin-Darby Bovine Kidney (MDBK) cells, or monkey kidney CV1 line transformed by SV40 (COS) cells.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B," the application also contemplates the alternative embodiments "a composition consisting of A and B" and "a composition consisting essentially of A and B."

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

What is claimed is:

1. A method of treating anemia in a subject having an anemia of chronic disease, the method comprising administering to the subject an effective amount of a composition comprising an isolated antibody that binds to human hemojuvelin (HJV) and a pharmaceutically acceptable carrier, wherein the isolated antibody comprises: a heavy chain comprising the amino acid sequence of SEQ ID NO: 120, and a light chain comprising the amino acid sequence of SEQ ID NO: 69.

2. The method of claim 1, wherein the composition is administered to the subject via subcutaneous injection.

3. The method of claim 1, wherein the composition is administered to the subject once monthly.

4. The method of claim 1, wherein the anemia results from hepcidin expression that is induced by at least one pro-inflammatory cytokine.

5. The method of claim 4, wherein the administration of the composition reduces the anemia.

6. The method of claim 4, wherein the at least one pro-inflammatory cytokine comprises Interleukin-6 (IL-6).

7. The method of claim 1, wherein the administration reduces hepcidin-25 in the subject within 24 hours of the administration.

8. The method of claim 7, wherein the administration reduces a hepcidin-25 level by at least 50% compared to the hepcidin-25 level in the subject prior to the administration.

9. The method of claim 1, wherein the subject has a serum hemoglobin level of less than 10 g/dL.

10. The method of claim 1, wherein the subject has a serum hemoglobin level of less than 8 g/dL.

11. The method of claim 1, wherein the subject is erythrocyte transfusion-dependent.

12. The method of claim 1, wherein the subject is erythrocyte transfusion-dependent.

13. The method of claim 1, wherein the anemia of chronic disease is an iron-restricted anemia.

14. The method of claim 1, wherein the anemia of chronic disease is associated with a chronic disease that involves inflammation selected from inflammatory bowel disease, diabetes, or heart failure.

15. A method of treating anemia in a subject having an anemia of chronic disease, the method comprising administering to the subject an effective amount of a composition comprising:
    (i) an isolated anti-human hemojuvelin (HJV) antibody comprising a heavy chain comprising the amino acid sequence of SEQ ID NO: 68, and a light chain comprising the amino acid sequence of SEQ ID NO: 69; and/or
    (ii) an isolated anti-human hemojuvelin (HJV) antibody comprising a heavy chain comprising the amino acid sequence of SEQ ID NO: 120, and a light chain comprising the amino acid sequence of SEQ ID NO: 69, wherein the composition further comprises a pharmaceutically acceptable carrier.

16. The method of claim 15, wherein the composition is administered to the subject via subcutaneous injection.

17. The method of claim 15, wherein the anemia results from hepcidin expression that is induced by at least one pro-inflammatory cytokine.

18. A method of treating anemia in a subject having an anemia of chronic disease, the method comprising: administering to the subject an effective amount of a composition comprising an isolated antibody that binds to human hemojuvelin (HJV) and a pharmaceutically acceptable carrier, wherein the isolated antibody comprises: a heavy chain comprising the amino acid sequence of SEQ ID NO: 68, and a light chain comprising the amino acid sequence of SEQ ID NO: 69.

19. The method of claim 18, wherein the composition is administered to the subject via subcutaneous injection.

20. The method of claim 18, wherein the anemia results from hepcidin expression that is induced by at least one pro-inflammatory cytokine.

*     *     *     *     *